United States Patent
Han

(10) Patent No.: US 10,626,156 B2
(45) Date of Patent: Apr. 21, 2020

(54) BIOREVERSABLE PROMOIETIES FOR NITROGEN-CONTAINING AND HYDROXYL-CONTAINING DRUGS

(71) Applicant: Jie Han, Bloomington, IN (US)

(72) Inventor: Jie Han, Bloomington, IN (US)

(73) Assignee: Jie Han, Bloomington, IN (US)

( * ) Notice: Subject to any disclaimer, the term of this patent is extended or adjusted under 35 U.S.C. 154(b) by 0 days.

(21) Appl. No.: 14/562,561

(22) Filed: Dec. 5, 2014

(65) Prior Publication Data

US 2015/0246958 A1 Sep. 3, 2015

Related U.S. Application Data

(60) Provisional application No. 61/913,166, filed on Dec. 6, 2013.

(51) Int. Cl.
| | | |
|---|---|---|
| *C07K 14/62* | (2006.01) | |
| *A61K 47/64* | (2017.01) | |
| *A61K 47/54* | (2017.01) | |
| *A61K 47/60* | (2017.01) | |
| *C07K 14/575* | (2006.01) | |
| *C07K 19/00* | (2006.01) | |

(52) U.S. Cl.
CPC ........... *C07K 14/62* (2013.01); *A61K 47/54* (2017.08); *A61K 47/542* (2017.08); *A61K 47/60* (2017.08); *A61K 47/643* (2017.08); *C07K 14/575* (2013.01); *C07K 19/00* (2013.01)

(58) Field of Classification Search
CPC ......... A61K 47/54; A61K 47/64; C07K 14/62
See application file for complete search history.

(56) References Cited

U.S. PATENT DOCUMENTS

| | | | |
|---|---|---|---|
| 4,100,346 A * | 7/1978 | Gottstein | ............. C07D 257/04 540/226 |
| 4,782,139 A | 11/1988 | DiMarchi et al. | |
| 8,697,838 B2 | 4/2014 | Dimarchi et al. | |
| 8,778,872 B2 | 7/2014 | DiMarchi et al. | |
| 8,962,547 B2 | 2/2015 | Jenkins et al. | |
| 8,980,242 B2 | 3/2015 | Vetter et al. | |
| 2008/0288176 A1 | 11/2008 | Tam et al. | |
| 2012/0230916 A1 | 9/2012 | Jenkins et al. | |
| 2013/0189328 A1 | 7/2013 | Cleemann et al. | |

FOREIGN PATENT DOCUMENTS

| | | | | |
|---|---|---|---|---|
| CN | 101066459 | | 11/2007 | |
| CN | 101066459 A | | 11/2007 | |
| CN | 101242859 | | 8/2008 | |
| CN | 101242859 A | | 8/2008 | |
| CN | 101541349 | | 9/2009 | |
| CN | 101541349 A | | 9/2009 | |
| CN | 101983066 | | 3/2011 | |
| CN | 101983066 A | | 3/2011 | |
| CN | 102695545 | | 9/2012 | |
| CN | 102695545 A | | 9/2012 | |
| CN | 103237561 | | 8/2013 | |
| CN | 103237561 A | | 8/2013 | |
| CN | 103384472 | | 11/2013 | |
| CN | 103384472 A | | 11/2013 | |
| EP | 2123305 A1 * | 11/2009 | | ............. A61K 47/60 |
| WO | WO-2005065361 A2 * | 7/2005 | | ............. C07C 69/65 |
| WO | WO 2007/064759 | | 6/2007 | |
| WO | WO 2007/064759 A2 | | 6/2007 | |
| WO | WO 2009/095479 | | 8/2009 | |
| WO | WO 2009/095479 A2 | | 8/2009 | |
| WO | WO/2010/080605 A1 | | 7/2010 | |
| WO | WO 2010/080609 A1 | | 7/2010 | |
| WO | WO 2011/012723 | | 2/2011 | |
| WO | WO2011012723 | | 2/2011 | |
| WO | WO 2011012723 A1 * | 2/2011 | | ........... A61K 31/428 |
| WO | WO 2011/082076 | | 7/2011 | |
| WO | WO 2011/082076 A1 | | 7/2011 | |
| WO | WO 2011/112978 | | 9/2011 | |
| WO | WO 2011/112978 A1 | | 9/2011 | |
| WO | WO 2011163460 A1 * | 12/2011 | | ............. C07K 14/65 |
| WO | WO 2012/122422 | | 9/2012 | |
| WO | WO 2012/122422 A2 | | 9/2012 | |
| WO | WO 2013/063204 | | 5/2013 | |
| WO | WO 2013/160340 | | 10/2013 | |
| WO | WO2013160340 | | 10/2014 | |

OTHER PUBLICATIONS

Li et al., International Journal of Biological Macromolecules, 50 (2012) 974-980.*
Beilfuss, Chelating Agents: their structure and properties, available on-line at: https://web.archive.org/web/20050528210454/www.westerhuis-restauratie.nl/pdf/chelating-agents.pdf, Apr. 6, 2004.*
Fife et al., "Intramolecular nucleophilic aminolysis of aliphatic esters. Cyclization of methyl 2-aminomethylbenzoate to phthalimidine," *Journal of the American Chemical Society*, 98: 6798-6982 (1976).
McDonald et al., "Intramolecular participation by the thiol group in amide hydrolysis: the general acid-catalyzed pathway," *Can. J. Chem.*, 61: 1846-1852 (1983).

(Continued)

*Primary Examiner* — James H Alstrum-Acevedo
*Assistant Examiner* — Kaipeen E Yang
(74) *Attorney, Agent, or Firm* — Sheppard Mullin Richter & Hampton LLP

(57) ABSTRACT

Disclosed are promoieties of the following formula which can be used to form prodrugs of nitrogen-containing or hydroxyl-containing drug or a pharmaceutically active agent:

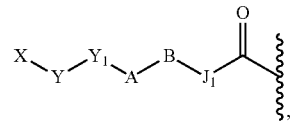

and pharmaceutical compositions comprising the prodrugs.

38 Claims, 6 Drawing Sheets

Specification includes a Sequence Listing.

(56) References Cited

OTHER PUBLICATIONS

Nielsen et al., "Prodrugs as drug delivery systems. Part 42. 2-Hydroxymethylbenzamides and 2-acyloxymethylbenzamides as potential prodrug forms for amines," *International Journal of Pharmaceutics*, 29: 9-18 (1986).
Petit et al., "New Family of Peptidomimetics Based on the Imidazole Motif," Organic Letters, 12(21): 4928-4931 (2010).
Suaifan et al., "Effects of steric bulk and stereochemistry on the rates of diketopiperazine formation from N-aminoacyl-2,2-dimethylthiazolidine-4-carboxamides (Dmt dipeptide amides)—a model for a new prodrug linker system," *Tetrahedron*, 62: 11245-11266 (2006).
PCT Notification of Transmittal of the International Search Report and the Written Opinion of the International Search Authority, or the Declaration for International Application No. PCT/CN2014/093165 dated Mar. 3, 2015.
Wenjun Li et al., "Synthesis, Drug Release and anti-HIV activity of a series of PEGylated zidovudine conjugates," International Journal of Biological Macromolecules, 2012, pp. 974-980, vol. 50, Elsevier B.V.
European Official Communication for EP Application No. 14868224.8 dated Sep. 21, 2018.
European Office Action for EP Application No. 14868224.8 dated Aug. 23, 2019.
Wenjun Li et al., (2012) "Synthesis, drug release and anti-HIV activity of a series of PEGylated zidovudine conjugates", International Journal of Biological Macromolecules, Elsevier BV, NL, vol. 50, No. 4, pp. 974-980, Feb. 18, 2012.
Examination Report for AU Appln. No. 2014359894 dated Nov. 6, 2019, 4 pages.

\* cited by examiner

SEQUENCE LISTING

<160> NUMBER OF SEQ ID NOS: 62

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 3
<211> LENGTH: 21
<212> TYPE: PRT
<213> ORGANISM: Homo sapiens

<400> SEQUENCE: 3

Gly Ile Val Asp Glu Cys Cys Phe Arg Ser Cys Asp Leu Arg Arg Leu
1               5                   10                  15

Glu Met Tyr Cys Ala
            20

<210> SEQ ID NO 4
<211> LENGTH: 29
<212> TYPE: PRT
<213> ORGANISM: Homo sapiens

<400> SEQUENCE: 4

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr
            20                  25

<210> SEQ ID NO 5
<211> LENGTH: 8
<212> TYPE: PRT
<213> ORGANISM: Homo sapiens

<400> SEQUENCE: 5

Pro Leu Lys Pro Ala Lys Ser Ala
1               5

<210> SEQ ID NO 6
<211> LENGTH: 12
<212> TYPE: PRT
<213> ORGANISM: Homo sapiens

<400> SEQUENCE: 6

Gly Tyr Gly Ser Ser Ser Arg Arg Ala Pro Gln Thr
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Tyr Gly Ser Ser Ser Arg Arg Ala Pro Gln Thr
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Gly Ser Ser Ser Arg Arg Ala Pro Gln Thr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Ser Gly Ser Ser Ser Ala Ala Ala Pro Gln Thr
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Ala Gly Ser Ser Ser Arg Arg Ala Pro Gln Thr
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Ala Gly Ser Ser Ser Ala Ala Ala Pro Gln Thr
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 12

Gly Tyr Gly Ser Ser Arg Arg
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Ser Gly Ser Ser Arg Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Arg Gly Pro Gly Gly Gly
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Arg Gly Gly Gly Gly Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Gly Gly Gly Lys Arg
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Ala Pro Gly Asp Val Lys Arg
1               5

<210> SEQ ID NO 18
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Arg Ala Pro Gly Asp Val Gly Gly
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Pro Gly Lys Arg
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Tyr Pro Gly Asp Val Lys Arg
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Arg Tyr Pro Gly Asp Val Gly Gly
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Gly His Pro Gly Asp Val Lys Arg
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Arg His Pro Gly Asp Val Gly Gly
```

```
<210> SEQ ID NO 24
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be promoiety modified
<220> FEATURE:
<221> NAME/KEY: MOD_RES
<222> LOCATION: (1)..(1)
<223> OTHER INFORMATION: Lysine, arginine, or not present
<220> FEATURE:
<221> NAME/KEY: MOD_RES
<222> LOCATION: (2)..(2)
<223> OTHER INFORMATION: Lysine, arginine, or not present
<220> FEATURE:
<221> NAME/KEY: MOD_RES
<222> LOCATION: (3)..(3)
<223> OTHER INFORMATION: Sarcosine, D-alanine, D-leucine, D-lysine,
      D-glutamic acid, D-tryptophan, p-benzoyl-L-phenylalanine (Bpa),
      or glycine
<220> FEATURE:
<221> NAME/KEY: MOD_RES
<222> LOCATION: (6)..(6)
<223> OTHER INFORMATION: Aspartic acid or glutamic acid
<220> FEATURE:
<221> NAME/KEY: MOD_RES
<222> LOCATION: (7)..(7)
<223> OTHER INFORMATION: Aspartic acid, glutamic acid, asparagine, or
      glutamine
<220> FEATURE:
<221> NAME/KEY: MOD_RES
<222> LOCATION: (10)..(10)
<223> OTHER INFORMATION: 2,4-diaminobutyric acid (DAB), leucine,
      isoleucine, threonine, histidine, arginine, lysine, asparagine,
      glutamine, tryptophan, tyrosine, alanine, phenylalanine, valine,
      or methionine
<220> FEATURE:
<221> NAME/KEY: MOD_RES
<222> LOCATION: (11)..(11)
<223> OTHER INFORMATION: Alanine, serine, arginine, or lysine
<220> FEATURE:
<221> NAME/KEY: MOD_RES
<222> LOCATION: (12)..(12)
<223> OTHER INFORMATION: Isoleucine, serine, lysine, or arginine
<220> FEATURE:
<221> NAME/KEY: MOD_RES
<222> LOCATION: (14)..(14)
<223> OTHER INFORMATION: Aspartic acid or serine
<220> FEATURE:
<221> NAME/KEY: MOD_RES
<222> LOCATION: (16)..(16)
<223> OTHER INFORMATION: Tyrosine, phenylalanine, tryptophan, arginine,
      alanine, glutamic acid, histidine, or lysine
<220> FEATURE:
<221> NAME/KEY: MOD_RES
<222> LOCATION: (17)..(17)
<223> OTHER INFORMATION: Glutamine, leucine, arginine, or lysine
<220> FEATURE:
<221> NAME/KEY: MOD_RES
<222> LOCATION: (20)..(20)
<223> OTHER INFORMATION: Asparagine, methionine, or threonine
<220> FEATURE:
<221> NAME/KEY: MOD_RES
<222> LOCATION: (23)..(23)
<223> OTHER INFORMATION: Asparagine, aspartic acid, alanine, glycine,
      lysine, or arginine
<220> FEATURE:
<221> NAME/KEY: misc_feature
<222> LOCATION: (24)..(25)
<223> OTHER INFORMATION: This region may encompass lysine, arginine,
      "lysine-lysine" dipeptide, "arginine-arginine" dipeptide, or may
      not be present
<220> FEATURE:
```

-continued

<223> OTHER INFORMATION: See specification as filed for detailed
      description of substitutions and preferred embodiments

<400> SEQUENCE: 24

Xaa Xaa Xaa Ile Val Xaa Xaa Cys Cys Xaa Xaa Xaa Cys Xaa Leu Xaa
1               5                   10                  15

Xaa Leu Glu Xaa Tyr Cys Xaa Xaa Xaa
            20                  25

<210> SEQ ID NO 25
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<221> NAME/KEY: misc_feature
<222> LOCATION: (1)..(4)
<223> OTHER INFORMATION: This region may encompass any codable amino
      acid except cysteine, a dipeptide or tripeptide comprising no
      cysteine, a tripeptide "Gly Pro Glu," a tetrapeptide "Phe Val Asn
      Gln," wherein some or all positions may be absent
<220> FEATURE:
<221> NAME/KEY: MOD_RES
<222> LOCATION: (5)..(5)
<223> OTHER INFORMATION: Histidine, threonine, arginine, or lysine
<220> FEATURE:
<221> NAME/KEY: MOD_RES
<222> LOCATION: (9)..(9)
<223> OTHER INFORMATION: Threonine, alanine, serine, glycine, or
      alpha-aminoisobutyric acid
<220> FEATURE:
<221> NAME/KEY: MOD_RES
<222> LOCATION: (10)..(10)
<223> OTHER INFORMATION: Histidine, aspartic acid, glutamic acid,
      homoglutamic acid, homocysteic acid, cysteic acid, arginine, or
      phenylalanine
<220> FEATURE:
<221> NAME/KEY: MOD_RES
<222> LOCATION: (13)..(13)
<223> OTHER INFORMATION: Glutamic acid or aspartic acid
<220> FEATURE:
<221> NAME/KEY: MOD_RES
<222> LOCATION: (14)..(14)
<223> OTHER INFORMATION: Alanine, threonine, or alpha-aminoisobutyric
      acid
<220> FEATURE:
<221> NAME/KEY: MOD_RES
<222> LOCATION: (16)..(16)
<223> OTHER INFORMATION: Tyrosine, phenylalanine, or tryptophan
<220> FEATURE:
<221> NAME/KEY: MOD_RES
<222> LOCATION: (17)..(17)
<223> OTHER INFORMATION: Phenylalanine, tryptophan, or leucine
<220> FEATURE:
<221> NAME/KEY: MOD_RES
<222> LOCATION: (20)..(20)
<223> OTHER INFORMATION: Glycine or alanine
<220> FEATURE:
<221> NAME/KEY: MOD_RES
<222> LOCATION: (21)..(21)
<223> OTHER INFORMATION: Glutamic acid, aspartic acid, or alanine
<220> FEATURE:
<221> NAME/KEY: MOD_RES
<222> LOCATION: (22)..(22)
<223> OTHER INFORMATION: Arginine, lysine, aspartic acid, glutamic acid,
      or alanine
<220> FEATURE:
<221> NAME/KEY: MOD_RES
<222> LOCATION: (24)..(24)
<223> OTHER INFORMATION: Phenylalanine, D-Phenylalanine, D-tyrosine,
      D-alanine, or glycine
<220> FEATURE:

```
<221> NAME/KEY: MOD_RES
<222> LOCATION: (25)..(25)
<223> OTHER INFORMATION: Tyrosine, phenylalanine, asparagine, or
      histidine
<220> FEATURE:
<221> NAME/KEY: MOD_RES
<222> LOCATION: (26)..(26)
<223> OTHER INFORMATION: Tyrosine, D-tyrosine, phenylalanine, alanine,
      serine, histidine, D-alanine, D-tyrosine, glutamic acid,
      sarcosine, or not present
<220> FEATURE:
<221> NAME/KEY: MOD_RES
<222> LOCATION: (27)..(27)
<223> OTHER INFORMATION: Threonine, asparagine, arginine, glutamic acid,
      aspartic acid, lysine, serine, proline, or not present
<220> FEATURE:
<221> NAME/KEY: MOD_RES
<222> LOCATION: (28)..(28)
<223> OTHER INFORMATION: Proline, arginine, lysine, orthonine, glutamic
      acid, aspartic acid, or not present
<220> FEATURE:
<221> NAME/KEY: MOD_RES
<222> LOCATION: (29)..(29)
<223> OTHER INFORMATION: Proline, lysine, glutamic acid, aspartic acid,
      or not present
<220> FEATURE:
<221> NAME/KEY: MOD_RES
<222> LOCATION: (30)..(30)
<223> OTHER INFORMATION: Threonine, alanine, glutamic acid, aspartic
      acid, or not present
<220> FEATURE:
<221> NAME/KEY: misc_feature
<222> LOCATION: (31)..(32)
<223> OTHER INFORMATION: This region may encompass "arginine-arginine"
      dipeptide, "glutamic acid-glutamic acid" dipeptide, "aspartic
      acid-aspartic acid" dipeptide, or may not be present
<220> FEATURE:
<223> OTHER INFORMATION: See specification as filed for detailed
      description of substitutions and preferred embodiments

<400> SEQUENCE: 25

Xaa Xaa Xaa Xaa Xaa Leu Cys Gly Xaa Xaa Leu Val Xaa Xaa Leu Xaa
1               5                   10                  15

Xaa Val Cys Xaa Xaa Xaa Gly Xaa Xaa Xaa Xaa Xaa Xaa Xaa Xaa
            20                  25                  30

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Phe Val Asn Gln
1

<210> SEQ ID NO 27
<211> LENGTH: 57
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<221> NAME/KEY: misc_feature
<222> LOCATION: (1)..(4)
<223> OTHER INFORMATION: This region may encompass any codable amino
      acid except cysteine, a dipeptide or tripeptide comprising no
      cysteine, a tripeptide "Gly Pro Glu," a tetrapeptide "Phe Val Asn
      Gln," wherein some or all positions may be absent
```

```
<220> FEATURE:
<221> NAME/KEY: MOD_RES
<222> LOCATION: (5)..(5)
<223> OTHER INFORMATION: Histidine, threonine, arginine, or lysine
<220> FEATURE:
<221> NAME/KEY: MOD_RES
<222> LOCATION: (9)..(9)
<223> OTHER INFORMATION: Threonine, alanine, serine, glycine, or
      alpha-aminoisobutyric acid
<220> FEATURE:
<221> NAME/KEY: MOD_RES
<222> LOCATION: (10)..(10)
<223> OTHER INFORMATION: Histidine, aspartic acid, glutamic acid,
      homoglutamic acid, homocysteic acid, cysteic acid, arginine, or
      phenylalanine
<220> FEATURE:
<221> NAME/KEY: MOD_RES
<222> LOCATION: (14)..(14)
<223> OTHER INFORMATION: Alanine, threonine, or alpha-aminoisobutyric
      acid
<220> FEATURE:
<221> NAME/KEY: MOD_RES
<222> LOCATION: (16)..(16)
<223> OTHER INFORMATION: Tyrosine, phenylalanine, or tryptophan
<220> FEATURE:
<221> NAME/KEY: MOD_RES
<222> LOCATION: (17)..(17)
<223> OTHER INFORMATION: Phenylalanine, tryptophan, or leucine
<220> FEATURE:
<221> NAME/KEY: MOD_RES
<222> LOCATION: (20)..(20)
<223> OTHER INFORMATION: Glycine or alanine
<220> FEATURE:
<221> NAME/KEY: MOD_RES
<222> LOCATION: (21)..(21)
<223> OTHER INFORMATION: Glutamic acid, aspartic acid, or alanine
<220> FEATURE:
<221> NAME/KEY: MOD_RES
<222> LOCATION: (22)..(22)
<223> OTHER INFORMATION: Arginine, lysine, aspartic acid, glutamic acid,
      or alanine
<220> FEATURE:
<221> NAME/KEY: MOD_RES
<222> LOCATION: (24)..(24)
<223> OTHER INFORMATION: Phenylalanine, D-phenylalanine, D-tyrosine,
      D-alanine, or glycine
<220> FEATURE:
<221> NAME/KEY: MOD_RES
<222> LOCATION: (25)..(25)
<223> OTHER INFORMATION: Tyrosine, phenylalanine, asparagine, or
      histidine
<220> FEATURE:
<221> NAME/KEY: MOD_RES
<222> LOCATION: (26)..(26)
<223> OTHER INFORMATION: Tyrosine, D-tyrosine, phenylalanine, alanine,
      serine, histidine, D-alanine, D-tyrosine, glutamic acid,
      sarcosine, or not present
<220> FEATURE:
<221> NAME/KEY: MOD_RES
<222> LOCATION: (27)..(27)
<223> OTHER INFORMATION: Threonine, asparagine, arginine, glutamic acid,
      aspartic acid, lysine, serine, proline, or not present
<220> FEATURE:
<221> NAME/KEY: MOD_RES
<222> LOCATION: (28)..(28)
<223> OTHER INFORMATION: Proline, arginine, lysine, orthonine, glutamic
      acid, aspartic acid, or not present
<220> FEATURE:
<221> NAME/KEY: MOD_RES
<222> LOCATION: (29)..(29)
<223> OTHER INFORMATION: Proline, lysine, glutamic acid, aspartic acid,
      or not present
<220> FEATURE:
<221> NAME/KEY: MOD_RES
<222> LOCATION: (30)..(30)
<223> OTHER INFORMATION: Threonine, alanine, glutamic acid, aspartic
      acid, or not present
<220> FEATURE:
<221> NAME/KEY: misc_feature
```

```
<222> LOCATION: (31)..(32)
<223> OTHER INFORMATION: This region may encompass "arginine-arginine"
      dipeptide, "glutamic acid-glutamic acid" dipeptide, "aspartic
      acid-aspartic acid" dipeptide, or may not be present
<220> FEATURE:
<221> NAME/KEY: misc_feature
<222> LOCATION: (32)..(33)
<223> OTHER INFORMATION: Residues at these positions are separated by a
      prodrug moiety
<220> FEATURE:
<221> NAME/KEY: MOD_RES
<222> LOCATION: (33)..(33)
<223> OTHER INFORMATION: Lysine, arginine, or not present
<220> FEATURE:
<221> NAME/KEY: MOD_RES
<222> LOCATION: (34)..(34)
<223> OTHER INFORMATION: Lysine, arginine, or not present
<220> FEATURE:
<221> NAME/KEY: MOD_RES
<222> LOCATION: (35)..(35)
<223> OTHER INFORMATION: Sarcosine, D-alanine, D-leucine, D-lysine,
      D-glutamic acid, D-tryptophan, p-benzoyl-L-phenylalanine (Bpa), or
      glycine
<220> FEATURE:
<221> NAME/KEY: MOD_RES
<222> LOCATION: (38)..(38)
<223> OTHER INFORMATION: Aspartic acid or glutamic acid
<220> FEATURE:
<221> NAME/KEY: MOD_RES
<222> LOCATION: (39)..(39)
<223> OTHER INFORMATION: Aspartic acid, glutamic acid, asparagine, or
      glutamine
<220> FEATURE:
<221> NAME/KEY: MOD_RES
<222> LOCATION: (42)..(42)
<223> OTHER INFORMATION: 2,4-diaminobutyric acid (DAB), leucine,
      isoleucine, threonine, histidine, arginine, lysine, asparagine,
      glutamine, tryptophan, tyrosine, alanine, phenylalanine, valine,
      or methionine
<220> FEATURE:
<221> NAME/KEY: MOD_RES
<222> LOCATION: (43)..(43)
<223> OTHER INFORMATION: Alanine, serine, arginine, or lysine
<220> FEATURE:
<221> NAME/KEY: MOD_RES
<222> LOCATION: (44)..(44)
<223> OTHER INFORMATION: Isoleucine, serine, lysine, or arginine
<220> FEATURE:
<221> NAME/KEY: MOD_RES
<222> LOCATION: (48)..(48)
<223> OTHER INFORMATION: Tyrosine, phenylalanine, tryptophan, arginine,
      alanine, glutamic acid, histidine, or lysine
<220> FEATURE:
<221> NAME/KEY: MOD_RES
<222> LOCATION: (49)..(49)
<223> OTHER INFORMATION: Glutamine, leucine, arginine, or lysine
<220> FEATURE:
<221> NAME/KEY: MOD_RES
<222> LOCATION: (52)..(52)
<223> OTHER INFORMATION: Asparagine, methionine, or threonine
<220> FEATURE:
<221> NAME/KEY: MOD_RES
<222> LOCATION: (55)..(55)
<223> OTHER INFORMATION: Asparagine, aspartic acid, alanine, glycine,
      lysine, or arginine
<220> FEATURE:
<221> NAME/KEY: misc_feature
<222> LOCATION: (56)..(57)
<223> OTHER INFORMATION: This region may encompass lysine, arginine,
      "lysine-lysine" dipeptide, "arginine-arginine" dipeptide, or may
      not be present
<220> FEATURE:
<223> OTHER INFORMATION: See specification as filed for detailed
      description of substitutions and preferred embodiments

<400> SEQUENCE: 27

Xaa Xaa Xaa Xaa Xaa Leu Cys Gly Xaa Xaa Leu Val Glu Xaa Leu Xaa
1               5                   10                  15
```

```
Xaa Val Cys Xaa Xaa Xaa Gly Xaa Xaa Xaa Xaa Xaa Xaa Xaa Xaa
        20                  25                  30

Xaa Xaa Xaa Ile Val Xaa Xaa Cys Cys Xaa Xaa Xaa Cys Ser Leu Xaa
            35                  40                  45

Xaa Leu Glu Xaa Tyr Cys Xaa Xaa Xaa
    50                  55

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be promoiety modified
<220> FEATURE:
<221> NAME/KEY: MOD_RES
<222> LOCATION: (8)..(8)
<223> OTHER INFORMATION: 2,4-diaminobutyric acid (DAB), leucine,
      isoleucine, threonine, histidine, arginine, lysine, asparagine,
      glutamine, tryptophan, tyrosine, alanine, phenylalanine, valine,
      or methionine
<220> FEATURE:
<221> NAME/KEY: MOD_RES
<222> LOCATION: (21)..(21)
<223> OTHER INFORMATION: Asparagine, aspartic acid, alanine, glycine,
      lysine, or arginine
<220> FEATURE:
<223> OTHER INFORMATION: See specification as filed for detailed
      description of substitutions and preferred embodiments

<400> SEQUENCE: 28

Gly Ile Val Glu Gln Cys Cys Xaa Ser Ile Cys Ser Leu Tyr Gln Leu
1               5                   10                  15

Glu Asn Tyr Cys Xaa
            20

<210> SEQ ID NO 29
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<221> NAME/KEY: misc_feature
<222> LOCATION: (1)..(4)
<223> OTHER INFORMATION: This region may encompass any codable amino
      acid except cysteine, a dipeptide or tripeptide comprising no
      cysteine, a tripeptide "Gly Pro Glu," a tetrapeptide "Phe Val Asn
      Gln," wherein some or all positions may be absent
<220> FEATURE:
<221> NAME/KEY: MOD_RES
<222> LOCATION: (25)..(25)
<223> OTHER INFORMATION: Tyrosine, phenylalanine, asparagine, or
      histidine
<220> FEATURE:
<221> NAME/KEY: MOD_RES
<222> LOCATION: (26)..(26)
<223> OTHER INFORMATION: Tyrosine, D-tyrosine, phenylalanine, alanine,
      serine, histidine, D-alanine, D-tyrosine, glutamic acid,
      sarcosine, or not present
<220> FEATURE:
<221> NAME/KEY: MOD_RES
<222> LOCATION: (27)..(27)
<223> OTHER INFORMATION: Threonine, asparagine, arginine, glutamic acid,
      aspartic acid, lysine, serine, proline, or not present
<220> FEATURE:
<221> NAME/KEY: MOD_RES
```

```
<222> LOCATION: (28)..(28)
<223> OTHER INFORMATION: Proline, arginine, lysine, orthonine, glutamic
      acid, aspartic acid, or not present
<220> FEATURE:
<221> NAME/KEY: MOD_RES
<222> LOCATION: (29)..(29)
<223> OTHER INFORMATION: Proline, lysine, glutamic acid, aspartic acid,
      or not present
<220> FEATURE:
<221> NAME/KEY: MOD_RES
<222> LOCATION: (30)..(30)
<223> OTHER INFORMATION: Threonine, alanine, glutamic acid, aspartic
      acid, or not present
<220> FEATURE:
<221> NAME/KEY: misc_feature
<222> LOCATION: (31)..(32)
<223> OTHER INFORMATION: This region may encompass "arginine-arginine"
      dipeptide, "glutamic acid-glutamic acid" dipeptide, "aspartic
      acid-aspartic acid" dipeptide, or may not be present
<220> FEATURE:
<223> OTHER INFORMATION: See specification as filed for detailed
      description of substitutions and preferred embodiments

<400> SEQUENCE: 29

Xaa Xaa Xaa Xaa His Leu Cys Gly Ser His Leu Val Glu Ala Leu Tyr
1               5                   10                  15

Leu Val Cys Gly Glu Arg Gly Phe Xaa Xaa Xaa Xaa Xaa Xaa Xaa Xaa
            20                  25                  30

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be promoiety modified
<220> FEATURE:
<221> NAME/KEY: MOD_RES
<222> LOCATION: (21)..(21)
<223> OTHER INFORMATION: Asparagine, aspartic acid, alanine, glycine,
      lysine, or arginine
<220> FEATURE:
<223> OTHER INFORMATION: See specification as filed for detailed
      description of substitutions and preferred embodiments

<400> SEQUENCE: 30

Gly Ile Val Glu Gln Cys Cys Thr Ser Ile Cys Ser Leu Tyr Gln Leu
1               5                   10                  15

Glu Asn Tyr Cys Xaa
            20

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<221> NAME/KEY: misc_feature
<222> LOCATION: (1)..(4)
<223> OTHER INFORMATION: This region may encompass any codable amino
      acid except cysteine, a dipeptide or tripeptide comprising no
      cysteine, a tripeptide "Gly Pro Glu," a tetrapeptide "Phe Val Asn
      Gln," wherein some or all positions may be absent
<220> FEATURE:
<221> NAME/KEY: MOD_RES
<222> LOCATION: (28)..(28)
<223> OTHER INFORMATION: Proline, arginine, lysine, orthonine, glutamic
```

```
       acid, aspartic acid, or not present
<220>  FEATURE:
<221>  NAME/KEY: MOD_RES
<222>  LOCATION: (29)..(29)
<223>  OTHER INFORMATION: Proline, lysine, glutamic acid, aspartic acid,
       or not present
<220>  FEATURE:
<221>  NAME/KEY: MOD_RES
<222>  LOCATION: (30)..(30)
<223>  OTHER INFORMATION: Threonine, alanine, glutamic acid, aspartic
       acid, or not present
<220>  FEATURE:
<223>  OTHER INFORMATION: See specification as filed for detailed
       description of substitutions and preferred embodiments

<400> SEQUENCE: 31

Xaa Xaa Xaa Xaa His Leu Cys Gly Ser His Leu Val Glu Ala Leu Tyr
1               5                   10                  15

Leu Val Cys Gly Glu Arg Gly Phe Phe Tyr Thr Xaa Xaa Xaa
            20                  25                  30

<210>  SEQ ID NO 32
<211>  LENGTH: 30
<212>  TYPE: PRT
<213>  ORGANISM: Artificial Sequence
<220>  FEATURE:
<223>  OTHER INFORMATION: Description of Artificial Sequence: Synthetic
       polypeptide
<220>  FEATURE:
<223>  OTHER INFORMATION: N-term may be promoiety modified
<220>  FEATURE:
<221>  NAME/KEY: MOD_RES
<222>  LOCATION: (28)..(28)
<223>  OTHER INFORMATION: Proline, arginine, lysine, orthonine, glutamic
       acid, aspartic acid, or not present
<220>  FEATURE:
<221>  NAME/KEY: MOD_RES
<222>  LOCATION: (29)..(29)
<223>  OTHER INFORMATION: Proline, lysine, glutamic acid, aspartic acid,
       or not present
<220>  FEATURE:
<221>  NAME/KEY: MOD_RES
<222>  LOCATION: (30)..(30)
<223>  OTHER INFORMATION: Threonine, alanine, glutamic acid, aspartic
       acid, or not present
<220>  FEATURE:
<223>  OTHER INFORMATION: See specification as filed for detailed
       description of substitutions and preferred embodiments

<400> SEQUENCE: 32

Phe Val Asn Gln His Leu Cys Gly Ser His Leu Val Glu Ala Leu Tyr
1               5                   10                  15

Leu Val Cys Gly Glu Arg Gly Phe Phe Tyr Thr Xaa Xaa Xaa
            20                  25                  30

<210>  SEQ ID NO 33
<211>  LENGTH: 30
<212>  TYPE: PRT
<213>  ORGANISM: Artificial Sequence
<220>  FEATURE:
<223>  OTHER INFORMATION: Description of Artificial Sequence: Synthetic
       polypeptide
<220>  FEATURE:
<223>  OTHER INFORMATION: N-term may be promoiety modified

<400> SEQUENCE: 33

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

```
<210> SEQ ID NO 34
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified

<400> SEQUENCE: 34

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 35
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be promoiety modified
<220> FEATURE:
<223> OTHER INFORMATION: C-term NH2

<400> SEQUENCE: 35

Phe Val Asn Gln His Leu Cys Gly Ser His Leu Val Glu Ala Leu Tyr
1               5                   10                  15

Leu Val Cys Gly Glu Arg Gly Phe Phe
            20                  25

<210> SEQ ID NO 36
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be promoiety modified
<220> FEATURE:
<221> NAME/KEY: MOD_RES
<222> LOCATION: (5)..(5)
<223> OTHER INFORMATION: Aspartic acid, glutamic acid, asparagine, or
      glutamine
<220> FEATURE:
<221> NAME/KEY: MOD_RES
<222> LOCATION: (8)..(8)
<223> OTHER INFORMATION: 2,4-diaminobutyric acid (DAB), leucine,
      isoleucine, threonine, histidine, arginine, lysine, asparagine,
      glutamine, tryptophan, tyrosine, alanine, phenylalanine, valine,
      or methionine
<220> FEATURE:
<221> NAME/KEY: MOD_RES
<222> LOCATION: (12)..(12)
<223> OTHER INFORMATION: Aspartic acid or serine
<220> FEATURE:
<221> NAME/KEY: MOD_RES
<222> LOCATION: (18)..(18)
<223> OTHER INFORMATION: Asparagine, methionine, or threonine
<220> FEATURE:
<221> NAME/KEY: MOD_RES
<222> LOCATION: (21)..(21)
<223> OTHER INFORMATION: Asparagine, aspartic acid, alanine, glycine,
      lysine, or arginine
<220> FEATURE:
<223> OTHER INFORMATION: See specification as filed for detailed
      description of substitutions and preferred embodiments
```

-continued

```
<400> SEQUENCE: 36

Gly Ile Val Asp Xaa Cys Cys Xaa Arg Ser Cys Xaa Leu Arg Arg Leu
1               5                   10                  15

Glu Xaa Tyr Cys Xaa
                20

<210> SEQ ID NO 37
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<221> NAME/KEY: misc_feature
<222> LOCATION: (1)..(4)
<223> OTHER INFORMATION: This region may encompass any codable amino
      acid except cysteine, a dipeptide or tripeptide comprising no
      cysteine, a tripeptide "Gly Pro Glu," a tetrapeptide "Phe Val Asn
      Gln," wherein some or all positions may be absent
<220> FEATURE:
<221> NAME/KEY: MOD_RES
<222> LOCATION: (5)..(5)
<223> OTHER INFORMATION: Histidine, threonine, arginine, or lysine
<220> FEATURE:
<221> NAME/KEY: MOD_RES
<222> LOCATION: (10)..(10)
<223> OTHER INFORMATION: Histidine, aspartic acid, glutamic acid,
      homoglutamic acid, homocysteic acid, cysteic acid, arginine, or
      phenylalanine
<220> FEATURE:
<221> NAME/KEY: MOD_RES
<222> LOCATION: (16)..(16)
<223> OTHER INFORMATION: Tyrosine, phenylalanine, or tryptophan
<220> FEATURE:
<221> NAME/KEY: MOD_RES
<222> LOCATION: (17)..(17)
<223> OTHER INFORMATION: Phenylalanine, tryptophan, or leucine
<220> FEATURE:
<221> NAME/KEY: MOD_RES
<222> LOCATION: (25)..(25)
<223> OTHER INFORMATION: Tyrosine, phenylalanine, asparagine, or
      histidine
<220> FEATURE:
<221> NAME/KEY: MOD_RES
<222> LOCATION: (26)..(26)
<223> OTHER INFORMATION: Tyrosine, D-tyrosine, phenylalanine, alanine,
      serine, histidine, D-alanine, D-tyrosine, glutamic acid,
      sarcosine, or not present
<220> FEATURE:
<221> NAME/KEY: MOD_RES
<222> LOCATION: (27)..(27)
<223> OTHER INFORMATION: Threonine, asparagine, arginine, glutamic acid,
      aspartic acid, lysine, serine, proline, or not present
<220> FEATURE:
<221> NAME/KEY: MOD_RES
<222> LOCATION: (28)..(28)
<223> OTHER INFORMATION: Proline, arginine, lysine, orthonine, glutamic
      acid, aspartic acid, or not present
<220> FEATURE:
<221> NAME/KEY: MOD_RES
<222> LOCATION: (29)..(29)
<223> OTHER INFORMATION: Proline, lysine, glutamic acid, aspartic acid,
      or not present
<220> FEATURE:
<221> NAME/KEY: MOD_RES
<222> LOCATION: (30)..(30)
<223> OTHER INFORMATION: Threonine, alanine, glutamic acid, aspartic
      acid, or not present
<220> FEATURE:
<221> NAME/KEY: misc_feature
<222> LOCATION: (31)..(32)
<223> OTHER INFORMATION: This region may encompass "arginine-arginine"
      dipeptide, "glutamic acid-glutamic acid" dipeptide, "aspartic
``` acid-aspartic acid" dipeptide, or may not be present
<220> FEATURE:
<223> OTHER INFORMATION: See specification as filed for detailed
      description of substitutions and preferred embodiments

<400> SEQUENCE: 37

Xaa Xaa Xaa Xaa Xaa Leu Cys Gly Ala Xaa Leu Val Asp Ala Leu Xaa
1               5                   10                  15

Xaa Val Cys Gly Asp Arg Gly Phe Xaa Xaa Xaa Xaa Xaa Xaa Xaa
            20                  25                  30

<210> SEQ ID NO 38
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<221> NAME/KEY: misc_feature
<222> LOCATION: (1)..(4)
<223> OTHER INFORMATION: This region may encompass any codable amino
      acid except cysteine, a dipeptide or tripeptide comprising no
      cysteine, a tripeptide "Gly Pro Glu," a tetrapeptide "Phe Val Asn
      Gln," wherein some or all positions may be absent
<220> FEATURE:
<221> NAME/KEY: MOD_RES
<222> LOCATION: (5)..(5)
<223> OTHER INFORMATION: Histidine, threonine, arginine, or lysine
<220> FEATURE:
<221> NAME/KEY: MOD_RES
<222> LOCATION: (10)..(10)
<223> OTHER INFORMATION: Histidine, aspartic acid, glutamic acid,
      homoglutamic acid, homocysteic acid, cysteic acid, arginine, or
      phenylalanine
<220> FEATURE:
<221> NAME/KEY: MOD_RES
<222> LOCATION: (16)..(16)
<223> OTHER INFORMATION: Tyrosine, phenylalanine, or tryptophan
<220> FEATURE:
<221> NAME/KEY: MOD_RES
<222> LOCATION: (17)..(17)
<223> OTHER INFORMATION: Phenylalanine, tryptophan, or leucine
<220> FEATURE:
<221> NAME/KEY: MOD_RES
<222> LOCATION: (28)..(28)
<223> OTHER INFORMATION: Proline, arginine, lysine, orthonine, glutamic
      acid, aspartic acid, or not present
<220> FEATURE:
<221> NAME/KEY: MOD_RES
<222> LOCATION: (29)..(29)
<223> OTHER INFORMATION: Proline, lysine, glutamic acid, aspartic acid,
      or not present
<220> FEATURE:
<221> NAME/KEY: MOD_RES
<222> LOCATION: (30)..(30)
<223> OTHER INFORMATION: Threonine, alanine, glutamic acid, aspartic
      acid, or not present
<220> FEATURE:
<223> OTHER INFORMATION: See specification as filed for detailed
      description of substitutions and preferred embodiments

<400> SEQUENCE: 38

Xaa Xaa Xaa Xaa Xaa Leu Cys Gly Ala Xaa Leu Val Asp Ala Leu Xaa
1               5                   10                  15

Xaa Val Cys Gly Asp Arg Gly Phe Tyr Phe Asn Xaa Xaa Xaa
            20                  25                  30

<210> SEQ ID NO 39
<211> LENGTH: 30
<212> TYPE: PRT

-continued

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<221> NAME/KEY: misc_feature
<222> LOCATION: (1)..(4)
<223> OTHER INFORMATION: This region may encompass any codable amino
      acid except cysteine, a dipeptide or tripeptide comprising no
      cysteine, a tripeptide "Gly Pro Glu," a tetrapeptide "Phe Val Asn
      Gln," wherein some or all positions may be absent
<220> FEATURE:
<221> NAME/KEY: MOD_RES
<222> LOCATION: (5)..(5)
<223> OTHER INFORMATION: Histidine, threonine, arginine, or lysine
<220> FEATURE:
<221> NAME/KEY: MOD_RES
<222> LOCATION: (10)..(10)
<223> OTHER INFORMATION: Histidine, aspartic acid, glutamic acid,
      homoglutamic acid, homocysteic acid, cysteic acid, arginine, or
      phenylalanine
<220> FEATURE:
<221> NAME/KEY: MOD_RES
<222> LOCATION: (28)..(28)
<223> OTHER INFORMATION: Proline, arginine, lysine, orthonine, glutamic
      acid, aspartic acid, or not present
<220> FEATURE:
<221> NAME/KEY: MOD_RES
<222> LOCATION: (29)..(29)
<223> OTHER INFORMATION: Proline, lysine, glutamic acid, aspartic acid,
      or not present
<220> FEATURE:
<221> NAME/KEY: MOD_RES
<222> LOCATION: (30)..(30)
<223> OTHER INFORMATION: Threonine, alanine, glutamic acid, aspartic
      acid, or not present
<220> FEATURE:
<223> OTHER INFORMATION: See specification as filed for detailed
      description of substitutions and preferred embodiments

<400> SEQUENCE: 39

Xaa Xaa Xaa Xaa Xaa Leu Cys Gly Ala Xaa Leu Val Asp Ala Leu Tyr
1               5                   10                  15

Leu Val Cys Gly Asp Arg Gly Phe Tyr Phe Asn Xaa Xaa Xaa
            20                  25                  30

<210> SEQ ID NO 40
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be promoiety modified
<220> FEATURE:
<221> NAME/KEY: MOD_RES
<222> LOCATION: (4)..(4)
<223> OTHER INFORMATION: Histidine, threonine, arginine, or lysine
<220> FEATURE:
<221> NAME/KEY: MOD_RES
<222> LOCATION: (27)..(27)
<223> OTHER INFORMATION: Proline, arginine, lysine, orthonine, glutamic
      acid, aspartic acid, or not present
<220> FEATURE:
<221> NAME/KEY: MOD_RES
<222> LOCATION: (28)..(28)
<223> OTHER INFORMATION: Proline, lysine, glutamic acid, aspartic acid,
      or not present
<220> FEATURE:
<221> NAME/KEY: MOD_RES
<222> LOCATION: (29)..(29)
<223> OTHER INFORMATION: Threonine, alanine, glutamic acid, aspartic
      acid, or not present
```

```
<220> FEATURE:
<223> OTHER INFORMATION: See specification as filed for detailed
      description of substitutions and preferred embodiments

<400> SEQUENCE: 40

Gly Pro Glu Xaa Leu Cys Gly Ala His Leu Val Asp Ala Leu Tyr Leu
1               5                   10                  15

Val Cys Gly Asp Arg Gly Phe Tyr Phe Asn Xaa Xaa Xaa
            20                  25

<210> SEQ ID NO 41
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be promoiety modified
<220> FEATURE:
<221> NAME/KEY: MOD_RES
<222> LOCATION: (4)..(4)
<223> OTHER INFORMATION: Histidine, threonine, arginine, or lysine
<220> FEATURE:
<221> NAME/KEY: MOD_RES
<222> LOCATION: (27)..(27)
<223> OTHER INFORMATION: Proline, arginine, lysine, orthonine, glutamic
      acid, aspartic acid, or not present
<220> FEATURE:
<221> NAME/KEY: MOD_RES
<222> LOCATION: (28)..(28)
<223> OTHER INFORMATION: Proline, lysine, glutamic acid, aspartic acid,
      or not present
<220> FEATURE:
<221> NAME/KEY: MOD_RES
<222> LOCATION: (29)..(29)
<223> OTHER INFORMATION: Threonine, alanine, glutamic acid, aspartic
      acid, or not present
<220> FEATURE:
<223> OTHER INFORMATION: See specification as filed for detailed
      description of substitutions and preferred embodiments

<400> SEQUENCE: 41

Gly Pro Glu Xaa Leu Cys Gly Ala His Leu Val Asp Ala Leu Phe Phe
1               5                   10                  15

Val Cys Gly Asp Arg Gly Phe Tyr Phe Asn Xaa Xaa Xaa
            20                  25

<210> SEQ ID NO 42
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be promoiety modified
<220> FEATURE:
<221> NAME/KEY: misc_feature
<222> LOCATION: (1)..(4)
<223> OTHER INFORMATION: This region may encompass any codable amino
      acid except cysteine, a dipeptide or tripeptide comprising no
      cysteine, a tripeptide "Gly Pro Glu," a tetrapeptide "Phe Val Asn
      Gln," wherein some or all positions may be absent
<220> FEATURE:
<221> NAME/KEY: MOD_RES
<222> LOCATION: (5)..(5)
<223> OTHER INFORMATION: Histidine, threonine, arginine, or lysine
<220> FEATURE:
<221> NAME/KEY: MOD_RES
<222> LOCATION: (10)..(10)
<223> OTHER INFORMATION: Histidine, aspartic acid, glutamic acid,
      homoglutamic acid, homocysteic acid, cysteic acid, arginine, or
```

```
             phenylalanine
<220> FEATURE:
<221> NAME/KEY: MOD_RES
<222> LOCATION: (16)..(16)
<223> OTHER INFORMATION: Tyrosine, phenylalanine, or tryptophan
<220> FEATURE:
<221> NAME/KEY: MOD_RES
<222> LOCATION: (17)..(17)
<223> OTHER INFORMATION: Phenylalanine, tryptophan, or leucine
<220> FEATURE:
<223> OTHER INFORMATION: C-term NH2
<220> FEATURE:
<223> OTHER INFORMATION: See specification as filed for detailed
      description of substitutions and preferred embodiments

<400> SEQUENCE: 42

Xaa Xaa Xaa Xaa Xaa Leu Cys Gly Ala Xaa Leu Val Asp Ala Leu Xaa
1               5                   10                  15

Xaa Val Cys Gly Asp Arg Gly Phe Tyr
            20                  25

<210> SEQ ID NO 43
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be promoiety modified

<400> SEQUENCE: 43

Gly Ile Val Glu Gln Cys Cys Thr Ser Ile Cys Ser Leu Tyr Gln Leu
1               5                   10                  15

Glu Asn Tyr Cys Asn Lys
            20

<210> SEQ ID NO 44
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Arg
            20                  25

<210> SEQ ID NO 45
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term NH2

<400> SEQUENCE: 45

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```

```
<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 46

Pro Ser Ser Gly Ala Pro Pro Pro Ser
1               5

<210> SEQ ID NO 47
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 47

Gly Pro Ser Ser Gly Ala Pro Pro Pro Ser
1               5                   10

<210> SEQ ID NO 48
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term NH2

<400> SEQUENCE: 48

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 49
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<221> NAME/KEY: MOD_RES
<222> LOCATION: (1)..(1)
<223> OTHER INFORMATION: L-histidine, D-histidine, desamino-histidine,
      2-amino-histidine, beta-hydroxy-histidine, homohistidine, alpha-
      fluoromethyl-histidine, alpha-methyl-histidine,
      imidazopropionyl, arginine, or tyrosine
<220> FEATURE:
<221> NAME/KEY: MOD_RES
<222> LOCATION: (2)..(2)
<223> OTHER INFORMATION: Serine, D-serine, alanine, glycine, 2-
      aminoisobutyric acid, or valine
<220> FEATURE:
<221> NAME/KEY: MOD_RES
<222> LOCATION: (3)..(3)
<223> OTHER INFORMATION: Glutamic acid, glutamine, or proline
```

```
<220> FEATURE:
<221> NAME/KEY: MOD_RES
<222> LOCATION: (6)..(6)
<223> OTHER INFORMATION: Phenylalanine, tryptophan, tyrosine, or alanine
<220> FEATURE:
<221> NAME/KEY: MOD_RES
<222> LOCATION: (10)..(10)
<223> OTHER INFORMATION: Valine, tryptophan, isoleucine, leucine,
      phenylalanine, tyrosine, lysine, or cysteine
<220> FEATURE:
<221> NAME/KEY: MOD_RES
<222> LOCATION: (12)..(12)
<223> OTHER INFORMATION: Serine, tryptophan, tyrosine, phenylalanine,
      lysine, isoleucine, leucine, valine, or cysteine
<220> FEATURE:
<221> NAME/KEY: MOD_RES
<222> LOCATION: (13)..(13)
<223> OTHER INFORMATION: Tyrosine, tryptophan, or phenylalanine,
      glutamine, or alanine
<220> FEATURE:
<221> NAME/KEY: MOD_RES
<222> LOCATION: (14)..(14)
<223> OTHER INFORMATION: Leucine, phenylalanine, tyrosine, tryptophan,
      lysine, cysteine, or methione
<220> FEATURE:
<221> NAME/KEY: MOD_RES
<222> LOCATION: (16)..(16)
<223> OTHER INFORMATION: Glycine, glutamic acid, aspartic acid, serine,
      cysteine, or lysine
<220> FEATURE:
<221> NAME/KEY: MOD_RES
<222> LOCATION: (17)..(17)
<223> OTHER INFORMATION: Glutamine, glutamic acid, arginine, isoleucine,
      lysine, or cysteine
<220> FEATURE:
<221> NAME/KEY: MOD_RES
<222> LOCATION: (18)..(18)
<223> OTHER INFORMATION: Alanine, histidine, or arginine
<220> FEATURE:
<221> NAME/KEY: MOD_RES
<222> LOCATION: (19)..(19)
<223> OTHER INFORMATION: Alanine, glutamine, valine, isoleucine, or
      leucine
<220> FEATURE:
<221> NAME/KEY: MOD_RES
<222> LOCATION: (20)..(20)
<223> OTHER INFORMATION: Lysine, cysteine, arginine, or glutamine
<220> FEATURE:
<221> NAME/KEY: MOD_RES
<222> LOCATION: (21)..(21)
<223> OTHER INFORMATION: Glutamic acid, aspartic acid, leucine, lysine,
      cysteine, or alanine
<220> FEATURE:
<221> NAME/KEY: MOD_RES
<222> LOCATION: (23)..(23)
<223> OTHER INFORMATION: Isoleucine or valine
<220> FEATURE:
<221> NAME/KEY: MOD_RES
<222> LOCATION: (24)..(24)
<223> OTHER INFORMATION: Alanine, asparagine, aspartic acid, glutamic
      acid, or glutamine
<220> FEATURE:
<221> NAME/KEY: MOD_RES
<222> LOCATION: (27)..(27)
<223> OTHER INFORMATION: Valine, leucine, lysine, cysteine, or
      methionine
<220> FEATURE:
<221> NAME/KEY: MOD_RES
<222> LOCATION: (28)..(28)
<223> OTHER INFORMATION: Lysine, alanine, asparagine, aspartic acid,
      arginine, cysteine, or glutamic acid
<220> FEATURE:
<221> NAME/KEY: MOD_RES
<222> LOCATION: (29)..(29)
<223> OTHER INFORMATION: Glycine, threonine, lysine, cysteine, or
      glutamine
<220> FEATURE:
<221> NAME/KEY: MOD_RES
<222> LOCATION: (30)..(30)
```

```
<223> OTHER INFORMATION: Glycine, lysine, cysteine, proline, or arginine
<220> FEATURE:
<221> NAME/KEY: MOD_RES
<222> LOCATION: (31)..(31)
<223> OTHER INFORMATION: Glycine, proline, serine, lysine, cysteine, or
      not present
<220> FEATURE:
<221> NAME/KEY: MOD_RES
<222> LOCATION: (32)..(32)
<223> OTHER INFORMATION: Serine, proline, histidine, cysteine, lysine,
      or not present
<220> FEATURE:
<221> NAME/KEY: MOD_RES
<222> LOCATION: (33)..(33)
<223> OTHER INFORMATION: Serine, arginine, threonine, tryptophan,
      lysine, cysteine, or not present
<220> FEATURE:
<221> NAME/KEY: MOD_RES
<222> LOCATION: (34)..(34)
<223> OTHER INFORMATION: Serine, glycine, asparagine, lysine, cysteine,
      or not present
<220> FEATURE:
<221> NAME/KEY: MOD_RES
<222> LOCATION: (35)..(35)
<223> OTHER INFORMATION: Alanine, aspartic acid, arginine, glutamic
      acid, lysine, cysteine, glycine, or not present
<220> FEATURE:
<221> NAME/KEY: MOD_RES
<222> LOCATION: (36)..(36)
<223> OTHER INFORMATION: Proline, alanine, tryptophan, or not present
<220> FEATURE:
<221> NAME/KEY: MOD_RES
<222> LOCATION: (37)..(37)
<223> OTHER INFORMATION: Proline, alanine, lysine, or not present
<220> FEATURE:
<221> NAME/KEY: MOD_RES
<222> LOCATION: (38)..(38)
<223> OTHER INFORMATION: Proline, alanine, arginine, lysine, histidine,
      or not present
<220> FEATURE:
<221> NAME/KEY: MOD_RES
<222> LOCATION: (39)..(39)
<223> OTHER INFORMATION: Serine, histidine, proline, lysine, arginine,
      cysteine, asparagine, or not present
<220> FEATURE:
<221> NAME/KEY: MOD_RES
<222> LOCATION: (40)..(40)
<223> OTHER INFORMATION: Histidine, serine, arginine, lysine, cysteine,
      isoleucine, or not present
<220> FEATURE:
<221> NAME/KEY: MOD_RES
<222> LOCATION: (41)..(41)
<223> OTHER INFORMATION: Histidine, serine, arginine, lysine, threonine,
      or not present
<220> FEATURE:
<221> NAME/KEY: MOD_RES
<222> LOCATION: (42)..(42)
<223> OTHER INFORMATION: May or may not be present
<220> FEATURE:
<223> OTHER INFORMATION: May be C-term NH2
<220> FEATURE:
<223> OTHER INFORMATION: See specification as filed for detailed
      description of substitutions and preferred embodiments

<400> SEQUENCE: 49

Xaa Xaa Xaa Gly Thr Xaa Thr Ser Asp Xaa Ser Xaa Xaa Xaa Glu Xaa
1               5                   10                  15

Xaa Xaa Xaa Xaa Xaa Phe Xaa Xaa Trp Leu Xaa Xaa Xaa Xaa Xaa Xaa
            20                  25                  30

Xaa Xaa Xaa Xaa Xaa Xaa Xaa Xaa Xaa Gln
            35                  40

<210> SEQ ID NO 50
<211> LENGTH: 31
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<221> NAME/KEY: MOD_RES
<222> LOCATION: (2)..(2)
<223> OTHER INFORMATION: Serine, D-serine, alanine, glycine,
      2-aminoisobutyric acid, or valine
<220> FEATURE:
<221> NAME/KEY: MOD_RES
<222> LOCATION: (10)..(10)
<223> OTHER INFORMATION: Valine, tryptophan, isoleucine, leucine,
      phenylalanine, tyrosine, lysine, or cysteine
<220> FEATURE:
<221> NAME/KEY: MOD_RES
<222> LOCATION: (12)..(12)
<223> OTHER INFORMATION: Serine, tryptophan, tyrosine, phenylalanine,
      lysine, isoleucine, leucine, valine, or cysteine
<220> FEATURE:
<221> NAME/KEY: MOD_RES
<222> LOCATION: (16)..(16)
<223> OTHER INFORMATION: Glycine, glutamic acid, aspartic acid, serine,
      cysteine, or lysine
<220> FEATURE:
<221> NAME/KEY: MOD_RES
<222> LOCATION: (20)..(20)
<223> OTHER INFORMATION: Lysine, cysteine, arginine, or glutamine
<220> FEATURE:
<221> NAME/KEY: MOD_RES
<222> LOCATION: (28)..(28)
<223> OTHER INFORMATION: Lysine, alanine, asparagine, aspartic acid,
      arginine, cysteine, or glutamic acid
<220> FEATURE:
<221> NAME/KEY: MOD_RES
<222> LOCATION: (31)..(31)
<223> OTHER INFORMATION: Glycine, proline, serine, lysine, cysteine, or
      not present
<220> FEATURE:
<223> OTHER INFORMATION: May be C-term NH2
<220> FEATURE:
<223> OTHER INFORMATION: See specification as filed for detailed
      description of substitutions and preferred embodiments

<400> SEQUENCE: 50

His Xaa Glu Gly Thr Phe Thr Ser Asp Xaa Ser Xaa Tyr Leu Glu Xaa
1               5                   10                  15

Gln Ala Ala Xaa Glu Phe Ile Ala Trp Leu Val Xaa Gly Arg Xaa
            20                  25                  30

<210> SEQ ID NO 51
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<221> NAME/KEY: MOD_RES
<222> LOCATION: (2)..(2)
<223> OTHER INFORMATION: Serine, D-serine, alanine, glycine,
      2-aminoisobutyric acid, or valine
<220> FEATURE:
<221> NAME/KEY: MOD_RES
<222> LOCATION: (16)..(16)
<223> OTHER INFORMATION: Glycine, glutamic acid, aspartic acid, serine,
      cysteine, or lysine
<220> FEATURE:
<221> NAME/KEY: MOD_RES
<222> LOCATION: (31)..(31)
<223> OTHER INFORMATION: Glycine, proline, serine, lysine, cysteine, or
      not present
```

```
<220> FEATURE:
<223> OTHER INFORMATION: May be C-term NH2
<220> FEATURE:
<223> OTHER INFORMATION: See specification as filed for detailed
      description of substitutions and preferred embodiments

<400> SEQUENCE: 51

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Val Lys Gly Arg Xaa
            20                  25                  30

<210> SEQ ID NO 52
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<221> NAME/KEY: MOD_RES
<222> LOCATION: (1)..(1)
<223> OTHER INFORMATION: L-histidine, D-histidine, desamino-histidine,
      2-amino-histidine, beta-hydroxy-histidine, homohistidine,
      alpha-fluoromethyl-histidine, alpha-methyl-histidine,
      imidazopropionyl, arginine, or tyrosine
<220> FEATURE:
<221> NAME/KEY: MOD_RES
<222> LOCATION: (12)..(12)
<223> OTHER INFORMATION: Serine, tryptophan, tyrosine, phenylalanine,
      lysine, isoleucine, leucine, valine, or cysteine
<220> FEATURE:
<221> NAME/KEY: MOD_RES
<222> LOCATION: (14)..(14)
<223> OTHER INFORMATION: Leucine, phenylalanine, tyrosine, tryptophan,
      lysine, cysteine, or methione
<220> FEATURE:
<221> NAME/KEY: MOD_RES
<222> LOCATION: (20)..(20)
<223> OTHER INFORMATION: Lysine, cysteine, arginine, or glutamine
<220> FEATURE:
<221> NAME/KEY: MOD_RES
<222> LOCATION: (27)..(27)
<223> OTHER INFORMATION: Valine, leucine, lysine, cysteine, or
      methionine
<220> FEATURE:
<221> NAME/KEY: MOD_RES
<222> LOCATION: (28)..(28)
<223> OTHER INFORMATION: Lysine, alanine, asparagine, aspartic acid,
      arginine, cysteine, or glutamic acid
<220> FEATURE:
<221> NAME/KEY: MOD_RES
<222> LOCATION: (29)..(29)
<223> OTHER INFORMATION: Glycine, threonine, lysine, cysteine, or
      glutamine
<220> FEATURE:
<221> NAME/KEY: MOD_RES
<222> LOCATION: (30)..(30)
<223> OTHER INFORMATION: Glycine, lysine, cysteine, proline or arginine
<220> FEATURE:
<221> NAME/KEY: MOD_RES
<222> LOCATION: (31)..(31)
<223> OTHER INFORMATION: Glycine, proline, serine, lysine, cysteine,
      or not present
<220> FEATURE:
<221> NAME/KEY: MOD_RES
<222> LOCATION: (32)..(32)
<223> OTHER INFORMATION: Serine, proline, histidine, cysteine, lysine,
      or not present
<220> FEATURE:
<221> NAME/KEY: MOD_RES
<222> LOCATION: (33)..(33)
<223> OTHER INFORMATION: Serine, arginine, threonine, tryptophan,
      lysine, cysteine, or not present
```

```
<220> FEATURE:
<221> NAME/KEY: MOD_RES
<222> LOCATION: (34)..(34)
<223> OTHER INFORMATION: Serine, glycine, asparagine, lysine, cysteine,
      or not present
<220> FEATURE:
<221> NAME/KEY: MOD_RES
<222> LOCATION: (35)..(35)
<223> OTHER INFORMATION: Alanine, aspartic acid, arginine, glutamic
      acid, lysine, cysteine, glycine, or not present
<220> FEATURE:
<221> NAME/KEY: MOD_RES
<222> LOCATION: (36)..(36)
<223> OTHER INFORMATION: Proline, alanine, tryptophan, or not present
<220> FEATURE:
<221> NAME/KEY: MOD_RES
<222> LOCATION: (37)..(37)
<223> OTHER INFORMATION: Proline, alanine, lysine, or not present
<220> FEATURE:
<221> NAME/KEY: MOD_RES
<222> LOCATION: (38)..(38)
<223> OTHER INFORMATION: Proline, alanine, arginine, lysine, histidine,
      or not present
<220> FEATURE:
<221> NAME/KEY: MOD_RES
<222> LOCATION: (39)..(39)
<223> OTHER INFORMATION: Serine, histidine, proline, lysine, arginine,
      cysteine, asparagine, or not present
<220> FEATURE:
<223> OTHER INFORMATION: May be C-term NH2
<220> FEATURE:
<223> OTHER INFORMATION: See specification as filed for detailed
      description of substitutions and preferred embodiments

<400> SEQUENCE: 52

Xaa Gly Glu Gly Thr Phe Thr Ser Asp Leu Ser Xaa Gln Xaa Glu Glu
1               5                   10                  15

Glu Ala Val Xaa Leu Phe Ile Glu Trp Leu Xaa Xaa Xaa Xaa Xaa Xaa
                20                  25                  30

Xaa Xaa Xaa Xaa Xaa Xaa Xaa
                35

<210> SEQ ID NO 53
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Serine, tryptophan, tyrosine, phenylalanine,
      lysine, isoleucine, leucine, valine, or cysteine
<220> FEATURE:
<221> NAME/KEY: MOD_RES
<222> LOCATION: (27)..(27)
<223> OTHER INFORMATION: Valine, leucine, lysine, cysteine, or
      methionine
<220> FEATURE:
<221> NAME/KEY: MOD_RES
<222> LOCATION: (39)..(39)
<223> OTHER INFORMATION: Serine, histidine, proline, lysine, arginine,
      cysteine, asparagine, or not present
<220> FEATURE:
<223> OTHER INFORMATION: May be C-term NH2
<220> FEATURE:
<223> OTHER INFORMATION: See specification as filed for detailed
      description of substitutions and preferred embodiments

<400> SEQUENCE: 53

His Gly Glu Gly Thr Phe Thr Ser Asp Leu Ser Xaa Gln Met Glu Glu
1               5                   10                  15
```

```
Glu Ala Val Arg Leu Phe Ile Glu Trp Leu Xaa Asn Gly Gly Pro Ser
            20                  25                  30

Ser Gly Ala Pro Pro Pro Xaa
        35

<210> SEQ ID NO 54
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<223> OTHER INFORMATION: C-term NH2

<400> SEQUENCE: 54

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 55
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<221> NAME/KEY: MOD_RES
<222> LOCATION: (2)..(2)
<223> OTHER INFORMATION: 2,4-diaminobutyric acid (DAB), leucine,
      isoleucine, threonine, histidine, arginine, lysine, asparagine,
      glutamine, tryptophan, tyrosine, alanine, phenylalanine, valine,
      methionine
<220> FEATURE:
<223> OTHER INFORMATION: C-term NH2
<220> FEATURE:
<223> OTHER INFORMATION: See specification as filed for detailed
      description of substitutions and preferred embodiments

<400> SEQUENCE: 55

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 56
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<223> OTHER INFORMATION: C-term NH2

<400> SEQUENCE: 56

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term NH2

<400> SEQUENCE: 57

Gly Ile Val Glu Gln Ala Ala
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Ile Val Glu Gln Ala Ala Tyr
1               5

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be promoiety modified
<220> FEATURE:
<221> NAME/KEY: misc_feature
<222> LOCATION: (1)..(2)
<223> OTHER INFORMATION: This region may encompass "Ala-Indo2CA," "Ala-
      Tic," "Phe-Indo2CA," "dK(C10)-dTic," "Val-Indo2CA," "K(C10)-Tic,"
      "K(C10)-Indo2CA" or may not be present
<220> FEATURE:
<223> OTHER INFORMATION: See specification as filed for detailed
      description of substitutions and preferred embodiments

<400> SEQUENCE: 59

Xaa Xaa Gly Ile Val Glu Gln Ala Ala Tyr
1               5                   10

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be promoiety modified

<400> SEQUENCE: 60

Gly Ile Val Glu Gln Ala Ala Tyr
1               5

<210> SEQ ID NO 61
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term may be promoiety modified
<220> FEATURE:
<223> OTHER INFORMATION: See specification as filed for detailed
      description of substitutions and preferred embodiments

<400> SEQUENCE: 61

Gly Ile Val Glu Gln Ala Ala
1               5

<210> SEQ ID NO 62
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term may be promoiety modified
<220> FEATURE:
<223> OTHER INFORMATION: C-term NH2
<220> FEATURE:
<223> OTHER INFORMATION: See specification as filed for detailed
      description of substitutions and preferred embodiments

<400> SEQUENCE: 62

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser
                35
```

BIOREVERSABLE PROMOIETIES FOR NITROGEN-CONTAINING AND HYDROXYL-CONTAINING DRUGS

SEQUENCE LISTING

The instant application contains a Sequence Listing which has been submitted electronically in ASCII format and is hereby incorporated by reference in its entirety. Said ASCII copy, created on Mar. 26, 2015, is named 11778.0002-00000_SL.txt and is 50,680 bytes in size.

BACKGROUND OF THE DISCLOSURE

The development of prodrugs—chemically modified versions of the pharmaceutically active agent that must undergo transformation in vivo prior to exerting their pharmacological or therapeutic action—has become one of the strategies to improve the physicochemical, pharmacokinetic and/or pharmacodynamic properties of pharmaceutically active agents, and thereby enhance their efficacy and/or reduce their side effects. For example, prodrugs provide possibilities to overcome various barriers to drug formulation and delivery such as poor aqueous solubility, physical and/or chemical instability, insufficient absorption, rapid pre-systemic metabolism, inadequate brain penetration, toxicity and/or local irritation. Prodrugs can also improve drug targeting and duration of action.

DETAILED DESCRIPTION OF THE DISCLOSURE

Conjugating one or more polymers to a pharmaceutically active agent can result in a conjugate having reduced immunogenicity and/or antigenicity. The conjugate often has greatly increased half-lives in vivo compared to its unconjugated counterpart as a result of decreased clearance through the kidney and/or decreased enzymatic degradation in the systemic circulation. As a result of longer half-life, the conjugate requires less frequent dosing. Moreover, pharmaceutically active agents that are only marginally soluble may demonstrate a significant increase in water solubility when conjugated to a water-soluble polymer. Attachment of low molecular weight drugs to macromolecular carriers can alter drug pharmacokinetics, and the drug targeting may be achieved.

Due to its documented safety as well as its approval by the FDA for both topical and internal use, polyethylene glycol (PEG) has been conjugated to active agents such as PEG-INTRON®, and administration of a conjugated form of an active agent can have significant advantages over the unconjugated counterpart.

Serum albumin and immunoglobulins (Igs) are serum proteins which account for 90% of plasma proteins with an unusually prolonged circulation, typically of 2 to 3 weeks, which is attributable to their specific interaction with the neonatal Fc receptor (FcRn). FcRn binds to Igs in a pH-dependent manner and protects Igs from degradation. The mechanism has been employed by producing fusion proteins with the Fc portion of Igs.

Despite these successes, conjugation of a polymer to an active agent to result in a commercially relevant drug is often challenging. For example, conjugation can result in the polymer being attached at or near a binding site on the active agent. Such conjugates may therefore have unacceptably low activity due to, for example, the steric effects introduced by the polymer.

Conjugation to a plasma protein gives a pharmaceutically active agent the circulating $t_{1/2}$ of the plasma protein to which it binds, but at the expense of potentially lowered receptor affinity.

Alkylation and acylation of a drug or pharmaceutically active agent is another means of extending its in vivo time of action. However, even linking a relatively small sized alkyl or acyl group to a drug may result in significant reduction of its biological activity. For example, insulin detemir ([LysB29-tetradecanoyl, des B30] insulin) retains only 15-20% of binding affinity of native insulin and 4-5 fold higher doses are necessary in clinical practice.

Attempts to remedy conjugates having unacceptably low activity can be frustrated when the active agent has few or no other sites suited for attachment to a polymer.

There are also disadvantages of Fc or albumin fusions. FcRn rescue mainly prevents pinocytosis rather than kidney clearance and some conjugated therapeutic proteins might not be stable in the recycling process. Fusion proteins are mostly expressed in eukaryotic cell culture and result in high production cost. Retention of fusion proteins in vascular space makes it difficult for some fusion proteins to reach their therapeutic targets.

Further, PEGylated proteins have been observed to cause renal tubular vacuolation in animal models. Renally cleared PEGylated proteins or their metabolites may accumulate in the kidney, causing formation of PEG hydrates that interfere with normal glomerular filtration. Some proteins have targets in pivotal organs such as central nerve system (CNS). Pegylated proteins can go through blood brain barrier. However, it is very difficult for PEG molecules to be metabolized in the brain or excreted after the conjugated proteins are degraded. Long time accumulation of PEG molecules in CNS may impose health risks for these patients. Conjugation of marcromolecules to the drugs or pharmaceutically active agents which are designed for intracellular actions can hamper their ability to reach their targets because macromolecules usually do not penetrate cell membrane easily. Thus, alternative conjugation methods have been desired.

One of our approaches for solving this and other problems is to connect an active agent to a modifying moiety via a hydrolysable or cleavable linker (promoiety), wherein the pharmaceutically active agent or a moiety having increased activity compared to the conjugated active agent is released.

It may be desirable in certain circumstances to attach more than one identical or different modifying moieties to a pharmaceutically active agent by hydrolysable linkers. Attaching multiple hydrolysable modifying moieties to a pharmaceutically active agent may be employed to improve circulation, delay onset of action, and/or optimize hydrophilicity of the pharmaceutically active agent. For example, administration of a mixture of drug-modifying moiety conjugates could ensure that some conjugates have almost immediate activity (i.e. only one or a few bonds to hydrolyze or bonds are easily hydrolysable) while others become active on a time-delayed basis as multiple hydrolysable bonds are hydrolyzed (or bonds are relatively more resistant to hydrolysis). The pharmaceutically active agent may be joined either directly to the modifying moiety by covalent bonding, indirectly through appropriate spacer groups or hydrolysable linkers. A spacer such as beta-alanine, gamma-aminobutyric acid, or gamma-glutamic acid can be inserted between a pharmaceutically active agent and its conjugated modifying moieties in order to regain some or most of its potency.

In some embodiments prodrugs in this disclosure can be constructed as follows:

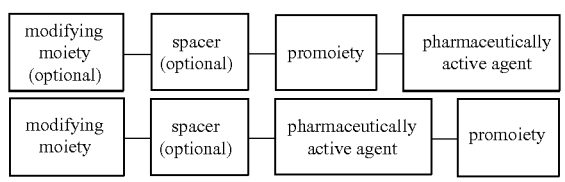

Most of the prodrugs now in clinical use require enzymatic catalysis in order to be converted into the active form of the drug. This is particularly true for those prodrugs designed to liberate the parent drug in the blood stream following gastro-intestinal absorption. It is known that enzyme levels vary significantly among people and are usually related to people's health state. Moreover, enzymatic activation may result in reduced regeneration of the parent drug. Limitations of enzyme activation of prodrugs can be evident and significant, inter and intra-individual variability have been observed in clinical applications.

Thus, the development of prodrugs that can liberate the parent drug through non-enzymatic pathways is an alternative approach in which prodrug activation is unlikely to be influenced by inter- and intra-individual variability that affects the enzymatic activity.

Some of the most common functional groups that are amenable to prodrug design include carboxylic acids, hydroxyl groups, thiols, amines, amides, phosphate/phosphonate and carbonyl groups. The prodrug approach has been particularly effective in addressing pharmaceutical problems with carboxyl- or hydroxyl-bearing drugs, mainly due to the wide possibilities for ester prodrug design. Amine prodrug design has been much more challenging. N-Mannich bases, N-hydroxymethyl derivatives, and N-acyloxyalkyl derivatives have been utilized as prodrugs for amides, imides, and NH-acidic compounds. Phosphamides, carbamates, imines, oximes, enaminones, N-Mannich bases, and amides have been described as prodrugs for amines. However, these amine prodrugs have certain limitations. The high chemical reactivity or instability of some types of the prodrugs precludes either liquid or solid formulation.

The major differences between amino derivatives such as amide or carbamates and carboxylic esters, from a prodrug point of view, could be the greater susceptibility of esters to undergo hydrolysis and the general chemical and enzymatic stability of amides and many other amine derivatives. There remains a dearth of amine-masking systems with suitable release kinetics applicable in prodrug design.

Amide bond is known for its stability. Strong acid (e.g. $H_2SO_4$, HCl) or strong base (e.g. NaOH) and high heat (e.g. 100° C.) is usually required for amide bond hydrolysis. N-acylation of amines to produce amide prodrugs has been used to a very limited extent due to the relative stability of amides in vivo. By taking advantage of intramolecular chemical catalysis, an amide bond can be hydrolized and the parent amine molecule can be released under milder conditions. For instance, 2-hydroxymethylbenzamides undergo cyclization in aqueous solution to give phthalide and free amine. However, the lactonization rate can be too slow at physiological pH and temperature. For example, pH-rate profile for the lactonization over the pH range 0-10 can show a "U" shape curve, which indicates much faster hydrolysis rates under both highly acidic and highly basic condition but slowest around the neutral pH. High reactivities at both acidic and basic conditions limit the scope of utility of this reaction.

The inventors have made extensive efforts to modulate the reaction rates at physiological conditions by designing and modifying chemical structures. It is found that a nucleophile can react with an intramolecular amide to release the amine when they are in designated positions of an appropriate backbone structure. Reaction rates can be further regulated by choices of steric, electron withdrawing or donating substituents in different positions of this backbone structure.

This approach is effective for a nitrogen-containing drug, especially a drug having an amine, amide, carbamate, imide, or sulfonamide substructure.

The same approach is also applicable to hydroxyl-bearing drugs.

All methods and promoieties for nitrogen-containing drugs in this disclosure can also be used in hydroxyl-bearing drugs.

The intramolecular reaction liberating the active nitrogen-containing drug is not enzyme initiated. The disclosed promoieties can be chemically conjugated to the active site amines or hydroxyl groups of a drug to form amides or esters. The prodrug will be automatically converted into a bioactive agent under physiological conditions (e.g., 37° C., pH 7.0-7.6) and requires no additional reagents. The speed of this chemical conversion largely determines the time of onset and duration of in vivo biological action. In addition, since physiological conditions are generally constant among people, the variation in the half life ($t_{1/2}$) of a prodrug is de minimus intra and interpatiently. The half life of a prodrug can be fine tuned in accordance with clinical and formulation requirements by structural modifications. In one embodiment the chemical cleavage half-life of a promoiety from the prodrug is at least about 30 minutes to about 720 hours under physiological conditions. In one embodiment promoieties are selected to inhibit enzymatic cleavage of the promoiety from a prodrug by enzymes found in mammalian serum.

The following definitions of the terms apply throughout the disclosure unless otherwise indicated. Terms not defined herein have the meaning commonly understood in the art to which the term pertains. It will be understood by those skilled in the art, with respect to any group containing one or more substituents, that such groups are not intended to introduce any substitution or substitution patterns that are sterically impractical, synthetically non-feasible and/or inherently unstable.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds, and groups having mixtures of single, double, and triple carbon-carbon bonds. Where a specific level of saturation is intended, the terms "alkanyl," "alkenyl," and "alkynyl" are used. "Alkyl" by itself or as part of another substituent refers to a saturated or unsaturated, branched or straight-chain monovalent hydrocarbon radical derived by the removal of one hydrogen atom from a single carbon atom of a parent alkane, alkene, or alkyne. Examples of alkyl groups include, but are not limited to, methyl; ethyls such as ethanyl, ethenyl, and ethynyl; propyls such as propan-1-yl, propan-2-yl, prop-1-en-1-yl, prop-1-en-2-yl, prop-2-en-1-yl(allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like. In certain embodiments, an alkyl group comprises from 1 to 6 carbon atoms, in certain embodiments, from 1 to 8 carbon atoms, in certain embodiments, from 1 to 10 carbon atoms, in certain embodiments, from 1 to 20 carbon atoms.

"Acyl" by itself or as part of another substituent refers to a radical) —C(O)R$^{(30)}$, where R$^{(30)}$ is hydrogen, alkyl, heteroalkyl, cycloalkyl, heterocycloalkyl, cycloalkylalkyl, heterocycloalkylalkyl, aryl, heteroaryl, arylalkyl, or heteroarylalkyl, which can be substituted, as defined herein. Examples of acyl groups include, but are not limited to, formyl, acetyl, cyclohexylcarbonyl, cyclohexylmethylcarbonyl, benzoyl, benzylcarbonyl, and the like.

"Alkoxy" by itself or as part of another substituent refers to a radical —OR$^{(31)}$ where R$^{(31)}$ is hydrogen, alkyl, cycloalkyl, heteroalkyl, heterocycloalkyl, cycloalkylalkyl, aryl, heteroaryl, arylalkyl, or heteroarylalkyl, which can be substituted, as defined herein. In some embodiments, alkoxy groups have from 1 to 8 carbon atoms. Examples of alkoxy groups include, but are not limited to, methoxy, ethoxy, propoxy, butoxy, cyclohexyloxy, and the like.

"Alkoxycarbonyl" by itself or as part of another substituent refers to a radical —C(O)OR$^{(32)}$ where R$^{(32)}$ represents a hydrogen, alkyl, cycloalkyl, heteroalkyl, heterocycloalkyl, cycloalkylalkyl, aryl, heteroaryl, arylalkyl, or heteroarylalkyl, which can be substituted, as defined herein. Examples of alkoxycarbonyl groups include, but are not limited to, methoxycarbonyl, ethoxycarbonyl, propoxycarbonyl, and butoxycarbonyl, and the like.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene.

Aryl also encompasses multiple ring systems having at least one carbocyclic aromatic ring fused to at least one carbocyclic aromatic ring, cycloalkyl ring, or heterocycloalkyl ring. For example, aryl includes 5- and 6-membered carbocyclic aromatic rings fused to a 5- to 7-membered heterocycloalkyl ring containing one or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Examples of aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In certain embodiments, an aryl group can comprise from 5 to 20 carbon atoms, and in certain embodiments, from 5 to 12 carbon atoms. Aryl, however, does not encompass or overlap in any way with heteroaryl, separately defined herein. Hence, a multiple, ring system in which one or more carbocyclic aromatic rings is fused to a heterocycloalkyl aromatic ring, is heteroaryl, not aryl, as defined herein.

"Arylalkyl" by itself or as part of another substituent refers to an acyclic alkyl radical in which one of the hydrogen atoms bonded to a carbon atom, typically a terminal or sp$^{(3)}$ carbon atom, is replaced with an aryl group. Examples of arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl, and the like. Where specific alkyl moieties are intended, the nomenclature arylalkanyl, arylalkenyl, or arylalkynyl is used.

"Cycloalkylalkyl" by itself or as part of another substituent refers to an acyclic alkyl radical in which one of the hydrogen atoms bonded to a carbon atom, typically a terminal or sp$^{(3)}$ carbon bon atom, is replaced with a cycloalkyl group. Where specific alkyl moieties are intended, the nomenclature cycloalkylalkanyl, cycloalkylalkenyl, or cycloalkylalkynyl is used.

"Monocyclic" refers to a compound in which a series of atoms is connected to form a loop or ring. The term "polycyclic" is used when more than one ring is formed in a single molecule for instance in naphthalene.

"Halogen" or "Halo" refers to a fluoro, chloro, bromo, or iodo group.

"Heteroalkyl" by itself or as part of another substituent refer to an alkyl group in which one or more of the carbon atoms (and any associated hydrogen atoms) are independently replaced with the same or different heteroatomic groups. In some embodiments, heteroalkyl groups have from 1 to 8 carbon atoms. Examples of heteroatomic groups include, but are not limited to, —O—, —S—, —O—O—, —S—S—, —O—S—, —NR$^{(37)}$R$^{(38)}$—, =N—N=, —N=N—, —N=N—NR$^{(39)}$R$^{(40)}$, —PR$^{(41)}$—, —P(O)$_{(2)}$—, —POR$^{(42)}$—, —O—P(O)$_{(2)}$—, —SO—, —SO$_{(2)}$—, —SnR$^{(43)}$R$^{(44)}$— and the like, where R$^{(37)}$, R$^{(38)}$, R$^{(39)}$, R$^{(40)}$, R$^{(41)}$, R$^{(42)}$, R$^{(43)}$, and R$^{(44)}$ are independently hydrogen, alkyl, substituted alkyl, aryl, substituted aryl, arylalkyl, substituted arylalkyl, cycloalkyl, substituted cycloalkyl, heterocycloalkyl, substituted heterocycloalkyl, heteroalkyl, substituted heteroalkyl, heteroaryl, substituted heteroaryl, heteroarylalkyl, or substituted heteroarylalkyl. Where a specific level of saturation is intended, the nomenclature "heteroalkanyl," "heteroalkenyl," or "heteroalkynyl" is used.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one aromatic ring fused to at least one other ring, which can be aromatic or non-aromatic in which at least one ring atom is a heteroatom. Heteroaryl encompasses 5- to 12-membered aromatic, monocyclic rings (such as 5- to 7-membered rings) containing one or more, for example, from 1 to 4, or in certain embodiments, from 1 to 3, heteroatoms chosen from N, O, and S, with the remaining ring atoms being carbon; and bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring. For example, heteroaryl includes a 5- to 7-membered heteroaromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. In certain embodiments, when the total number of N, S, and O atoms in the heteroaryl group exceeds one, the heteroatoms are not adjacent to one another. In certain embodiments, the total number of N, S, and O atoms in the heteroaryl group is not more than two. In certain embodiments, the total number of N, S, and O atoms in the aromatic heterocycle is not more than one. Heteroaryl does not encompass or overlap with aryl as defined herein.

Examples of heteroaryl groups include, but are not limited to, groups derived from acridine, arsindole, carbazole, beta-carboline, chromane, chromene, cinnoline, furan, furazan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenantbxoline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In certain embodiments, a heteroaryl group is from 5- to 20-membered heteroaryl, and in certain embodiments from 5- to 12-membered heteroaryl or from 5- to 10-membered heteroaryl. In certain embodiments heteroaryl groups are those derived from thiophene, pyrrole, benzothiophene, benzofuran, indole, pyridine, quinoline, imidazole, oxazole, and pyrazine.

"Heteroarylalkyl" by itself or as part of another substituent refers to an acyclic alkyl radical in which one of the hydrogen atoms bonded to a carbon atom, typically a terminal or sp$^{(3)}$ carbon atom, is replaced with a heteroaryl group. Where a specific level of saturation is intended, the nomenclature heteroarylalkanyl, heteroarylalkenyl, or heteroarylalkynyl is used. In certain embodiments, a heteroarylalkyl group is a 6- to 30-membered heteroarylalkyl, e.g., the alkanyl, alkenyl, or alkynyl moiety of the heteroarylalkyl is 1- to 10-membered and the heteroaryl moiety is a 5- to 20-membered heteroaryl, and in certain embodiments, 6- to 20-membered heteroarylalkyl, e.g., the alkanyl, alkenyl, or alkynyl moiety of the heteroarylalkyl is 1- to 8-membered and the heteroaryl moiety is a 5- to 12-membered heteroaryl.

"Heterocycloalkyl" by itself or as part of another substituent refers to a saturated, partially saturated or unsaturated cyclic alkyl radical in which one or more carbon atoms (and any associated hydrogen atoms) are independently replaced with the same or different heteroatom. Examples of heteroatoms to replace the carbon atom(s) include, but are not limited to, N, P, O, S, Si, etc. Where a specific level of saturation is intended, the nomenclature "heterocycloalkanyl", "heterocycloalkenyl", or "heterocycloalkynyl" is used. Examples of heterocycloalkyl groups include, but are not limited to, groups derived from aziridine, azirine, epoxides, oxirene, thiiranes, thiirene, dioxirane, diazirine, azetidine, azete, oxetane, oxete, thietane, thiete, diazetidine, dioxetane, dioxetene, dithietane, dithiete, dihydrofuran, imidazoline, imidazolidine, morpholine, oxazolidine, isoxazolidine, thiazolidine, isothiazolidine, dithiazole, dioxolane, oxathiolane, dithiolane, oxazoline, isoxazoline, piperazine, piperidine, pyrazoline, pyrazolidine, pyrrolidine, pyrroline, quinuclidine, tetrahydrofuran, dihydrothiophene, tetrahydrothiophene, thiazoline, isothiazoline, tetrahydropyran, thiane, thiopyran, dithiane, dioxane, trioxane, azepane, oxepane, thiepane, azocane, oxecane, thiocane, and the like.

"Heterocycloalkylalkyl" by itself or as part of another substituent refers to an acyclic alkyl radical in which one of the hydrogen atoms bonded to a carbon atom, typically a terminal or sp$^{(3)}$ carbon atom, is replaced with a heterocycloalkyl group. Where specific alkyl moieties are intended, the nomenclature heterocycloalkylalkanyl, heterocycloalkylalkenyl, or heterocycloalkylalkynyl is used. In certain embodiments, a heterocycloalkylalkyl group is a 6- to 30-membered heterocycloalkylalkyl, e.g., the alkanyl, alkenyl, or alkynyl moiety of the heterocycloalkylalkyl is 1- to 10-membered and the heterocycloalkyl moiety is a 5- to 20-membered heterocycloalkyl.

"Haloformyl" by itself or as part of another substituent refers to a radical —COX, where X is a halogen group. Examples of haloformyl group include, but are not limited to, acetyl chloride.

"Carboxamido" or "Carboxamide" by itself or as part of another substituent refers to a radical —C(O)NR$^{(45)}$R$^{(46)}$, where R$^{(45)}$ and R$^{(46)}$ are each an hydrogen, alkyl, heteroalkyl, cycloalkyl, heterocycloalkyl, cycloalkylalkyl, heterocycloalkylalkyl, aryl, heteroaryl, arylalkyl, or heteroarylalkyl, which can be substituted, as defined herein. Examples of carboxamido group include, but are not limited to, acetamide.

"Ammonio" or "ammonium" by itself or as part of another substituent refers to a radical —N$^+$R$^{(47)}$R$^{(48)}$R$^{(49)}$, where R$^{(47)}$, R$^{(48)}$, and R$^{(49)}$ are each an alkyl, heteroalkyl, cycloalkyl, heterocycloalkyl, cycloalkylalkyl, heterocycloalkylalkyl, aryl, heteroaryl, arylalkyl, or heteroarylalkyl, which can be substituted, as defined herein. Examples of ammonio group include, but are not limited to, choline.

"Imino" or "imine" by itself or as part of another substituent refers to a radical)) —C(=NR$^{(50)}$R$^{(51)}$, where R$^{(50)}$ and R$^{(51)}$ are each an hydrogen, alkyl, heteroalkyl, cycloalkyl, heterocycloalkyl, cycloalkylalkyl, heterocycloalkylalkyl, aryl, heteroaryl, arylalkyl, or heteroarylalkyl, which can be substituted, as defined herein.

"Imido" or "imide" by itself or as part of another substituent refers to a radical —C(=O)N(—R$^{(52)}$)C(=O)R$^{(53)}$, where R$^{(52)}$ and R$^{(53)}$ are each an hydrogen, alkyl, heteroalkyl, cycloalkyl, heterocycloalkyl, cycloalkylalkyl, heterocycloalkylalkyl, aryl, heteroaryl, arylalkyl, or heteroarylalkyl, which can be substituted, as defined herein.

"Azido" or "azide" by itself or as part of another substituent refers to a radical —N$_3$. Examples of azido group include, but are not limited to, phenyl azide.

"Azo" by itself or as part of another substituent refers to a radical —N$_2$R$^{(54)}$, where R$^{(54)}$ is an alkyl, heteroalkyl, cycloalkyl, heterocycloalkyl, cycloalkylalkyl, heterocycloalkylalkyl, aryl, heteroaryl, arylalkyl, or heteroarylalkyl, which can be substituted, as defined herein. Examples of azo group include, but are not limited to, methyl orange (p-dimethylamino-azobenzenesulfonic acid).

"Cyanato" or "cyanate" by itself or as part of another substituent refers to a radical —OCN. Examples of cyanato group include, but are not limited to, cyanatomethane.

"Isocyano" or "isocyanide" by itself or as part of another substituent refers to a radical —NC. Examples of isocyano group include, but are not limited to, isocyanoethane.

"Isocyanato" or "isocyanate" by itself or as part of another substituent refers to a radical —NCO. Examples of isocyanato group include, but are not limited to, methyl isocyanate.

"Isothiocyanato" or "isothiocyanate" by itself or as part of another substituent refers to a radical —NCS. Examples of isothiocyanato group include, but are not limited to, allyl isothiocyanate.

"Phosphino" by itself or as part of another substituent refers to a radical —PR$^{(55)}$R$^{(56)}$R$^{(57)}$, where R$^{(55)}$, R$^{(56)}$, and R$^{(57)}$ are each hydrogen, alkyl, heteroalkyl, cycloalkyl, heterocycloalkyl, cycloalkylalkyl, heterocycloalkylalkyl, aryl, heteroaryl, arylalkyl, or heteroarylalkyl, which can be substituted, as defined herein. Examples of phosphino group include, but are not limited to, methylpropylphosphane.

"Thiocyano" or "thiocyanate" by itself or as part of another substituent refers to a radical —SCN. Examples of thiocyano group include, but are not limited to, phenyl thiocyanate.

"Nitroso" by itself or as part of another substituent refers to a radical —NO. Various nitroso groups can be categorized as C-nitroso compounds (e.g., nitrosoalkanes; R—N=O), S-nitroso compounds (nitrosothiols; RS—N=O), N-nitroso compounds (e.g., nitrosamines, $R^1N(-R^2)-N=O$).

"Acyloxy" by itself or as part of another substituent refers to a radical —OC(O)$R^{(58)}$ where $R^{(58)}$ represents an alkyl, cycloalkyl, heteroalkyl, heterocycloalkyl, cycloalkylalkyl, aryl, heteroaryl, arylalkyl, or heteroarylalkyl, which can be substituted, as defined herein.

"Carbonate group" by itself or as part of another substituent refers to a radical —OC(O)O$R^{(58)}$ where $R^{(58)}$ represent an alkyl, cycloalkyl, heteroalkyl, heterocycloalkyl, cycloalkylalkyl, aryl, heteroaryl, arylalkyl, or heteroarylalkyl, which can be substituted, as defined herein. Examples of carbonate esters include, but are not limited to, dimethyl carbonate, diphenyl carbonate, and ethylene carbonate.

"Carbamate group" by itself or as part of another substituent refers to a radical —NHC(O)O$R^{(59)}$, —$NR^{(60)}$C(O) O$R^{(59)}$, or —OC(O)$NR_{(61)}R^{(62)}$, where $R^{(59)}$, $R_{(60)}$, $R^{(61)}$, and $R^{(62)}$ represent an alkyl, cycloalkyl, heteroalkyl, heterocycloalkyl, cycloalkylalkyl, aryl, heteroaryl, arylalkyl, or heteroarylalkyl. In some embodiments, $R^{(64)}$ can be a hydrogen (H).

"Sulfonate group" refers to a radical —$SO_2OR^{(63)}$, where $R^{(63)}$ represent an alkyl, cycloalkyl, heteroalkyl, heterocycloalkyl, cycloalkylalkyl, aryl, heteroaryl, arylalkyl, or heteroarylalkyl, which can be substituted, as defined herein.

"Sulfamide group" refers to a radical —$R^{(64)}NSO_2NR^{(65)}R^{(66)}$ where $R^{(64)}$, $R^{(65)}$, and $R^{(66)}$ represent a hydrogen, alkyl, cycloalkyl, heteroalkyl, heterocycloalkyl, cycloalkylalkyl, aryl, heteroaryl, arylalkyl, or heteroarylalkyl, which can be substituted, as defined herein.

"Sulfonamide group" refers to a radical —$SO_2NR^{(67)}R^{(68)}$, or —$N(R^{(67)})SO_2R^{(69)}$ where $R^{(67)}$, $R^{(58)}$, and $R^{(69)}$ represent an alkyl, cycloalkyl, heteroalkyl, heterocycloalkyl, cycloalkylalkyl, aryl, heteroaryl, arylalkyl, or heteroarylalkyl, which can be substituted, as defined herein. In one embodiment $R^{(67)}$ or $R^{(68)}$ or both can be a hydrogen.

"Sulfonyl" refers to a radical —$SO_2R^{(69)}$ where $R^{(69)}$ represents an alkyl, cycloalkyl, heteroalkyl, heterocycloalkyl, cycloalkylalkyl, aryl, heteroaryl, arylalkyl, or heteroarylalkyl, which can be substituted, as defined herein.

"Sulfoxide group" refers to a radical —$SOR^{(70)}$ where $R^{(70)}$ represents an alkyl, cycloalkyl, heteroalkyl, heterocycloalkyl, cycloalkylalkyl, aryl, heteroaryl, arylalkyl, or heteroarylalkyl, which can be substituted, as defined herein.

"Sulfide group" refers to a radical —$SR^{(71)}$ where $R^{(71)}$ represents an alkyl, cycloalkyl, heteroalkyl, heterocycloalkyl, cycloalkylalkyl, aryl, heteroaryl, arylalkyl, or heteroarylalkyl, which can be substituted, as defined herein. "Disulfide group" contains a —S—S— disulfide bond.

"Thione group" or "thiocarbonyl" by itself or as part of another substituent refers to a radical —C(S) $R^{(72)}$ where $R^{(72)}$ represent an alkyl, cycloalkyl, heteroalkyl, heterocycloalkyl, cycloalkylalkyl, aryl, heteroaryl, arylalkyl, or heteroarylalkyl, which can be substituted, as defined herein.

"Phosphate ester group" by itself or as part of another substituent refers to a radical —OP(O)(O$R^{(73)}$)(O$R^{(74)}$) where $R^{(73)}$ and $R^{(74)}$ represent a hydrogen, alkyl, cycloalkyl, heteroalkyl, heterocycloalkyl, cycloalkylalkyl, aryl, heteroaryl, arylalkyl, or heteroarylalkyl, which can be substituted, as defined herein.

"Phosphoramide group" by itself or as part of another substituent refers to a radical —N($R^{(75)}$)P(O) (N$R^{(76)}R^{(77)}$) (N$R^{(78)}R^{(79)}$) where $R^{(75)}$, $R^{(76)}$, $R^{(77)}$, $R^{(78)}$, $R^{(79)}$ represent a hydrogen, alkyl, cycloalkyl, heteroalkyl, heterocycloalkyl, cycloalkylalkyl, aryl, heteroaryl, arylalkyl, or heteroarylalkyl, which can be substituted, as defined herein. Phosphoramide groups include —N($R^{(75)}$)P(O)(OH)(N$R^{(76)}R^{(77)}$), and —N($R^{(75)}$)P(=O)(OH)$_2$.

"Acetal group" by itself or as part of another substituent refers to a radical —CH(O$R^{(80)}$)(O$R^{(81)}$), and "hemiacetal group" by itself or as part of another substituent refers to a radical —CH(O$R^{(80)}$)(OH), where $R^{(80)}$ and $R^{(81)}$ represent an alkyl, cycloalkyl, heteroalkyl, heterocycloalkyl, cycloalkylalkyl, aryl, heteroaryl, arylalkyl, or heteroarylalkyl, which can be substituted, as defined herein.

"Ketal group" by itself or as part of another substituent refers to a radical —C($R^{(82)}$)(O$R^{(83)}$)(O$R^{(84)}$), and "hemiketal group" by itself or as part of another substituent refers to a radical —C($R^{(82)}$)(O$R^{(83)}$)(OH), where $R^{(82)}$, $R^{(83)}R^{(84)}$ represent an alkyl, cycloalkyl, heteroalkyl, heterocycloalkyl, cycloalkylalkyl, aryl, heteroaryl, arylalkyl, or heteroarylalkyl, which can be substituted, as defined herein.

"Orthoester group" by itself or as part of another substituent refers to a radical —C(O$R^{(85)}$)(O$R^{(86)}$) (O$R^{(87)}$) where $R^{(85)}$, $R^{(86)}$, $R^{(87)}$ represent an alkyl, cycloalkyl, heteroalkyl, heterocycloalkyl, cycloalkylalkyl, aryl, heteroaryl, arylalkyl, or heteroarylalkyl, which can be substituted, as defined herein.

"Carboxyalkyl" by itself or as part of another substituent refers to a radical —$R^{(88)}$COOH where $R^{(88)}$ represents an alkyl, cycloalkyl, heteroalkyl, heterocycloalkyl, cycloalkylalkyl, aryl, heteroaryl, arylalkyl, or heteroarylalkyl, which can be substituted, as defined herein.

"Parent aromatic ring system" refers to an unsaturated cyclic or polycyclic ring system having a conjugated [pi] (pi) electron system. Included within the definition of "parent aromatic ring system" are fused ring systems in which one or more of the rings are aromatic and one or more of the rings are saturated or unsaturated. Examples of parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, alphay-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like.

"Parent heteroaromatic ring system" refers to a parent aromatic ring system in which one or more carbon atoms (and any associated hydrogen atoms) are independently replaced with the same or different heteroatom. Examples of heteroatoms to replace the carbon atoms include, but are not limited to, N, P, O, S, etc. Specifically included within the definition of "parent heteroaromatic ring systems" are fused ring systems in which one or more of the rings are aromatic and one or more of the rings are saturated or unsaturated. Examples of parent heteroaromatic ring systems include, but are not limited to, arsindole, carbazole, beta-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

A "biologically active agent" or "pharmaceutically active agent" refers to a therapeutic or pharmacological agent that is conjugatable in the manner of the present disclosure. A pharmaceutically active agent can be a small molecule, peptide, or protein. Examples of pharmaceutically active agents include, but are not limited to, those falling into the following therapeutic categories: ACE-inhibitors; anti-anginal drugs; anti-arrhythmias; anti-asthmatics; anti-cholesterolemics; anti-convulsants; anti-depressants; anti-diarrhea preparations; anti-histamines; antihypertensive drugs; anti-infectives; anti-inflammatory agents; anti-lipid agents; anti-manics; anti-nauseants; antistroke agents; anti-thyroid preparations; anti-tumor drugs; anti-tussives; anti-uricemic drugs; anti-viral agents; acne drugs; alkaloids; amino acid preparations; anabolic drugs; analgesics; anesthetics; angiogenesis inhibitors; antacids; anti-arthritics; antibiotics; anticoagulants; antiemetics; antiobesity drugs; antiparasitics; antipsychotics; antipyretics; antispasmodics; antithrombotic drugs; anxiolytic agents; appetite stimulants; appetite suppressants; beta blocking agents; bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypnotics; hypoglycemic agents; laxatives; migraine treatments; mucolytics; narcotics; neuroleptics; neuromuscular drugs; NSAIDS; peripheral vasodilators; prostaglandins; psychotropics; renin inhibitors; respiratory stimulants; steroids; stimulants; sympatholytics; thyroid preparations; tranquilizers; uterine relaxants; vaginal preparations; vasoconstrictors; vasodilators; vertigo agents; vitamins; and wound healing agents.

"Prodrug" refers to a derivative of a drug or a pharmaceutically active agent that is administered in an inactive or less than fully active form, and is then converted to its active form within the body. In some cases, the transformation releases the parent drug or pharmaceutically active agent. In some cases a bioactive derivative of the parent drug or pharmaceutically active agent is generated. Prodrugs can be obtained by bonding a promoiety (defined herein) to a drug or a pharmaceutically active agent typically via a functional group.

The prodrugs of our disclosure can be used to treat any condition for which the parent drugs or pharmaceutical active agents are useful for. For example, if insulin is the parent drug of choice, the prodrug can be used for any condition or treatment for which insulin would be administered.

"Promoiety" refers to a group bonded to a drug, typically to a functional group of the drug, via bond(s) that are cleavable under specified conditions of use, for example, following administration to a patient. The bond(s) between the drug and promoiety may be cleaved by enzymatic or non-enzymatic means to release the parent drug. The cleavage of the promoiety may proceed spontaneously, such as via a hydrolysis reaction, or it may be catalyzed or induced by another agent, such as by an enzyme, by light, by acid, by base, or by a change of or exposure to a physical or environmental parameter, such as temperature, pH, etc. The agent may be endogenous to the conditions of use, such as an enzyme present in the systemic circulation of a patient to which the prodrug is administered or the acidic conditions of the stomach or the agent may be supplied exogenously.

"Protecting group" refers to a grouping of atoms, which when attached to a reactive group in a molecule masks, reduces, or prevents that reactivity. Examples of protecting groups can be found in Wuts and Greene, "Protective Groups in Organic Synthesis," John Wiley & Sons, 4th ed. 2006. Examples of amino protecting groups include, but are not limited to, formyl, acetyl, trifluoroacetyl, benzyl, benzyloxycarbonyl (CBZ), tert-butoxycarbonyl (Boc), trityl and substituted trityl groups, allyloxycarbonyl, and 9-fluorenylmethyloxycarbonyl (FMOC). Examples of hydroxy protecting groups include, but are not limited to, those in which the hydroxy group is either acylated or alkylated such as benzyl, trityl ethers, alkyl ethers, tetrahydropyranyl ethers, trialkylsilyl ethers, and allyl ethers.

The term "polypeptide" or "peptide" used herein is intended to indicate any structural form (e.g., primary, secondary or tertiary form) of an amino acid sequence comprising more than 5 amino acid residues, which may or may not be further modified (e.g., acetylated, carboxylated, phosphorylated, lipidated, or acylated). The term "native" refers to a polypeptide that has an amino acid sequence that is identical to one found in nature. The term "native" is intended to encompass allelic variants of the polypeptide in question. A number may be included to designate the position of an amino acid in a polypeptide. For example, amino acids that are located within an insulin or GLP-1 sequence are designated by positive numbers numbered consecutively from the N-terminus of insulin or GLP-1. Additional amino acids linked to the insulin receptor binding peptide at the N-terminus are numbered starting with 0 and increasing in negative integer value as they are further removed from the insulin receptor binding sequence.

In the present disclosure, the amino acid sequence of a biologically active peptide can be altered without affecting its biological activity. For example, one of the insulin derivatives may comprise one or more of conservative amino acid substitutions. The conservative amino acid substitution is the one where an amino acid residue is replaced with another amino acid residue having a similar side chain. Amino acid residues can be classified according to the nature of the side chain of an amino acid residue in literatures. Amino acid residues with a basic side chain comprise lysine, arginine, histidine; amino acid residues with an acidic side chain and an acylamide side chain comprise aspartic acid, glutamic acid, asparagine, glutamine; amino acid residues with small aliphatic, non-polar, or weak polar side chains comprise glycine, alanine, threonine, serine, praline; amino acid residues with large aliphatic and non-polar side chains comprise leucine, isoleucine, valine; aromatic amino acid residues comprise phenylalanine, tryptophan, tyrosine; amino acid residues with a sulphur-containing side chain comprise cysteine and methionine.

The term "amino acid" is used herein in its broadest sense, and includes naturally occurring amino acids as well as non-naturally occurring amino acids, including amino acid variants and derivatives. One skilled in the art will recognize, in view of this broad definition, that reference herein to an amino acid includes, for example, naturally occurring proteogenic L-amino acids; D-amino acids; chemically modified amino acids such as amino acid variants and derivatives; naturally occurring non-proteogenic amino acids such as norleucine, β-alanine, ornithine, etc.; and chemically synthesized compounds having properties known in the art to be characteristic of amino acids. Examples of amino acids include α-methyl amino acids (e.g., α-methyl alanine), β-amino acids, histidine-like amino acids (e.g., 2-amino-histidine, β-hydroxy-histidine, homohistidine, α-fluoromethyl-histidine and α-methyl-histidine), amino acids having an extra methylene in the side chain ("homo" amino acids) and amino acids in which a carboxylic acid functional group in the side chain is replaced with a sulfonic acid group (e.g., cysteic acid).

For the purposes of the present disclosure designation of an amino acid without specifying its stereochemistry is intended to encompass either the L or D form of the amino acid, or a racemic mixture. However, in the instance where an amino acid is only designated by its one letter code (i.e., K), such a designation is intended to specify the native L form of the amino acid, whereas the D form will be specified by inclusion of a lower case d before the one letter code (i.e., dK).

The term "hydroxyl acid" refers to amino acids that have been modified to replace the alpha carbon amino group with a hydroxyl group.

The term "albumin" includes serum albumin from a variety of species and sources, e.g., native human serum albumin (HSA), recombinant albumin such as Albagen, a recombinant human albumin with deletion of the N-terminal residue (Asp), human albumin derivatives, or a fragment of human albumin as provided in EP322,094, including HSA (1-373), HSA (1-388), HSA (1-389), HSA (1-369), and HSA (1-419). EP399666 provides sequences including HSA (1-177) and HSA (1-200).

The numbering of the positions in albumin is done so that the parent compound is human serum albumin. The term like Cys34, indicate a Cys in position 34. In Albagen, which is recombinant human serum albumin lacking the first amino acid, the free Cys is referred to as Cys34.

The term "thiol reactive groups" includes, but is not limited to, for example, haloacetyl groups and un-symmetric disulfides. Non-limiting examples of such unsymmetrical disulfides are pyridyldisulfides, methoxy- or ethoxycarbonyl disulfides, and o-nitrophenyl disulfides.

The term "Michael acceptors" includes, but is not limited to, for example, α,β-unsaturated carbonyl moieties, maleimido groups and vinyl sulfone groups.

The term "immunoglobulin" (Ig) includes all five antibody isotypes known as IgA, IgD, IgE, IgG, IgM in mammals or portion thereof (e.g. variable region, CDR, or Fc region). Fc of an immunoglobulin can be a human immunoglobulin Fc, a human immunoglobulin Fc derivative, or a fragment of human immunoglobulin Fc, etc. Fc may comprise the hinge-region, $C_{H2}$, and $C_{H3}$ up to the C-terminus. Binding of Fc to FcRn results in prolonged circulation time of a Fc conjugate in vivo. Suitable conjugate moieties include portions of immunoglobulin sequence that contain the FcRn binding site. The major contact area of the Fc with the FcRn is near the junction of the $C_{H2}$ and $C_{H3}$ domains. The major contact sites include amino acid residues 248, 250-257, 272, 285, 288, 290-291, 308-311, and 314 of the $C_{H2}$ domain and amino acid residues 385-387, 428, and 433-436 of the $C_{H3}$ domain. Amino acid modifications may be made to the Fc region of an immunoglobulin. Such variant Fc regions comprise at least one amino acid modification in the $C_{H3}$ domain of the Fc region (residues 342-447) and/or at least one amino acid modification in the $C_{H2}$ domain of the Fc region (residues 231-341). Mutations believed to impart an increased affinity for FcRn include T256A, T307A, E380A, and N434A (Shields et al. 2001, J. Biol. Chem. 276:6591). Variations at the interface between $C_{H2}$ and $C_{H3}$ may extend the half-time of Igs (Hinton et at, 2004. J Biol Chem. 279(8):6213-6; Vaccaro et al., 2005. Nat Biotechnol. 23(10):1283-8). References made to amino acid numbering of immunoglobulins or immunoglobulin fragments, or regions, are based on Kabat et al. 1991, Sequences of Proteins of Immunological Interest, U.S. Department of Public Health, Bethesda, Md. Some conjugate moieties may or may not include FcγR binding site(s) responsible for antibody dependent cell-mediated cytotoxicity (ADCC) and complement dependent cytotoxicity (CDC).

The term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by FDA or listed in the US Pharmacopeia for use in humans.

The term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Figure 1A:
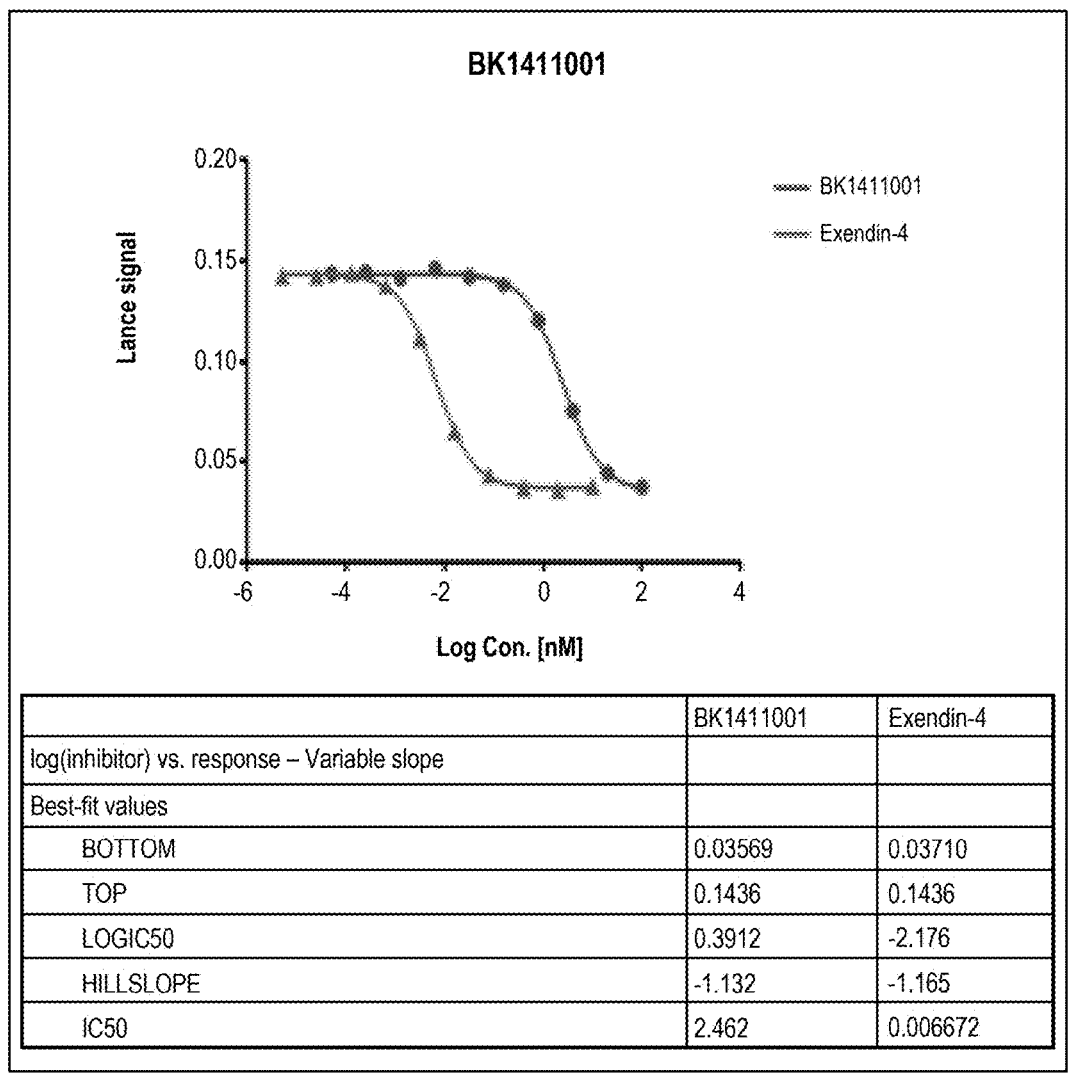
FIG. 1A-FIG. 1D show $IC_{50}$ data obtained from GLP-1 receptor functional assay of exenatide prodrug 1 (FIG. 1A), exenatide prodrug 1 human serum albumin conjugate (FIG. 1B), exenatide prodrug 2 PEG40K conjugate (FIG. 1C), and exenatide prodrug 3 albumin conjugate (FIG. 1D). The samples were incubated in serum at 37° C. and collected at different time points.
Figure 1B:
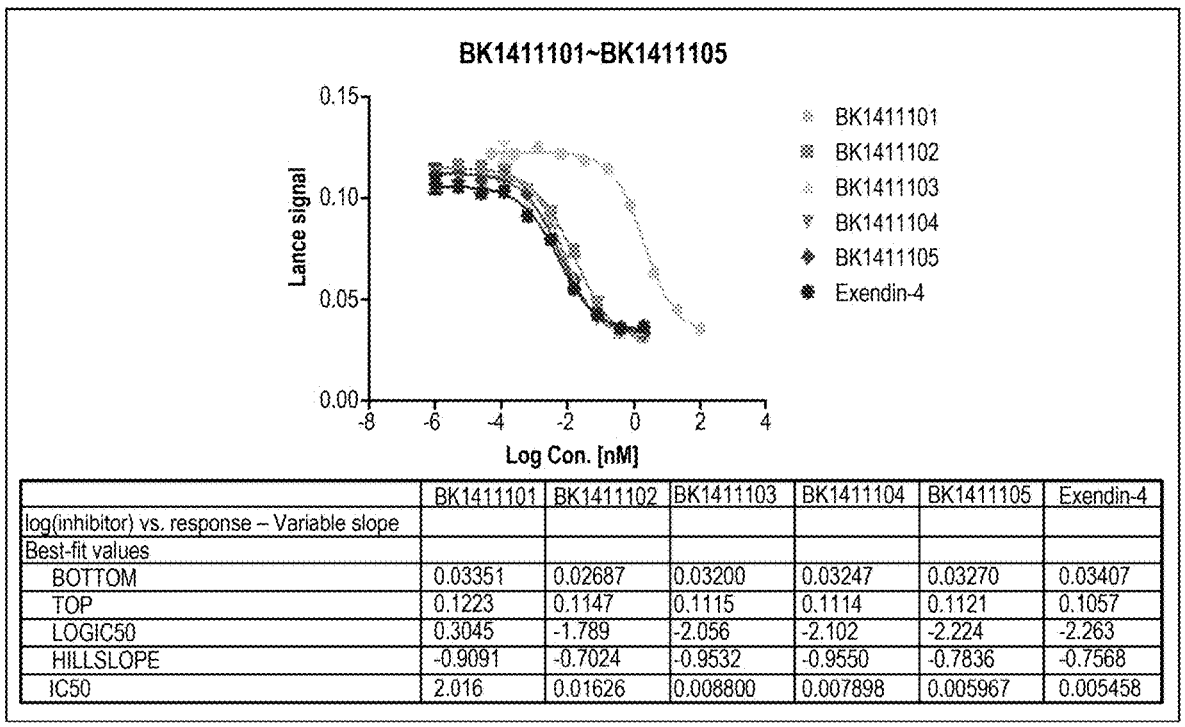
Figure 1C:
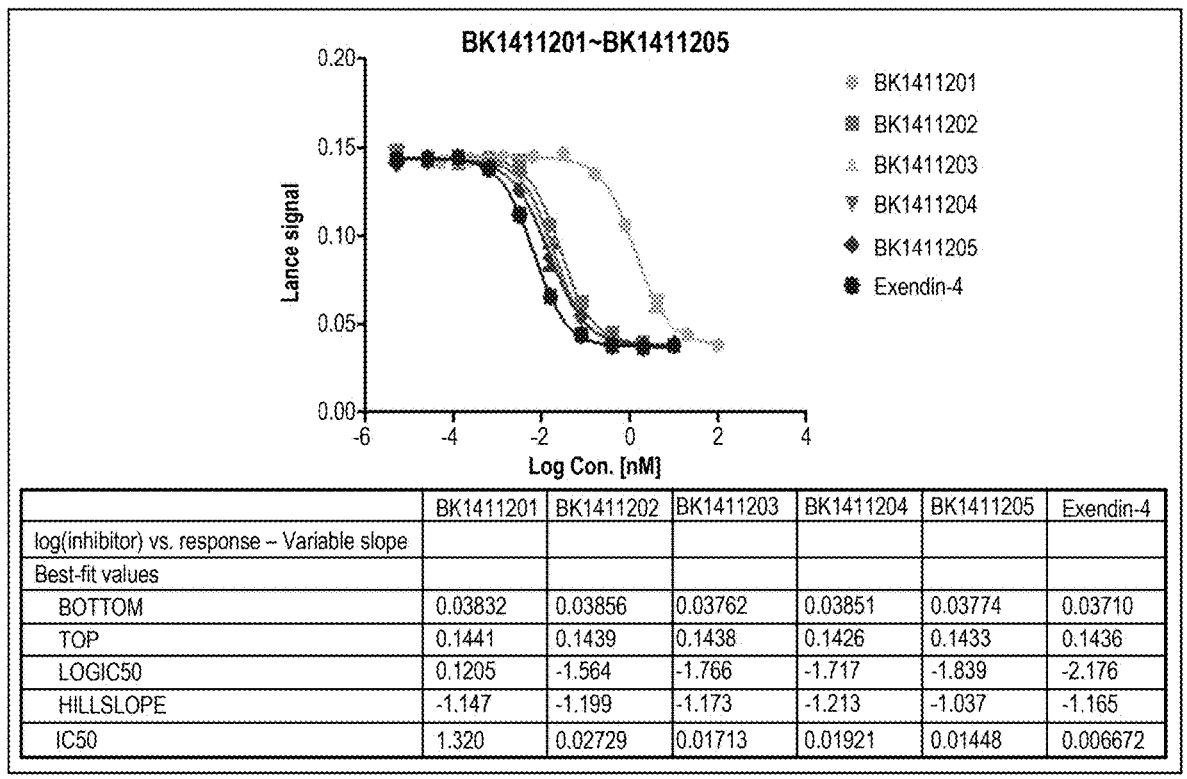
Figure 1D:
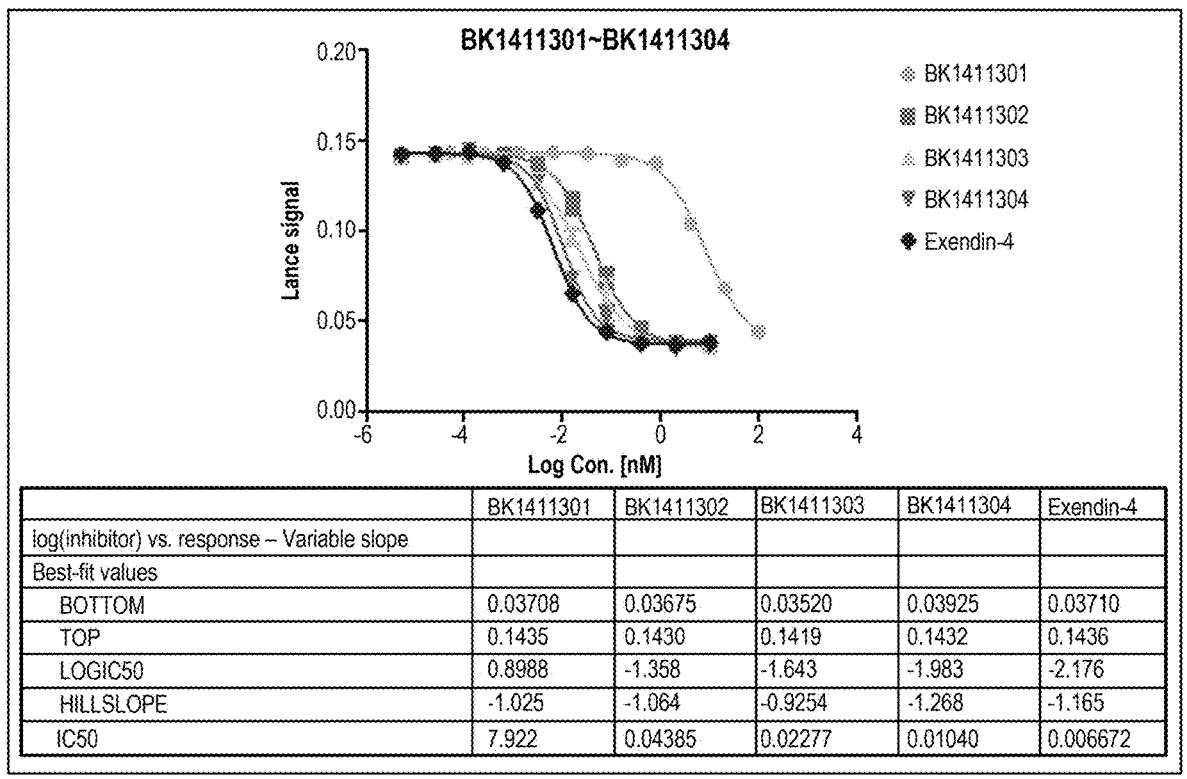

The present disclosure relates to a prodrug or its pharmaceutically acceptable salt thereof comprising a nitrogen-containing or hydroxyl-containing drug or a pharmaceutically active agent and a promoiety. A promoiety is biologically inactive and is of the following formula, wherein the wavy line indicates the attachment point to a drug or a pharmaceutically active agent via an amide or ester bond:

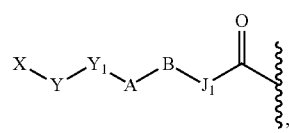

wherein X is selected from —OH, —SH, and —HN—R$_O$;
Y is selected from:
(1) —N—R$_O$;
(2) —C(R$_p$R$_q$);
(3) —O or —S, provided that X is not —OH or —SH;
(4) —C(R$_p$R$_q$), when X is —HN—R$_O$; and
(5) C(O);
Y$_1$ is selected from
(1) —C(R$_3$R$_4$);
(2) —C(O) or —C(S), provided that none of Y and A is C(O), C(S), SO, or SO$_2$;
(3) O, S, SO, or SO$_2$, provided that none of Y and A is —O or —S;
(4) —N—R$_a$; and
(5) bond;
J$_1$ is —C(R$_{10}$R$_{11}$) or a bond.

A and B together form a ring system, or are independently selected from —NR'—, —S—, —O—, straight and branched chain alkyl having from 1 to 20 carbon atoms; aryl having from 6 to 15 carbon atoms; cycloalkyl having a 3, 4, 5, 6, 7, 8, 9, or 10 membered ring; alkenyl having from 2 to 20 carbon atoms; cycloalkenyl having a 4, 5, 6, 7, 8, 9, or 10 membered ring; alkynyl having from 2 to 20 carbon atoms; cycloalkynyl having a 5, 6, 7, 8, 9, or 10 membered ring; monocyclic and polycyclic; aralkyl; aralkenyl; aralkynyl; alkaryl; alkenylaryl; alkynylaryl; loweracyloxyalkyl; and carboxyalkyl, wherein alkyl, aryl, alkenyl and alkynyl are defined as above; ether, thioether, or substituted amine; saturated and unsaturated monoheterocyclic, polyheterocyclic; and fused heterocyclic, containing one or more heteroatoms N, S or O in each heterocyclic ring thereof and each such ring being from 3- to 8-membered. Each of aforementioned alkyl, aryl, cycloalkyl, cycloalkenyl, cycloalkynyl, monocyclic and polycyclic aralkyl, aralkenyl, aralkynyl, alkaryl, alkenylaryl, alkynylaryl, loweracyloxyalkyl, carboxyalkyl, saturated and unsaturated monoheterocyclic, polyheterocyclic, and fused heterocyclic is optionally substituted with one or more groups selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiments A and B together form a C3-C10 cycloalkyl ring (e.g. cycloalkane, cycloalkene, and cycloalkyne) optionally substituted by at least one group; or saturated or unsaturated monocyclic or polycyclic, or fused cyclic ring optionally substituted by at least one group; or saturated or unsaturated monoheterocyclic or polyheterocyclic, or fused heterocyclic ring optionally substituted by at least one group. Examples of the rings include, but not limited to, acridine, azepane, azepine, azocane, benzofuran, benzimidazole, benzothiophene, benzo[c]thiophene, benzoxazole, benzisoxazole, benzothiazole, cinnoline, diazepine, dioxolane, dithiolane, furan, furazan, imidazolidine, imidazole, indazole, indole, isoindole, isobenzofuran, isothiazole, isothiazolidine, isoxazole, isoxazolidines, morpholine, oxazines, oxadiazole, oxazole, oxazolidine, oxepane, quinazoline, quinoline, isoquinoline, quinoxaline, phosphole, phthalazine, piperidine, purine, pyridine, pyran, pyrrolidine, pyrrole, pyrazolidine, pyrazine, pyrazole, piperazine, pyrimidine, pyridazine, thiazole, tetrazole, 1,2,3-triazine, 1,2,4-triazine, 1,3,5-triazine, triazole, thiane, thiazolidine, thiopyran, tetrahydrofuran, tetrahydrothiophene, thiadiazole, thiophene, thiomorpholine, thiazine, thiazepine, zocine. The "at least one group" is selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy. Or A and B together form an aromatic ring optionally substituted by the at least one group as defined above; or A and B together with the atoms to which they are attached form a polyaromatic ring optionally substituted by the at least one group as defined above.

In some embodiments, A and/or B can be —NR'—, —S—, or —O—. In one embodiment A and B together form a saturated or unsaturated monocyclic, polycyclic, fused cyclic, monoheterocyclic, polyheterocyclic, or fused heterocyclic ring optionally substituted by the at least one group as defined above.

R$_O$, R$_O$, R$_3$, R$_4$, R$_{10}$, R$_{11}$, R$_n$, R$_p$, R$_q$, and R' are independently selected from hydrogen (H), straight and branched chain alkyl having from 1 to 20 carbon atoms; aryl having from 6 to 15 carbon atoms; cycloalkyl having a 3, 4, 5, 6, 7, 8, 9, or 10 membered ring; alkenyl having from 2 to 20 carbon atoms; cycloalkenyl having a 4, 5, 6, 7, 8, 9, or 10 membered ring; alkynyl having from 2 to 20 carbon atoms; cycloalkynyl having a 5, 6, 7, 8, 9, or 10 membered ring; monocyclic or polycyclic; aralkyl, aralkenyl, aralkynyl, alkaryl, alkenylaryl, alkynylaryl, loweracyloxyalkyl, and carboxyalkyl, wherein alkyl, aryl, alkenyl and alkynyl are defined as above; saturated and unsaturated monoheterocyclic, polyheterocyclic, and fused heterocyclic, containing one or more heteroatoms N, S or O in each heterocyclic ring thereof and each such ring being from 3- to 8-membered. Each of aforementioned alkyl, aryl, cycloalkyl, cycloalkenyl, cycloalkynyl, monocyclic and polycyclic, aralkyl, aralkenyl, aralkynyl, alkaryl, alkenylaryl, alkynylaryl, lower acyloxyalkyl, carboxyalkyl, saturated and unsaturated monoheterocyclic, polyheterocyclic; and fused heterocyclic is optionally substituted with one or more groups selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy. Or $R_0$, $R_O$, $R_3$, $R_4$, $R_{10}$, $R_{11}$, $R_n$, $R_p$, $R_q$, and R' can also be independently selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, lower alkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiments, $R_0$, $R_O$, $R_3$, $R_4$, $R_{10}$, $R_{11}$, $R_n$, $R_p$, $R_q$, and R' are independently selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiments, $R_0$, $R_O$, $R_3$, $R_4$, $R_{10}$, $R_{11}$, $R_n$, $R_p$, $R_q$, and R' are independently selected from H, $C_1$-$C_{18}$ alkyl, $C_2$-$C_{18}$ alkenyl, ($C_1$-$C_{10}$ alkyl)OH, ($C_1$-$C_{10}$ alkyl)SH, ($C_2$-$C_3$ alkyl)SCH$_3$, ($C_1$-$C_4$ alkyl)CONH$_2$, ($C_1$-$C_{10}$ alkyl)COOH, ($C_1$-$C_{10}$ alkyl)NH$_2$, ($C_1$-$C_4$ alkyl)NHC(NH$_2$+)NH$_2$, ($C_0$-$C_4$ alkyl)($C_3$-$C_5$ cycloalkyl), ($C_0$-$C_4$ alkyl)($C_2$-$C_5$ heterocyclic), ($C_0$-$C_4$ alkyl)($C_6$-$C_{10}$ aryl), ($C_0$-$C_4$ alkyl)($C_6$-$C_{10}$ aryl)$R_{16}$, ($C_1$-$C_4$ alkyl)($C_3$-$C_9$ heteroaryl), and $C_1$-$C_{12}$ alkyl(W$_1$)$C_1$-$C_{12}$ alkyl, wherein $W_1$ is a heteroatom selected from N, S and O; $R_{16}$ is selected from H, OH, halo, ($C_1$-$C_7$ alkyl), ($C_2$-$C_7$ alkenyl), CF$_3$, OCF$_3$, NO$_2$, CN, NC, O($C_1$-$C_7$ alkyl), CO$_2$H, CO$_2$($C_1$-$C_7$ alkyl), NHC$_1$-$C_{10}$ alkyl, O(C$_1$-$C_{10}$ alkyl), aryl, and heteroaryl.

In some embodiments, two R groups (selected from $R_0$, $R_3$, $R_4$, $R_{10}$, $R_{11}$, $R_O$, $R_n$, $R_p$, $R_q$, and R') that are attached to the same atom or attached to two atoms separated by one bond, together with the atom(s) to which they are attached form a $C_3$-$C_8$ cycloalkyl, cycloalkenyl, or cycloalkynyl ring, or saturated or unsaturated heterocyclic ring optionally substituted by the at least one group other than hydrogen (H); or two R groups together with the atom(s) to which they are attached form an aromatic ring optionally substituted by the at least one group other than hydrogen (H). The at least one group is selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

Such promoiety and a nitrogen containing or hydroxyl-containing drug (such as $R_{14}R_{15}$NH or $R_{14}$OH) form an amide or ester prodrug. Intramolecular reaction of the prodrug under physiological conditions (e.g., 37° C., pH 7.0-7.5) releases the nitrogen containing or hydroxyl-containing drug. Those two processes are illustrated as follows:

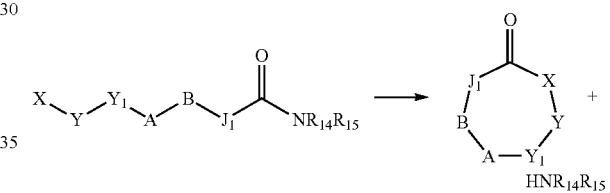

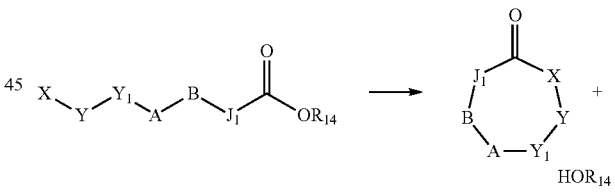

wherein $R_{14}$ and $R_{15}$ are substructures of a nitrogen-containing or hydroxyl-containing drug or pharmaceutically active agent of this disclosure.

In some embodiments, $J_1$ is $C(R_{10}R_{11})$ and $Y_1$ is a bond, and one class of promoieties is of the following formula:

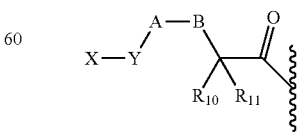

In some embodiments, $Y_1$ is $C(R_3R_4)$ and $J_1$ is a bond, and one class of promoieties is of the following formula:

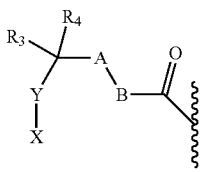

In some embodiments, $Y_1$ is $C(R_3R_4)$, $J_1$ is $C(R_{10}R_{11})$, and one class of promoieties is of the following formula:

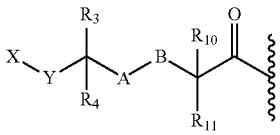

In some embodiments, one class of promoieties is of the following formula:

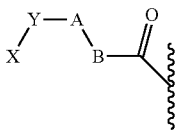

Subclass 1

In some embodiments, one class of promoieties is of the following formula:

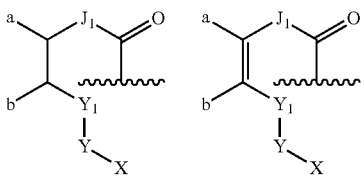

wherein X is OH, SH, or HN—$R_0$;
Y is selected from
(1) N—$R_O$;
(2) $C(R_pR_q)$;
(3) O or S, provided that X is not OH or SH;
(4) $C(R_pR_q)$, when X is HN—$R_0$, wherein $R_0$ and $R_p$ together with the atoms to which they are attached can form a 4, 5, or 6 membered heterocyclic ring; and
(5) C(O).
$Y_1$ is selected from
(1) $C(R_3R_4)$;
(2) C(O) or C(S), provided that none of Y and A is C(O), C(S), SO, or $SO_2$;
(3) O, S, SO, or $SO_2$, provided that none of Y and A is O or S;
(4) N—$R_n$; and
(5) a covalent bond.
$J_1$ is $C(R_{10}R_{11})$ or a covalent bond;
a and b are independently selected from hydrogen (H), straight and branched chain alkyl having from 1 to 20 carbon atoms; aryl having from 6 to 15 carbon atoms; cycloalkyl having a 3, 4, 5, 6, 7, 8, 9, or 10 membered ring; alkenyl having from 2 to 20 carbon atoms; cycloalkenyl having a 4, 5, 6, 7, 8, 9, or 10 membered ring; alkynyl having from 2 to 20 carbon atoms; cycloalkynyl having a 5, 6, 7, 8, 9, or 10 membered ring; monocyclic or polycyclic; aralkyl, aralkenyl, aralkynyl, alkaryl, alkenylaryl, alkynylaryl, lower acyloxyalkyl, and carboxyalkyl, wherein alkyl, aryl, alkenyl and alkynyl are defined as above; saturated or unsaturated monoheterocyclic, polyheterocyclic, and fused heterocyclic, containing one or more heteroatoms N, S or O in each heterocyclic ring thereof and each such ring being from 3- to 8-membered. Each of aforementioned alkyl, aryl, cycloalkyl, cycloalkenyl, cycloalkynyl, monocyclic and polycyclic aralkyl; aralkenyl; aralkynyl; alkaryl; alkenylaryl; alkynylaryl; loweracyloxyalkyl; carboxyalkyl, saturated and unsaturated monoheterocyclic, polyheterocyclic; and fused heterocyclic is optionally substituted with one or more groups selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiments, a and b together with the atoms to which they are attached form a C3-C10 cycloalkyl ring (e.g. cycloalkane, cycloalkene, and cycloalkyne) optionally substituted by the at least one group; or saturated or unsaturated monocyclic or polycyclic, or fused cyclic ring optionally substituted by the at least one group; or saturated or unsaturated monoheterocyclic or polyheterocyclic, or fused heterocyclic ring optionally substituted by the at least one group. Examples of the rings include, but not limited to, acridine, azepane, azepine, azocane, benzofuran, benzimidazole, benzothiophene, benzo[c]thiophene, benzoxazole, benzisoxazole, benzothiazole, cinnoline, diazepine, dioxolane, dithiolane, furan, furazan, imidazolidine, imidazole, indazole, indole, isoindole, isobenzofuran, isothiazole, isothiazolidine, isoxazole, isoxazolidines, morpholine, oxazines, oxadiazole, oxazole, oxazolidine, oxepane, quinazoline, quinoline, isoquinoline, quinoxaline, phosphole, phthalazine, piperidine, purine, pyridine, pyran, pyrrolidine, pyrrole, pyrazolidine, pyrazine, pyrazole, piperazine, pyrimidine, pyridazine, thiazole, tetrazole, 1,2,3-triazine, 1,2,4-triazine, 1,3,5-triazine, triazole, thiane, thiazolidine, thiopyran, tetrahydrofuran, tetrahydrothiophene, thiadiazole, thiophene, thiomorpholine, thiazine, thiazepine, zocine. The at least one group is selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy. Or a and b together with the atoms to which they are attached form an aromatic ring optionally substituted by the at least one group selected from the above; or a and b together with the atoms to which they are attached form a polyaromatic ring, such as a fused aromatic ring, for example, naphthalene, optionally substituted by the at least one group as defined above.

In some embodiments, a and b are independently selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiments a and b are independently selected from —NR', —SR'', and —OR'''. R' is defined as above. R'' and R''' are independently selected from hydrogen (H), straight or branched chain alkyl having from 1 to 20 carbon atoms; aryl having from 6 to 15 carbon atoms; cycloalkyl having a 3, 4, 5, 6, 7, 8, 9, or 10 membered ring; alkenyl having from 2 to 20 carbon atoms; cycloalkenyl having a 4, 5, 6, 7, 8, 9, or 10 membered ring; alkynyl having from 2 to 20 carbon atoms; cycloalkynyl having a 5, 6, 7, 8, 9, or 10 membered ring; monocyclic or polycyclic; aralkyl; aralkenyl; aralkynyl; alkaryl; alkenylaryl; alkynylaryl; loweracyloxyalkyl; and carboxyalkyl; wherein alkyl, aryl, alkenyl and alkynyl are defined as above; and saturated or unsaturated monoheterocyclic, polyheterocyclic, or fused heterocyclic, containing one or more heteroatoms N, S or O in each heterocyclic ring thereof and each such ring being from 3- to 8-membered; mono- or poly-substituted derivatives of the above. Each of aforementioned alkyl, aryl, cycloalkyl, cycloalkenyl, cycloalkynyl, monocyclic and polycyclic aralkyl; aralkenyl; aralkynyl; alkaryl; alkenylaryl; alkynylaryl; loweracyloxyalkyl; carboxyalkyl, and saturated and unsaturated monoheterocyclic, polyheterocyclic is optionally substituted with one or more groups selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiments, R'' and R''' are independently selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiments, R'' and R''' are independently selected from H, $C_1$-$C_{18}$ alkyl, $C_2$-$C_{18}$ alkenyl, ($C_1$-$C_{10}$ alkyl)OH, ($C_1$-$C_{10}$ alkyl)SH, ($C_2$-$C_3$ alkyl)SCH$_3$, ($C_1$-$C_4$ alkyl)CONH$_2$, ($C_1$-$C_{10}$ alkyl)COOH, ($C_1$-$C_{10}$ alkyl)NH$_2$, ($C_1$-$C_4$ alkyl)NHC(NH$_2$$^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl), ($C_0$-$C_4$ alkyl)($C_6$-$C_{10}$ aryl)$R_{16}$, ($C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from N, S and O; $R_{16}$ is selected from H, OH, halo, ($C_1$-$C_7$ alkyl), ($C_2$-$C_7$ alkenyl), CF$_3$, OCF$_3$, NO$_2$, CN, NC, O($C_1$-$C_7$ alkyl), CO$_2$H, CO$_2$($C_1$-$C_7$ alkyl), NH $C_1$-$C_{10}$ alkyl, O($C_1$-$C_{10}$ alkyl), aryl, and heteroaryl.

In some embodiments, a and b together with the atoms to which they are attached form a saturated or unsaturated monocyclic, polycyclic, fused cyclic, monoheterocyclic, polyheterocyclic, or fused heterocyclic ring optionally substituted by the at least one group as defined above.

Subclass 2

In some embodiments, promoieties in this class are of the following formulae, wherein X, Y, a, and b are defined as above:

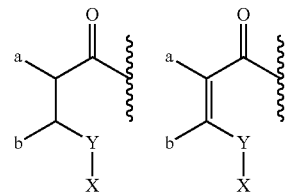

In some embodiment, promoieties in this class are of the following formulae, wherein X, Y, $R_3$, $R_4$, a, and b are defined as above:

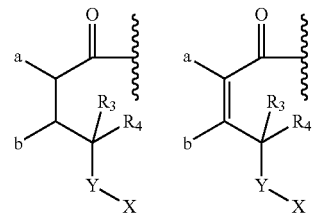

in some embodiments, promoieties in this class are of the following formulae, wherein X, Y, $R_{10}$, $R_{11}$, a, and b are defined as above:

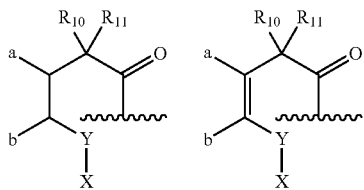

Subclass 3

In some embodiments, one class of promoieties containing a 6-member ring is of the following formula:

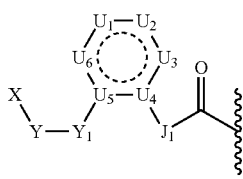

wherein $U_1$, $U_2$, $U_3$, $U_4$, $U_5$, and $U_6$ are independently selected from $CR_{12}$ and N;
X is OH, SH, or HN—$R_0$;
Y is selected from:
(1) N—$R_o$;
(2) $C(R_pR_q)$;
(3) O or S, provided that X is not OH or SH;
(4) $C(R_pR_q)$, when X is HN—$R_O$, wherein $R_0$ and $R_p$ together with the atoms to which they are attached can form a 4, 5, or 6 membered heterocyclic ring; and
(5) C(O);
$Y_1$ is selected from
(1) $C(R_3R_4)$;
(2) C(O) or C(S), provided that none of Y and A is C(O), C(S), SO, or $SO_2$;
(3) O, S, SO, or $SO_2$, provided that none of Y and A is O or S;
(4) N—$R_n$; and
(5) a bond;
$J_1$ is $C(R_{10}R_{11})$ or a bond;
$R_{12}$ is selected from hydrogen (H), straight or branched chain alkyl having from 1 to 20 carbon atoms; aryl having from 6 to 15 carbon atoms; cycloalkyl having a 3, 4, 5, 6, 7, 8, 9, or 10 membered ring; alkenyl having from 2 to 20 carbon atoms; cycloalkenyl having a 4, 5, 6, 7, 8, 9, or 10 membered ring; alkynyl having from 2 to 20 carbon atoms; cycloalkynyl having a 5, 6, 7, 8, 9, or 10 membered ring; monocyclic or polycyclic; aralkyl, aralkenyl, aralkynyl, alkaryl, alkenylaryl, alkynylaryl, loweracyloxyalkyl, and carboxyalkyl, wherein alkyl, aryl, alkenyl and alkynyl are defined as above; saturated and unsaturated monoheterocyclic, polyheterocyclic, and fused heterocyclic, containing one or more heteroatoms N, S or O in each heterocyclic ring thereof and each such ring being from 3- to 8-membered. Each of the aforementioned alkyl, aryl, cycloalkyl, cycloalkenyl, cycloalkynyl, monocyclic and polycyclic aralkyl; aralkenyl; aralkynyl; alkaryl; alkenylaryl; alkynylaryl; loweracyloxyalkyl; carboxyalkyl, saturated and unsaturated monoheterocyclic, polyheterocyclic, and fused heterocyclic is optionally substituted with one or more groups selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy. Or $R_{12}$ can be selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiment, $R_{12}$ is selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

Subclass 4

In some embodiments, one class of promoieties containing a 6-member ring is of the following formula:

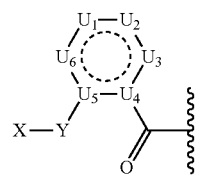

wherein X is OH, SH, or HN—$R_0$;
Y is selected from
(1) N—$R_O$;

(2) $C(R_pR_q)$;
(3) O or S, provided that X is not OH or SH; and
(4) $C(R_pR_q)$, when X is HN—$R_0$, wherein $R_0$ and $R_p$ together with the atoms to which they are attached can form a 4, 5, or 6 membered heterocyclic ring; and
$U_1$, $U_2$, $U_3$, $U_4$, $U_5$, $U_6$, $R_0$, $R_O$, $R_p$ and $R_q$ are defined as above.

Subclass 5

The promoities in this class include, but are not limited to, the following examples:

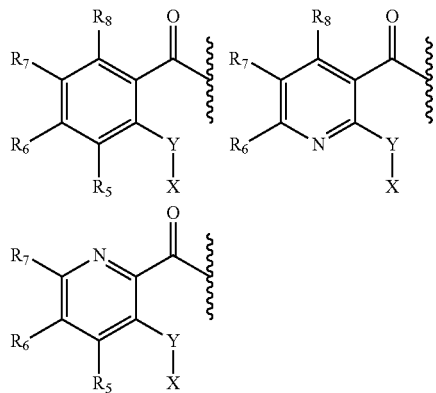

In some embodiments, Y in above three formulae is selected from NH, N—$R_O$, O (provided that X is not OH or SH).

In some embodiments, Y is N—$R_O$, X is HN—$R_0$ or OH. Promoieties in this class are of the following formulae:

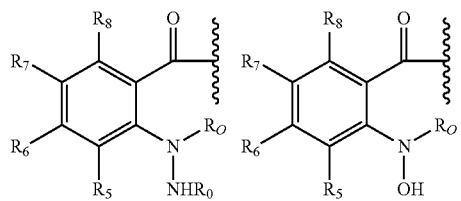

In some embodiments, $R_O$ is hydrogen (H) and the promoieties in this class are of the following formulae:

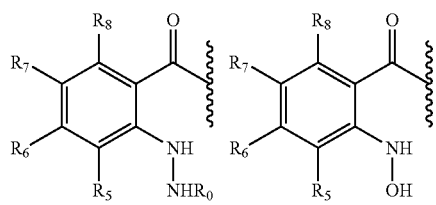

In each of the above formulae containing $R_5$, $R_6$, $R_7$, and $R_8$, $R_5$, $R_6$, $R_7$, and $R_8$ are independently selected from hydrogen (H), straight or branched chain alkyl having from 1 to 20 carbon atoms; aryl having from 6 to 15 carbon atoms; cycloalkyl having a 3, 4, 5, 6, 7, 8, 9, or 10 membered ring; alkenyl having from 2 to 20 carbon atoms; cycloalkenyl having a 4, 5, 6, 7, 8, 9, or 10 membered ring; alkynyl having from 2 to 20 carbon atoms; cycloalkynyl having a 5, 6, 7, 8, 9, or 10 membered ring; monocyclic or polycyclic; aralkyl, aralkenyl, aralkynyl, alkaryl, alkenylaryl, alkynylaryl, loweracyloxyalkyl, and carboxyalkyl, wherein alkyl, aryl, alkenyl and alkynyl are defined as above; saturated or unsaturated monoheterocyclic, polyheterocyclic, and fused heterocyclic, containing one or more heteroatoms N, S or O in each heterocyclic ring thereof and each such ring being from 3- to 8-membered. Each of the aforementioned alkyl, aryl, cycloalkyl, cycloalkenyl, cycloalkynyl, monocyclic and polycyclic aralkyl; aralkenyl; aralkynyl; alkaryl; alkenylaryl; alkynylaryl; loweracyloxyalkyl; carboxyalkyl, saturated and unsaturated monoheterocyclic, polyheterocyclic, and fused heterocyclic is optionally substituted with one or more groups selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiments, $R_5$, $R_6$, $R_7$, and $R_8$ are independently selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiments, two R groups (selected from $R_5$, $R_6$, $R_7$, $R_8$, $R_0$, $R_O$, $R_p$, and $R_q$) that are attached to the same atom or attached to two atoms separated by one bond form a $C_3$-$C_8$ cycloalkyl, cycloalkenyl, or cycloalkynyl ring, or saturated or unsaturated heterocyclic ring optionally substituted by the at least one group; or two R groups together with the atoms to which they are attached form an aromatic ring optionally substituted by the at least one group. The at least one group is selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfonic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiments, Y is O, and the promoieties in this class are of the following formula, wherein $R_5$, $R_6$, $R_7$, and $R_8$ are defined as above:

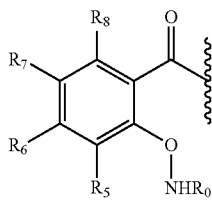

Subclass 6

In some embodiments, Y is $C(R_pR_q)$. Promoieties in this class are of the following formula wherein X, $U_1$, $U_2$, $U_3$, $U_4$, $U_5$, and $U_6$ are defined as above:

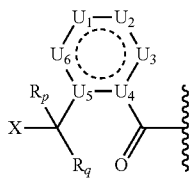

In some embodiments, promoieties in this class include, but are not limited to the following examples wherein X, $R_5$, $R_6$, $R_7$, and $R_8$ are defined as above:

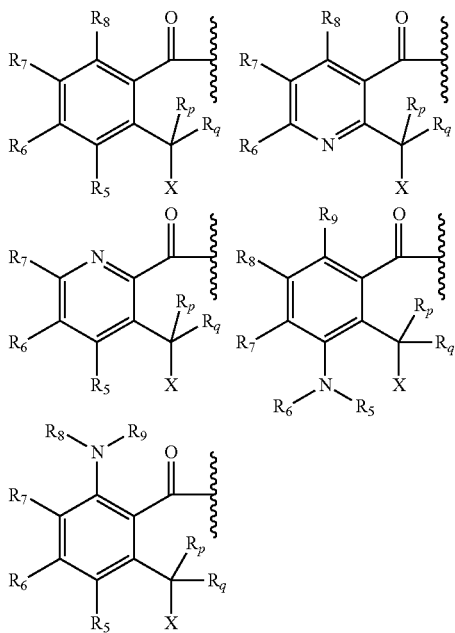

$R_9$ is selected from hydrogen (H), straight and branched chain alkyl having from 1 to 20 carbon atoms; aryl having from 6 to 15 carbon atoms; cycloalkyl having a 3, 4, 5, 6, 7, 8, 9, or 10 membered ring; alkenyl having from 2 to 20 carbon atoms; cycloalkenyl having a 4, 5, 6, 7, 8, 9, or 10 membered ring; alkynyl having from 2 to 20 carbon atoms; cycloalkynyl having a 5, 6, 7, 8, 9, or 10 membered ring; monocyclic or polycyclic; aralkyl, aralkenyl, aralkynyl, alkaryl, alkenylaryl, alkynylaryl, loweracyloxyalkyl, and carboxyalkyl, wherein alkyl, aryl, alkenyl and alkynyl are defined as above; saturated and unsaturated monoheterocyclic, polyheterocyclic, and fused heterocyclic, containing one or more heteroatoms N, S or O in each heterocyclic ring thereof and each such ring being from 3- to 8-membered. Each of the aforementioned alkyl, aryl, cycloalkyl, cycloalkenyl, cycloalkynyl, monocyclic and polycyclic aralkyl; aralkenyl; aralkynyl; alkaryl; alkenylaryl; alkynylaryl; loweracyloxyalkyl; carboxyalkyl, saturated and unsaturated monoheterocyclic, polyheterocyclic, and fused heterocyclic is optionally substituted with one or more groups selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiments, $R_9$ is selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiment when Y is $C(R_pR_q)$, two R groups (selected from $R_p$, $R_q$, $R_0$, $R_5$, $R_6$, $R_7$, $R_8$, and $R_9$) that are attached to the same atom or two atomes separated by one bond form a $C_3$-$C_8$ cycloalkyl, cycloalkenyl, or cycloalkynyl ring, or saturated or unsaturated heterocyclic ring optionally substituted by at least one group; or two R groups together with the atoms to which they are attached form an aromatic ring optionally substituted by at least one group. The at least one group is selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

In some embodiments $R_p$ and $R_q$ are hydrogen (H). A group of promoieties in this class are of the following formula wherein X, $R_5$, $R_6$, $R_7$, and $R_8$ are defined as above:

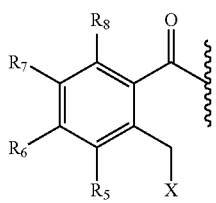

In some embodiments, promoieties in this group are of the following formulae:

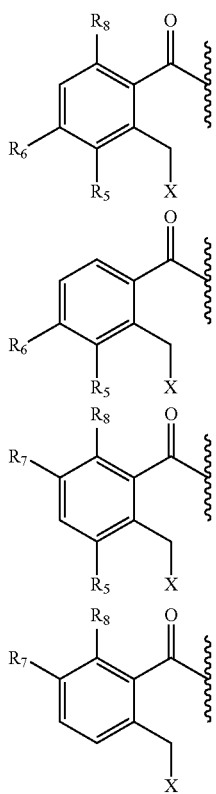
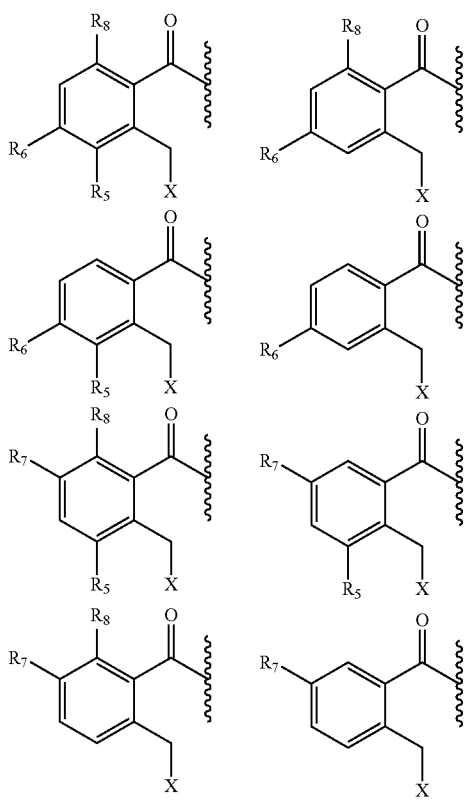

In some embodiments, $R_5$, $R_6$, $R_7$, and $R_8$ are independently selected from the group hydrogen (H), loweralkyl, loweralkoxy, acyl, hydroxyl, amino, halogen, trifluoromethyl, trifloromethoxy, nitrile, nitro, carboxylic acid, —$SO_2$—OH, —$SO_2$—$NR_{m1}R_{m2}$, —$SO_2$—$R_{m3}$, —O—$R_{m4}$, —S—$R_{m5}$, —N—$R_{m6}R_{m7}$, —C(O)$R_{m8}$, —C(O)O$R_{m9}$, —OC(O)$R_{m10}$, —NHC(O)$R_{m11}$, —C(O)N$R_{m12}R_{m13}$, —NHC(O)N$R_{m14}R_{m15}$, wherein $R_{m1}$, $R_{m2}$, $R_{m3}$, $R_{m4}$, $R_{m5}$, $R_{m6}$, $R_{m7}$, $R_{m8}$, $R_{m9}$, $R_{m10}$, $R_{m11}$, $R_{m12}$, $R_{m13}$, $R_{m14}$, and $R_{m15}$ are independently selected from hydrogen (H), ($C_1$-$C_{18}$) alkyl, aryl, ($C_1$-$C_{18}$ alkyl)OH, ($C_1$-$C_{18}$ alkyl)SH, ($C_1$-$C_{18}$ alkyl)COOH, ($C_1$-$C_{18}$ alkyl)$NH_2$, ($C_0$-$C_4$ alkyl)($C_3$-$C_6$ cycloalkyl), ($C_0$-$C_{10}$ alkyl)($C_2$-$C_5$ heterocyclic), ($C_0$-$C_4$ alkyl)($C_6$-$C_{10}$ aryl), ($C_1$-$C_4$ alkyl)($C_3$-$C_9$ heteroaryl), and ($C_1$-$C_{18}$) alkyl. In some embodiments, OH, $NH_2$, COOH, and SH functional groups can be used to connect to an optional linker or a modifying moiety. In some embodiments, $R_5$, $R_6$, $R_7$, or $R_8$ contains an azide or alkyne which can react with another alkyne or azide on an optional linker or a modifying moiety by click chemistry.

In some embodiments, promoieties in this group are of the following formula wherein X, $R_6$, and $R_7$ are defined as above:

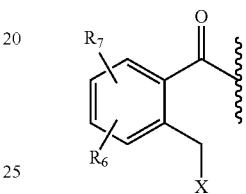

In some embodiments, promoieties in this group are of the following formulae wherein X, $R_6$, and $R_7$ are defined as above:

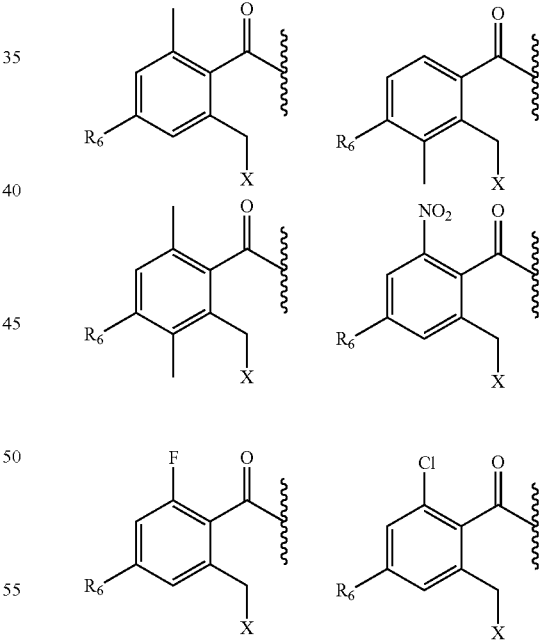

-continued
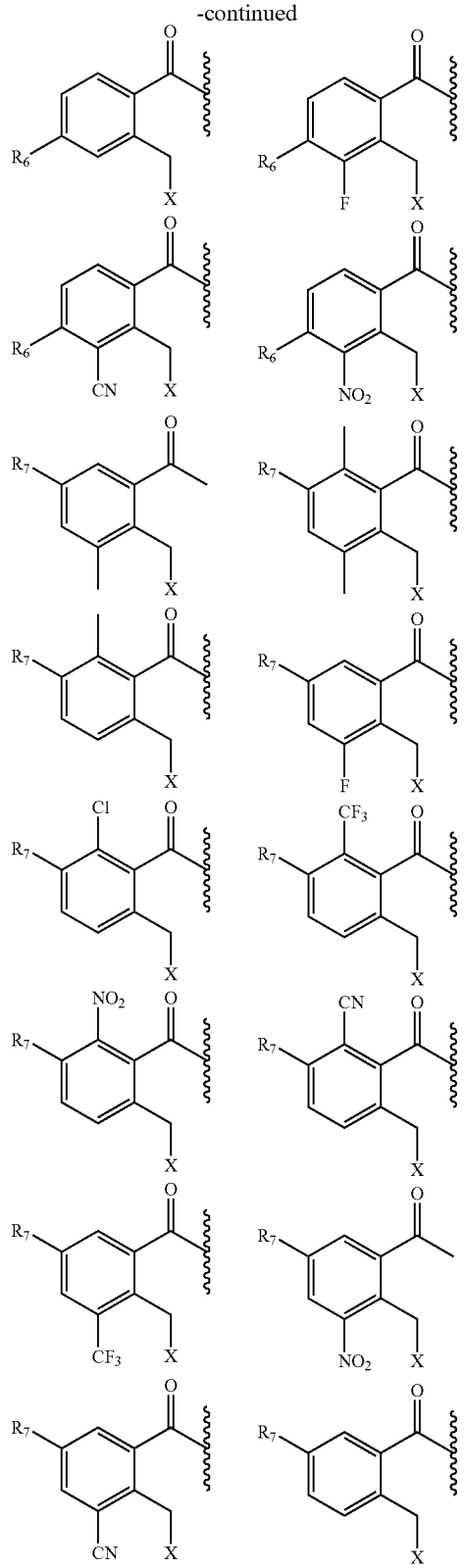
In some embodiments, X in above formulae is OH or HN—R₀.
In some embodiments, X in above formulae is OH.
In some embodiments, X in above formulae is HN—R₀.
In some embodiments, X in above formulae is NH₂.
Illustrative, non-limiting examples of promoieties in this group include:
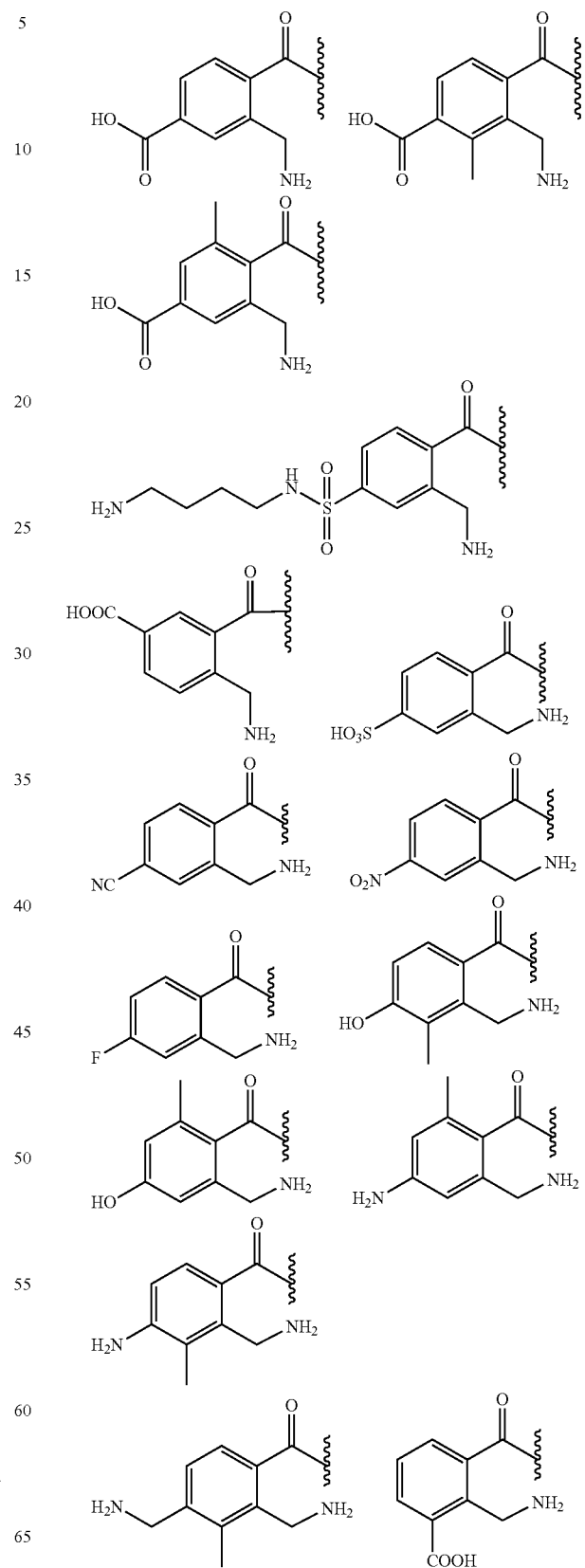

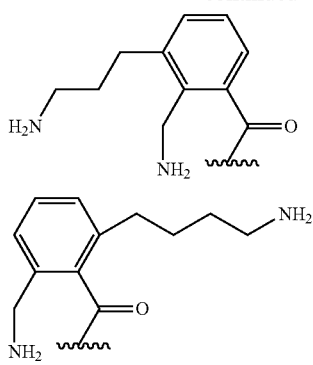

Subclass 7

In some embodiments, $Y_1$ is $C(R_3R_4)$ and one class of promoieties containing a 6-member ring is of the following formula:

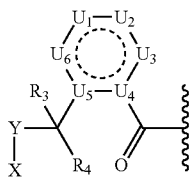

wherein X is OH, SH, or HN—$R_0$;
Y is selected from
(1) N—$R_O$;
(2) $C(R_pR_q)$;
(3) O or S, provided that X is not OH or SH; and
(4) $C(R_pR_q)$, when X is HN—$R_0$, wherein $R_0$ and $R_p$ together with the atoms to which they are attached can form a 4, 5, or 6 membered heterocyclic ring, and wherein $U_1$, $U_2$, $U_3$, $U_4$, $U_5$, $U_6$, $R_3$, $R_4$, $R_0$, $R_O$, $R_p$ and $R_q$ are defined as above.

In some embodiments, the promoieties in this class include, but are not limited to the following examples wherein X, Y, and $R_3$-$R_9$ are defined as above:

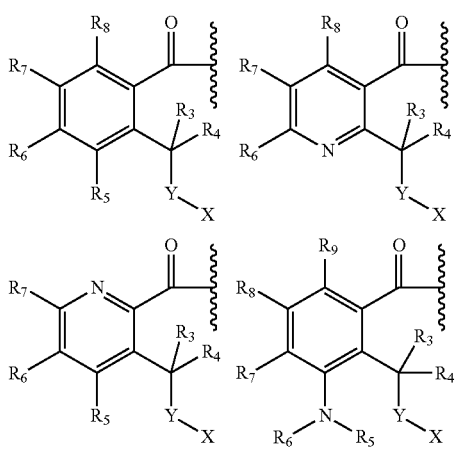

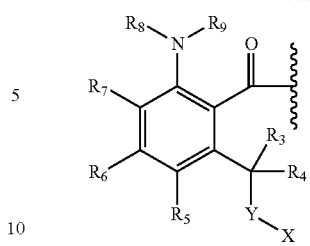

In some embodiments, Y is selected from
(1) N—$R_O$;
(2) O or S, provided that X is not OH or SH.
In some embodiments Y is N—$R_O$.
In some embodiments Y is $C(R_pR_q)$ and the promoieties in this class are of the formula, wherein X, $R_3$-$R_9$, $R_p$, and $R_q$ are defined as above:

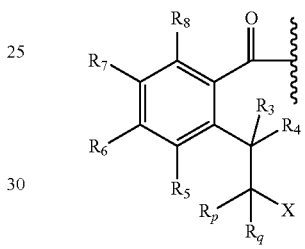

Examples of promoieties in this group include, but not limited to, the following formulae:

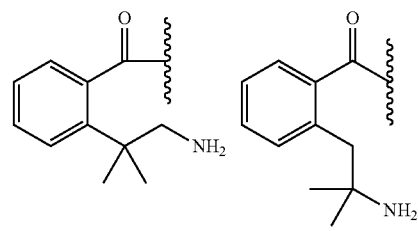

In some embodiments, Y is $CH_2$, and the promoieties in this class are of the following formula, wherein X and $R_5$-$R_8$ are defined above:

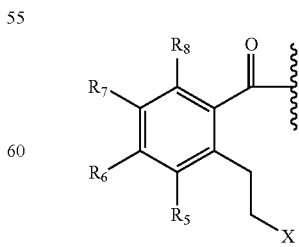

In some embodiments, the promoieties in this class are of the following formulae, wherein $R_5$-$R_8$ are defined above:

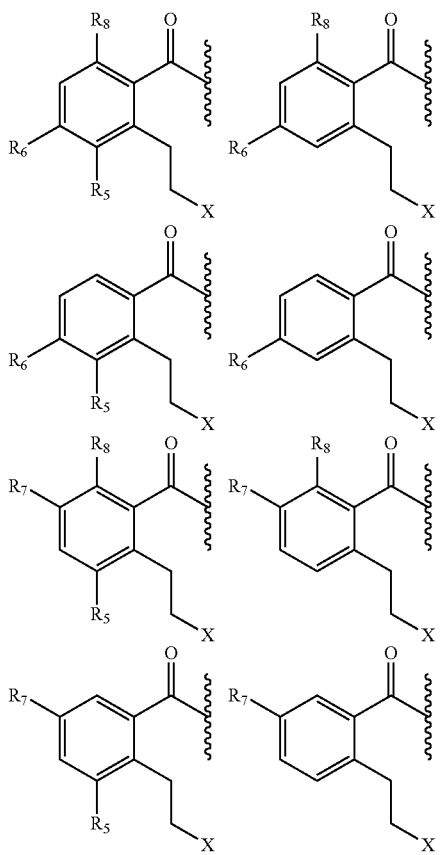

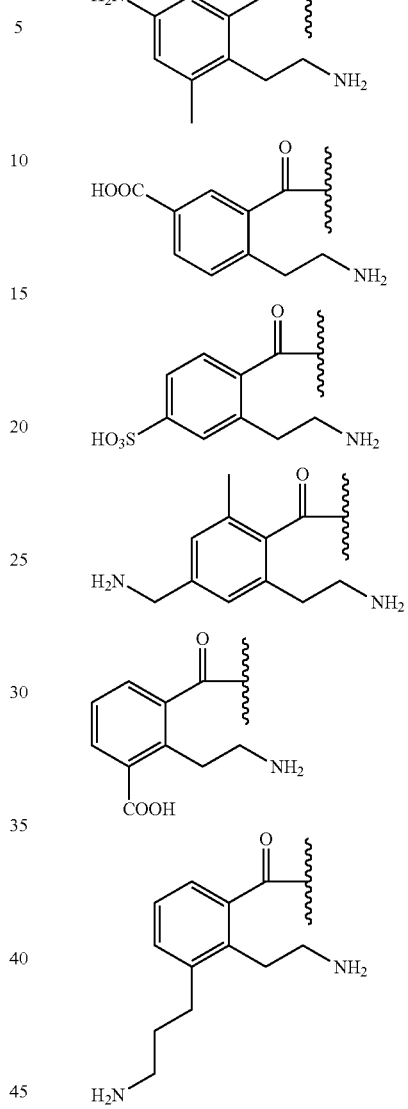

In some embodiments, $R_5$, $R_6$, $R_7$, and $R_8$ are independently selected from hydrogen (H), loweralkyl, loweralkoxy, acyl, hydroxyl, amino, halogen, trifluoromethyl, triflorometrhoxy, nitrile, nitro, carboxylic acid, $-SO_2-OH$, $-SO_2-NR_{m1}R_{m2}$, $-SO_2-R_{m3}$, $-O-R_{m4}$, $-S-R_{m5}$, $-N-R_{m6}R_{m7}$, $-C(O)R_{m8}$, $-C(O)OR_{m9}$, $-OC(O)R_{m10}$, $-NHC(O)R_{m11}$, $-C(O)NR_{m12}R_{m13}$, $-NHC(O)NR_{m14}R_{m15}$, wherein $R_{m1}$, $R_{m2}$, $R_{m3}$, $R_{m4}$, $R_{m5}$, $R_{m6}$, $R_{m7}$, $R_{m8}$, $R_{m9}$, $R_{m10}$, $R_{m11}$, $R_{m12}$, $R_{m13}$, $R_{m14}$, and $R_{m15}$ are defined above.

In some embodiments, X is OH or HN—$R_0$.

In some embodiments, X is OH.

In some embodiments, X is HN—$R_0$.

Examples of promoieties in this group include, but not limited to, the following formulae:

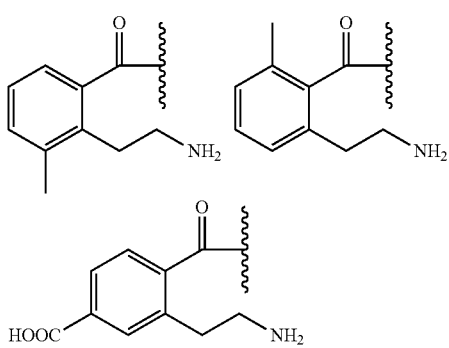

Subclass 8

In some embodiments, $U_5$ is C, $Y_1$ is N—$R_n$, Y is $C(R_pR_q)$, and one class of promoieties containing a 6-member ring is of the following formula, wherein $U_1$-$U_4$, $U_6$, $R_n$, $R_p$, $R_q$, and X are defined as above:

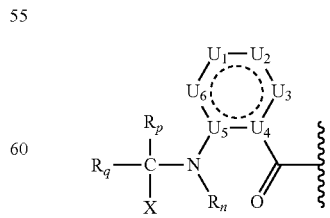

In some embodiments, the promoieties in this class include, but are not limited to, the following formula, wherein $R_5$-$R_8$, $R_n$, $R_p$, $R_q$, and X are defined as above:

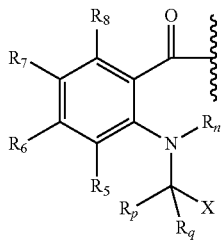

Subclass 9

In some embodiments, $U_5$ is C, $Y_1$ is O, Y is C—$R_pR_q$, and one class of promoieties containing a 6-member ring is of the following formula, wherein $U_1$-$U_4$, $U_6$, $R_p$, $R_q$, and X are the same defined as above:

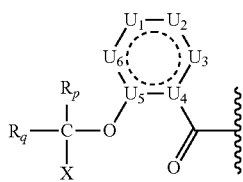

In some embodiments, the promoieties in this class include, but are not limited to, the following formula, wherein $R_5$-$R_8$, $R_p$, $R_q$, and X are defined as above:

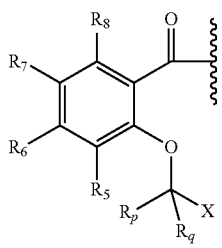

Subclass 10

In some embodiments, $Y_1$ is C(O), C(S), SO, or $SO_2$, and promoieties in this group are of the following formula:

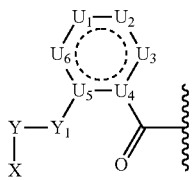

wherein X is OH, SH, or HN—$R_0$;
Y is
(1) N—$R_O$;
(2) C($R_pR_q$);
(3) O or S, provided that X is not OH or SH; or
(4) C($R_pR_q$), when X is HN—$R_0$, wherein $R_0$ and $R_p$ together with the atoms to which they are attached can form a 4, 5, or 6 membered heterocyclic ring,
wherein $R_O$, $R_0$, $R_p$, $R_q$, and $U_1$-$U_6$ are the same as defined above.

In some embodiments, the promoieties in this group are of the following formulae, wherein $R_5$-$R_8$ are the same as defined above:

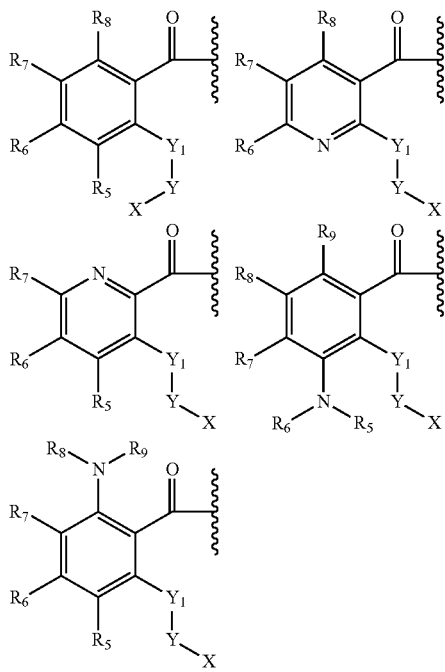

In some embodiments, $Y_1$ is C(O) and the promoieties in this group are of the following formulae, wherein $R_5$-$R_8$ are the same as defined above:

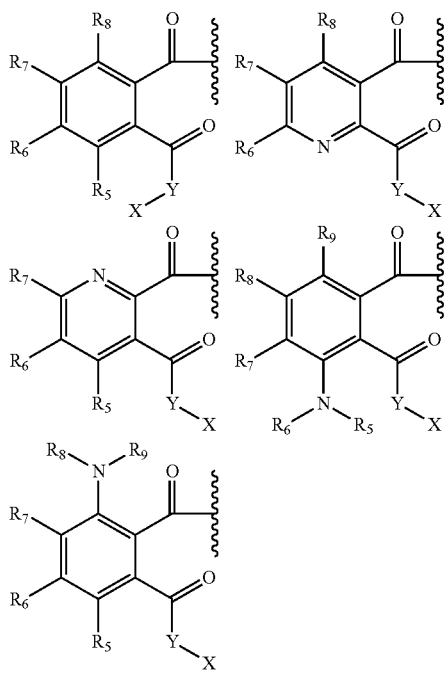

In some embodiments, Y is N—$R_O$ wherein $R_O$ is the same as defined above.

In some embodiments, Y is C—$R_pR_q$, wherein $R_p$ and $R_q$ are the same as defined above.

In some embodiments, X is OH or HN—$R_0$, wherein $R_0$ is the same as defined above.

In some embodiments, X is OH.

Subclass 11

In some embodiments, $J_1$ is $C(R_{10}R_{11})$ and one class of promoieties containing a 6-member ring is of the following formula:

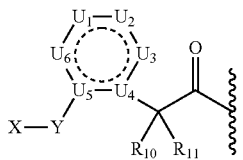

wherein $U_1$, $U_2$, $U_3$, $U_4$, $U_5$, $U_6$ are independently selected from $CR_{12}$ and N;

X is OH, SH, or HN—$R_0$;

Y is (1) N—$R_O$;

(2) $C(R_pR_q)$;

(3) O or S, provided that X is not OH or SH; or (4) $C(R_pR_q)$, when X is HN—$R_0$, wherein $R_0$ and $R_p$ together with the atoms to which they are attached can form a 4, 5, or 6 membered heterocyclic ring, wherein $R_0$, Ro, $R_p$, $R_q$, and $R_{10}$-$R_{12}$ are the same as defined above.

In some embodiments, Y is selected from N—$R_O$ and O (provided that X is not OH or SH).

In some embodiments, Y is $C(R_pR_q)$.

In some embodiments, promoieties in this class are of the following formulae, wherein $R_5$-$R_8$, $R_p$, $R_q$, $R_{10}$, and $R_{11}$ are the same as defined above:

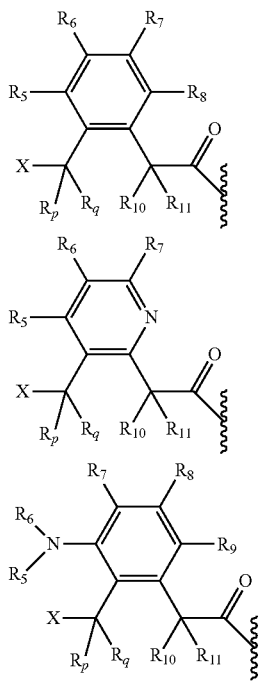

In some embodiments, $R_{10}$, $R_{11}$, $R_p$, $R_q$ are hydrogen (H) and the promoieties in this class are of the following formula, wherein $R_5$-$R_8$ are the same as defined above:

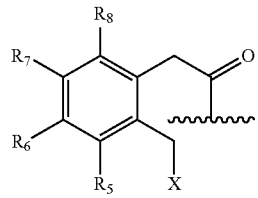

In some embodiments, $R_{10}$, $R_{11}$, $R_p$, $R_q$ are hydrogen (H) and the promoieties in this class are of the following formulae, wherein $R_5$-$R_8$ are the same as defined above:

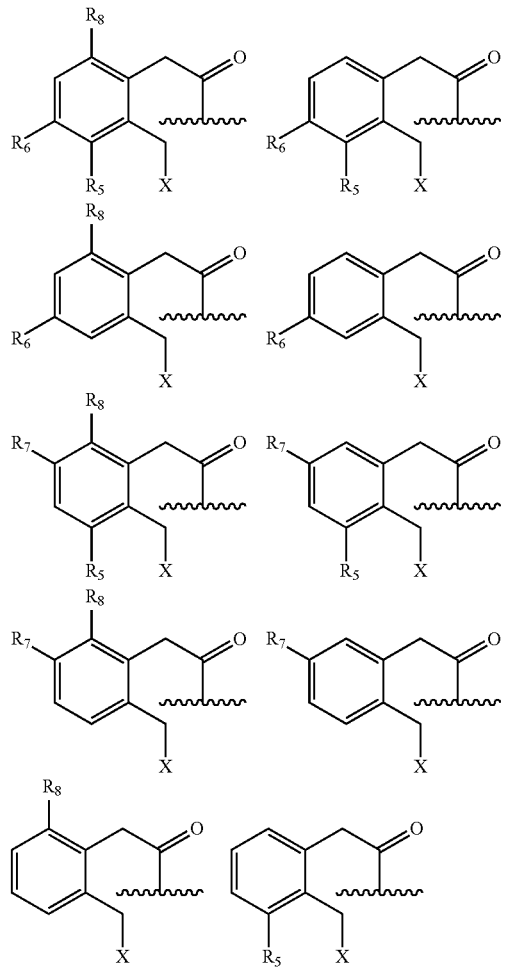

In some embodiments, $R_5$, $R_6$, $R_7$, $R_8$ are independently selected from hydrogen (H), lower alkyl, lower alkoxy, acyl, hydroxyl, amino, halogen, trifluoromethyl, trifloromethoxy, nitrile, nitro, carboxylic acid, —$SO_2$—OH, —$SO_2$—$NR_{m1}R_{m2}$, —$SO_2$—$R_{m3}$, —O—$R_{m4}$, —S—$R_{m5}$, —N—$R_{m6}R_{m7}$, —C(O)$R_{m8}$, —C(O)O$R_{m9}$, —OC(O)$R_{m10}$, —NHC(O)$R_{m11}$, —C(O)N$R_{m12}R_{m13}$, —NHC(O)N$R_{m14}R_{m15}$ wherein $R_{m1}$-$R_{m13}$ are the same as defined above.

In some embodiments, X is OH or HN—$R_0$ wherein $R_0$ is the same as defined above.

In some embodiments, X is OH.

In some embodiments, X is HN—$R_0$ wherein $R_0$ is the same as defined above.

In one embodiment, X is $NH_2$.

Examples of promoieties in this class include, but are not limited to, the following formulae:

Subclass 12

In some embodiments, one class of promoieties containing a 5-member ring is of the following formula:

wherein $Z_1$, $Z_2$, $Z_3$, $Z_4$, $Z_5$ are independently selected from $CR_{12}$, N, $NR_{13}$, O, and S;
X is OH, SH, or HN—$R_0$;
Y is
(1) N—$R_O$;
(2) $C(R_pR_q)$;
(3) O or S, provided that X is not OH or SH;
(4) $C(R_pR_q)$, when X is HN—$R_0$, wherein $R_0$ and $R_p$ together with the atoms to which they are attached can form a 4, 5, or 6 membered heterocyclic ring; or
(5) C(O).
$Y_1$ is selected from
(1) $C(R_3R_4)$;
(2) C(O) or C(S), provided that none of Y and A is C(O), C(S), SO, or $SO_2$;
(3) O, S, SO, or $SO_2$, provided that none of Y and A is O or S;
(4) N—$R_n$; and
(5) a covalent bond.
$J_1$ is $C(R_{10}R_{11})$ or a covalent bond;
$R_{13}$ is selected from hydrogen (H), straight or branched chain alkyl having from 1 to 20 carbon atoms; aryl having from 6 to 15 carbon atoms; cycloalkyl having a 3, 4, 5, 6, 7, 8, 9, or 10 membered ring; alkenyl having from 2 to 20 carbon atoms; cycloalkenyl having a 4, 5, 6, 7, 8, 9, or 10 membered ring; alkynyl having from 2 to 20 carbon atoms; cycloalkynyl having a 5, 6, 7, 8, 9, or 10 membered ring; monocyclic or polycyclic; aralkyl; aralkenyl; aralkynyl; alkaryl; alkenylaryl; alkynylaryl; loweracyloxyalkyl, and carboxyalkyl; saturated or unsaturated monoheterocyclic, polyheterocyclic, and fused heterocyclic, containing one or more heteroatoms N, S or O in each heterocyclic ring thereof and each such ring being from 3- to 8-membered Each of the aforementioned alkyl, aryl, cycloalkyl, cycloalkenyl, cycloalkynyl, monocyclic and polycyclic aralkyl; aralkenyl; aralkynyl; alkaryl; alkenylaryl; alkynylaryl; loweracyloxyalkyl; carboxyalkyl, saturated and unsaturated monoheterocyclic, polyheterocyclic, and fused heterocyclic is optionally substituted with one or more groups selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy;
wherein $R_0$, Ro, $R_p$, $R_q$, $R_3$, $R_4$, and $R_{10}$-$R_{12}$ are the same as defined above.

In some embodiments $R_{13}$ is selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, ammonio, imino, imido, amino lower alkyl, lower alkylamino, lower dialkylamino, hydroxyl, hydroxyl alkyl, nitro, nitrate, nitrite, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl), sulfinic acid group, thione group, thial, phosphino, phosphono, phosphate ester group, phosphoramide group, acetal group, hemiacetal group, hemiketal group, ketal group, orthoester group, methylenedioxy, and ethylenedioxy.

Some examples of these 5-member rings formed by $Z_1$-$Z_5$ are tetrazoles and triazoles wherein $R_5$ is the same as defined above:

Some examples of these 5-member rings formed by $Z_1$-$Z_5$ are imidazoles wherein $R_5$ and $R_6$ are the same as those defined above:

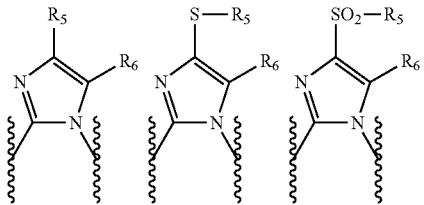

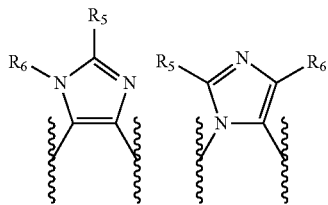

Some examples of these 5-member rings formed by $Z_1$-$Z_5$ are pyrroles wherein $R_5$-$R_7$ are the same as those defined above:

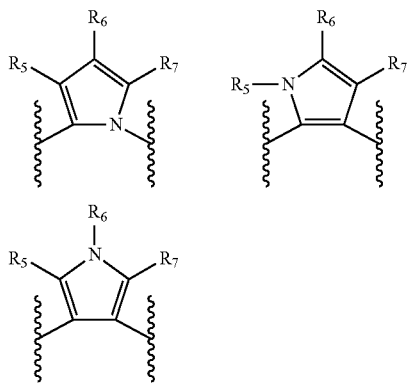

Some examples of these 5-member rings formed by $Z_1$-$Z_5$ are pyrazoles wherein $R_5$ and $R_6$ are the same as those defined above:

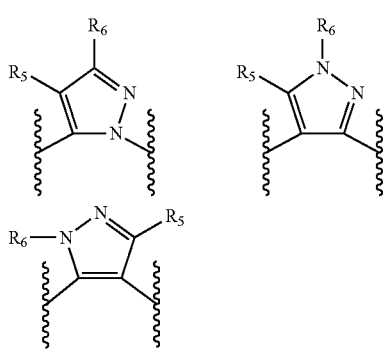

Some other examples of these 5-member rings formed by $Z_1$-$Z_5$ are furans wherein $R_5$ and $R_6$ are the same as those defined above:

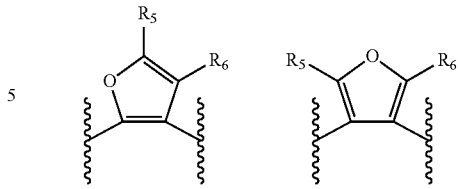

Some other examples of these 5-member rings formed by $Z_1$-$Z_5$ are thiophene wherein $R_5$ and $R_6$ are the same as those defined above:

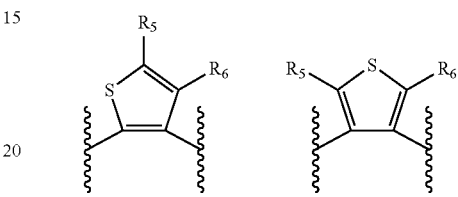

Some other examples of these 5-member rings formed by $Z_1$-$Z_5$ are thiazoles, isothiazole, oxazole, and isoxazole wherein $R_5$ is the same as defined above:

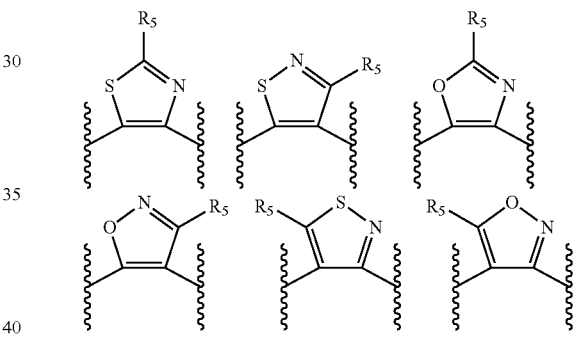

In some embodiments, $Y_1$ is a bond and $J_1$ is $C(R_{10}R_{11})$ and one class of promoieties containing a 5-member ring is of the following formula:

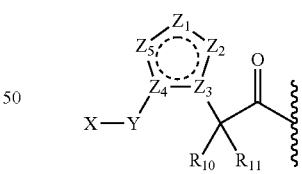

In some embodiments, $J_1$ is $C(R_{10}R_{11})$, $Y_1$ is a bond, and $Y$ is $C(R_pR_q)$ and one class of promoieties containing a 5-member ring is of the following formula:

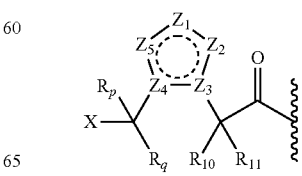

In some embodiments, Y is $C(R_pR_q)$, $J_1$ is $C(R_{10}R_{11})$, and one class of triazole based promoieties is of the following formula:

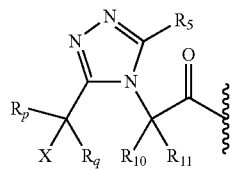

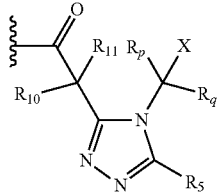

In some embodiments, X is OH, or HN—$R_0$;

In some embodiments, X is OH;

In some embodiment, X is HN—$R_0$.

In some embodiments, X is $NH_2$.

In some embodiments a class of triazole based promoieties is of the following formulae, wherein $R_5$ is the same as defined above:

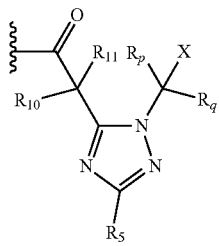

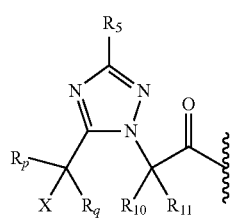

In some embodiments, Y is $C(R_pR_q)$, $J_1$ is $C(R_{10}R_{11})$, and one class of triazole based promoieties is of the following formulae wherein $R_5$ is the same as defined above:

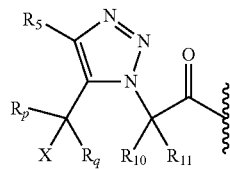 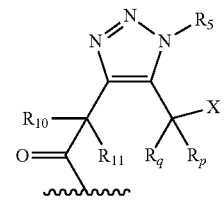

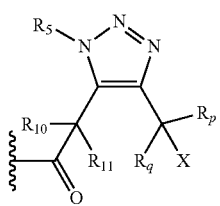 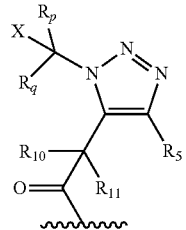

In some embodiments, X is OH or HN—$R_0$;

In some embodiments, X is OH;

In some embodiments, X is HN—$R_0$.

In some embodiments, X is $NH_2$.

In some embodiments, Y is $C(R_pR_q)$, $J_1$ is $C(R_{10}R_{11})$, and one class of tetrazole based promoieties is of the following formulae, wherein all of the variables are defined above:

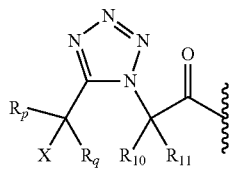

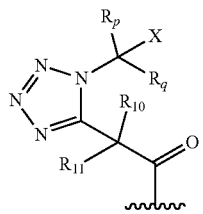

In some embodiments, X is OH or HN—$R_0$;

In some embodiments, X is OH;

In some embodiments, X is HN—$R_0$.

In some embodiments, X is $NH_2$.

In some embodiments, Y is $C(R_pR_q)$, $J_1$ is $C(R_{10}R_{11})$, and one class of imidazole based promoieties is of the following formulae, wherein $R_5$ and $R_6$ are the same as defined above:

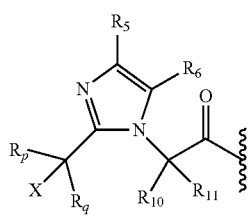 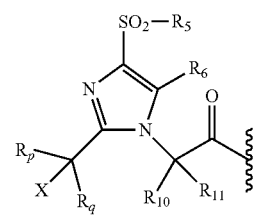

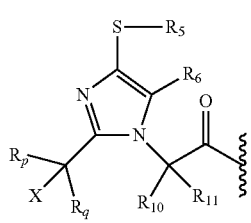 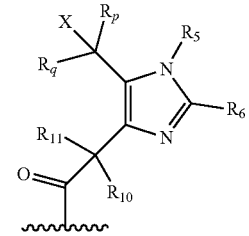

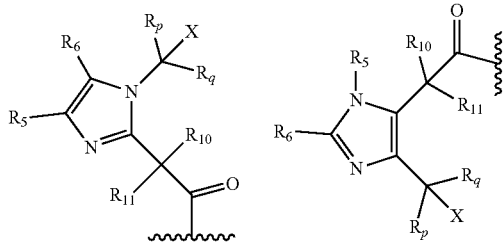
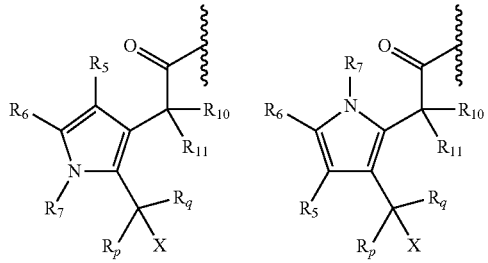

Examples of imidazole based promoieties include, but are not limited to, the following formulae:

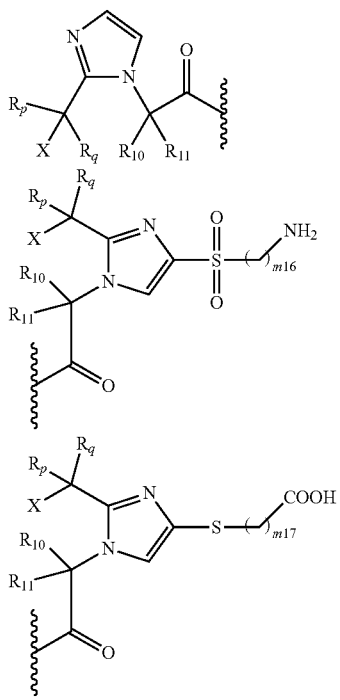

wherein m16 and m17 are each an integer in the range of 1-10.

In some embodiments, X is OH or HN—$R_0$;
In some embodiments, X is OH;
In some embodiments, X is or HN—$R_0$.
In some embodiments, X is $NH_2$.

In some embodiments, Y is $C(R_pR_q)$, $J_1$ is $C(R_{10}R_{11})$, and one class of pyrrole based promoieties is of the following formulae wherein $R_5$-$R_7$ are the same as defined above:

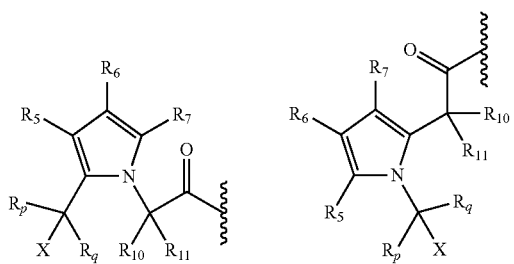

In some embodiments, X is OH or HN—$R_0$;
In some embodiments, X is OH;
In some embodiments, X is HN—$R_0$.
In some embodiments, X is $NH_2$.

In some embodiments, Y is $C(R_pR_q)$, $J_1$ is $C(R_{10}R_{11})$, and one class of pyrazole based promoieties is of the following formula wherein $R_5$ and $R_6$ are the same as defined above:

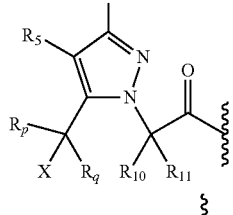
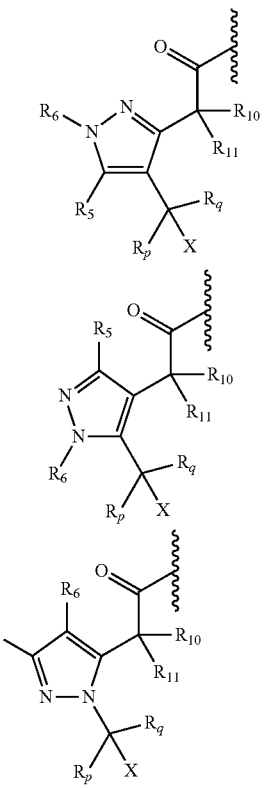

In some embodiments, X is OH or HN—$R_0$;
In some embodiments, X is OH;
In some embodiments, X is HN—$R_0$.
In some embodiments, X is $NH_2$.
In some embodiments, $R_5$ and $R_6$ are each hydrogen (H).

In some embodiments, each of $Y_1$ and $J_1$ is a bond and one class of promoieties is of the following formula:

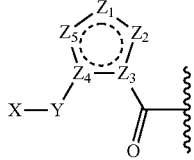

In some embodiments, Y is $C(R_pR_q)$.

In some embodiments, a class of triazole based promoieties is of the following formula, wherein $R_5$ is the same as define above:

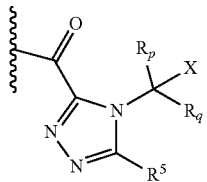

In some embodiments, a class of triazole based promoieties is of the following formula wherein $R_5$ is the same as defined above:

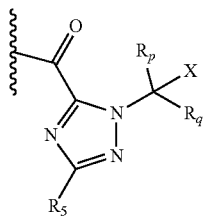

In some embodiments, a class of triazole based promoieties is of the following formula wherein $R_5$ is the same as define above:

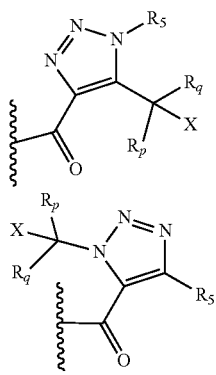

In some embodiments, a class of tetrazole based promoieties is of the following formula:

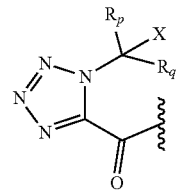

In some embodiments, a class of imidazole based promoieties are of the following formulae, wherein $R_5$ and $R_6$ are the same as defined above:

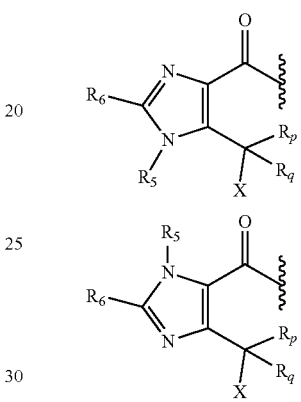

In some embodiments a class of pyrrole based promoieties are of the following formula wherein $R_5$-$R_7$ are the same as those defined above:

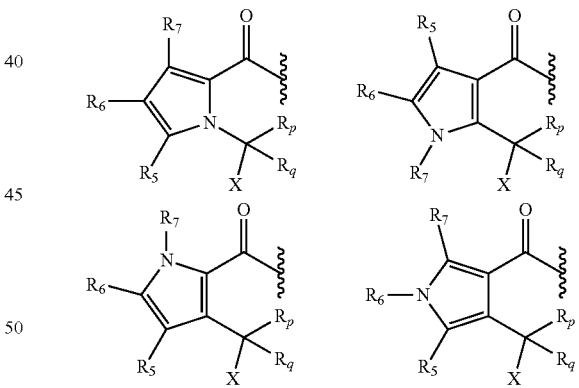

In some embodiments, a class of pyrazole based promoieties are of the following formulae, wherein $R_5$ and $R_6$ are the same as defined above:

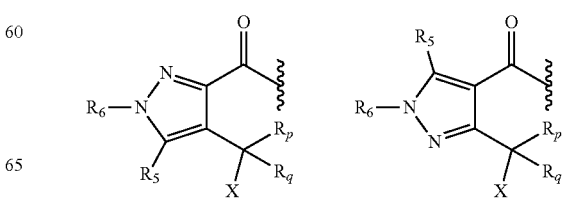

-continued

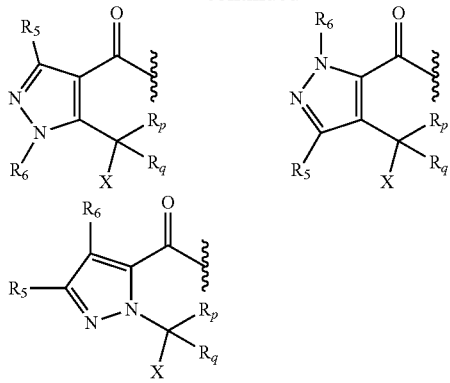

In some embodiments, X is OH or HN—R₀.
In some embodiments, X is OH.
In some embodiments, X is HN—R₀.
In some embodiments, X is NH₂.
In some embodiments, $Y_1$ is $C(R_3R_4)$ and one class of promoieties is of the following formula:

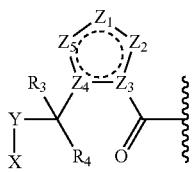

In some embodiments, Y is $C(R_pR_q)$.

In some embodiments, a class of triazole based promoieties is of the following formula wherein $R_5$ is the same as defined above:

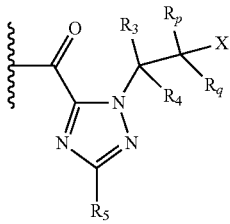

In some embodiments, a class of triazole based promoieties is of the following formula wherein $R_5$ is the same as defined above:

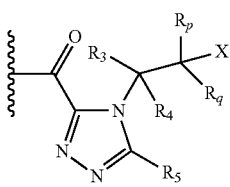

In some embodiments, a class of triazole based promoieties is of the following formula wherein $R_5$ is the same as defined above:

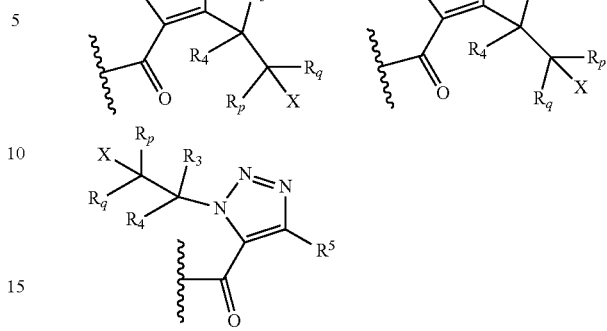

In some embodiments, a class of tetrazole based promoieties is of the following formula:

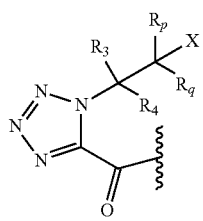

In some embodiments, a class of imidazole based promoieties is of the following formulae wherein $R_5$ and $R_6$ are the same as defined above:

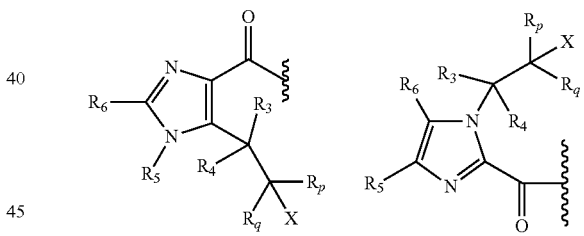

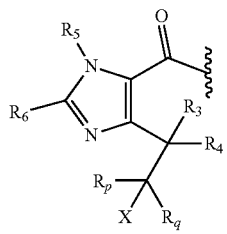

In some embodiments, a class of pyrrole based promoieties is of the following formulae, wherein $R_6$ and $R_7$ are the same as those defined above:

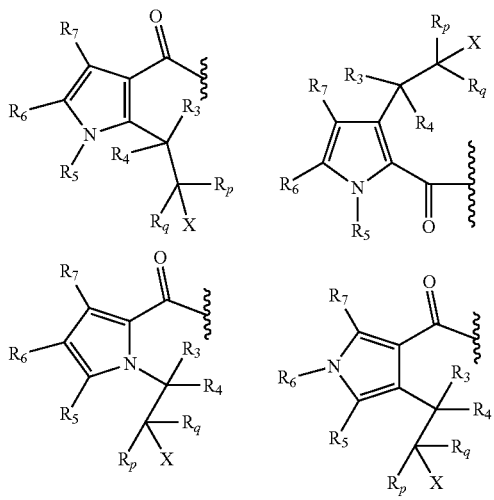

In some embodiments, a class of pyrazole based promoieties is the following formulae wherein $R_5$ and $R_6$ are the same as defined above:

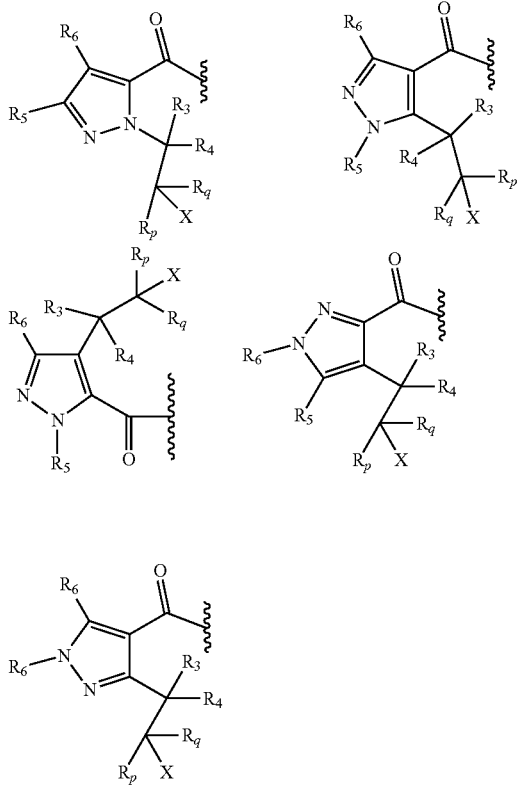

In some embodiments, X is OH or HN—$R_0$.
In some embodiments, X is OH.
In some embodiments, X is HN—$R_0$.
In some embodiments, X is $NH_2$.

Subclass 13

In some embodiments, $Y_1$ is C(O), and one class of promoieties are of the following formula:

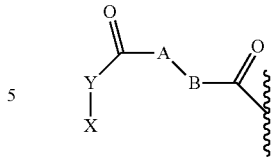

wherein X is OH, SH, or HN—$R_0$;

Y is:

(1) N—$R_O$;

(2) $C(R_pR_q)$;

(3) O or S, provided that X is not OH or SH; or (4) $C(R_pR_q)$, when X is HN—$R_0$, wherein $R_0$ and $R_p$ together with the atoms to which they are attached can form a 4, 5, or 6 membered heterocyclic ring;

wherein A, B, Ro, $R_0$, $R_p$, and $R_q$ are the same as defined above.

In some embodiments, promoieties in this class are of the following formula:

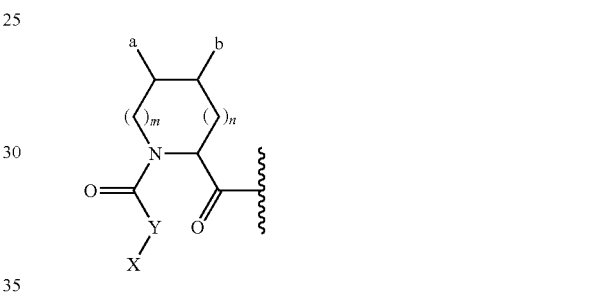

wherein a and b are the same as defined above, m and n are each an integer independently selected from 0, 1, 2, 3, 4, 5, and 6.

In some embodiments, promoieties in this class are of the following formulae wherein $R_5$ and $R_6$ are the same as defined above:

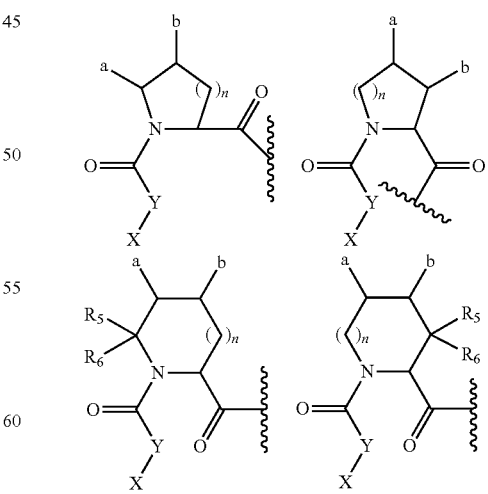

In some embodiments, Y is $C(R_pR_q)$ and promoieties in this class are of the following formulae wherein $R_5$ and $R_6$ are the same as defined above:

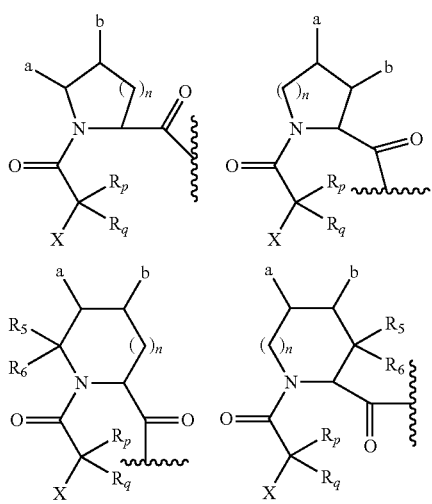
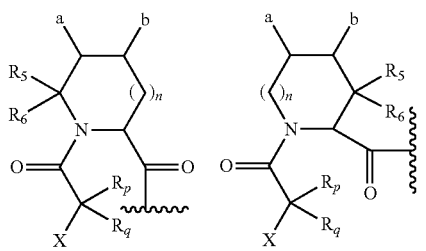

In some embodiments, X, Y, and $Y_1$ (C(O)) constitute a natural or unnatural amino acid or hydroxyl acid. Non limiting examples include alanine, arginine, asparagine, aspartic acid, cysteine, glycine, glutamic acid, histidine, isoleucine, leucine, lysine, methionine, proline, glutamine, phenylalanine, serine, threonine, valine, tryptophan, tyrosine, aminoisobutyric acid, sarcosine, glycolic acid, and phenyllactic acid.

Examples of promoieties in this class include, but not limited to:

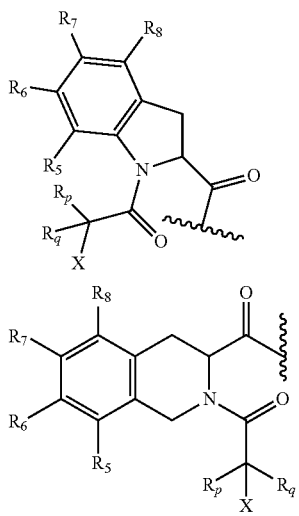
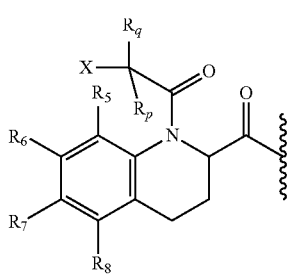
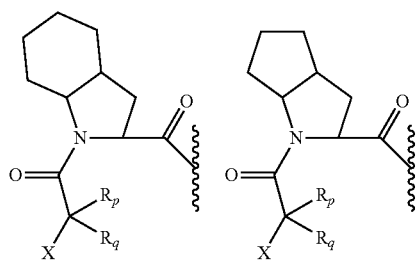
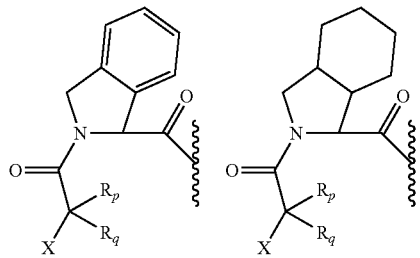
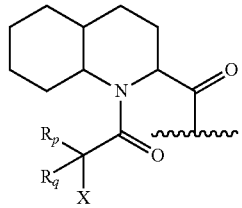
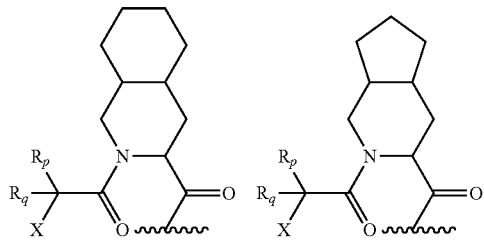
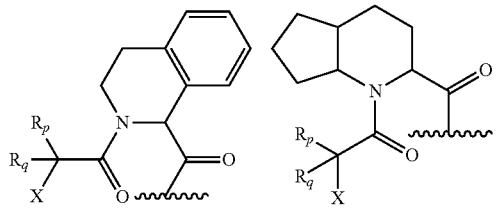

wherein $R_5$ and $R_6$ are the same as defined above.

Some more specific examples of promoieties in this class include, but not limited to:

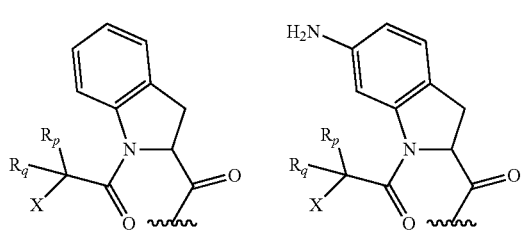

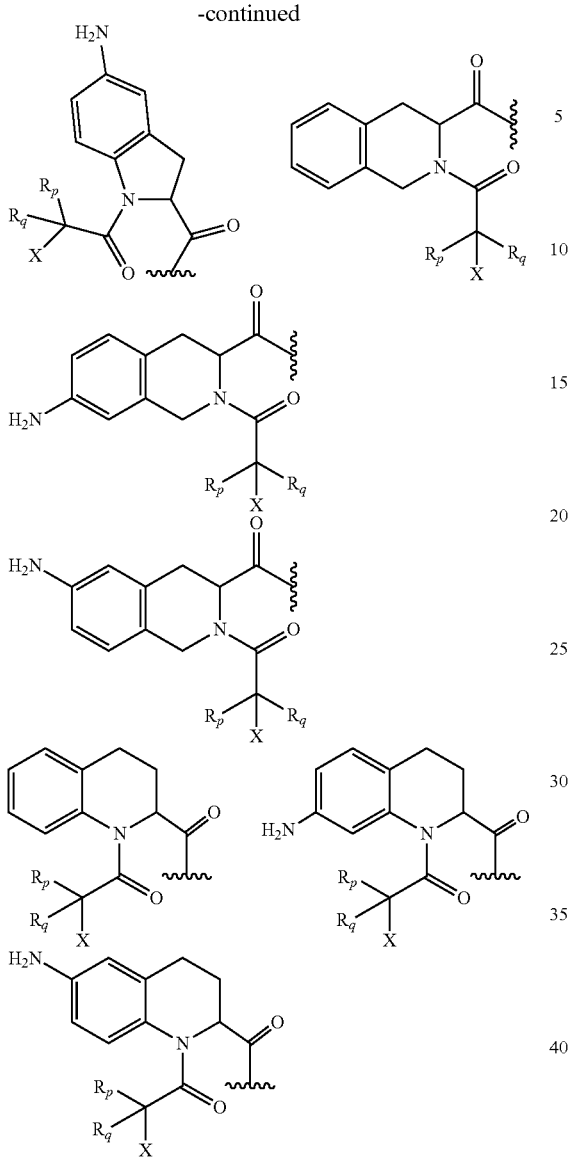

In some embodiments, X is OH or HN—$R_0$.
In some embodiments, X is OH.
In some embodiments, X is HN—$R_0$.
In some embodiments, X is $NH_2$.

Subclass 14

In some embodiments, X is OH and Y is C(O) and one class of promoieties is of the following formula:

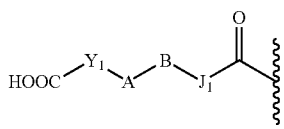

wherein $Y_1$ is $C(R_3R_4)$ or a covalent bond; $J_1$ is $C(R_{10}R_{11})$ or a covalent bond between B and C(O)-drug/pharmaceutically active agent, $R_3$, $R_4$, $R_{10}$, $R_{11}$, A and B are the same as defined above.

In some embodiments, one class of promoieties is of the following formulae wherein a and b are the same as defined above:

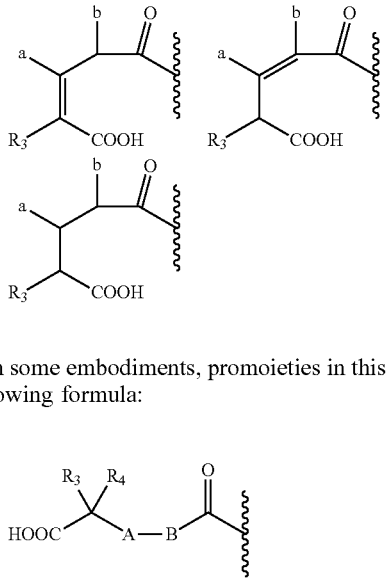

In some embodiments, promoieties in this class are of the following formula:

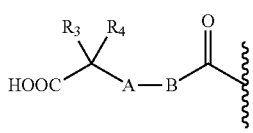

In some embodiments, promoieties in this class are of the following formulae, wherein $Z_1$-$Z_5$ and $U_1$-$U_6$ are the same as defined above:

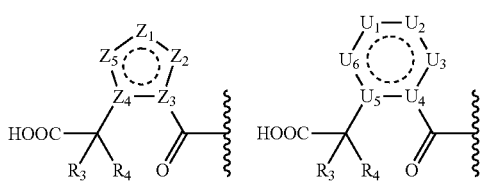

In some embodiments, promoieties in this class are of the following formula wherein $R_5$-$R_8$ are the same as defined above:

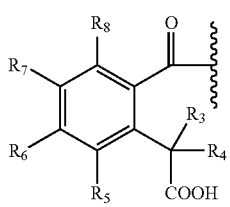

In some embodiments, $R_3$ and $R_4$ are hydrogen (H) and promoieties in this class are of the following formula:

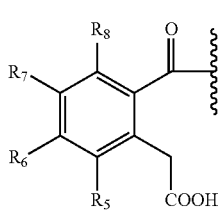

In some embodiments, one class of promoieties is of the following formula:

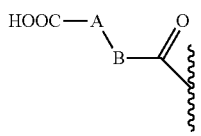

In some embodiments, the promoieties in this class are of the following formulae:

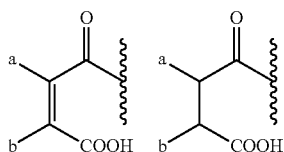

In some embodiments, the promoieties in this class are of the following formulae:

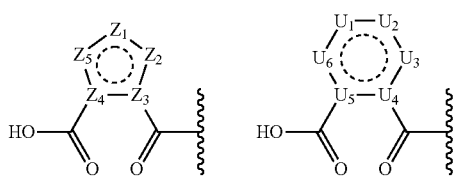

In some embodiments, $J_1$ is $C(R_{10}R_{11})$ and one class of promoieties is of the following formula:

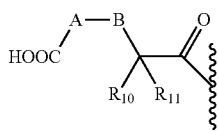

In some embodiments, $J_1$ is $C(R_{10}R_{11})$ and one class of promoieties is of the following formula:

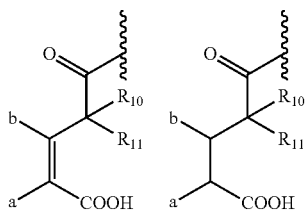

In some embodiments, two R groups (selected from $R_0$, $R_1$, $R_2$, $R_3$, $R_4$, $R_5$, $R_6$, $R_7$, $R_8$, $R_9$, $R_{10}$, $R_{11}$, $R_{12}$, $R_{13}$, $R_O$, $R_m$, $R_n$, $R_p$, $R_q$, R', R", and R''') that are attached to the same atom or to two atoms separated by one bond form a $C_3$-$C_8$ cycloalkyl, cycloalkenyl, or cycloalkynyl ring, or saturated or unsaturated heterocyclic ring optionally substituted by at least one group other than hydrogen (H); or two R groups together with the atoms to which they are attached form an aromatic ring optionally substituted by at least one group other than hydrogen (H).

In some embodiments, when appropriate, X may be OH, HN—$R_0$, or SH. And the nature of X determines reactivity and optimal pH for ring closure reactions. Generally, the amino and thiol groups are more nucleophilic. When X is OH, the reaction rates are higher in acidic or basic solution but slowest at neutral pH. When X is an amine, the reaction becomes faster when pH goes up, which makes it more suitable for clinical use. Therefore, choices of X may dramatically change the reaction profiles. Substituents can alter the steric and/or electronic properties of the aromatic ring and regulate ring closure rates. Moreover, a substituent can provide a handle to which one or more modifying moieties can be attached. These types of modifications may significantly change the biophysical, biochemical, and pharmacokinetic properties of the prodrug.

In some embodiments, the nucleophilic group X is protected with a protecting group capable of being hydrolyzed or otherwise degraded in vivo. When the protecting group is removed, hydrolysis of the prodrug and resultant release of the parent drug is facilitated. Such cascade latentiation is a useful prodrug design which gives a prodrug in vitro stability and in vivo lability.

In some embodiments a prodrug can also be prepared as a double prodrug, where the second promoiety is attached to the first promoiety linked to the parent drug molecule. These promoieties are usually different and are cleaved by a dissimilar mechanism.

In some embodiments the techniques disclosed in this disclosure can be used to construct co-drugs (mutual prodrugs, multiple prodrugs), a prodrug is formed from two pharmacologically active agents coupled together into a single molecule, and act as promoieties of each other.

The present disclosure also encompasses modifying moieties to which pharmaceutically active agents or prodrugs of the disclosure are linked, optionally via covalent bonding, and optionally via a linker. Linkage can be accomplished by covalent chemical bonds, physical forces such electrostatic, hydrogen, ionic, van der Waals, or hydrophobic or hydrophilic interactions. A pharmaceutically active agent conjugate complex include a modifying moiety coupled to a pharmaceutical agent. Modifying moieties provide a pharmaceutically active agent with desired properties as described herein. For example, the modifying moiety can reduce the rate of degradation of the pharmaceutical agent in various environments (e.g., GI tract, bloodstream). Further, preferred modifying moieties render the pharmaceutical agent amphiphilic, hydrophilic, lipophilic than a scientifically acceptable control, such as a corresponding unconjugated pharmaceutical agent.

The modifying moieties may include degradable linkages in their backbones. For example, the PAGs (polyalkylene glycols) can include hydrolytically unstable linkages, such as lactide, glycolide, carbonate, ester, carbamate and the like, which are susceptible to hydrolysis. This approach allows the polymers to be cleaved into lower molecular weight fragments.

In some embodiments, a prodrug can be conjugated to a modifying moiety which has the general formula:-L-M, wherein L is a covalent bond or an optional linker include, but are not limited to, PEG, long chain fatty acids, natural or unnatural amino acids (e.g., β-alanine, γ-aminobutyric acid, γ-glutamic acid), short peptides (e.g., β-alanine-β-alanine, γ-glutamic acid-γ-glutamic acid), —(CH$_2$)$_n$—, —(CH$_2$CH$_2$O)$_n$—, —O—, —S—, —C(O)—, —C(O)O—, —NH—, —NHC(O)CH$_2$—, —C(O)NH—, —SO$_2$CH$_2$CH$_2$—, —HNSO$_2$—, maleimide, or a combination of two or more of the above thereof (e.g., a long chain formed by linking together optional long-chain fatty acids, PEG, amino acids, short peptides, etc through covalent bonds), or any structure connecting a modifying moiety to a prodrug through a covalent bond; n is an integer in the range from 1 to 30.

M is a modifying moiety, which includes but are not limited to hydrophilic moieties, lipophilic moieties, amphiphilic moieties, salt forming moieties, carrier proteins (e.g. serum albumin, immunoglobulin or portion thereof (e.g. variable region, CDR, or Fc region)), a targeting agent, a diagnostic label such as a radioisotope, fluorophore or enzymatic label, or combinations of two or more of the above thereof with appropriate spacer moieties, linker moieties, and terminating moieties. The various moieties can be covalently coupled to one another by either hydrolyzable or non-hydrolyzable bonds.

In some embodiments, a pharmaceutically active agent is bound to a modifying moiety via a linker, wherein the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from C, O, N, and S. Chain atoms and linkers may be selected according to their expected solubility so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce steric hindrance. If the linker is a peptide, such peptidyl linkers may be any length. Exemplary linkers are from about 1 to 50 amino acids in length, 5 to 50, 3 to 5, 5 to 10, 5 to 15, or 10 to 30 amino acids in length. Alternatively, a modifying moiety can be linked to a pharmaceutically active agent indirectly through linkers or intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

In some embodiments, L is a covalent bond or is chosen from the following moieties: —NH—(CH$_2$—CH$_2$—O)$_{n4}$—(CH$_2$)$_{n5}$—CO—, —NH—(CH$_2$)$_{n6}$—CO—, —(CH$_2$)$_{n7}$—CO—, —(CH$_2$)$_{n8}$—NH—, —HN—(CH$_2$)$_{n9}$—NH—CO, —CO—(CH$_2$)$_{n10}$—CO, —(CH$_2$—CH$_2$—O)$_{n11}$—(CH$_2$)$_{12}$—CO—, —NH—C$_6$H$_4$—CO—, —NH—(CH$_2$)$_{n13}$—O—(CH$_2$CH$_2$O)$_{n14}$—(CH$_2$)$_{n15}$—CO—, [—NH—(CH$_2$CH$_2$O)$_2$—CH$_2$—CO—]$_{n16}$, [—NH—CH$_2$—(CH$_2$CH$_2$O)$_3$—(CH$_2$)$_3$—NHCO—(CH$_2$)$_2$—CO—]$_{n17}$, —NH—(CH$_2$)$_{n18}$—CO—NH—(CH$_2$—CH$_2$—O)$_{n19}$—(CH$_2$)$_{n20}$—CO—, and a combination of two or more of the above thereof, wherein n4, n5, n6, n7, n8, n9, n10, n11, n12, n13, n14, n15, n16, n17, n18, n19, n20 are an integer in the range from 1 to 20; —C$_6$H$_4$— is para-phenylene.

In some embodiments, a modifying moiety derived from immunoglobulins includes the whole or parts of the constant regions in the heavy or light chain of a human immunoglobulin. An immunoglobulin modifying moiety may comprise all constant regions except the first domain in the heavy chain constant regions of a human immunoglobulin. Amino acid residues in the immunoglobulin modifying moiety can be deleted or substituted with one or more of amino acid residues, or can be inserted with one or more of amino acid residues so long as said immunoglobulin exhibits one or more of its characteristic properties.

In some embodiments, a prodrug comprises a pharmaceutically active agent, a promoiety, an optional linker and a plasma protein, wherein the plasma protein is selected from albumin, transferin and fibrinogen. In one embodiment the plasma protein moiety of the prodrug is albumin or transferin. In one embodiment a modifying moiety derived from albumin comprises the partial or whole sequence of human albumin. Amino acid residues in the albumin modifying moiety can be deleted or substituted with one or more of amino acid residues, or can be inserted with one or more of amino acid residues as long as said albumin exhibits one or more of its characteristic properties.

In some embodiments, a modifying moiety is attached to a pharmaceutically active agent throught a promoiety. This connection can resist cleavage of the covalent bond between the promoiety and the pharmaceutically active agent by peptidases present in the plasma, including for example dipeptidyl peptidase IV (DPP-IV), making the prdrug half life mostly dependent on the promoiety structure and less prone to enzymatic interference.

In some embodiments, a modifying moiety is directly attached to a pharmaceutically active agent while a promoiety is attached to the pharmaceutically active agent at another site.

Any means of reaction known in the art can be used, including acylation, reductive alkylation, Michael addition, thiol alkylation or other chemoselective conjugation/ligation methods through a reactive group on the modifying moiety (e.g., an aldehyde, amino, ester, thiol, α-haloacetyl, maleimido, N-hydroxysuccinimide ester, or hydrazino group) to a reactive group on a pharmaceutically active agent or its promoiety (e.g., an aldehyde, amino, ester, thiol, α-haloacetyl, maleimido, N-hydroxysuccinimide ester, or hydrazino group). Activating groups used in the reactions include but are not limited to N-hydroxysuccinimide ester, sulfone, maleimide, triflate, tresylate, azidirine, oxirane, and 5-pyridyl. Derivatizing agents include, for example, glutaraldehyde, succinic anhydride or other agents known in the art. In one embodiment an azide or alkyne on a pharmaceutically active agent or its promoiety can react with another alkyne or azide on an optional linker or a modifying moiety by Cu catalized or Cu-free click chemistry. A series of cyclooctyne reagents have been developed to directly couple with azide without addition of copper catalyst. Non-limiting examples include dibenzocyclooctyl (DBCO) reagents.

Two examples of modifying moiety-conjugated promoieties are of the formulae as follows:

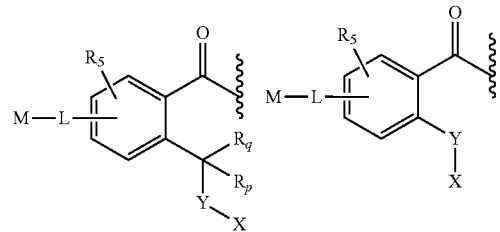

Representative hydrophilic, amphiphilic, and lipophilic polymers and modifying moieties are described in more detail below.

1. Hydrophilic Moieties

Examples of suitable hydrophilic moieties include PAG moieties, polysaccharides, polysorbate moieties, and combinations of two or more of the above thereof.

1.1 Polyalkylene Glycol Moieties

PAGs are compounds with repeat alkylene glycol units. In some embodiments, the units are all identical (e.g., polyethylene glycol (PEG) or polypropylene glycol (PPG)). In other embodiments, the alkylene units are different. The polymers can be random copolymers (for example, where ethylene oxide and propylene oxide are co-polymerized) or branched or graft copolymers.

PEG is a preferred PAG and generally has the formula H—(CH$_2$CH$_2$O)$_n$—H, where n can range from about 2 to about 10000 or more, though the capping moieties may vary, e.g., mono-methoxy or di-hydroxy. The PEG can be linear, branched, forked, multi-armed, dumbbell shaped, or comb shaped.

Numerous derivatives of PEG exist in the art and are suitable for use in the disclosure. (See, e.g., U.S. Pat. Nos. 5,445,090; 5,900,461; 5,932,462; 6,436,386; 6,448,369; 6,437,025; 6,448,369; 6,495,659; 6,515,100 and 6,514,491 and Zalipsky, S. Bioconjugate Chem. 6:150-165, 1995).

Based on reactive sites in the substrate entities, pegylation requires different functionalities on PEG reagents. For amine pegylation PEG reagents include PEG-NHS, PEG-aldehyde, PEG-epoxide, PEG-isothiocyanate, PEG-COOH, PEG-NPC (nitrophenyl carbonate), and PEG-acrylate. For carboxyl pegylation PEG reagents include PEG-amine, PEG-hydrazide, and PEG-halide/sulfonate (chloride, bromide, iodide, tosylate and mesylate). For thiol pegylation PEG reagents include PEG-maleimide, PEG-OPSS (orthopyridyl disulfide), PEG-vinylsulfone, PEG-thiol, and PEG-halide. For hydroxyl pegylation PEG reagents include PEG-isocyanate, PEG-NPC, and PEG-epoxide. Click pegylation reagents include PEG-azide and PEG-alkyne. Reversabile pegylation reagents include PEG-hydrazide and PEG-thiol.

1.2 Sugar Moieties

The modifying moieties described herein can include sugar moieties. Representative sugar moieties include, but are not limited to, glycerol moieties, mono-, di-, oligosaccharides, and polysaccharides such as starches, glycogen, cellulose and polysaccharide gums. Specific monosaccharides include C6 and above (preferably C6 to C8) sugars such as glucose, fructose, mannose, galactose, ribose, and sedoheptulose; di- and tri-saccharides include moieties having two or three monosaccharide units (preferably C5 to C8) such as sucrose, cellobiose, maltose, lactose, and raffinose.

1.3 Polysorbate Moieties

The modifying moieties may include one or more polysorbate moieties.

1.4 Other Hydrophilic Moieties

The modifying moieties may also include other hydrophilic polymers. Biocompatible polycationic moieties include polyamines having amine groups on either the modifying moiety backbone or the modifying moiety side chains, such as poly-L-Lys and other positively charged natural or synthetic amino acids or mixtures of amino acids, including poly(ornithine), poly(arginine), and poly(histidine), and nonpeptide polyamines such as poly(aminostyrene), poly(aminoacrylate), poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly (N-ethylaminomethacrylate), poly(N,N-dimethyl aminomethacrylate), poly(N,N-diethyl aminomethacrylate), poly(ethyleneimine), polymers of quaternary amines, such as poly(N,N, N-trimethylaminoacrylate chloride), poly(m-ethyacrylamidopropyltrimethyl ammonium chloride), and natural or synthetic polysaccharides such as chitosan. Other hydrophilic moieties include poly(oxyethylated polyols) such as poly(oxyethylated glycerol), poly(oxyethylated sorbitol), and poly(oxyethylated glucose); poly(vinyl alcohol) ("PVA"); dextran; carbohydrate-based polymers and the like. The polymers can be homopolymers or random or block copolymers and terpolymers based on the monomers of the above polymers, linear chain or branched.

Specific examples of suitable additional polymers include, but are not limited to, poly(oxazoline), difunctional poly(acryloylmorpholine) ("PAcM"), and poly(vinylpyrrolidone) ("PVP").

2. Bioadhesive Polyanionic Moieties

Certain hydrophilic polymers appear to have potentially useful bioadhesive properties. Examples of such polymers are found, for example, in U.S. Pat. No. 6,197,346, to Mathiowitz, et al. Those polymers containing carboxylic groups (e.g., poly(acrylic acid)) exhibit bioadhesive properties, and are also readily conjugated with the insulin compounds described herein. Rapidly bioerodible polymers that expose carboxylic acid groups on degradation, such as poly(lactide-co-glycolide), polyanhydrides, and polyorthoesters, are also bioadhesive polymers. These polymers can be used to deliver the insulin conjugates to the gastrointestinal tract. As the polymers degrade, they can expose carboxylic acid groups to enable them to adhere strongly to the gastrointestinal tract, and can aid in the delivery of the insulin conjugates.

3. Lipophilic Moieties

In some embodiments, the modifying moieties include one or more lipophilic moieties, which include, but are not limited to, alkyl moieties, alkenyl moieties, alkynyl moieties, aryl moieties, arylalkyl moieties, alkylaryl moieties, fatty acid moieties, adamantanyl, and cholesteryl, as well as lipophilic polymers and/or oligomers.

The alkyl moiety can be a saturated or unsaturated, linear, branched, or cyclic hydrocarbon chain. In some embodiments, the alkyl moiety has 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or more carbon atoms. Examples include saturated, linear alkyl moieties such as methyl, ethyl, propyl, butyl, pentyl, hexyl, heptyl, octyl, nonyl, decyl, undecyl, dodecyl, tridecyl, tetradecyl, pentadecyl, hexadecyl, octadecyl, nonadecyl and eicosyl; saturated, branched alkyl moieties such as isopropyl, sec-butyl, tert-butyl, 2-methylbutyl, tert-pentyl, 2-methyl-pentyl, 3-methylpentyl, 2-ethylhexyl, 2-propylpentyl; and unsaturated alkyl moieties derived from the above saturated alkyl moieties including, but not limited to, vinyl, allyl, 1-butenyl, 2-butenyl, ethynyl, 1-propynyl, and 2-propynyl. The alkyl groups can either be unsubstituted or substituted with one or more substituents The lipophilic moiety may be a fatty acid moiety, such as a natural or synthetic, saturated or unsaturated, linear or branched fatty acid moiety. In some embodiments, the fatty acid moiety has 2, 3, 4, 5, 6, 7, 8, 9, 10, 11, 12, 13, 14, 15, 16, 17, 18, 19, 20, 21, 22, 23, 24, or more carbon atoms.

4. Amphiphilic Moieties

In some embodiments, the modifying moiety includes an amphiphilic moiety. Many polymers and oligomers are amphiphilic. These are often block co-polymers, branched copolymers or graft co-polymers that include hydrophilic and lipophilic moieties, which can be in the form of oligomers and/or polymers, such as linear chain, branched, or graft polymers or co-polymers.

The amphiphilic modifying moieties may include combinations of any of the lipophilic and hydrophilic moieties described herein. Such modifying moieties typically include at least one reactive functional group, for example, halo, hydroxyl, amine, thiol, sulfonic acid, carboxylic acid, isocyanate, epoxy, ester, and the like, which is often at a terminal end of the modifying moiety. These reactive functional groups can be used to attach a lipophilic linear or branched chain alkyl, alkenyl, alkynyl, arylalkyl, or alkylaryl group, or a lipophilic polymer or oligomer, thereby increasing the lipophilicity of the modifying moiety (and thereby rendering them generally amphiphilic).

The lipophilic groups can, for example, be derived from mono- or di-carboxylic acids, or where appropriate, reactive equivalents of carboxylic acids such as anhydrides or acid chlorides. Examples of suitable precursors for the lipophilic groups are acetic acid, propionic acid, butyric acid, valeric acid, isobutyric acid, trimethylacetic acid, caproic acid, caprylic acid, heptanoic acid, capric acid, pelargonic acid, lauric acid, myristic acid, palmitic acid, stearic acid, behenic acid, lignoceric acid, ceratic acid, montanoic acid, isostearic acid, isononanoic acid, 2-ethylhexanoic acid, oleic acid, ricinoleic acid, linoleic acid, linolenic acid, erucic acid, soybean fatty acid, linseed fatty acid, dehydrated castor fatty acid, tall oil fatty acid, tung oil fatty acid, sunflower fatty acid, safflower fatty acid, acrylic acid, methacrylic acid, maleic anhydride, orthophthalic anhydride, terephthalic acid, isophthalic acid, adipic acid, azelaic acid, sebacic acid, tetrahydrophthalic anhydride, hexahydrophthalic anhydride, succinic acid and polyolefin carboxylic acids.

The terminal lipophilic groups need not be equivalent, i.e., the resulting copolymers can include terminal lipophilic groups that are the same or different. The lipophilic groups can be derived from more than one mono or di-functional alkyl, alkenyl, alkynyl, cycloalkyl, arylalkyl or alkylaryl group as defined above.

4.1 PAG-alkyl Modifying Moieties

The modifying moiety may be a linear or branched polymeric moiety having one or more linear or branched PAG moieties and/or one or more linear or branched, substituted or unsubstituted alkyl moieties. In certain cases, such moieties are considered amphiphilic; however, the PAG and alkyl moieties may be varied to render such moieties more lipophilic or more hydrophilic. In certain embodiments, the modifying moiety specifically does not consist of an alkyl moiety and in other embodiments, the modifying moiety specifically does not consist of an alkane moiety.

The PAG moieties in some embodiments include 1, 2, 3, 4, 5, 6, 7, 8, 9, 10, 11, 12, 13, 14, 15, 16, 17, 18, 19, 20, 21, 22, 23, 24, or 25 PAG subunits arranged in linear or branched form. The PAG moieties in some embodiments include PEG, PPG and/or PEG subunits. The alkyl moieties in some embodiments preferably have 2, 3, 4, 5, 6, 7, 8, 9, 10, 11, 12, 13, 14, 15, 16, 17, 18, 19, or 20 carbon atoms. The alkyl moieties are preferably alkane moieties. The modifying moiety may include a capping moiety, such as —OCH$_3$. Further, the modifying moiety may include a hydrophobic group, such as a pivaloyl group.

In some embodiments, the modifying moiety may include a linear or branched, substituted carbon chain moiety having a backbone of 3, 4, 5, 6, 7, 8, 9, 10, 11, 12, 13, 14, 15, 16, 17, 19, 20, 21, 22, 23, 24 or 25 atoms. The modifying moiety may be coupled to an available group on an amino acid, such as an amino group, a hydroxyl group or a free carboxylic acid group in the polypeptide by a linking group, such as a carbamate, carbonate, ether, ester, amide, or secondary amine group, or by a disulfide bond.

5. Salt-Forming Moieties

In some embodiments, the modifying moiety comprises a salt-forming moiety, which may include, but not limited to, carboxylate and ammonium. In some embodiments where the modifying moiety includes a salt forming moiety, the insulin compound conjugate is provided in salt form. In these embodiments, the insulin conjugate is associated with a suitable pharmaceutically acceptable counterion as will be understood by those skilled in the art including, but not limited to, negative ions such as chloro, bromo, iodo, phosphate, acetate, carbonate, sulfate, tosylate, and mesylate, or positive ions such as sodium, potassium, calcium, lithium, and ammonium.

The foregoing examples of modifying moieties are intended as illustrative and should not be taken as limiting in any way. One skilled in the art will recognize that suitable moieties for conjugation to achieve particular functionality will be possible within the bounds of the chemical conjugation mechanisms disclosed and claimed herein. Accordingly, additional moieties can be selected and used according to the principles as disclosed herein.

One of the reasons for short circulation time of low molecular weight pharmaceutically active agents in the plasma is rapid renal clearance. Several mechanisms can be exploited. 1. "depot" formation in the site of injection; 2. association with a plasma protein to prevent glomerular filtration; 3. covalent binding to a plasma protein; 4. binding to large molecular weight synthetic polymers (e.g., PEG).

Hydrophobic depoting involves dramatically increasing the hydrophobicity of a pharmaceutically active agent in order to decrease the solubility and cause it to form a "depot" at the injection site in the body. Thus the depot dissolves slowly, with the pharmaceutically active agent then binding to a plasma protein (e.g., albumin). While bound to albumin, the pharmaceutically active agent would not be cleared by glomerular filtration or degraded by proteases.

Increasing the molecular weight of pharmaceutically active agents over glomerular filtration cutoff will significantly reduce their renal clearance rate and prolong their duration of action. One approach is to conjugate a pharmaceutically active agent to a natural or synthetic large molecule via a hydrolysable or non-hydrolysable bond. Synthetic polymers include PEG and biomolecules include plasma proteins (e.g., albumin, Igs, or Fc portion of an immunoglobin), and polysaccharides (e.g., dextran). Conjugation of a pharmaceutically active agent to a natural or synthetic large molecule can also reduce their immunogenicity and susceptibility to peptidase degradation. In one embodiment at least one PEG chain having a molecular weight of about 40,000 Daltons or about 20,000 Daltons is linked to the promoiety of a prodrug either directly or through a linker/spacer.

The duration of in vivo action of a pharmaceutically active agent can be improved by conjugation with hydrophobic moieties. In one embodiment the hydrophobic moiety is a long chain fatty acid (e.g. myristic acid, palmitic acid, stearic acid, arachidic acid, tetradecanedioic acid, hexadecanedioic acid, octadecanedioic acid, icosanedioic acid). In one embodiment the hydrophobic moiety is a cholesterol or a bile acid (e.g. cholic acid, chenodeoxycholic acid, glycocholic acid, taurocholic acid, deoxycholic acid, cholesterol acid, lithocholic acid). An non-limiting, illustrative example is as follows:

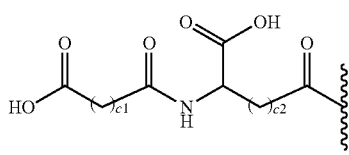

wherein c1 and c2 are an integer in the range from 1 to 30. When a long chain fatty acid is linked to the side chain thiol group of a cysteine in a protein/peptide drug, several non-limiting, illustrative examples include

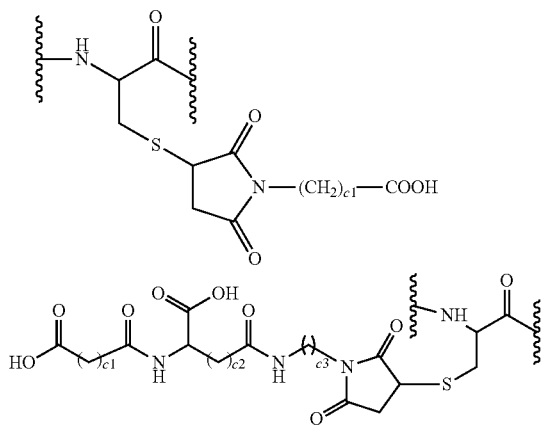

wherein c3 is an integer in the range from 1 to 20.

In some embodiments a PEG spacer may be inserted between a hydrophobic moiety and a prodrug to reduce steric hinderance, enhance binding to albumin, or improve solubility. When a long chain fatty acid is linked to the side chain thiol group of a cysteine in a protein/peptide drug, an non-limiting, illustrative example is as follows:

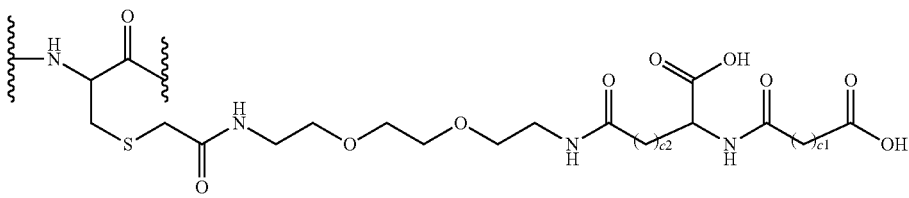

When a long chain fatty acid is linked to the ε-amino group of a lysine in a protein/peptide drug, an non-limiting, illustrative example is as follows:

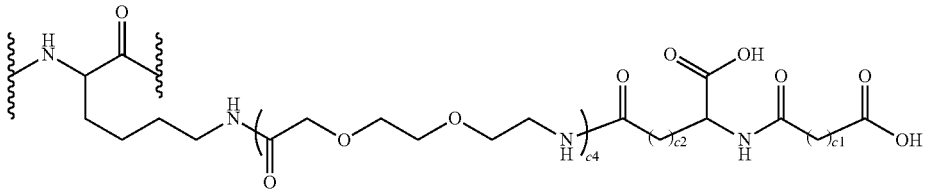

wherein c4 is an integer in the range from 1 to 10.

The solubility in aqueous solutions and duration of in vivo action of a pharmaceutically active agent can be improved by conjugation with hydrophilic moieties. In one embodiment the hydrophilic moiety is a plasma protein, PEG, or polysaccharides.

The duration of in vivo action of a pharmaceutically active agent can be improved by conjugation with an albumin affinity tag (Zobel et al, 2003, Bioorganic & Medicinal Chemistry Letters 13, 1513-1515; Jonsson et al, 2008, Protein Engineering, Design & Selection vol. 21 no. 8 pp. 515-527), an anti-serum albumin domain antibody (Holt et al, 2008, Protein Engineering, Design & Selection vol. 21 no. 5 pp. 283-288), or an albumin-binding Fab (Nguyen et al, 2006, Protein Engineering, Design & Selection vol. 19 no. 7 pp. 291-297).

Most conjugates with albumin involve ex vivo conjugate formation with an exogenous albumin. While homogeneity of the conjugate product can be guaranteed potential drawbacks to using exogenous sources of albumin are cost, possible contamination, or immunogenic response. The in vivo attachment of a therapeutic agent to albumin has the advantage, relative to the ex vivo approach, in that endogenous albumin is used, thus obviating problems associated with contamination or an immunogenic response to the exogenous albumin. Yet, the prior art approach of in vivo formation of drug conjugates with endogenous albumin involves a permanent covalent linkage between the drug and the albumin. To the extent the linkage is cleavable or reversible, the drug or peptide released from the conjugate is in a modified form of the original compound.

The drug albumin conjugates of this disclosure consist of a drug (or a pharmaceutically active agent), a promoiety, an optional linker and albumin.

In some embodiments, one end of a linker shall be connected to a promoiety on the drug. In some embodiments, one end of a linker shall be directly bound to a drug while a promoiety is attached to the drug at another site. The other end of the linker shall be attached to albumin. The attachment from the linker to albumin shall preferably be to the free Cys at position 34.

In some embodiments the monofunctional linker is of the formula $M_r$-L-, wherein $M_r$ is a Michael acceptor (e.g., a malimido group, a vinylsulfone) or a thiol reactive group (e.g., pyridyldisulfide, methoxy- or ethoxycarbonyldisulfide, o-nitrophenyldisulphide, iodoacetamide); L is a linker moiety as defined above.

In some embodiments the monofunctional linker has one of the following structures

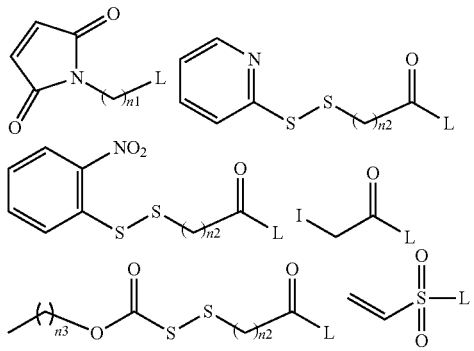

Wherein n1, n2, and n3 are an integer in the range from 1 to 20 [what is "I."?].

In one embodiment L is a covalent bond or is chosen from the following moieties: —NH—$(CH_2—CH_2—O)_{n4}$—$(CH_2)_{n5}$—CO—, —NH—$(CH_2)_{n6}$—CO—, —$(CH_2)_{n7}$—CO—, —$(CH_2)_{n8}$—NH—, —HN—$(CH_2)_{n9}$—NH—CO, —CO—$(CH_2)_{n10}$—CO, —$(CH_2—CH_2—O)_{n11}$—$(CH_2)_{n12}$—CO—, —NH—$C_6H_4$—CO—, —NH—$(CH_2)_{n13}$—O—$(CH_2CH_2O)_{n14}$—$(CH_2)_{n15}$—CO—, [—NH—$(CH_2CH_2O)_2$—$CH_2$—CO—]$_{n16}$, [—NH—$CH_2$—$(CH_2CH_2O)_3$—$(CH_2)_3$—NHCO—$(CH_2)_2$—CO—]$_{n17}$, —NH—$(CH_2)_{n18}$—CO—NH—$(CH_2—CH_2—O)_{n19}$—$(CH_2)_{n20}$—CO—, or a combination of two or more of the above thereof, wherein n4, n5, n6, n7, n8, n9, n10, n11, n12, n13, n14, n15, n16, n17, n18, n19, n20 are an integer in the range from 1 to 20; —$C_6H_4$— is para-phenylene.

For a pharmaceutically active agent designed for in vivo attachment to albumin the formula shall be: $M_r$-L-promoiety-drug (Drug mean active agent) or $M_r$-L -drug-promoiety. In one embodiment, non-limiting, illustrative examples of $M_r$-L- include

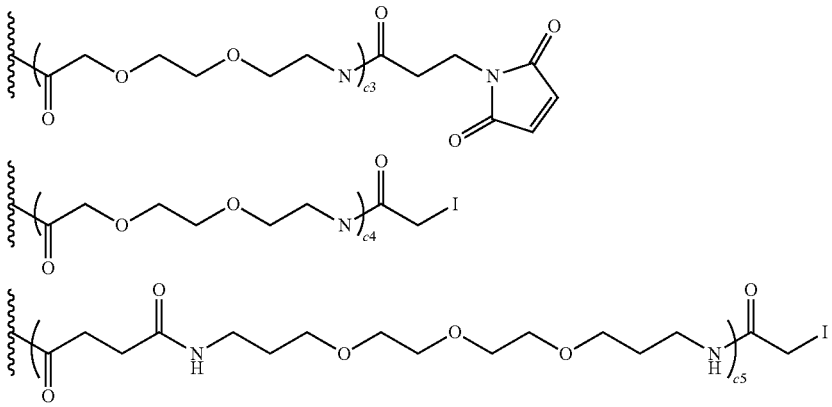

wherein c3, c4, and c5 are an integer in the range from 1 to 8.

In some embodiments, an ex vivo albumin conjugate prodrug is of the formula: alb-$M_{r'}$-L-promoiety-drug or alb-$M_{r'}$-L-drug-promoiety, wherein alb is albumin as defined herein linked through a free thiol group of a Cys residue, preferably the Cys34 residue; $M_{r'}$ is the $M_r$ after reaction with a thiol-group of albumin.

In one embodiment, $M_{r'}$ is of one of the following formulae:

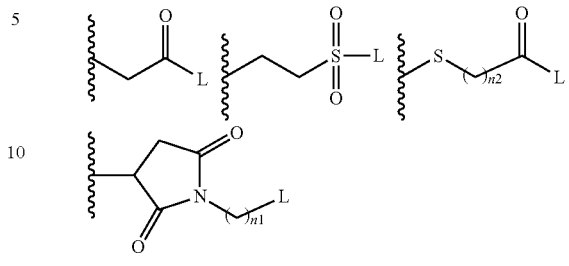

wherein the wavy line indicates the attachment to the thiol group of a cysteine residue.

In some embodiments, a modifying moiety is linked to a pharmaceutically active agent or a promoiety on the active agent via a homobifunctional or heterobifunctional linker. The choices of functional groups on the linker depend upon the target functional groups on the pharmaceutically active agent and the modifying moiety as well as requirements for a particular reaction. In one embodiment, a linker may have two activating groups (e.g., N-hydroxyl succinimide (NHS ester) or maleimide), each of which reacts with the amino or mercapto group on the prodrug and the modifying moiety, linking the three components as a whole. In one embodiment, a linker may have an activating group (e.g., NHS ester, maleimide, iodoacetyl, or vinylsulfone) and a nucleophilic functional group (e.g., an amino or mercapto group), each of which reacts respectively with another nucleophilic functional group (e.g., an amino or mercapto group) and another activating group (e.g., NHS ester, maleimide, iodoacetyl, or vinylsulfone) on the prodrug and the modifying moiety, linking the three components as a whole. In another embodiment, a linker may have two nucleophilic functional groups (e.g., an amino or mercapto group), each of which reacts with the activating groups (e.g., NHS, maleimide, iodoacetyl, or vinylsulfone) on the prodrug and the modifying moiety, linking the three components as a whole.

The commercial bifunctional PEG reagents used in the disclosure include, but are not limited to, NHS-PEG-NHS, ALD-PEG-ALD (acetaldehyde-PEG-acetaldehyde), Ts-PEG-Ts (toluenesulfonic acid-PEG-toluenesulfonic acid), CDI-PEG-CDI (carbonyl imidazole-PEG-carbonyl imidazole), ISC-PEG-ISC (isocyanate-PEG-isocyanate), EPO-PEG-EPO (epoxide-PEG-epoxide), Mal-PEG-Mal (maleimide-PEG-maleimide), maleimide-PEG-NHS, maleimide-PEG-NH$_2$, maleimide-PEG-COOH, PEG-vinyl sulfone derivatives, (VS-PEG-X, X=NHS, maleimide, NH$_2$, COOH, etc), PEG-iodoacetamide derivatives (IA-PEG-X, X=NHS, maleimide, NH$_2$, COOH, etc.), OPSS-PEG-NHS (orthopyridyldisulfide-PEG-succinimidyl ester), OPSS-PEG-NH$_2$, OPSS-PEG-OPSS.

When the modifying moiety is an immunoglobulin or Fc portion of an immunoglobulin, one end of the linker is connected to a prodrug while the other end is an aldehyde group which is reacted with the amino group on an immunoglobulin or the Fc of an immunoglobulin through reductive amination to form a covalent linkage.

6. Conjugation Strategies

Factors such as the degree of conjugation of a drug or a pharmaceutically active agent with modifying moieties, selection of conjugation sites, and selection of modifying moieties play a significant role in the physical, chemical, pharmacokinetic, and pharmacodynamic properties of a drug conjugate. A pharmaceutically active agent may be coupled to a modifying moiety through a hydrolyzable bond (e.g., an ester, carbonate or hydrolyzable carbamate bond) or a non-hydrolyzable bond (e.g., an amide or ether bond). Use of a hydrolyzable coupling can make a conjugate act as a prodrug. When a modifying moiety conjugation site is in a region throught which a drug interacts with its target the conjugate loses the ability to affect the body through its primary mechanism of action. The pharmaceutically active agent is released as the modifying moiety is detached from the conjugate. Use of a hydrolyzable coupling can also provide a delayed-release or controlled-release effect. Use of a non-hydrolyzable bond may be preferable when it is desirable to allow therapeutically significant amounts of the conjugate to circulate in the bloodstream for an extended period of time.

One or more modifying moieties may be coupled to a pharmaceutically active agent. The modifying moieties may be same or may be different from one another, or, alternatively, some of the modifying moieties may be same and some may be different. When a plurality of modifying moieties are coupled to a pharmaceutically active agent, it may be preferable to couple one or more of the modifying moieties to the pharmaceutically active agent with hydrolyzable bonds and couple one or more of the modifying moieties to the pharmaceutically active agent with non-hydrolyzable bonds. Alternatively, all of the bonds coupling the plurality of modifying moieties to a pharmaceutically active agent may be hydrolyzable but have varying degrees of hydrolyzability such that, for example, one or more of the modifying moieties may be relatively rapidly removed from the pharmaceutically active agent by hydrolysis in the body and one or more of the modifying moieties is more slowly removed from the pharmaceutically active agent by hydrolysis in the body. For example, the number of modifying moieties on the insulin analog is limited only by the number of conjugation sites on an insulin analog. An insulin analog may be modified to include modifying moieties at one, two, or more appropriate conjugation sites on the insulin analog structure suitable for facilitating the association of a modifying moiety thereon. In still other embodiments, the insulin conjugates are a mixture of mono-conjugates, di-conjugates, tri-conjugates, tetra-conjugates, and/or penta-conjugates.

A modifying moiety may be coupled to a pharmaceutically active agent or its derivative at various nucleophilic residues, including, but not limited to, nucleophilic hydroxyl functions and/or amino functions. In proteins and peptides nucleophilic hydroxyl functions may be found, for example, at serine, threonine, or tyrosine residues, and nucleophilic amino functions may be found, for example, at histidine and/or Lys residues, and/or at the one or more N-terminus of the A or B chains of the insulin or insulin analogs. A modifying moiety may be coupled to a protein at a free mercapto group, e.g., by forming a thioester, thioether or sulfonate bond.

A wide variety of drugs or pharmaceutically active agents may be employed in the broad practice of the present disclosure. Nitrogen-containing drugs or pharmaceutically active agents amenable to the present technology include, but are not limited to, insulin (including insulin lispro, aspart, glulisine, glargine, detemir, degludec), erythropoietin (or epoetin beta, epoetin alfa), growth hormone, glucagon-like peptide-1 (GLP-1), exenatide, glucose-dependent insulinotropic peptide (GIP), interferon (including interferon alpha 2a, interferon alpha 2b, human leukocyte interferon-alpha (HuIFN-alpha-Le), interferon beta 1a, interferon beta 1b, interferon gamma 1b, PEGylated interferon alpha 2a, PEGylated interferon alpha 2b), granulocyte colony-stimulating factor (G-CSF or GCSF) (including filgrastim (Neupogen), PEG-filgrastim (Neulasta), and lenograstim).

Nitrogen-containing drugs or pharmaceutically active agents amenable to the present technology also include bevacizumab, trastuzumab, trastuzumab emtansine, adalimumab, infliximab, rituximab, enalapril, lisinopril, ranibizumab, interleukin-1 receptor antagonist (IL-1Ra), coagulation factor IX, coagulation factor VIIa, saralasin, calcitonin (human calcitonin, salmon calcitonin, elcatonin acetate, sermorelin, thymalfasin, thymopentin, copaxone, octreotide, tanercept, pregabalin, memantine, amphetamine, dextroamphetamine, Levoamphetamine, fingolimod, ustekinumab, abatacept, levothyroxine, metoprolol, omalizumab, riociguat, natalizumab, dabigatran, denosumab, cinacalcet, anthracycline, duloxetine, ibrutinib, ceritinib, crizotinib, pertuzumab, ipilimumab, sitagliptin, lenalidomide.

Also included are buserelin, goserelin, histrelin, leuprolide, triptorelin, abarelix, degarelix, thymopetidum, somatostatin, teriparatide, oxytocin, carbetocin, chorionic gonadotrophin, desmopressin, terlipressin, interferon alfacon-1, sargramostim, lisdexamfetamine, methylphenidate, pemetrexed, doxorubicin, irbesartan, carfilzomib, basiliximab, daclizumab, alemtuzumab, nimotuzumab, cetuximab, palivizumab, abciximab, darbepoetin alfa, teriflunomide, leflunomide, sofosbuvir, ribavirin, ciprofloxacin, dabrafenib, trametinib, cytarabine, votrient, siltuximab, ramucirumab, imatinib, nivolumab, elotuzumab, etanercept, prevnar 13, aflibercept, eculizumab, linagliptin, pomalidomide, natriuretic peptide (including atrial natriuretic peptide, brain natriuretic peptide, C-type natriuretic peptide), palbociclib, lampalizumab, evolocumab, alirocumab, secukinumab, ocrelizumab, pembrolizumab, ofatumumab, obinutuzumab, brentuximab vedotin, rilotumumab, ibrutinib, idelalisib, dabrafenib, odanacatib, omarigliptin, alogliptin, vildagliptin.

Also included are depreotide, edotreotide, pentetreotide, vapreotide, argipressin, phenypressin, ADH-1, afamelanotide, glutathione, oglufanide, macrophage-activating lipopeptide-2 synthetic, interferon alfa-n3, alglucerase, alteplase, anistreplase, antihemophilic factor or factor VIII antithrombin III, antithymocyte globulin, sinapultide, spaglumat, vasoactive intestinal peptide, pancrelipase (amylase; lipase; protease), urokinase, pegaspargase, eptotermin alfa, galsulfase, imiglucerase, chymotrypsin, chymopapain, bococizumab, lutropin alfa or luteinizing hormone, insulin like growth factor 1 (IGF-1), mecasermin rinfabate, insulin like growth factor 2 (IGF-2), glucagon, glucagon-like peptide-2 (GLP-2), exendin-3, teduglutide, ghrelin, melanin-concentrating hormone (MCH), vasopressin (e.g. arginine vasopressin (AVP)), lypressin, adrenocorticotropic hormone (ACTH, also known as corticotrophin), parathyroid hormone (PTH), pituitary adenylate cyclase-activating peptide, corticotropin-releasing hormone (CRH), gonadotropin releasing hormone (GnRH), angiotensin, bombesin, gastrin releasing peptide, growth hormone releasing hormone (GHRH), neuromedin B (NMB), neuromedin U, neuromedin S, neuromedin N, bradykinin, gastrin, laronidase, alglucosidase alfa, BMN-701, secretin (human and porcine), alglucerase, imiglucerase, rasburicase, uricase, pegloticase, asparaginase, agalsidase alfa, agalsidase beta, lactase, oxyntomodulin, peptide histidine methionine, peptide histidine isoleucine, osteocalcin, octrotide, zicontide, pasireotide, peginesatide, linaclotide, lixisenatide, tesamorelin, tildrakizumab, velaglucerase alfa, andexanet alfa, idursulfase, RG7446, oprelvekin, nesiritide, elcatonin, bivalirudin, botulinum toxin type a, botulinum toxin type B, palifermin, papain, sacrosidase, somatotropin, enfuvirtide, palifermin, urokinase, romiplostim, aldesleukin, metreleptin, elosulfase alfa, somatrem, dornase alfa, reteplase, lanreotide, streptokinase, pegvisomant, pramlintide, amylin, tenecteplase, somatropin, sertraline, bupropion, salmeterol, darunavir, acivicin, allopurinol, 5-amino salicylic acid (5-ASA), dapsone, dopamine, 5-fluorouracil, (−)-ephedrine, (+)-pseudoephedrine, L-dopa, (R)-a-methylhistamine, morpholine, phenyethylamine, phenylenediamine, celecoxib, entecavir, lamivudine, amikacin, sunitinib, oseltamivir, atomoxetine, timolol, tigecycline, pazopanib, ponatinib, neratinib, lapatinib, afatinib.

Also included nitrogen containing drugs are fluoxetine, bleomycin, dactinomycin, kanamycin, vancomycin, lorcaserin, phenytoin, sulfamethoxazole, theophylline, teicoplanin, atosiban, cilazapril, delapril, imidapril, ramipril, temocapril, seractide, pegademase bovine, adenosine, tirofiban, imiquimod, aminocaproic acid, para-aminohippuric acid (PAH), flucytosine, icatibant, rilonacept, argatroban, nelarabine, amoxapine, dutasteride, rasagiline, brinzolamide, arformoterol, piperazine, bumetanide, nebivolol, amodiaquine, caspofungin, capreomycin, ceftibuten, cetrorelix, varenicline, clofarabine, colistin, carvedilol, dactinomycin, daptomycin, cysteamine, aminoglutethimide, decitabine, daunorubicin, penciclovir, famciclovir, penicillamine, deferoxamine, desloratadine, acetazolamide, mesalazine, dobutamine, doxazosin, dacarbazine, epirubicin, esmolol, amifostine, thyroxine, triiodothyronine, gemifloxacin, pyrimethamine, sulfadoxine, fenoldopam, hyaluronidase, colestipol, cyclothiazide, flutamide, dexmethylphenidate, pralatrexate, alendronic acid, dalteparin, frovatriptan, amphotericin b, levoleucovorin, gemcitabine, arbutamine, follitropin alfa or beta, adefovir, hydroxyurea, fibrinogen, idarubicin, inamrinone, eptifibatide, etravirine, hirudin, desirudin, lepirudin, gefitinib, dexlansoprazole, betaxolol, ketamine, clonazepam, sapropterin, lamotrigine, clofazimine, butalbital, furosemide, letrozole, droxidopa, simeprevir, ledipasvir, daclatasvir, asunaprevir, tofacitinib, cladribine, penbutolol, levetiracetam.

Also included are aminolevulinic acid, regadenoson, fosamprenavir, amprenavir, baclofen, lorazepam, benazepril, talbutal, fluvoxamine, tranexamic acid, pegaptanib, sorafenib, proguanil, cycloguanil, maprotiline, isocarboxazid, procarbazine, pirbuterol, lomefloxacin, meclofenamate, mefloquine, melphalan, chlordiazepoxide, metaraminol, methamphetamine, chlorothiazide, methyldopa, urofollitropin, mexiletine, glyburide, amiloride, benzamil, plerixafor, dronedarone, mitomycin, ethambutol, rifabutin, nadolol, galsulfase, phenelzine, natamycin, bendroflumethiazide, methazolamide, netilmicin, gabapentin, trimetrexate, niclosamide, nimodipine, mitoxantrone, armodafinil, nystatin, fludarabine, saxagliptin, denileukin diftitox, choriogonadotropin alfa, nortriptyline, pamidronate, norpholedrine, 3-hydroxyamphetamine, paromomycin, enoxacin, pentamidine, pentostatin, famotidine, perindopril, desipramine, paroxetine, 4-Aminosalicylic acid, apremilast, apixaban, pioglitazone, hydroxychloroquine, cilostazol, mefenamic acid, pramipexole, nordazepam, prazosin, chlorphentermine, dexmedetomidine, phenylephrine, dibotermin alfa, ziconotide, primaquine, cilastatin, primidone, midodrine, nifedipine, eltrombopag, metaproterenol, procainamide, propranolol, modafinil, mercaptopurine, quinaprilat, ramipril, silodosin, norepinephrine, phentolamine, metoclopramide, zanamivir, sulfacytine, spiraprilat, riluzole, propafenone, vigabatrin, collagenase, milnacipran, levonordefrin, acebutolol, cycloserine.

Other nitrogen-containing drugs which can be used in prodrugs include sotalol, dasatinib, carbidopa, levodopa, isoniazid, streptomycin, sulfaphenazole, phenazopyridine, sulfanilamide, sulfameter, formoterol, nafarelin, tetracaine, flecainide, tamsulosin, erlotinib, nilotinib, 4-aminosalicylic acid, MTIC (3-methyl-(triazen-1-yl)imidazole-4-carboxamide), guanfacine, atenolol, terazosin, carbamazepine, chlorthalidone, thalidomide, sulfadiazine, minoxidil, thioguanine, sulfamethizole, protirelin, thyroglobulin, liotrix, thyrotropin, dofetilide, tocainide, topiramate, phentermine, torsemide, tolterodine, bosentan, labetalol, trandolapril, tranylcypromine, oxprenolol, aprotinin, methotrexate, triamterene, pseudoephedrine, trimethoprim, liothyronine, sulfamerazine, sulfamethazine, spectinomycin, emtricitabine, epinephrine, amlodipine, ceruletide, cilengitide, taltirelin, gentamicin, febuxostat, hydralazine, moexipril, trimethoprim, alfuzosin, diazepam, valacyclovir, aciclovir, aliskiren, eflornithine, candicidin, oxamniquine, isoproterenol, sulfacetamide, bortezomib, protokylol, mebendazole, sildenafil, telavancin, diphenhydramine, azacitidine, didanosine, moxifloxacin, lacosamide, vincristine, vinorelbine, viomycin, vidarabine, nelfinavir, nevirapine, tenofovir, pindolol, cidofovir, fomivirsen, protriptyline, diclofenac, albuterol, miconazole, colesevelam, leucovorin, GLPG0634 mephentermine, guanabenz, alprazolam, bromfenac, levalbuterol, tizanidine, metolazone, omeprazole, stavudine, bisoprolol, hydrochlorothiazide, zidovudine, neomycin, polymyxin, dexrazoxane, ziprasidone, ganciclovir, zoledronic acid, vorinostat, zonisamide, acyclovir, tobramycin, olanzapine, linezolid, (9S)-erythromycyclamine.

Other therapeutic monoclonal antibodies which can be used in prodrugs include 3F8, 8H9, abagovomab, actoxumab, adecatumumab, afelimomab, afutuzumab, alacizumab pegol (or non-PEGylated form), ALD518, altumomab pentetate, amatuximab, anatumomab mafenatox, anifrolumab, anrukinzumab (IMA-638), apolizumab, arcitumomab, aselizumab, atinumab, atlizumab, atorolimumab, bapineuzumab, bavituximab, bectumomab, belimumab, benralizumab, bertilimumab, besilesomab, bezlotoxumab, biciromab, bimagrumab, bivatuzumab mertansine, blinatumomab, blosozumab, briakinumab, brodalumab, canakinumab, cantuzumab mertansine, cantuzumab ravtansine, caplacizumab, carlumab, catumaxomab, cedelizumab, certolizumab pegol (or non-PEGylated form), citatuzumab bogatox, cixutumumab, clazakizumab, clenoliximab, clivatuzumab tetraxetan, conatumumab, concizumab, crenezumab, CR6261, dacetuzumab, dalotuzumab, daratumumab, demcizumab, detumomab, dorlirnomab aritox, drozitumab, duligotumab, dupilumab, dusigitumab, ecromeximab, edobacomab, edrecolornab, efalizumab, efungumab, eldelumab, elotuzumab, elsilirnomab, enavatuzumab, enlimomab pegol (or non-PEGylated form), enokizumab, enoticumab, ensituximab, epitumomab cituxetan, epratuzumab, erlizumab, ertumaxomab, etaracizurnab, etrolizumab, exbivirumab, fanolesomab, faralimomab, farletuzumab, fasinumab, FBTA05, felvizumab, fezakinumab, ficlatuzumab, figitumumab, flanvotumab, fontolizurnab, foralumab, foravirumab, fresolimumab, fulranumab, futuximab, galiximab, ganitumab, gantenerumab, gavilimomab, gemtuzumab ozogamicin, gevokizumab, girentuximab, glembatumumab vedotin, golimumab, gorniliximab, GS6624, guselkumab, guselkumab, ibalizumab, ibritumomab or ibritumomab tiuxetan, icrucumab, igovomab, imciromab, imgatuzumab, inclacumab, indatuximab ravtansine, intetumumab, inolimomab, inotuzumab ozogamicin, iratumumab, itolizumab, ixekizumab, keliximab, labetuzumab, lebrikizumab, lemalesomab, lerdelimumab, lexatumumab, libivirumab, ligelizumab, lintuzumab, lirilumab, lodelcizumab, lorvotuzumab mertansine, lucatumurnab, mapatumumab, margetuximab, maslirnomab, mavrilimumab, matuzumab, MEDI3902, mepolizumab, metelimumab, milatuzumab, minretumomab, mitumomab, mogamulizumab, morolimumab, motavizumab, moxetumomab pasudotox, muromonab-CD3, nacolomab tafenatox, namilumab, naptumomab estafenatox, narnatumab, nebacumab, necitumumab, nerelimomab, nesvacumab, nofeturnornab merpentan, ocaratuzumab, odulimomab, olaratumab, olokizumab, onartuzumab, ontuxizumab, oportuzumab monatox, oregovomab, orticumab, otelixizumab, oxelumab, ozanezumab, ozoralizumab, pagibaximab, panitumumab, panobacurnab, parsatuzumab, pascolizumab, pateclizumab, patritumab, pemtumomab, perakizumab, pexelizumab, pidilizumab, pinatuzumab vedotin, pintumomab, placulumab, polatuzumab vedotin, ponezumab, priliximab, pritoxaximab, priturnumab, PRO 140, quilizumab, racotumomab, radretumab, rafivirumab, raxibacumab, regavirumab, reslizumab, robaturnumab, roledumab, romosozumab, rontalizumab, rovelizumab, ruplizumab, samalizumab, sarilumab, satumomab pendetide, seribantumab, setoxaximab, sevirumab, sibrotuzurnab, sifalimumab, simtuzumab, siplizumab, sirukumab, solanezumab, solitomab, sonepcizumab, sontuzumab, stamulumab, sulesomab, suvizumab, tabalumab, tacatuzumab tetraxetan, tadocizurnab, talizumab, tanezumab, taplitumomab paptox, tefibazumab, telimomab aritox, tenatumomab, teneliximab, teplizumab, teprotumumab, TGN1412, ticilimumab (tremelimurnab), tigatuzumab, TNX-650, tocilizumab (atlizumab), toralizumab, tositumomab, tovetumab, tralokinumab, trbs07, tregalizumab, tremelimumab, tucotuzumab celmoleukin, tuvirumab, ubliruximab, urelumab, urtoxazumab, ustekinumab, vantictumab, vapaliximab, vatelizumab, vedolizumab, veltuzumab, vepalimomab, vesencumab, visilizumab, volociximab, vorsetuzumab mafodotin, votumumab, zalutumumab, zanolimumab, zatuximab, ziralimumab, zolimomab aritox.

Drugs with one or more than one hydroxyl group(s) amenable to the present technology include, but are not limited to, rosuvastatin, ezetimibe, buprenorphine, quetiapine, testosterone, oxycodone, doxycycline, ciclosporin, raltegravir, budesonide, atazanavir, simvastatin, raloxifene, abiraterone, olmesartan, paliperidone, dapagliflozin, 4-hydroxybutanoic acid, dolutegravir, eltrombopag, everolimus.

Also included hydroxyl containing drugs such as tetracycline, micafungin, ivacaftor, biperiden, indinavir, quinupristin/dalfopristin, rentiapril, methylprednisolone, masoprocol, risedronic acid, acetyldigitoxin, canagliflozin, empagliflozin, dapagliflozin, ipragliflozin, tofogliflozin, remogliflozin, retapamulin, oxymetholone, apomorphine, misoprostol, meprednisone, calcifediol, mepenzolate, deslanoside, nabilone, ibutilide, dromostanolone, difluprednate, estramustine, dienestrol, fulvestrant, miglitol, doxercalciferol, homatropine, hydroxyprogesterone, inulin, saquinavir, procyclidine, digoxin, phenprocoumon, acetohydroxamic acid, flumetasone, loperamide, bimatoprost, hydrocortamate, dronabinol, ethylestrenol, megestrol acetate, lovastatin, mifepristone, plicamycin, trilostane, atropine, guaifenesin, flunisolide, rotigotine, ethinyl estradiol, norethindrone, nalbuphine, tapentadol, etonogestrel, ciclesonide, oxyrnorphone, chloramphenicol, fluoxymesterone, norelgestromin, norgestrel, mestranol, oxandrolone, oxybutynin, cycrimine, rnethscopolamine, tridihexethyl, ciclopirox, cyclopentolate, desoxycorticosterone, dipyridamole, podofilox, lactulose, acarbose, prednicarbate, levonorgestrel, clarithromycin, isosorbide, carphenazine, fluphenazine, pralidoxime, medroxyprogesterone, diflorasone, clidinium bromide, piperacetazine, sirolimus, galantamine, indinavir, nelfinavir, glycopyrrolate, menthol, methyl salicylate, tolvaptan, trospium chloride, prednisone, oxybenzone, calcipotriene, mequinol, codeine, tiotropium, entacapone, diethylstilbestrol, ivermectin, beractant, dihydrocodeine, menadiol, estrogen, bazedoxfiene, naloxone, pentazocine, oxyphenbutazone, tolcapone, paclitaxel, docetaxel, clobetasol, edrophonium, estrone, acetophenazine, dexamethasone, fluorometholone, desoximetasone, temsirolimus, hexocyclium, travoprost, fluocinolone acetonide, hydroquinone, norgestimate, desonide, trihexyphenidyl, perphenazine, azithromycin, triamcinolone acetonide, tubocurarine, benzyl alcohol, chlophedianol, tramadol, halobetasol, ursodiol, betamethasone, beclomethasone, fluocinonide, prednisolone, calcitriol, desogestrel, iloprost, etoposide, venlafaxine, rimexolone, methyltestosterone, hydroxyzine, estradiol, naltrexone, teniposide, hydrocortisone, erythromycin, latanoprost, xylose, 4-hydroxybutanoic acid, streptozocin, miglustat, paricalcitol, rocuronium, clindamycin, ethinyl estradiol, ethynodiol diacetate, loteprednol, pravastatin, dinoprostone, dinoprost, alprostadil, clavulanate, treprostinil, cefpiramide, carboprost, fexofenadine, epoprostenol, fluvastatin, levocarnitine, atorvastatin, lubiprostone, cerivastatin, chenodiol, bentiromide, mycophenolate, cortisone, fludrocortisone, desoximetasone, flurandrenolide, norethynodrel, paramethasone, amcinonide, clocortolone, danazol, diflunisal, halofantrine, haloperidol, topotecan, irinotecan, ixabepilone, lincomycin, lopinavir, cefamandole, pitavastatin, deferasirox, alvimopan, demeclocycline, ganirelix, levorphanol, methylergonovine, nandrolone, dyphylline, ritonavir, posaconazole, clioquinol, cromoglicic acid, hydromorphone, bromocriptine, piroxicam, rifapentine, finasteride, quinine, quinidine, capsaicin, ranolazine, methylnaltrexone, nalmefene, captopril, risedronate, methocarbamol, cyclosporine, SN-38, montelukast, minocycline, idoxuridine, tacrolimus, oxytetracycline, testosterone, rifampin, scopolamine, telbivudine, valrubicin, metronidazole, vinblastine, voriconazole, trifluridine, warfarin, ergotamine, stanozolol, rifaximin, oxazepam, capecitabine, chlortetracycline.

It is understood by those skilled in the art the present disclosure is also applicable to analogs and derivatives of the drugs and pharmaceutically active agents listed above. The foregoing examples are intended as illustrative and should not be taken as limiting in any way. One skilled in the art will recognize that suitable pharmaceutically active agents for prodrug modifications to achieve particular functionality will be possible within the bounds of the mechanisms disclosed and claimed herein. Accordingly, additional pharmaceutically active agents can be selected and used according to the principles as disclosed herein.

Pharmaceutical Compositions

In some embodiments a pharmaceutical composition comprises one prodrug. In some embodiments, a composition comprises a mixture of prodrugs, wherein the prodrugs differ from one another in the promoiety structures. More particularly, one prodrug may comprise a promoiety that has a half life substantially different from the promoieties of other prodrugs. Accordingly, selection of different combinations of promoieties will allow for the preparation of compositions that comprise a mixture of prodrugs that are activated in a controlled manner over a desired time frame and at specific time intervals. For example, the compositions can be formulated to release active insulin at mealtimes followed by a subsequent activation of insulin during night time with suitable dosages being released based on time of activation. In another embodiment the pharmaceutical composition comprises a mixture of prodrugs disclosed herein and the corresponding parent drug.

The prodrugs may be administered orally, topically, parenterally, nasally, pulmonarily, or rectally in dosage unit formulations containing conventional, non-toxic pharmaceutically acceptable carriers, adjuvants and vehicles.

The pharmaceutical compositions containing one or more prodrugs may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from sweetening agents, flavoring agents, coloring agents and preserving agents in order to provide pharmaceutically elegant and palatable preparation.

Formulations for oral use include tablets which contain one or more prodrugs in admixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, maize starch or alginic acid; binding agents, for example, starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

The prodrugs of this disclosure may be delivered by inhalation to achieve slow absorption and/or reduced systemical clearance thereof. Different inhalation devices typically provide similar pharmacokinetics when similar particle sizes and similar levels of lung deposition are compared. The prodrugs of this disclosure may be delivered by any of a variety of inhalation devices known in the art for administration of a therapeutic agent by inhalation. These devices include metered dose inhalers, nebulizers, dry powder generators, sprayers, and the like. Preferably, the compounds of this are delivered by a dry powder inhaler or a sprayer. There are several desirable features of an inhalation device for administering compounds of this disclosure. For example, delivery by the inhalation device is advantageously reliable, reproducible, and accurate. A composition for nasal administration of prodrugs of this disclosure may, e.g., be prepared as described in European Patent No. 272,097.

Pharmaceutical compositions containing a prodrug of this disclosure may also be administered parenterally to patients in need of such a treatment. Parenteral administration may be performed by subcutaneous, intramuscular or intravenous injection by means of a syringe, optionally a pen-like syringe. Alternatively, parenteral administration can be performed by means of an infusion pump.

Injectable compositions of the prodrugs of this disclosure can be prepared using the conventional techniques of the pharmaceutical industry which involve dissolving and mixing the ingredients as appropriate to give the desired end product. Thus, according to one procedure, a prodrug is dissolved in an amount of water which is somewhat less than the final volume of the composition to be prepared. An isotonic agent, a preservative and/or a buffer is/are added as required and the pH value of the solution is adjusted, if necessary, using an acid, e.g., hydrochloric acid, or a base, e.g., aqueous sodium hydroxide as needed. Finally, the volume of the solution is adjusted with water to give the desired concentration of the ingredients.

In a further embodiment of this disclosure the buffer is selected from sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, acetic acid and other organic acids or their salts, or mixtures thereof. Each one of these specific buffers constitutes an alternative embodiment of this disclosure. Examples of suitable buffers are sodium acetate, glycylglycine, HEPES (4-(2-hydroxyethyl)-1-piperazineethanesulfonic acid) and sodium phosphate.

In a further embodiment of this disclosure the formulation further comprises a pharmaceutically acceptable preservative which may be selected from phenol, o-cresol, tricresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3-(4-chlorophenoxy)-1,2-propanediol) or mixtures thereof. In a further embodiment of this disclosure the preservative is present in a concentration from about 0.1 mg/ml to 20 mg/ml. In a further embodiment of this disclosure the preservative is present in a concentration from about 0.1 mg/ml to 5 mg/ml. In a further embodiment of this disclosure the preservative is present in a concentration from about 5 mg/ml to 10 mg/ml. In a further embodiment of this disclosure the preservative is present in a concentration from about 10 mg/ml to 20 mg/ml. Each one of these specific preservatives constitutes an alternative embodiment of this disclosure. The use of a preservative in pharmaceutical compositions is well-known to the skilled person. For convenience reference is made to Remington. The Science and Practice of Pharmacy, 19$^{th}$ edition, 1995.

In a further embodiment of this disclosure, the formulation further comprises an isotonic agent which may be selected from a salt (e.g., sodium chloride), a sugar or sugar alcohol, an amino acid (for example, L-glycine, L-histidine, arginine, lysine, isoleucine, aspartic acid, tryptophan or threonine), an alditol (e.g. glycerol (glycerine), 1,2-propanediol (propyleneglycol), 1,3-propanediol or 1,3-butanediol), polyethyleneglycol (e.g., PEG400) or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and sodium carboxymethylcellulose may be used. In one embodiment the sugar additive is sucrose. Sugar alcohol is defined as a C4-C8 hydrocarbon having at least one —OH group and includes, e.g., mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of this disclosure. In one embodiment, the sugar or sugar alcohol concentration is between about 1 mg/ml and about 150 mg/ml. In a further embodiment of this disclosure the isotonic agent is present in a concentration from about 1 mg/ml to 50 mg/mi. In a further embodiment of this disclosure the isotonic agent is present in a concentration from about 1 mg/ml to 7 mg/ml. In a further embodiment of this disclosure the isotonic agent is present in a concentration from about 8 mg/ml to 24 mg/ml. In a further embodiment of this disclosure the isotonic agent is present in a concentration from about 25 mg/ml to 50 mg/ml. Each one of these specific isotonic agents constitutes an alternative embodiment of this disclosure. The use of an isotonic agent in pharmaceutical compositions is well-known to the skilled person. For convenience reference is made to Remington. The Science and Practice of Pharmacy, 19$^{th}$ edition, 1995. Typical isotonic agents are sodium chloride, mannitol, dimethyl sulfone and glycerol and typical preservatives are phenol, m-cresol, methyl p-hydroxybenzoate and benzyl alcohol.

1. Prodrug of Insulin Receptor Binding Peptides

Insulin receptor binding peptides include native insulin, insulin derivatives, IGF-1 derivatives, and peptides which have at least 1% of activity of native human insulin at human insulin receptor.

"Native insulin" means mammalian insulin (e.g., human insulin, bovine insulin, or porcine insulin etc.) from natural, synthetic, or genetically engineered sources. Human insulin is comprised of a 21 amino acid A-chain GIVEQCCTSICSLYQLENYCN (SEQ ID NO: 1) and a 30 amino acid B-chain FVNQHLCGSHLVEALYLVCGERGFFYTPKT. (SEQ ID NO: 2). A chain and B chain are cross-linked by three disulfide bonds: one between A7 and B7, a second between A20 and B19, and a third between A6 and A11.

"Insulin analog" or "insulin derivative" designates a modified insulin peptide, comprising an A chain and B chain dimer, as well as single-chain insulin analogs thereof, that retains sequence homology with a native insulin. "Insulin analog" exhibits some, all or enhanced activity relative to a corresponding native insulin or is converted in vivo or in vitro into a polypeptide exhibiting some, all or enhanced activity relative to a corresponding native insulin, e.g., a polypeptide having the structure of a human insulin with one or more amino acid additions, deletions and/or substitutions. Examples of insulin analogs include insulin glargine, insulin detemir, insulin degludec, insulin lispro, insulin aspart, insulin glulisine. Proinsulins, pre-proinsulins, insulin precursors, single chain insulin precursors of humans and non-human animals, and analogs of any of the foregoing are also referred to herein as insulin analogs. Many insulin analogs are known in the art (see discussion below). Insulin analog used to prepare the insulin conjugates can be prepared by a variety of peptide synthesis techniques such as classical (solution) methods, solid phase methods, semi-synthetic methods, and recombinant DNA methods. Unless context specifically indicates otherwise (e.g., were a specific insulin is referenced, such as "human insulin" or the like), the term "insulin analog" is used broadly to include native insulins and insulin analogs.

"Single chain insulin receptor binding peptide" encompasses a group of polypeptide sequences or modified polypeptide sequences with the general structure of B chain-$C_L$-A chain, where the B chain is the B chain of insulin or a derivative thereof, the A chain is the A chain of insulin or a derivative thereof, and $C_L$ is a linker (e.g., a peptide segment) connecting the C-terminus of the B chain to the N-terminus of the A chain.

Human IGF-I is a 70 amino acid peptide consisting of 4 domains (A, B, C, D) and has a 43% homology with proinsulin (Rinderknecht et al. (1978) J. Biol. Chem. 253: 2769-2776). "IGF-1 analog" or "IGF-1 derivative" includes A chain and B chain dimers, as well as single-chain IGF-1 and IGF-1 analogs thereof, wherein the A chain comprises the peptide sequence GIVDECCFRSCDLRRLEMYCA (SEQ ID NO: 3)and the B chain comprises the sequence GPETLCGAELVDALQFVCGDRGFYFNKPT (SEQ ID NO: 4) as well as derivatives of those sequences wherein the derivative of the A chain and/or B chain comprise 1-5 further amino acid substitutions. In some cases, D domain comprising the peptide sequence PLKPAKSA (SEQ ID NO: 5) may be present and connected to the C terminal of A domain; in some cases, C domain comprising the peptide sequence GYGSSSRRAPQT (SEQ ID: 6)is present and connected to the C terminal of B domain. In one embodiment IGF-1 derivatives have amino acid substitutions at positions corresponding to positions B16, B17 of native insulin,as disclosed in WO2010/080607, WO 2011/163460, and WO 2013/086786.

In one embodiment insulin or IGF-1 A chain and B chain are connected with a linker, including a peptide linker that covalently joins the amino-terminus of the A chain to the carboxy-terminus of the B chain. In one embodiment the peptide linker comprises 4 to 12 amino acids. In accordance with one embodiment the peptide linker is 5 to 30 amino acids in length. In one embodiment the peptide linker comprises a sequence selected from GYGSSSRRAPQT (SEQ ID NO: 7), GSGSSSRRAPQT (SEQ ID NO: 8), GSGSSSAAAPQT (SEQ ID NO: 9), GAGSSSRRAPQT (SEQ ID NO: 10), GAGSSSAAAPQT (SEQ ID NO: 11), GYGSSRR (SEQ ID NO: 12), GSGSSRR (SEQ ID NO: 13), RRGPGGG (SEQ ID NO: 14), RRGGGGG (SEQ ID NO: 15), GGGGGKR (SEQ ID NO: 16), GGAPGDVKR (SEQ ID NO: 17), RRAPGDVGG (SEQ ID NO: 18), GGGPGKR SEQ ID NO: 19), GGYPGDVKR (SEQ ID NO: 20), RRYPGDVGG (SEQ ID NO: 21), GGHPGDVKR (SEQ ID NO: 22), RRHPGDVGG (SEQ ID NO: 23), and a sequence that differs from the above sequences by 1 to 3 amino acid substitutions, or 1 to 2 amino acid substitutions.

All insulin analogs and IGF-1 analogs in this disclosure have the same three properly cross-linked disulfide bridges as native insulin.

Prodrug chemistry offers the opportunity to precisely control the onset and duration of insulin action after clearance from the site of administration and equilibration in the plasma at a highly defined concentration. Insulin receptor binding prodrugs with minimal receptor binding affinity can avoid clearance by receptor mediated endocytosis and degradation. These insulin receptor binding prodrugs circulate in human plasma for prolonged period of time and undergo a spontaneous hydrolysis under physiological conditions (e.g. pH 7.0-7.6, 37° C.), gradually regenerating insulin receptor binding analogs with full biological potency. A major challenge in the development of an extra long acting insulin derivative is that a high dose of the insulin analog needs to be injected at a time to minimize the time of injections and initial high concentration of insulin in the plasma can easily lead to severe hypoglycemia. The prodrug strategy in this disclosure can effectively regulate plasma concentration of insulin by slowly releasing the active insulin binding peptide in the plama, effectively lower the risks caused by peak activities upon administration and increases the therapeutic index of the parent drug. Moreover, frequent injections of high doses of an extra long acting insulin analog using subcutaneous fatty tissue as the insulin reservoir, just as current long-acting insulin analogs and formulations, may lead to injection site irritation or other side effects. Insulin receptor binding prodrugs use blood compartment rather than injection sites as the reservoir, eliminating the variability in absorption encountered with prior art delayed onset insulin derivatives. Prodrug chemistry also enables administration of the insulin derivative by routes other than a subcutaneous injection.

Human insulin possesses three free amino groups: B1-Phenylalanine, A1-Glycine, and B29-Lysine. The promoiety can be linked via an amide bond to an amino group present on the insulin or IGF-1 analog, or an amino group introduced into an insulin receptor binding peptides at or near the active site by modification of the peptide sequence. The amino group provides a handle for covalent attachment of a promoiety.

In some embodiments, the prodrug of an insulin receptor binding peptide can be conjugated to a modifying moiety which has the general formula: -L-M, wherein L and M are defined above in this disclosure. In some embodiments, a modifying moiety is conjugated to a prodrug through a promoiety. In some embodiments a modifying moiety is conjugated directly to a prodrug and at least one promoiety is covalently bound to the prodrug at another active site. In both cases covalent attachment of the promoiety to an active site of the insulin receptor binding peptide inhibits the activity of the polypeptide until cleavage of the promoiety.

In some embodiments, a modifying moiety can be conjugated optionally via a linker to either the N-terminus amino acid of the A chain or B chain, or to the side chain of an internal amino acid (e.g., ε-amino group of a lysine, hydroxyl group of a serine or threonine), or the C terminus of the a chain or B chain (e.g. B28, B29, or B30) through a promoiety. A thiol containing moiety such as cysteine or an amino containing moiety such as lysine can be introduced into an insulin derivative. In one embodiment the amino acid at the C-terminus of B chain is a cysteine or lysine. In another embodiment, C-terminus of A chain or B chain is extended by 1, 2, 3, 4, 5, 6, 7, 8, 9, 10, 11, 12, 13, 14, 15 or more amino acids where the side chain of an added cysteine or lysine is used for conjugation. In one embodiment a linker peptide connecting N terminus of A chain and C terminus of B chain contains a cysteine or lysine residue for conjugation. In one embodiment the modifying moiety is a plasma protein, PEG, the Fe portion of an immunoglobin, or a long chain fatty acid. In one embodiment the presently disclosed prodrugs are further modified to comprise one or more modifying moieties covalently linked to the side chains of amino acids of the peptide.

In accordance with some embodiments, insulin receptor binding peptides are modified by amino acid substitutions, wherein the substituting amino acid comprises a side chain suitable for conjugation. In one embodiment an amino acid at a position selected from A-1, A0, A1, A4, A5, A8, A9, A10, A12, A14, A15, A17, A18, A19, A21, A22, B1, B2, B3, B4, B5, B9, B10, B13, B14, B16, B17, B20, B21, B22, B23, B26, B27, B28, B29 and B30, B31, B32 is substituted with a moiety comprising a side chain $NH_2$, SH, OH, or COOH for conjugation of a modifying moiety or a promoiety. In one embodiment such moieties include but are not limited to lysine, homolysine, 2,2-diaminoacetic acid, 2,3-diaminopropanoic acid, 2,4-diaminobutanoic acid, 2,5-diaminopetanoic acid, cysteine, homocysteine, 2-amino-5-mercaptopentanoic acid, 2-amino-6-mercaptohexanoic acid, ornithine, serine, aspartic acid, and glutamic acid. In one embodiment, an insulin receptor binding peptide includes amino acid substitutions at positions selected from A5, A8, A9, A10, A14, A15, A17, A18, A19 and A21, B1, B2, B3, B4, B5, B9, B10, B13, B14, B17, B20, B22, B23, B26, B27, B28, B29 and B30 or deletions of any or all of positions B1-4 and B26-30.

In some embodiments insulin receptor binding peptides are modified to comprise an acyl group by acylation of an amine, hydroxyl, or thiol of a spacer which is attached to a side chain of an amino acid. The amino acid to which the spacer is attached can be any amino acid comprising a moiety which permits linkage to the spacer. For example, an amino acid comprising a side chain $NH_2$, OH, or COOH (e.g., Lys, Orn, Ser, Asp, or Glu) is suitable. In one embodiment, the spacer is an amino acid comprising a side chain amine, hydroxyl, or thiol, or a peptide comprising an amino acid comprising a side chain amine, hydroxyl, or thiol.

Insulin probably changes its conformation upon binding to the insulin receptor. The single chain insulin precursor miniproinsulin, in which LysB29 is coupled directly to GlyA1 via a peptide bond, crystallizes into conformations identical to those of native human insulin. However, the in vitro potency of miniproinsulin is less than 0.1% of that of insulin, probably due to conformational restrictions in this molecule and loss of the free amino group of GlyA1. Other insulin analogues with conformational restrictions (e.g. chemically cross-linked between B29 and A1) have also been shown to exhibit low affinity for the insulin receptor.

In some embodiments the promoiety cross-links between the α-amino group of GlyA1 of the A-chain and the α-COOH group or the side chain carboxylic acid of an amino acid at the C-terminal of B chain, or between the α-amino group of GlyA1 of the A-chain and the ε-amino group of Lysine located at the carboxy terminus of the B chain (e.g., α-GlyA1/ε-LysB29, des B30 human insulin), which decreases markedly the receptor binding potencies of the corresponding analogs.

In some embodiments the promoiety cross-links between the α-amino group of GlyA1 of the A-chain and the side chain of A8, or A9, A10, A14, or A15, wherein an original amino acids at those positions are substituted by a natural or an unnatural amino acid having a COOH or $NH_2$ on its side chain. Examples include, but not limited to, lysine, ornithine, glutamic acid, and aspartic acid.

In some embodiments the promoiety cross-links between the α-amino group of GlyA1 and the C terminus α-COOH of A-chain AsnA21.

In accordance with some embodiments a prodrug derivative of an insulin receptor binding analog comprises a modified A chain and B chain, wherein the A chain comprises a sequence of $Z\text{-}X_{-1}X_0X_1IVX_4X_5CCX_8X_9X_{10}CX_{12}LX_{14}X_{15}LEX_{18}YCX_{21}X_{22}$ (SEQ ID NO: 24)and the B chain comprises a sequence of $J\text{-}X_{23\text{-}26}X_{27}LCGX_{31}X_{32}LVX_{35}X_{36}LX_{38}X_{39}VCX_{42}X_{43}X_{44}GX_{46}X_{47}X_{48}X_{49}X_{50}X_{51}X_{52}X_{53}$ (SEQ ID NO 25); Z and J are independently hydrogen (H) or comprise the general structure wherein X, Y, $Y_1$, A, B, and $J_1$ are the same as defined above:

In some embodiments Z and J are independently hydrogen (H) or comprise the general structure wherein $Z_1$-$Z_5$ are the same as defined above:

In some embodiments $J_1$ is $C(R_{10}R_{11})$ or a covalent bond wherein $R_{10}$ and $R_{11}$ are the same as defined above.

In some embodiments $J_1$ is $C(R_{10}R_{11})$, Y is C—$R_pR_q$, and Z and J are independently hydrogen (H) or comprise the general structure wherein $R_p$ and $R_q$ are the same as defined above:

In some embodiments Z and J are independently hydrogen (H) or comprise the general structure wherein $U_1$-$U_6$, X, Y, $Y_1$, and $J_1$ are the same as defined above:

In some embodiments $J_1$ is a covalent bond, $Y_1$ is C—$R_3R_4$ wherein $R_3$ and $R_4$ are the same as defined above.

In some embodiments $J_1$ is a covalent bond, $Y_1$ is $C(R_3R_4)$, Y is $C(R_pR_q)$, wherein $R_p$ and $R_q$ are the same as defined above.

In some embodiments Z and J are independently hydrogen (H) or comprise the general structure wherein $R_5$-$R_8$ are the same as defined above:

In some embodiments $J_1$ is a covalent, and $Y_1$ is covalent bond.

In some embodiments $J_1$ is a covalent bond, $Y_1$ is covalent bond, and Y is C—$R_pR_q$.

In some embodiments Z and J are independently hydrogen (H) or comprise the general structure:

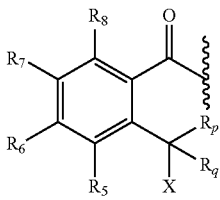

In some embodiments J is hydrogen (H) or comprise the general structure:

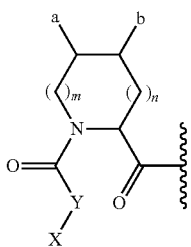

In some embodiments J is hydrogen (H) or comprise the general structure:

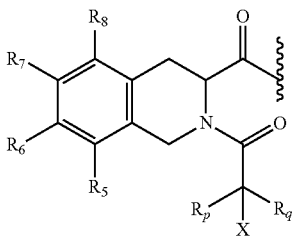

In some embodiments X is OH, $NH_2$, or HN—$R_0$;
In some embodiments X is OH;
In some embodiments X is $NH_2$, or HN—$R_0$.
In some embodiments X is $NH_2$.
$X_1$ is lysine, arginine, or deleted;
$X_0$ is lysine, arginine, or deleted;
$X_1$ is selected from sarcosine, D-alanine, D-leucine, D-lysine, D-glutamic acid, D-tryptophan, p-benzoyl-L-phenylalanine (Bpa), glycine;
$X_4$ is aspartic acid or glutamic acid;
$X_5$ is aspartic acid, glutamic acid, asparagine, glutamine;
$X_8$ is selected from 2,4-diaminobutyric acid (DAB), leucine, isoleucine, threonine, histidine, arginine, lysine, asparagine, glutamine, tryptophan, tyrosine, alanine, phenylalanine, valine, methionine;
$X_9$ is alanine, serine, arginine, or lysine;
$X_{10}$ is isoleucine, serine, lysine, or arginine;
$X_{12}$ is aspartic acid or serine;
$X_{14}$ is tyrosine, phenylalanine, tryptophan, arginine, alanine, glutamic acid, histidine, or lysine;
$X_{15}$ is glutamine, leucine, arginine, or lysine;
$X_{18}$ is asparagine, methionine, or threonine;
$X_{21}$ is asparagine, aspartic acid, alanine, glycine, lysine, or arginine;
$X_{22}$ is lysine, or arginine, lysine-lysine dipeptide, arginine-arginine dipeptide, or deleted;
$X_{23-26}$ is any codable amino acid except cysteine, a dipeptide or tripeptide comprising no cysteine, a tripeptide GPE, a tetrapeptide FVNQ (SEQ ID NO: 26), or deleted;

$X_{27}$ is histidine, threonine, arginine, or lysine;
$X_{31}$ is selected from threonine, alanine, serine, glycine, or α-aminoisobutyric acid;
$X_{32}$ is selected from histidine, aspartic acid, glutamic acid, homoglutamic acid, homocysteic acid, cysteic acid, arginine, phenylalanine;
$X_{35}$ is glutamic acid or aspartic acid;
$X_{36}$ is alanine, threonine, or α-aminoisobutyric acid;
$X_{38}$ is selected from tyrosine, phenylalanine, tryptophan;
$X_{39}$ is phenylalanine, tryptophan, or leucine;
$X_{42}$ is glycine, or alanine;
$X_{43}$ is glutamic acid, aspartic acid, or alanine;
$X_{44}$ is selected from arginine, lysine, aspartic acid, glutamic acid, alanine;
$X_{46}$ is selected from phenylalaine, D-phenylalaine, D-tyrosine, D-alanine, glycine;
$X_{47}$ is selected from tyrosine, phenylalanine, asparagine, histidine;
$X_{48}$ is selected from tyrosine, D-tyrosine, phenylalanine, alanine, serine, histidine, D-alanine, D-tyrosine, glutamic acid, sarcosine, or deleted;
$X_{49}$ is selected from threonine, asparagine, arginine, glutamic acid, aspartic acid, lysine, serine, proline, or deleted;
$X_{50}$ is selected from proline, arginine, lysine, orthonine, glutamic acid, aspartic acid, or deleted;
$X_{51}$ is selected from proline, lysine, glutamic acid, aspartic acid, or deleted;
$X_{52}$ is threonine, alanine, glutamic acid, aspartic acid, or deleted;
$X_{53}$ is an arginine-arginine dipeptide, glutamic acid-glutamic acid dipeptide, aspartic acid-aspartic acid dipeptide, or deleted;

In accordance with some embodiments a single-chain insulin receptor binding prodrug is provided wherein the C terminus of the B chain, or a functional analog thereof, is covalently linked to the N terminus of the A chain, or functional analog thereof, and further wherein a promoiety is covalently bound at the N terminus of the peptide, C terminus of the peptide, or at the side chain of an amino acid via an amide bond. In accordance with one embodiment the single-chain insulin receptor binding peptide comprises a compound of the formula: B-$L_i$-A, wherein: B represents the B chain of insulin receptor binding peptide or one of the functional or prodrug analogs of a B chain as disclosed herein, A represents the A chain of insulin receptor binding peptide or one of the functional or prodrug analogs of an A chain as disclosed herein, and $L_i$ represents a linker covalently joining the A chain to the B chain. In one embodiment the linker is a peptide linker of about 5 to about 30, or about 10 to about 15, or about 4 to about 8 amino acids. In one embodiment the peptide linker of the single chain analog is selected from the above linker sequences or a sequence that differs from the above linker sequences by 1 to 3 amino acid substitutions, or 1 to 2 amino acid substitutions. Optionally, the linker of the single chain analogs can also serve as a site for the attachment of the promoiety. In one embodiment the linker is a peptide that comprises an amino acid having a side chain group suitable for attaching the promoiety of the present disclosure via an amide linkage.

In accordance with one embodiment single-chain insulin receptor binding prodrugs are provided. In this embodiment the α-amino group of N terminus of the A-chain, or a functional analog, is covalently linked to the C terminus of the B chain, or a functional analog thereof, via a promoiety. In one embodiment, the single chain insulin receptor binding prodrug has the sequence J-$X_{23-26}$ $X_{27}LCGX_{31}X_{32}LVEX_{36}LX_{38}X_{39}VCX_{42}X_{43}X_{44}GX_{46}X_{47}$ X₄₈X₄₉X₅₀X₅₁X₅₂X₅₃-U-X₋₁
X₀X₁IVX₄X₅CCX₈X₉X₁₀CSLX₁₄X₁₅LEX₁₈YCX₂₁X₂₂
(SEQ ID NO: 27), wherein U has the general structure as defined above.

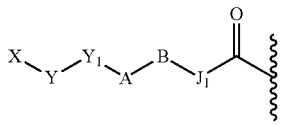

In some embodiments Z and J are independently hydrogen (H) or comprise the general structure:

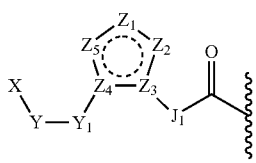

In some embodiments $J_1$ is $C(R_{10}R_{11})$ or a covalent bond between $Z_3$ and C(O)NH-insulin.

In some embodiments $J_1$ is $C(R_{10}R_{11})$, Y is $C-R_pR_q$, and Z and J are independently hydrogen (H) or comprise the general structure:

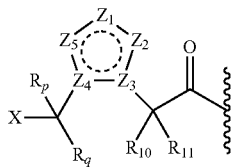

In some embodiments Z and J are independently hydrogen (H) or comprise the general structure:

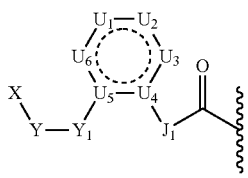

In some embodiments $J_1$ is a covalent bond and $Y_1$ is $C(R_3R_4)$.

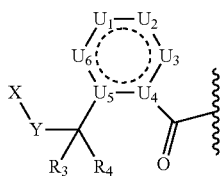

In some embodiments $J_1$ is a covalent bond and $Y_1$ is $C(R_3R_4)$, Y is $C(R_pR_q)$.

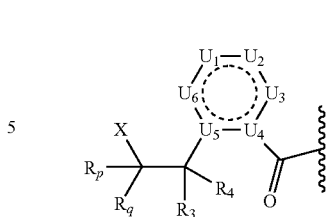

In some embodiments Z and J are independently hydrogen (H) or comprise the general structure:

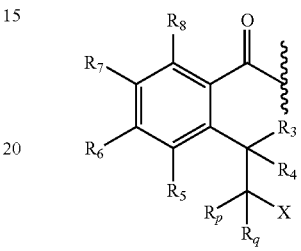

In some embodiments $J_1$ is a covalent bond and $Y_1$ is covalent bond.

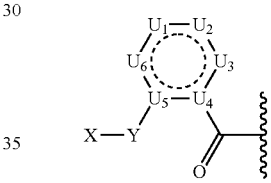

In some embodiments $J_1$ is a covalent bond, $Y_1$ is covalent bond, and Y is $C-R_pR_q$.

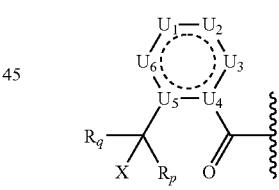

In some embodiments Z and J are independently hydrogen (H) or comprise the general structure:

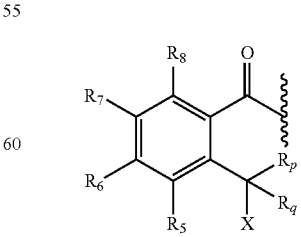

In some embodiments, J is hydrogen (H) or comprise the general structure:

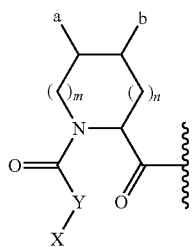

In some embodiments, J is hydrogen (H) or comprise the general structure:

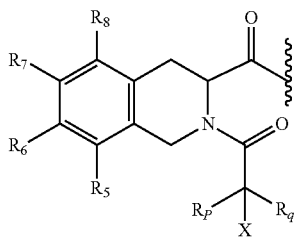

Wherein at least one substituent among $R_p$, $R_q$, $R_3$, $R_4$, $R_5$, $R_6$, $R_7$, $R_8$, or at least one substituent among $R_p$, $R_q$, $R_{10}$, $R_{11}$, $R_{12}$ and $R_{13}$ has an amino group which can form an amide bond with a carboxyl group at the C terminal of the B chain. U also has a carboxyl group which can form an amide bond with an amino group at the N terminal of the A chain.

In some embodiments, U has the structure

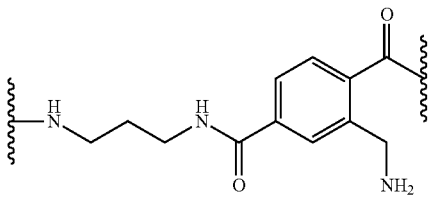 [SMILES: *NCCCNC(=O)c1ccc(C(*)=O)c(CN)c1]

In some embodiments, U has the structure

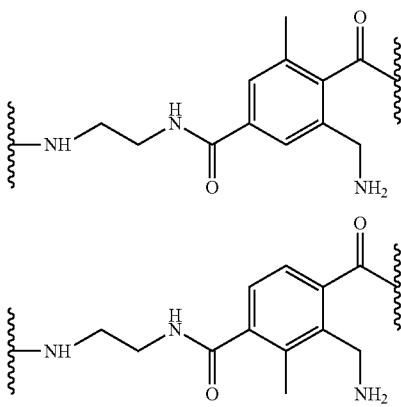

-continued

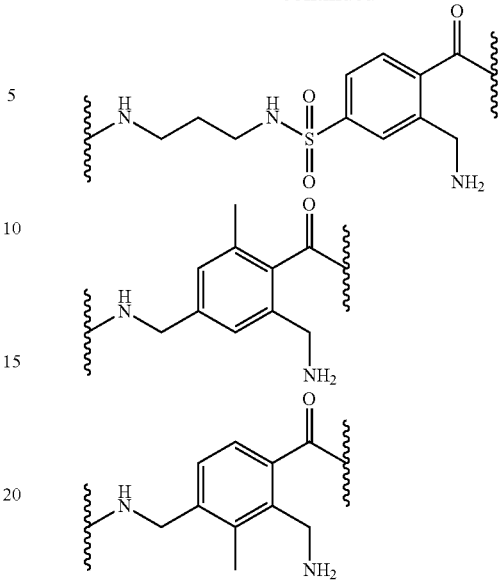

In some embodiments an insulin receptor binding peptide comprises an A chain having the sequence of Z-GIVEQCC$X_8$SICSLYQLENYC$X_{21}$ (SEQ ID NO: 28) (and a B chain having the sequence J-$X_{23\text{-}26}$HLCGSHLVEALYLVCGERGF$X_{47}X_{48}X_{49}X_{50}X_{51}X_{52}X_{53}$ (SEQ ID NO: 29)

In some embodiments an insulin receptor binding peptide comprises an A chain having the sequence of Z-GIVEQCCTSICSLYQLENYC$X_{21}$ (SEQ ID NO: 30)

In some embodiments an insulin receptor binding peptide comprises a B chain having the sequence J-$X_{23\text{-}26}$HLCGSHLVEALYLVCGERGFFYT$X_{50}X_{51}X_{52}$ (SEQ ID NO: 31)

In some embodiments an insulin receptor binding peptide comprises a B chain having the sequence J-FVNQHLCGSHLVEALYLVCGERGFFYT$X_{50}X_{51}X_{52}$ (SEQ ID NO: 32).

In some embodiments an insulin receptor binding peptide comprises a B chain having the sequence J-FVNQHLCGSHLVEALYLVCGERGFFYTPKT (SEQ ID NO: 33).

In some embodiments an insulin receptor binding peptide comprises a B chain having the sequence J-FVNQHLCGSHLVEALYLVCGERGFFYTKPT (SEQ ID NO: 34).

In some embodiments an insulin receptor binding peptide comprises a B chain having the sequence J-FVNQHLCGSHLVEALYLVCGERGFF-$NH_2$ (SEQ ID NO; 35).

In some embodiments an insulin receptor binding peptide comprises an A chain having the sequence of Z-GIVD$X_5$CC$X_8$RSC$X_{12}$LRRLE $X_{18}$YC$X_{21}$ (SEQ ID NO: 36) and a B chain having the sequence J-$X_{23\text{-}26}X_{27}$LCGA$X_{32}$LVDAL$X_{38}X_{39}$VCGDRGF$X_{47}X_{48}X_{49}X_{50}X_{51}X_{52}X_{53}$ (SEQ ID NO: 37).

In some embodiments an insulin receptor binding peptide comprised a B chain having the sequence J-$X_{23\text{-}26}X_{27}$LCGA$X_{32}$LVDAL$X_{38}X_{39}$VCGDRGFYFN$X_{50}X_{51}X_{52}$ (SEQ ID NO: 38).

In some embodiments an insulin receptor binding peptide comprised a B chain having the sequence J-$X_{23\text{-}26}X_{27}$LCGA$X_{32}$LVDALYLVCGDRGFYFN$X_{50}X_{51}X_{52}$ (SEQ ID NO: 39).

In some embodiments an insulin receptor binding peptide comprised a B chain having the sequence J-GPE$X_{27}$LCGAHLVDALYLVCGDRGFYFN$X_{50}X_{51}X_{52}$ (SEQ ID NO: 40).

In some embodiments an insulin receptor binding peptide comprised a B chain having the sequence J-GPEX$_{27}$LCGAHLVDALFFVCGDRGFYFNX$_{50}$X$_{51}$X$_{52}$ (SEQ ID NO: 41).

In some embodiments an insulin receptor binding peptide comprised a B chain having the sequence J-X$_{23-26}$X$_{27}$LCGAX$_{32}$LVDALX$_{38}$X$_{39}$VCGDRGFY-NH$_2$(SEQ ID NO: 42).

In some embodiments, Z or J can be conjugated to a modifying moiety which has the general formula: -L-M, wherein L and M are defined above in this disclosure.

In some embodiments the conjugate of an insulin receptor binding peptide prodrug is of the formula M-L-promoiety-insulin receptor binding peptide, wherein M-L-promoiety-promoiety can be linked to N-terminus amino acid of the peptide, or to the side chain of an internal amino acid (e.g., ε-amino group of a lysine, hydroxyl group of a serine or threonine). In some embodiments, the modifying moiety is a PEG or a fatty acid.

In some embodiments an insulin receptor binding peptide prodrug is of the formula M$_r$-L-promoiety-insulin receptor binding peptide, wherein L and M$_r$ are defined above in this disclosure. An illustrative, non-limiting example is as follows

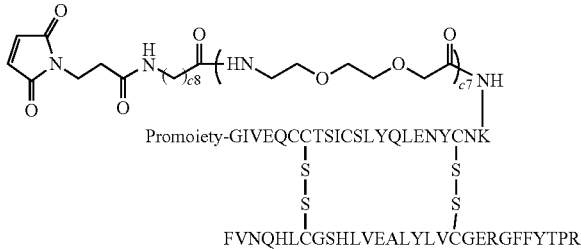

wherein c7 is an integer in the range from 1 to 8, and c8 is an integer in the range from 1 to 30.

In some embodiments the ex vivo albumin conjugate of an insulin receptor binding peptide prodrug is of the formula promoiety-insulin receptor binding peptide-L-M$_{r'}$-alb, wherein L, M$_{r'}$ and alb are defined above in this disclosure (SEQ ID NOS 43-44, respectively, in order of appearance).

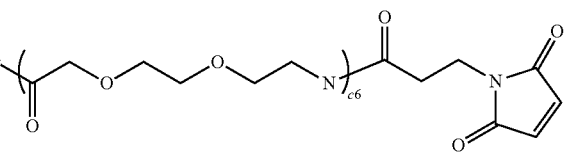

wherein c6 is an integer in the range from 1 to 8.

In some embodiments the ex vivo albumin conjugate of an insulin receptor binding peptide prodrug is of the formula alb-M$_{r'}$-L-promoiety-insulin receptor binding peptide, wherein L, M$_{r'}$ and alb are defined above in this disclosure.

In some embodiments the conjugate of an insulin receptor binding peptide prodrug is of the formula promoiety-insulin receptor binding peptide-L-M, wherein the promoiety can be linked to N-terminus amino acid of the peptide, or to the side chain of an internal amino acid (e.g., ε-amino group of a lysine, hydroxyl group of a serine or threonine); -L-M can be conjugated to the side chain of an internal amino acid (e.g., ε-amino group of a lysine, or thiol group of a cysteine) at a different site, or the C-terminus section of A chain or B chain. In one embodiment, the conjugate sites include ε-amino group of a lysine or thiol group of a cysteine at the N-terminus of B chain or positions X$_{22}$, X$_{48}$, X$_{49}$, X$_{50}$, X$_{51}$, X$_{52}$, or X$_{53}$, originally present or introduced after substitution or insertion. In one embodiment, the modifying moiety is a PEG or a fatty acid.

In some embodiments an insulin receptor binding peptide prodrug is of the formula promoiety-insulin receptor binding peptide-L-M$_r$. Insulin receptor binding peptides and linkers disclosed in US 20110039769 may be used in connection with a promoiety provided in this disclosure. An illustrative, non-limiting example is as follows (SEQ ID NOS 43-44, respectively, in order of appearance):

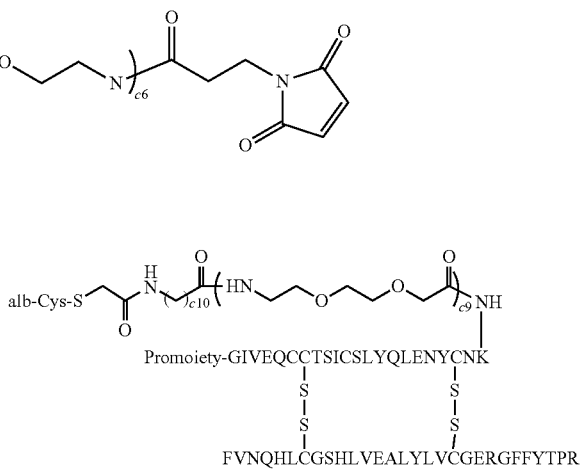

Wherein c9 is an integer in the range from 1 to 8, and c10 is an integer in the range from 1 to 30.

Prodrug of GLP-1 Receptor Binding Peptides

Glucagon-like peptide-1 (GLP-1) induces numerous biological effects such as stimulating insulin secretion, inhibiting glucagon secretion, inhibiting gastric emptying, inhibiting gastric motility or intestinal motility, enhancing glucose utilization, and inducing weight loss. GLP-1 may further act to prevent the pancreatic β-cell deterioration that occurs as non-insulin dependent diabetes mellitus (NIDDM) progresses. A significant characteristic of GLP-1 is its ability to stimulate insulin secretion without the associated risk of hypoglycemia that is seen when using insulin therapy or some types of oral therapies that act by increasing insulin expression.

The usefulness of therapy involving GLP-1 peptides has been limited by the fact that GLP-1(1-37) is poorly active, and the two naturally occurring truncated peptides, GLP-1(7-37)-OH and GLP-1(7-36)-NH$_2$, are rapidly cleared in vivo and have extremely short in vivo half lives. It is known that endogenously produced dipeptidyl-peptidase IV (DPP-IV) inactivates circulating GLP-1 peptides by removing the N-terminal histidine and alanine residues and is a major reason for the short in vivo half-life.

GLP-1(7-36)-NH$_2$ comprises the amino acid sequence HAEGTFTSDVSSYLEGQAAKEFIAWLVKGR-NH$_2$ (SEQ ID NO: 45)

The amino acid residues 7-21 in GLP-1 (7-36)-NH$_2$ are essential for receptor binding, though the full length sequence can play a concerted role. In addition to the skeleton of the long amino acid chain, the side chains on the amino acid residues at positions 7 (histidine), 10 (glycine), 12 (phenylalanine), 13 (threonine) and 15 (aspartic acid) are directly involved in interaction with the receptor. Furthermore, the amino acid residues at positions 28 (phenylalanine) and 29 (isoleucine) are very critical for GLP-1 to form a conformation that can be recognized by the receptor. Some studies have demonstrated that the amino acid residues at positions 10 (glycine), 15 (aspartic acid) and 17 (serine) in the sequence as well as the C-terminus of the sequence are very important for insulinotropic effect of GLP-1. Amidation at the C-terminus and the last amino acid residue at C-terminus are also helpful.

"GLP-1 analogue" or "GLP-1 derivative" is defined as the one in which one or more of amino acid residues of GLP-1 (1-37)-OH are deleted or substituted with other amino acid residues, or the one of which one or more of amino acid residues are inserted into the original polypeptide sequence. In a preferred embodiment, total number of amino acid residues that are different between the GLP-1 analogues and the corresponding GLP-1(1-37)-OH is no more than 20, or no more than 15, 10, 5, 4, 3, or 2, and most preferably is 1. GLP-1 analogues may be truncated fragments of GLP-1(1-37). "GLP-1 fragment" or "fragment of a GLP-1 compound" as used herein, is a biologically active polypeptide obtained after truncation of one or more amino acids from the N-terminus and/or C-terminus of a GLP-1 receptor binding peptide. GLP-1 analogues may also be sequences obtained by extending from the N-or C-terminus of GLP-1. In certain embodiments, GLP-1 analogues comprise an extension of 1-20 of amino acids at the C-terminus. In one embodiment, the sequence extending from the C-terminus is a PSSGAP-PPS-NH$_2$ (SEQ ID NO: 46) or GPSSGAPPPS-NH$_2$ (SEQ ID NO: 47). In one embodiment, C-terminal extension comprises 1-6 of positively charged amino acids, such as arginine or lysine. In one embodiment, C-terminal extension comprises 1-6 of negatively charged amino acids, such as glutamic acid or aspartic acid. In certain embodiments, the GLP-1 analogues may be a modified product, such as a product subjected to alkyl substitution, acylation, polyethylene glycol modification, etc.

In some embodiments a GLP-1 derivative has the amino acid sequence of GLP-1(7-36)-NH$_2$, GLP-1(7-37)-OH or an extended GLP-1 peptide as described in U.S. Patent Application Ser. No. 60/346,474 or 60/405,097 published as WO/2003/058203, both entitled "Extended Glucagon-Like Peptide-1 Analogs" or a fragment thereof modified so that 1, 2, 3, 4, 5 6, 7, 8, 9, 10 amino acids differ from the amino acid in the corresponding position of GLP-1(7-37)-OH or a fragment of GLP-1(7-37)-OH or modified so that 1, 2, 3, 4, 5, 6, 7, 8, 9, 10 amino acids differ from the amino acid in the corresponding position of an extended GLP-1 peptide, including substitutions and modifications at one or more positions 11, 12, 16, 22, 23, 24, 25, 26, 27, 30, 33, 34, 35, 36, 37. Positions 18, 20, 23, 30, 31, 34, 36, 37 or C terminus of these peptide can be used for conjugation to modifying moieties.

The nomenclature used to describe GLP-1 (7-37)-OH applies to GLP-1 analogs. The amino acids in these analogs are denoted by the same number as the corresponding amino acid in GLP-1(7-37)-OH. For example, the N-terminal glutamic acid in GLP-1(9-36)-OH is at position 9; position 12 is phenylalanine; and position 22 is glycine, as in GLP-1 (7-37)-OH.

Exendin-4 consists of 39 amino acids and has a sequence homology of up to 53% with GLP-1 and the identical biological function. The sequence thereof is HGEGTFTS-DLSKQMEEEAVRLFIEWLKNGGPSSGAPPPS-NH$_2$ (SEQ ID NO: 48).

"Exendin-4 derivative" is defined as the one in which one or more of the amino acid residues of Exendin-4 are deleted or substituted with other amino acid residues, or the one of which one or more of amino acid residues are inserted into the original polypeptide sequence. In a preferred embodiment, total number of amino acid residues that are different between the exendin-4 analogue and exendin-4 may be not more than 15, 10, 5, 4, 3, and 2, most preferably be 1. For consistency the amino acids in these analogs are denoted by the same number as the corresponding amino acid in GLP-1(7-37)-OH. For example, the N-terminal histidine in exendin-4 is at position 7. Exendin-4 derivatives may be truncated fragments of exendin-4 such as exendin-4 (7-34)-NH$_2$, exendin-4 (7-36), exendin-4 (7-36)-NH$_2$, leucine 20, phenylalanine 31-exendin-4(7-34)-NH$_2$, leucine 20, alanine 28, phenylalanine 31-exendin-4 (7-34)-NH$_2$.

The present disclosure comprises the sequences extending from C-terminus of exendin-4. In one embodiment, C-terminal extension comprises 1-6 of positively charged amino acids such as arginine or lysine. In one embodiment, C-terminal extension comprises 1-6 of negatively charged amino acids such as glutamic acid or aspartic acid. In certain embodiments, an exendin-4 derivative may be a modified product (e.g., a product subjected to alkyl substitution, acylation, polyethylene glycol modification, etc).

The term "GLP-1 receptor binding peptide" as used herein, includes native GLP-1 [GLP-1(7-37)-OH or GLP-1 (7-36)-NH$_2$], GLP-1 derivatives, biologically active GLP-1 fragments, extended GLP-1 or an derivative or fragment of an extended GLP-1 peptide (see, e.g., WO 03/058203), exendin-4, exendin-4 derivatives, and exendin-4 fragments. Other exemplary GLP-1 receptor binding peptides include liraglutide, albiglutide, taspoglutide, lixisenatide, and dulaglutide.

GLP-1 receptor binding peptides include peptides and peptide derivatives whose binding affinity for GLP-1 receptor is 1%, 5%, 10%, 20%, 30%, 40%, 50%, 60%, 70%, 80%, 90%, or over 100% of GLP-1(7-36)-NH$_2$. Preferably a GLP receptor binding peptides comprise an amino acid sequence that is at least about 40%, 45%, 50%, 55%, 60%, 65%, 70%, 75%, 80%, 85%, 90%, or 95% identical to the corresponding sequence of native exendin-4 or native GLP-1(7-37)-OH. GLP-1 receptor binding peptides include GLP-1 receptor agonists, GLP-1 receptor antagonists, GLP-1 receptor and glucagon receptor coagonists, GLP-1 receptor and GIP receptor coagonists, GLP-1 receptor agonist and glucagon antagonist chimera as well as derivatives of these peptides. Examples include but not limited to, WO97/46584, WO 98/05351, WO 99/07404, WO 99/24210, WO 99/25727, WO 99/25728, WO 99/40788, WO 99/043708, WO 00/41546, WO 00/41548, WO/2002/048192, WO/2003/011892, WO/2003/011892, WO/2003/018516, WO/2003/103572, WO/2004/022004, WO/2004/093823, WO/2005/058954, WO/2006/124529, WO/2006/134340, WO/2007/030519, WO/2007/124461, WO/2008/023050, WO/2008/101017, WO/2009/058662, WO/2009/058734, WO/2009/155257, WO/2009/155258, WO/2010/070253, WO/2010/

070255, WO 2010011439, WO/2011/073328, WO/2011/075393, WO/2011/080102, WO 2011143208, WO 2012088379, WO/2013/002580, WO/2013/164483, WO/2013/186240, WO/2014/0213513, U.S. Pat. Nos. 7,235,627, 7,691,963, 7,407,932, 8,030,273, 5,424,286 A, EP2322545, EP 2322546, CN200710138718.7, CN200910135363.5. In accordance with some embodiments a promoiety can be attached via an amide linkage to any of the bioactive peptides disclosed in those patent applications either through the N-terminal amine or to the side chain amino group of a lysine.

By custom in the art, the amino terminus of native GLP-1(7-37)-OH has been assigned residue number 7 and the carboxy-terminus, number 37. The other amino acids in the peptide are numbered consecutively. For example, position 12 is phenylalanine and position 22 is glycine in the native molecule.

In some embodiments the prodrug of a GLP-1 receptor binding peptide can be conjugated to a modifying moiety which has the general formula: -L-M, wherein L and M are defined above in this disclosure. In one embodiment, a modifying moiety is conjugated to a prodrug through a promoiety. In another embodiment a modifying moiety is conjugated directly to a prodrug and at least one promoiety is covalently bound to the prodrug at another active site. In both cases covalent attachment of the promoiety to an active site of the GLP-1 receptor binding peptide inhibits the activity of the polypeptide until cleavage of the promoiety.

In some embodiments, a modifying moiety can be conjugated optionally via a linker to either the N-terminus amino acid of the peptide, or to the side chain of an internal amino acid (e.g., ε-amino group of a lysine, hydroxyl group of a serine or threonine). A thiol containing moiety such as cysteine or an amino containing moiety such as lysine can be introduced into a GLP-1 derivative. In one embodiment the C-terminus section of a GLP-1 receptor binding peptide contains a lysine or a cysteine for conjugation. In another embodiment, C-terminus of a GLP-1 receptor binding peptide is extended by 1, 2, 3, 4, 5, 6, 7, 8, 9, 10, 11, 12, 13, 14, 15 or more amino acids where the side chain of an added cysteine or lysine is used for conjugation. In one embodiment the modifying moiety is a plasma protein, PEG, the Fc portion of an immunoglobin, or a long chain fatty acid. In one embodiment the presently disclosed prodrugs are further modified to comprise one or more modifying moieties covalently linked to the side chains of amino acids of the peptide.

In accordance with some embodiments a GLP-1 receptor binding peptide prodrugs has the sequence J-Xg$_7$Xg$_8$Xg$_9$GTXg$_{12}$TSDXg$_{16}$SXg$_{18}$Xg$_{19}$Xg$_{20}$EXg$_{22}$Xg$_{23}$Xg$_{24}$Xg$_{25}$Xg$_{26}$Xg$_{27}$FXg$_{29}$Xg$_{30}$WLXg$_{33}$Xg$_{34}$Xg$_{35}$Xg$_{36}$Xg$_{37}$Xg$_{38}$Xg$_{39}$Xg$_{40}$Xg$_{41}$Xg$_{42}$Xg$_{43}$Xg$_{44}$Xg$_{45}$Xg$_{46}$Xg$_{47}$Xg$_{48}$Xg$_{49}$ (SEQ ID NO: 49), wherein J is hydrogen (H) or has the general structure as defined above:

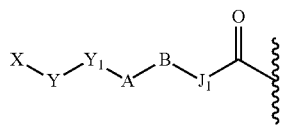

In some embodiments J is hydrogen (H) or has the following structures:

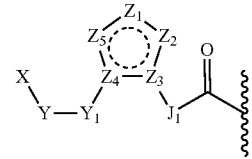

In some embodiments $J_1$ is $C(R_{10}R_{11})$ or a covalent bond between $Z_3$ and C(O)NH-insulin, In some embodiments $J_1$ is $C(R_{10}R_{11})$, Y is C—$R_pR_q$, and J is hydrogen (H) or comprise the general structure:

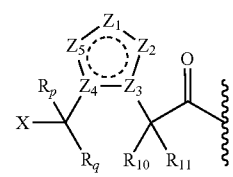

In some embodiments J is hydrogen (H) or comprise the general structure:

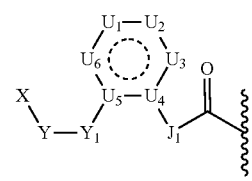

In some embodiments, $J_1$ is a covalent bond, $Y_1$ is C—$R_3R_4$.

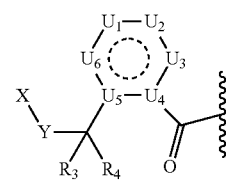

In some embodiments $J_1$ is a covalent bond, $Y_1$ is C—$R_3R_4$, and Y is C—$R_pR_q$.

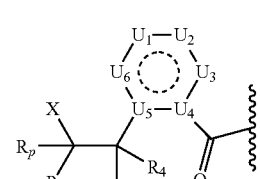

In some embodiments J is hydrogen (H) or comprise the general structure:

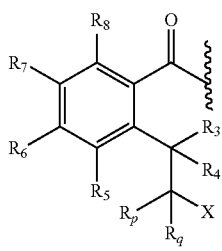

In some embodiments $J_1$ is a covalent bond and $Y_1$ is covalent bond.

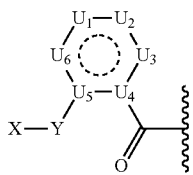

In some embodiments $J_1$ is a covalent bond, $Y_1$ is covalent bond, and Y is C—$R_p R_q$.

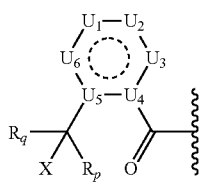

In some embodiments J is hydrogen (H) or comprise the general structure:

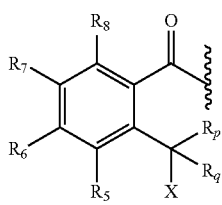

In some embodiments J is hydrogen (H) or comprise the general structure:

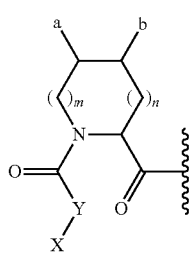

In some embodiments J is hydrogen (H) or comprise the general structure:

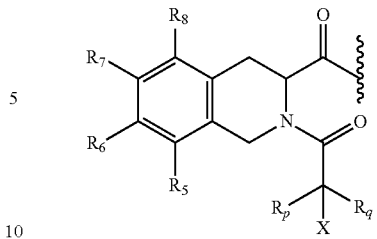

In some embodiments X is OH, $NH_2$, or HN—$R_0$;
In some embodiments X is OH;
In some embodiments X is $NH_2$, or HN—$R_0$.
In some embodiments X is $NH_2$.

$Xg_7$ is selected from L-histidine, D-histidine, desamino-histidine, 2-amino-histidine, β-hydroxy-histidine, homohistidine, α-fluoromethyl-histidine, α-methyl-histidine, imidazopropionyl, arginine, or tyrosine;

$Xg_8$ is serine, D-serine, alanine, glycine, 2-aminoisobutyric acid, or valine;

$Xg_9$ is glutamic acid, glutamine, or proline;

$Xg_{12}$ is phenylalanine, tryptophan, tyrosine, or alanine;

$Xg_{16}$ is valine, tryptophan, isoleucine, leucine, phenylalanine, tyrosine, lysine, or cysteine;

$Xg_{18}$ is serine, tryptophan, tyrosine, phenylalanine, lysine, isoleucine, leucine, valine, or cysteine;

$Xg_{19}$ is tyrosine, tryptophan, or phenylalanine, glutamine, or alanine;

$Xg_{20}$ is leucine, phenylalanine, tyrosine, tryptophan, lysine, cysteine, or methione;

$Xg_{22}$ is glycine, glutamic acid, aspartic acid, serine, cysteine, or lysine;

$Xg_{23}$ is glutamine, glutamic acid, arginine, isoleucine, lysine, or cysteine;

$Xg_{24}$ is alanine, histidine, or arginine;

$Xg_{25}$ is alanine, glutamine, valine, isoleucine, or leucine;

$Xg_{26}$ is lysine, cysteine, arginine, or glutamine;

$Xg_{27}$ is glutamic acid, aspartic acid, leucine, lysine, cysteine, or alanine;

$Xg_{29}$ is isoleucine or valine;

$Xg_{30}$ is alanine, asparagine, aspartic acid, glutamic acid, or glutamine;

$Xg_{33}$ is valine, leucine, lysine, cysteine, or methionine;

$Xg_{34}$ is lysine, alanine, asparagine, aspartic acid, arginine, cysteine, or glutamic acid;

$Xg_{35}$ is glycine, threonine, lysine, cysteine, or glutamine;

$Xg_{36}$ is glycine, lysine, cysteine, proline or arginine;

$Xg_{37}$ is glycine, proline, serine, lysine, cysteine, $NH_2$, or deleted;

$Xg_{38}$ is serine, proline, histidine, cysteine, lysine, or deleted;

$Xg_{39}$ is serine, arginine, threonine, tryptophan, lysine, cysteine, or deleted;

$Xg_{40}$ is serine, glycine, asparagine, lysine, cysteine, or deleted;

$Xg_{41}$ is alanine, aspartic acid, arginine, glutamic acid, lysine, cysteine, glycine, or deleted;

$Xg_{42}$ is proline, alanine, tryptophan, $NH_2$, or deleted;

$Xg_{43}$ is proline, alanine, lysine, $NH_2$, or deleted;

$Xg_{44}$ is praline, alanine, arginine, lysine, histidine, $NH_2$, or deleted;

$Xg_{45}$ is serine, histidine, proline, lysine, arginine, cysteine, asparagine, $NH_2$ or deleted;

$Xg_{46}$ is histidine, serine, arginine, lysine, cysteine, isoleucine, $NH_2$ or deleted;

Xg$_{47}$ is histidine, serine, arginine, lysine, threonine, NH2 or deleted;

Xg$_{48}$ is glutamine or deleted;

Xg$_{49}$ is NH$_2$ or deleted

In accordance with some embodiments a GLP-1 receptor binding peptide prodrug based on GLP-1 (7-36)-NH$_2$ has the sequence J-HXg$_8$EGTFTSDXg$_{16}$SXg$_{18}$YLEXg$_{22}$QAAXg$_{26}$EFIAWLVXg$_{34}$GRXg$_{37}$ (SEQ ID NO: 50)

In some embodiments a GLP-1 receptor binding peptide prodrugs based on GLP-1 (7-36)-NH$_2$ has the sequence J-HXg$_8$EGTFTSDVSSYLEXg$_{22}$QAAKEFIAWLVKGRXg$_{37}$ (SEQ ID NO: 51)

In accordance with some embodiments an exendin-4 based GLP-1 receptor binding peptide prodrug has the sequence J-X$_7$GEGTFTSDLSXg$_{18}$QXg$_{20}$EEEAVXg$_{26}$LFIEWLXg$_{33}$Xg$_{34}$Xg$_{35}$Xg$_{36}$Xg$_{37}$Xg$_{38}$Xg$_{39}$Xg$_{40}$Xg$_{41}$Xg$_{42}$Xg$_{43}$Xg$_{44}$Xg$_{45}$ (SEQ ID NO: 52)

In some embodiments an exendin-4 based GLP-1 receptor binding peptide has one or more substitutions with cysteine or lysine in comparison to wild type exendin-4, including lysine or cysteine substitutions at the C terminus, positions 26 (Arg), 31 (Trp), 36 (Gly), 41 (Ala), or 45 (Ser).

In some embodiments an exendin-4 based GLP-1 receptor binding peptide prodrugs has the sequence HGEGTFTSDLSXg$_{18}$QMEEEAVRLFIEWLXg$_{33}$NGGPSSGAPPPXg$_{45}$ (SEQ ID NO: 53)

In some embodiments an exendin-4 based GLP-1 receptor binding peptide prodrugs has the sequence J-HGEGTFTSDLSKQMEEEAVRLFIEWLKNGGPSSGAPPPS-NH$_2$ (SEQ ID NO: 54).

In accordance with some embodiments J can be conjugated to a modifying moiety which has a general formula: -L-M, wherein L and M are defined above in this disclosure.

In some embodiments a GLP-1 receptor binding peptide prodrug is of the formula M$_r$-L-promoiety-GLP-1 receptor binding peptide, wherein L and M$_r$ are defined above in this disclosure.

In some embodiments the ex vivo albumin conjugate of a GLP-1 receptor binding peptide prodrug is of the formula alb-M$_r$-L-promoiety-GLP-1 receptor binding peptide, wherein L, M$_r$, and alb are defined above in this disclosure.

In some embodiments a GLP-1 receptor binding peptide prodrug is of the formula promoiety-GLP-1 receptor binding peptide-L-M, wherein the promoiety can be linked to N-terminus amino acid of the peptide, or to the side chain of an internal amino acid (e.g., ε-amino group of a lysine, a hydroxyl group of a serine or threonine); -L-M can be conjugated to the side chain of an internal amino acid (e.g., ε-amino group of a lysine, or thiol group of a cysteine) at a different site, or the C-terminus section of the peptide. The conjugation sites used commonly in a GLP-1 derivative include the amino group on the side chain of a lysine or the mercapto group on the side chain of a cysteine at position Xg$_{16}$, Xg$_{26}$, Xg$_{30}$, or Xg$_{34}$, originally present or introduced after substitution or insertion, or the amino group on the side chain of a lysine or the mercapto group on the side chain of a cysteine introduced after substitution or insertion at the C-terminus section. The conjugation sites used commonly in an exendin-4 derivative include the amino group on the side chain of a lysine or the mercapto group on the side chain of a cysteine at positions Xg$_{18}$, Xg$_{26}$, Xg$_{33}$, Xg$_{34}$, or Xg$_{38}$, originally present or introduced after substitution or insertion, or the amino group on the side chain of a lysine or the mercapto group on the side chain of a cysteine substituted or inserted at the C-terminus section. In one embodiment, the modifying moiety is a PEG or a fatty acid.

In some embodiments a GLP-1 receptor binding peptide prodrug is of the formula promoiety-GLP-1 receptor binding peptide-L-M$_r$. An illustrative, non-limiting example of albumin reactive peptides includes (SEQ ID NOS 55-56, respectively, in order of appearance)

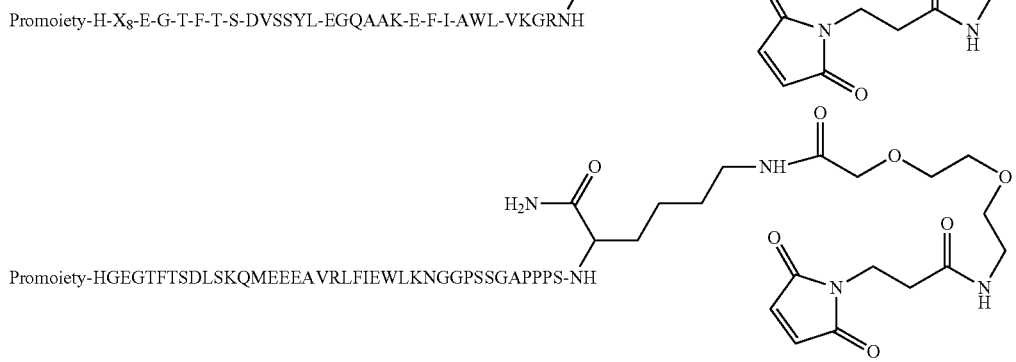

Promoiety-H-X$_8$-E-G-T-F-T-S-DVSSYL-EGQAAK-E-F-I-AWL-VKGRNH

Promoiety-HGEGTFTSDLSKQMEEEAVRLFIEWLKNGGPSSGAPPPS-NH

In some embodiments the conjugate of a GLP-1 receptor binding peptide prodrug is of the formula M-L-promoiety-GLP-1 receptor binding peptide, wherein M-L-promoiety can be linked to N-terminus amino acid of the peptide, or to the side chain of an internal amino acid (e.g., ε-amino group of a lysine, a hydroxyl group of a serine or threonine). In one embodiment, the modifying moiety is a PEG or a fatty acid.

In some embodiments the ex vivo albumin conjugate of a GLP-1 receptor binding peptide prodrug is of the formula promoiety-GLP-1 receptor binding peptide-L-M$_r$-alb, wherein L, M$_r$, and alb are defined above in this disclosure. Illustrative, non-limiting examples of albumin prodrug conjugates formed ex vivo include (SEQ ID NOS 55-56, respectively, in order of appearance)

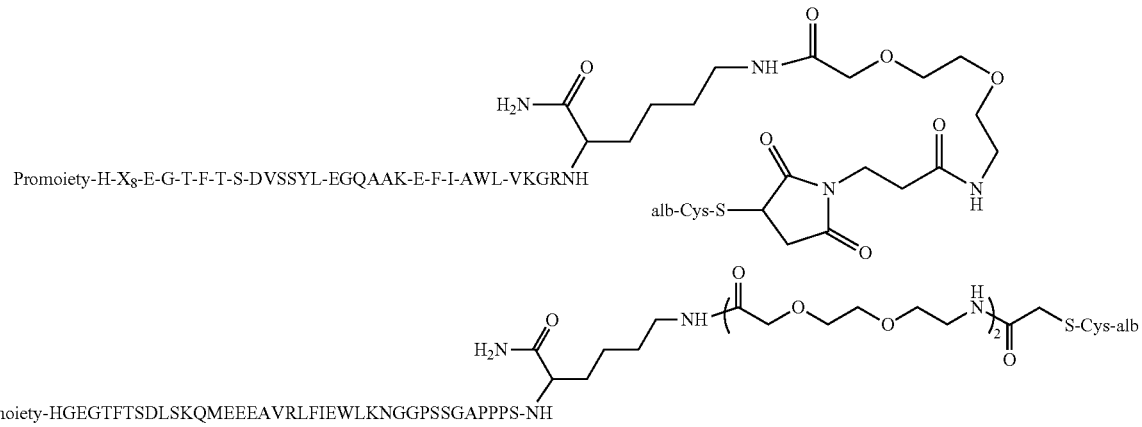

The disclosed peptide prodrugs are believed to be suitable for any use that has previously been described for their corresponding parent drugs. Accordingly, the prodrug of an insulin receptor binding peptide or GLP-1 receptor binding peptide described herein can be used to treat hyperglycemia, or treat other metabolic diseases that result from high blood glucose levels. Accordingly, the present disclosure encompasses pharmaceutical compositions comprising the prodrug of a pharmaceutically active peptide of the present disclosure, and a pharmaceutically acceptable carrier for use in treating a patient suffering from high blood glucose levels.

One method of treating hyperglycemia in accordance with the present disclosure comprises the steps of administering the presently disclosed prodrugs to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the prodrug composition is prepackaged in a syringe.

The prodrugs of insulin or GLP-1 receptor binding peptides of the disclosure may be administered alone or in combination with other anti-diabetic agents. Anti-diabetic agents known in the art or under investigation include native insulin, native glucagon and functional derivatives thereof, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; or FBPase (fructose 1,6-bisphosphatase) inhibitors.

In some embodiments, the GLP-1 receptor binding peptide prodrugs are used to reduce or suppress appetite, reduce food intake, induce weight loss, or assist in weight maintenance. Such methods for reducing appetite or body weight are expected to be useful in treating obesity of various causes and reducing complications associated with obesity including vascular disease (coronary artery disease, stroke, peripheral vascular disease, ischemia reperfusion, etc.), hypertension, onset of diabetes type H, hyperlipidemia and musculoskeletal diseases.

The GLP-1 receptor binding peptide prodrugs may be administered alone or in combination with another anti-obesity agents. Anti-obesity agents known in the art or under investigation include but are not limited to appetite suppressants, including phenethylamine type stimulants, phentermine (optionally with fenfluramine or dexfenfluramine), Qsymia (phentermine and topiramate), diethylpropion (Tenuate®), phendimetrazine (Prelu-2®, Bontril®), benzphetamine (Didrex®), sibutramine (Meridia®, Reductil®); rimonabant (Acomplia®), other cannabinoid receptor antagonists; oxyntomodulin; fluoxetine hydrochloride (Prozac); Excalia (bupropion and zonisamide) or Contrave (bupropion and naltrexone); lorcaserin (Belviq®); or lipase inhibitors, similar to xenical (Orlistat) or Cetilistat, or GT 389-255.

Pharmaceutical compositions comprising the peptide prodrugs disclosed herein can be formulated and administered to patients using standard pharmaceutically acceptable carriers and routes of administration known to those skilled in the art. Accordingly, the present disclosure also encompasses pharmaceutical compositions comprising one or more peptide prodrugs disclosed herein, or a pharmaceutically acceptable salt thereof, in combination with a pharmaceutically acceptable carrier. In one embodiment the pharmaceutical composition comprises a 1 mg/ml concentration of the peptide prodrug at pH about 4.0 to about 7.0 in a phosphate buffer system. The pharmaceutical compositions may comprise a peptide prodrug as the sole pharmaceutically active component, or a peptide prodrug can be combined with one or more additional active agents. In accordance with one embodiment a pharmaceutical composition is provided comprising one of the peptide prodrugs disclosed herein, preferably sterile and preferably at a purity level of at least 90%, 91%, 92%, 93%, 94%, 95%, 96%, 97%, 98% or 99%, and a pharmaceutically acceptable diluent, carrier or excipient. Such compositions may contain a peptide prodrug wherein the resulting active peptide is present at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored within various containers. The compounds of the present disclosure can be used in accordance with one embodiment to prepare pre-formulated solutions ready for injection. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

All therapeutic methods, pharmaceutical compositions, kits and other similar embodiments described herein contemplate that peptide prodrugs include all pharmaceutically acceptable salts thereof.

In some embodiments the kit is provided with a device for administering the peptide prodrug composition to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the pharmaceutically active peptide composition is prepackaged within the syringe. The compounds of this disclosure may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this disclosure that encompass non-peptide portions may be synthesized by standard organic chemistry reactions, in addition to standard peptide chemistry reactions when applicable.

EXAMPLES

Abbreviations

Bz, benzoyl; Bzl, benzyl; Boc, t-butoxycarbonyl; BOP, benzotriazol-1-yloxytris(dimethylamino)phosphonium hexafluorophosphate; CHO, formyl; Cbz or Z, benzyloxycarbonyl; DCC, N,N'-Dicyclohexylcarbodiimide; DCM, dichloromethane; DEPBT, 3-(Diethoxyphosphoryloxy)-1,2,3-benzotriazin-4(3H)-one; DIC, N,N'-Diisopropylcarbodiimide; DIPEA (or DIEA), diisopropylethylamine; DMAP, 4-N,N-dimethylaminopyridine; DMF, dimethylformamide; DMSO, dimethyl sulfoxide; DTT, dithiothreitol; EDC or EDCI, 1-ethyl-3-(3-dimethylaminopropyl)carbodiimide; EtOAc, ethyl acetate; Fm, 9-fluorenylmethyl; Fmoc, 9-fluorenylmethoxycarbonyl; Pmc, (2,2,5,7,8-pentametylchroman-6-sulphonyl; HBTU, O-(1H-benzotriazole-1-yl)-N,N,N',N'-tetramethyluronium hexafluorophosphate; HOBT, 1-hydroxybenzotriazole; Su, succinimide; tBu, t-butyl; TEA, triethylamine; TFA, trifluoroacetic acid; TFE 2,2,2-Trifluoroethanol; THF, tetrahydrofuran; TIS, triisopropylsilane; Tos, 4-toluenesulphonyl; Trt, tripheylmethyl; rt, room temperature.

(S)-2-(4-((2-((2-((((9H-fluoren-9-yl)methoxy)carbonyl)amino)ethyl)amino)-2-oxoethyl)thio)-2-((S)-1-((tert-butoxycarbonyl)amino)ethyl)-1H-imidazol-1-yl)propanoic acid

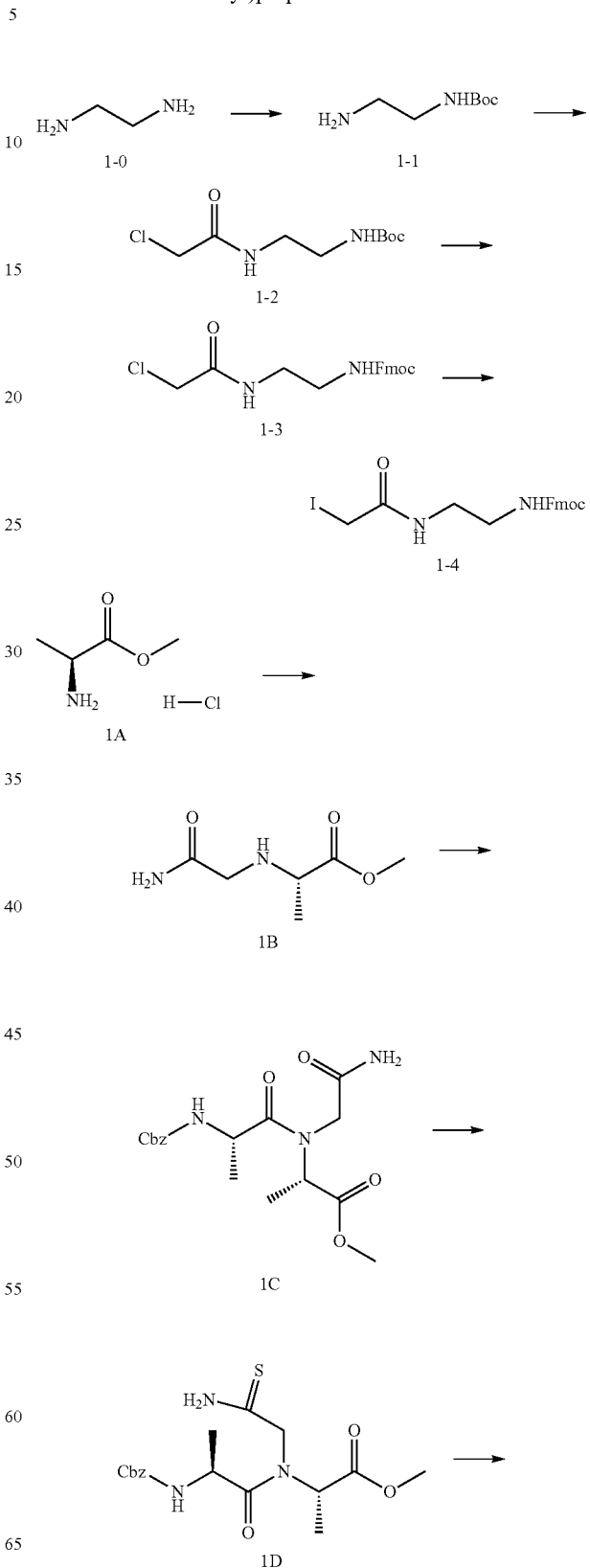

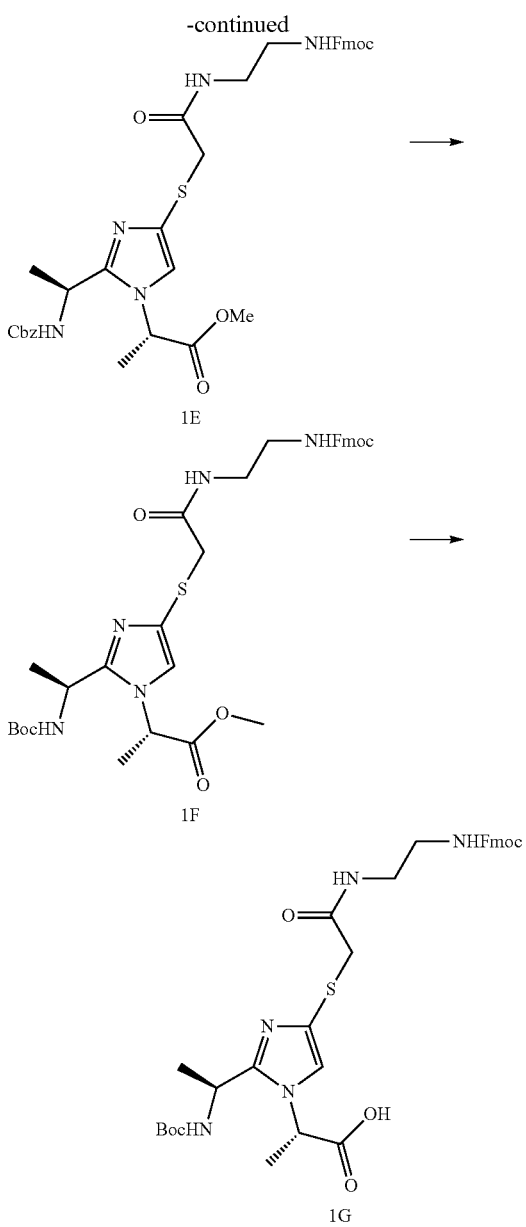

To a solution of 1-0 (28 mL, 400 mmol) in DCM (400 mL) was added a solution of (Boc)$_2$O (8.74 g, 40 mmol) in DCM (200 mL). After stirring at rt for 14 h the mixture was washed with water, brine, dried over MgSO$_4$ and concentrated in vacuo to afford 1-1 as a colorless oil (4.7 g, crude), which used in next step without further purification.

A solution of chloroacetyl chloride (2.82 g, 25 mmol) in dry THF (50 mL) was added to a solution of 1-1 (4.0 g, 25.0 mmol) and DIEA (3.15 g, 27.5 mmol) in dry THF (100 mL) at −10° C. The resulting solution was stirred for 30 min and the solvent was evaporated under vacuum. The residue was dissolved in a mixture of DCM and H$_2$O. The aqueous layer was extracted with DCM. The combined organic layers were washed with brine, dried (Na$_2$SO$_4$), and concentrated. The residue was purified by flash column chromatography on silica gel to give 1-2 as a white solid (4.6 g).

To a solution of 1-2 (1.0 g, 4.24 mmol) in DCM (20 mL) was added TFA (10 mL) and the mixture was stirred at r.t for 1 h. Then the mixture was evaporated to dryness and dissolved in 10% Na$_2$CO$_3$ (40 mL). FmocCl (1.3 g, dissolved in 10 mL of dioxane) was added. After stirring at r.t for 2 h the reaction was quenched and extracted with DCM. The combined organic layers were dried over Na$_2$SO$_4$, concentrated under reduced pressure and the residue was purified by flash column chromatography on silica gel to give 1-3 as an off-white solid (1.3 g).

To a stirred solution of 1-3 (1.3 g, 3.66 mmol) in 2-butanone (30 ml) was added KI (0.9 g, 5.50 mmol). The mixture was refluxed for 2 h and then concentrated. DCM was added and washed with aqueous Na$_2$SO$_3$. The organic layers were combined and dried over Na$_2$SO$_4$, evaporated to dryness to give 1-4 as brown crude oil (1.5 g), which was used in next step without further purification.

A mixture of 1A (50 g, 0.358 mol), 2-iodoacetamide (79.5 g, 0.430 mol) and DIPEA (164 mL, 0.895 mol) in CH$_3$CN (300 ml) was stirred at rt for 14 h. The reaction mixture was concentrated in vacuo and the residue was purified by flash column chromatography on silica gel to give 1B as a brown oil (12.0 g).

To a solution of 1B (8.3 g, 51.80 mmol) and Cbz-Ala-OH (17.3g) in dry CH$_3$CN was added DIEA (41.8 mL) followed by addition of T$_3$P (43.6 mL, 50% in DMF). The mixture was stirred overnight at rt. Water was added and the aqueous layer was extracted with EtOAc. The combined organic layers were washed with NaHCO$_3$, brine, dried over Na$_2$SO$_4$, filtered and concentrated in vacuo. The residue was purified by flash column chromatography on silica gel to give 1C as a yellow oil (2.7 g).

To a solution of 1C (2.7 g, 7.40 mmol) in dry DME (30 mL) was added Lawesson's reagent (1.49 g, 3.70 mmol). The mixture was stirred at 50° C. for 4 h. The reaction mixture was concentrated in vacuo and extracted with EtOAc. The combined organic layers were washed with brine, dried over Na$_2$SO$_4$, filtered and concentrated. The residue was purified by flash column chromatography on silica gel to give 1D as a yellow solid (1.5 g).

A solution of 1D (1.0 g, 2.62 mmol) in toluene (10 mL) and DCM (1 mL) under argon atmosphere was cooled to −78° C. Et$_3$N (3.0 mL) and TMSOTf (2.4 mL) were added and the mixture was allowed to warm to rt then stirred for an additional 12 h at rt. MeOH (3 mL) was added and stirring was kept for 15 min. Volatiles were then removed in vacua. The residue was dissolved in dry toluene and heated under reflux for 2 h. After concentration in vacuo DCM (2 L) was added followed by Dithiothreitol (DTT, 0.76 g). The reaction mixture was stirred overnight. Et$_3$N (1 mL) and 1-4 (1.4 g) were subsequently added and the mixture was stirred at rt for 30 min. The reaction mixture was extracted with EtOAc, washed with Na$_2$CO$_3$, dried over Na$_2$SO$_4$, filtered and concentrated in vacuo. The residue was purified by flash column chromatography on silica gel to give 1E as a yellow foam (490 mg).

A solution of 1E (400 mg, 0.584 mmol) and anisole (500 µL) in DCM (10 mL) under argon atmosphere was treated with HBr (4 mL, 33% wt in AcOH). The mixture was stirred at rt for 1 h. Volatiles were removed in vacuo and Et$_2$O was added. The solid was filtered and dried under vacuum. It was dissolved in DCM (5 mL), cooled to 0° C. then treated by a solution of Boc$_2$O (619 mg) in DCM (2 mL) and Et$_3$N (0.1 mL). The reaction medium was stirred for 16 h. The reaction was quenched by NaHCO$_3$, extracted with DCM, dried over Na$_2$SO$_4$, filtered and concentrated in vacuo. The residue was purified by flash column chromatography on silica gel to give 1F as a yellow solid (70 mg).

To a solution of 1F (40 mg, 0.058 mmol) in 5 mL of 50% THF/H$_2$O was added LiOH.H$_2$O (4.9 mg, 0.116 mmol). The mixture was stirred at r.t for 1 h. Then the mixture was adjusted to pH=3, concentrated, and the residue was purified by prep-HPLC to give 1G (10 mg) as a white solid.

$^1$NMR (400 MHz, d$_6$-DMSO): δ 10.36 (br s, 1H), 8.24 (t, J=5.2 Hz, 1H), 7.89 (d, J=7.2 Hz, 2H), 7.68 (d, J=7.2 Hz, 2H), 7.60 (br s, 1H), 7.49 (br s, 1H), 7.42 (d, J=7.2 Hz, 2H), 7.35-7.31 (m, 3H), 5.24-5.16 (m, 1H), 4.98-4.80 (m, 1H), 4.32-4.28 (m, 2H), 4.23-4.17 (m, 1H), 3.67 (s, 1H), 3.14-3.09 (t, J=6.0 Hz, 2H), 3.07-3.01 (t, J=6.4 Hz, 2H), 1.62 (d, J=7.2 Hz, 3H), 1.42 (d, J=6.8 Hz, 3H), 1.34 (s, 9H). LC-MS (ESI): m/z 638 [M+H]$^+$ 3-(((tert-butoxycarbonyl)amino)methyl)picolinic acid

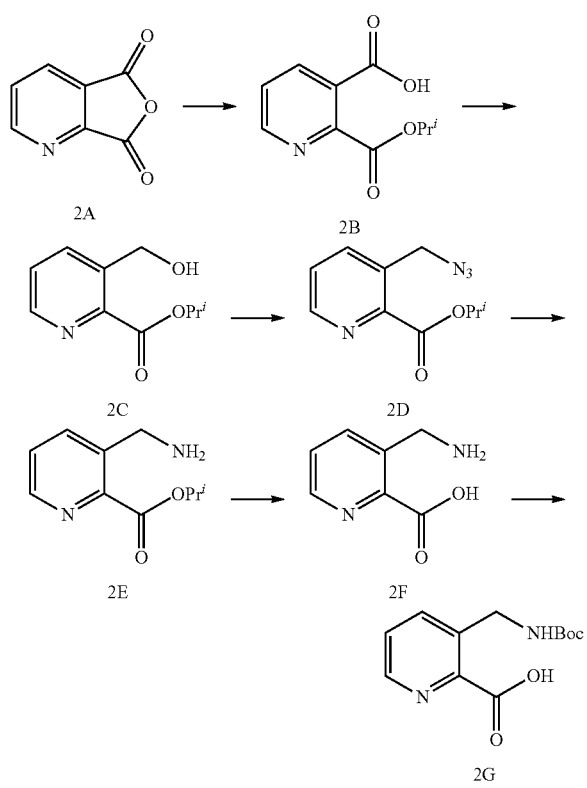

2A (5 g, 33.6 mmol) was added to isopropanol (50 mL) and refluxed overnight.

The liquid was evaporated in vacuo. The solid residue was added to ethyl acetate (150 mL) and refluxed. After cooling, white solid 2B (6.356 g) was obtained.

SOCl$_2$ (32 mL) was added to 2B (6.356g, 30.38 mmol) and heated to 80° C. for 2.5 hours. After removal of SOCl$_2$ in vacuo the residue was dissolved in THF (32 mL) and cooled below 0° C. NaBH$_4$ (1.15 g, 30.4 mmol) was added and the reaction was stirred for 1 hour. The mixture was poured into icy water and extracted with CH$_2$Cl$_2$. The combined organic layer was dried over anhydrous MgSO$_4$, filtered, and concentrated in vacuo to give 2C (3.2 g).

Triethylamine (1.9 g, 20 mmol) was added to 2C (3.2 g, 16.4 mmol) in CH$_2$Cl$_2$. The reaction was cooled to 0° C. and MsCl (1.8 g, 16.4 mmol) was added. The reaction was warmed to room temperature and stirred for 2 hours. The reaction was quenched with saturated NH$_4$Cl and extracted with CH$_2$Cl$_2$. The combined organic layer was dried over MgSO$_4$, filtered, and concentrated in vacuo. The residue was dissolved in DMF (20 mL), followed by NaN$_3$ (1.0 g, 16.4 mmol). The reaction was complete after 1 hour and H$_2$O (100 mL) was added. The reaction was extracted with ethyl acetate (3×100 mL). The combined organic layer was dried over MgSO$_4$, filtered, and concentrated in vacuo. Purification with flash chromatography (petroleum ether: ethyl acetate 5:1) gave yellow liquid 2D (2.6 g).

Pd/C (10%, 606 mg, 0.57 mmol) was added to 2D (2.6 g, 11.8 mmol) in ethyl alcohol (50 mL). The reaction was stirred under H$_2$ overnight. The reaction was filtered and concentration of filtrate gave crude product 2E (3.0 g, wet weight).

6N HCl (50 mL) was added to 2E (3.0 g, wet weight) and the reaction was refluxed overnight. After removal of water in vacuo, crude 2F (1.8 g) was obtained.

NaHCO$_3$ (5.0 g, 59 mmol) was added to 2F (1.8 g, 11.8 mmol) in THF (40 mL) and H$_2$O (10 mL). The reaction was stirred for 10 minutes before addition of Di-tert-butyl dicarbonate (Boc$_2$O) (3.8 g, 17.7 mmol). The reaction was stirred overnight pH was adjusted to 2 with HCl. The reaction was extracted with CH$_2$C$_{12}$, dried over MgSO$_4$, filtered, and concentrated in vacuo. Purification with HPLC gave 2G (130 mg)

HNMR: (400 MHz, D$_2$O) δ 8.62 (d, 1H), 8.22 (d, 1H), 7.83(t, 1H), 4.71 (s, 2H), 1.42 (s, 9H) MS (m/z): 253.4 [M+H]$^+$ 2-(((tert-butoxycarbonyl)amino)methyl)nicotinic acid

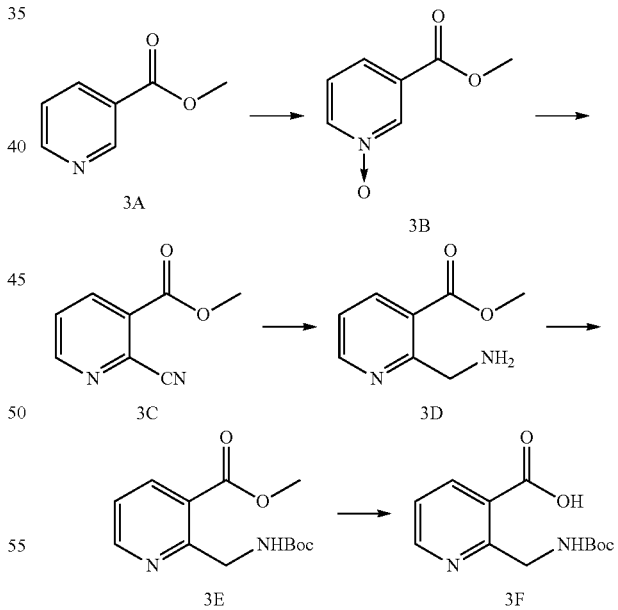

H$_2$O$_2$ (30%, 1.65 mL, 14.6 mmol) was added to methyl nicotinate 3A (2.0 g, 14.6 mmol) in glacial acetic acid (20 mL). The reaction was refluxed overnight. After cooling to room temperature, the reaction was diluted with H$_2$O (50 mL), pH was adjusted to 7 with Na$_2$CO$_3$, and extracted with CH$_2$Cl$_2$. The organic layer was dried over MgSO$_4$, filtered, and concentrated in vacuo to give solid 3B (1.5 g), which was used directly in the next reaction without purification.

TMSCN (6.8 mL, 54.9 mmol) was added dropwise to 3B (7 g, 45.7 mmol) in anhydrous $CH_2Cl_2$ under $N_2$. The reaction was cooled on ice bath and $Et_2NCOCl$ (7.4 g, 54.9 mmol) was added. The reaction was stirred at room temperature for two days. Aqueous $K_2CO_3$ solution (10%, 100 mL) was added to the reaction. After 10 minutes of stirring, the reaction was extracted with ethyl acetate, dried over $MgSO_4$, filtered, and concentrated in vacuo. The residue was purified with flash chromatography to give 3C (1.5 g)

Concentrated HCl (0.5 mL) was added to 3C (0.3 g, 1.84 mmol) in $CH_3OH$ (30 mL) and the reaction was stirred at room temperature for 3 hours. Filtration and concentration in vacuo gave yellow solid 3D (0.35 g), which was used directly in the next reaction without purification.

$NaHCO_3$ (0.35 g, 4.2 mmol) and Di-tert-butyl dicarbonate ($Boc_2O$) (0.46 g, 2.1 mmol) were added to crude 3D (0.35 g) in THF (30 mL) and $H_2O$ (10 mL). The reaction was stirred at room temperature overnight. The reaction was acidified to pH3, extracted with ethyl acetate, dried over $MgSO_4$, filtered, and concentrated in vacuo to give yellow oil 3E (0.5 g), which was used directly in the next reaction without purification.

$LiOH.H_2O$ (263 mg, 5.64 mmol) was added to crude 3E (500 mg) in $CH_3OH$ (20 mL) and $H_2O$ (10 mL) and the reaction was stirred at room temperature for 1 hour. $CH_3OH$ was removed under reduced pressure. The aqueous layer was washed with ethyl acetate, and pH was adjusted to 3. The reaction was extracted with ethyl acetate. The organic layer was dried over $MgSO_4$, filtered, and concentrated in vacuo. The residue was purified with HPLC to give 3F (200 mg).

HNMR: (400 MHz, DMSO-$d_6$) δ 8.73 (d, 1H), 8.30 (d, 1H), 7.50(t, 1H), 6.98 (s, 1H), 4.63 (s, 2H), 1.39 (s, 9H) MS (m/z): 253.4 $[M+H]^+$

Synthesis of 5-((((9H-fluoren-9-yl)methoxy)carbonyl)amino)-2-(((tert-butoxycarbonyl)amino)methyl)-3-methylbenzoic acid

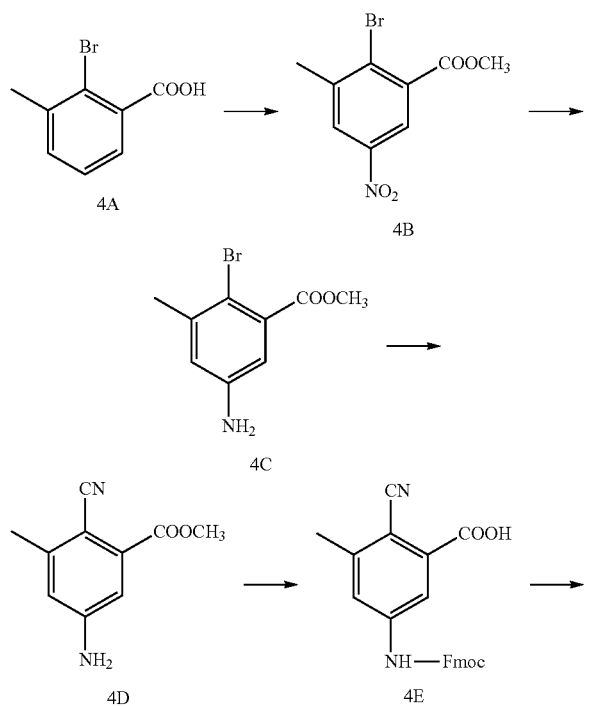

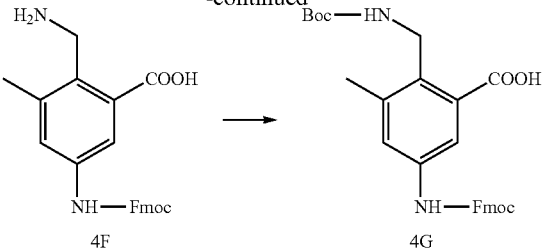

4A (10 g, 45.6 mmol) was dissolved in sulfuric acid (30 mL) at 0° C., and fuming nitric acid (4 mL) was added dropwise over 10 minutes. After stirring for 2 hours at room temperature, the reaction mixture was poured onto ice and the solids were isolated by filtration. The residue was refluxed for 1 h in thionyl chloride (30 mL) and concentrated to oil. Methanol (80 mL) was added slowly to the oil and the mixture refluxed for 1 hour. The reaction mixture was concentrated in vacuo, extracted with ethyl acetate to give a crude product, which was purified through column chromatography to give compound 4B (9.3 g, 67.9%).

$^1$H NMR: (400 MHz DMSO-d6) δ 8.38~8.29 (m, 2H), 3.90 (s, 3H), 2.51 (s, 3H).

4B (5 g, 18.3 mmol) was heated at 90° C. for 4 hours in methanol (60 mL) with iron powder (1.5 g, 27.5 mmol) and Con. HCl (5 mL). After cooling to room temperature, the resulting mixture was filtered through Celite. The filtrate was concentrated in vacuo, diluted with ethyl acetate, washed with water, brine and dried over anhydrous $Na_2SO_4$ and concentrated in vacuo to give a crude product, which was purified through column chromatography to give 4C (4.1 g, 92.1%).

$^1$H NMR: (400 MHz DMSO-d6) δ 10.15 (s, 1H), 7.76-7.76 (d, 1H), 7.61-7.62 (m, 1H), 3.82 (s, 3H), 2.34 (s, 3H).

To a solution of 4C (2.4 g, 9.9 mmol) in DMF (15 mL) was added CuCN (1.1 g, 12.3 mmol). The mixture was heated at 150° C. for 2 hours under nitrogen atmosphere. The reaction was cooled to room temperature, quenched with a solution of $NH_4OH/H_2O$ (1:1, 50 mL). The mixture was stirred for 5 minutes and filtered through Celite. The filter cake was washed with ethyl acetate and the combined organic phases were washed with water, brine, dried over anhydrous $Na_2SO_4$, and concentrated to give oil, which was purified through silica gel column chromatography to give 4D (1 g, 53.5%).

$^1$H NMR: (400 MHz DMSO-d6) δ 7.05~7.04(d, 1H), 6.68~6.67 (m, 1H), 6.31 (s, 2H), 3.82 (s, 3H), 2.34 (s, 3H).

To a solution of 4D (0.7 g, 3.68 mmol) in water (10 mL) and THF (20 mL) was added NaOH (0.22 g, 5.53 mmol). The reaction mixture was stirred at room temperature for 2 hours. After dilution with THF (20 mL), Fmoc-Cl (1.43 g, 5.54 mmol) was added at 0° C. The mixture was stirred at room temperature for 2 hours. The reaction mixture was poured into water and acidified with HCl solution, extracted with ethyl acetate, washed with water, brine and dried over anhydrous $Na_2SO_4$. The crude product was purified by prep-HPLC to give 4E (0.5 g, 34%).

1H NMR: (400 MHz DMSO-d6) δ 10.24 (s, 1H), 8.02 (s, 1H), 7.88~7.86 (d, 2H), 7.71~7.69 (d, 2H), 7.41~7.37 (m, 2H), 7.33~7.29 (m, 2H), 4.50-4.49 (d, 2H), 4.29 (m, 1H), 2.43 (s, 3H).

To a solution of 4E (0.5 g, 1.24 mmol) in 50 mL of ethanol and 5 mL of $NH_4OH$ was added Raney-Ni (200 mg). The resulting suspension was stirred under a hydrogen atmosphere for 12 hours. The mixture was filtered through Celite and the filtrate was concentrated to give 4F (0.8 g crude) and used for next step without further purification.

To a solution of 4F (0.8 g crude) in DCM (20 mL) was added di-tert-butyl dicarbonate (0.33 g, 1.5 mmol). The mixture was stirred at room temperature for 12 hours. After solvent removal under reduced pressure the residue was purified by Prep-HPLC to give 4G (100 mg, 16% from compound E) as a white solid.

1H NMR: (400 MHz MeOD) δ 7.80~7.78 (d, 2H), 7.69~7.67 (d, 2H), 7.62 (br, 1H), 7.40~7.36 (t, 2H), 7.30~7.28 (m, 3H), 4.46~4.44 (d, 2H), 4.37 (s, 2H), 4.27~4.23 (t, 1H), 2.36 (s, 3H), 1.41 (s, 9H). LC-MS: m/z=501.1 [M−1]

Synthesis of 4-((allyloxy)carbonyl)-2-(((tert-butoxycarbonyl)amino)methyl)-6-methylbenzoic acid

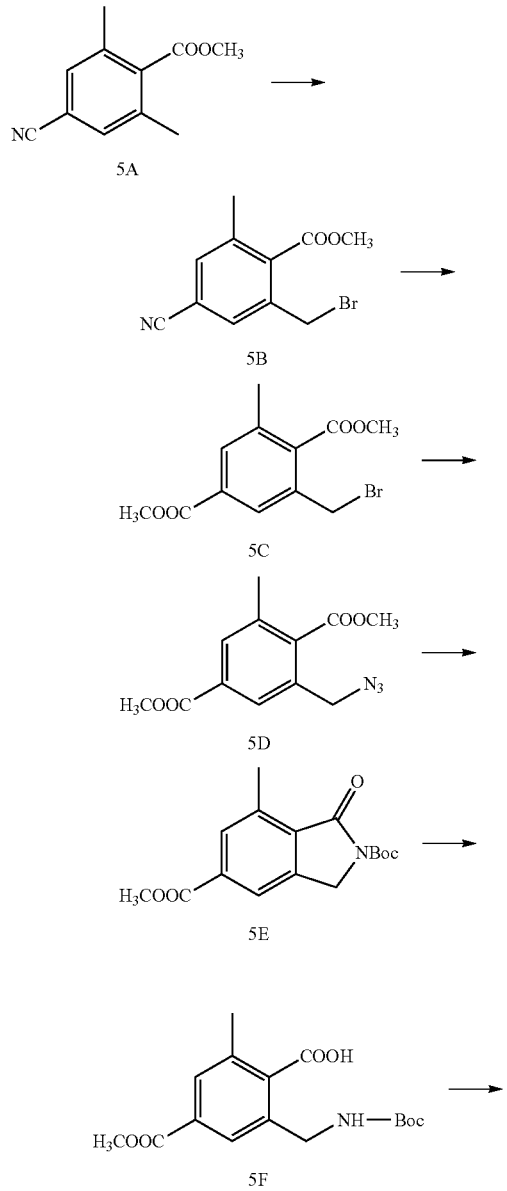

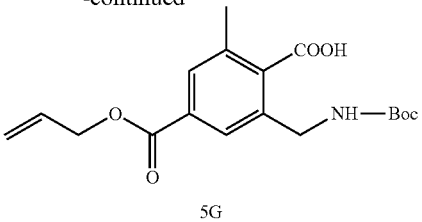

To a stirred solution of 5A (3.6 g, 19.0 mmol) in DCM (150 mL) was added BPO (462 mg, 20.9 mmol) followed by NBS (3.6 g, 20.9 mmol). The reaction was stirred at 60° C. overnight. The reaction was cooled to room temperature and treated with saturated NaHCO$_3$, extracted with ethyl acetate, washed with water, brine, dried over anhydrous Na$_2$SO$_4$ and concentrated in vacua to give a crude product, which was purified through silica gel column chromatography to give 5B (2.0 g, 39.2%).

5B (0.6 g, 2.24 mmol) was dissolved into methanol solution of HCl (100 mL). The reaction mixture was stirred at 50° C. overnight. The reaction mixture was concentrated in vacua, extracted with ethyl acetate (100 mL), washed with water, brine, dried over anhydrous Na$_2$SO$_4$ and concentrated in vacua to give a crude product, which was purified through silica gel column chromatography to give SC (0.6 g, 89.6%).

HNMR: (400 MHz CDCl$_3$) δ 7.91 (s, 1H), 7.86 (s, 1H), 4.66 (d, 2H), 3.97 (t, 3H), 3.92 (t, 3H), 2.39 (t, 3H).

The mixture of 5C (0.6 g, 2.0 mmol) and NaN$_3$ (0.26 mg, 4 mmol) in DMF (10 mL) was stirred at 50° C. for 16 hrs. The reaction was cooled to room temperature, diluted with water, and extracted with ethyl acetate. The combined organic phase was washed with brine, dried over anhydrous Na$_2$SO$_4$, concentrated in vacuo and purified through column chromatography to give 5D (0.3 g, 58%).

$^1$H NMR: (400 MHz CDCl$_3$) δ 7.84-7.85 (m, 2H), 4.41 (s, 2H), 3.89 (s, 3H), 3.86 (s, 3H), 2.33 (s, 3H).

To a solution of 5D (2.5 g, 9.5 mmol) in MeOH (100 mL) was added Pd/C (10%, 1.0 g). The resulting suspension was stirred under a hydrogen atmosphere for 18 hours and then filtered through celite. The filtrate was concentrated in vacuo. The residue (0.85 g, 4.1 mmol), Boc$_2$O (1.8 g, 8.2 mmol), triethylamine (1 mL) and DMAP (0.5 g, 4.1 mmol) in DCM (30 mL) were stirred at room temperature under nitrogen atmosphere for 5 hours. The reaction mixture was concentrated and purified through silica gel column chromatography to give 5E (0.85 g, 68%).

$^1$H NMR: (400 MHz CDCl$_3$) δ 7.90 (s, 1H), 7.86 (s, 1H), 4.71~4.70 (d, 2H), 3.93~3.92 (d, 3H), 2.72~2.71 (d, 3H), 1.45~1.44 (d, 9H).

To a solution of 5E (0.85 g, 2.8 mmol) in THF (15 mL) was added aqueous lithium hydroxide (0.6 g, 14 mmol) in H$_2$O (10 mL) and the mixture was stirred at room temperature for 5 hours. The crude 5F was used for next step without further purification.

To a solution of 5F (0.86 g, 2.8 mmol) in DMF (30 mL) was added Cs$_2$CO$_3$ (0.91 g, 2.8 mmol) and 3-bromoprop-1-ene (340 mg, 2.8 mmol), the mixture was stirred for 12 hours at 60° C. The mixture was cooled and water was added, then extracted with ethyl acetate, washed with brine, dried over anhydrous Na$_2$SO$_4$ and concentrated. The residue was purified by Prep-TLC to give 5G (100 mg, 10.2%) as off-white solid.

$^1$H NMR: (400 MHz CDCl$_3$) δ 7.88 (s, 1H), 7.84 (s, 1H), 6.05~5.90 (m, 1H), 5.38~5.33 (dd, 1H), 5.27~5.24 (dd, 1H), 4.79~4.77 (m, 2H), 4.67 (s, 2H), 2.68 (s, 3H), 1.544(s, 9H).

113

Synthesis of 4-((3-((((9H-fluoren-9-yl)methoxy)carbonyl)amino)propyl)carbamoyl)-2-(((tert-butoxycarbonyl)amino)methyl)benzoic acid

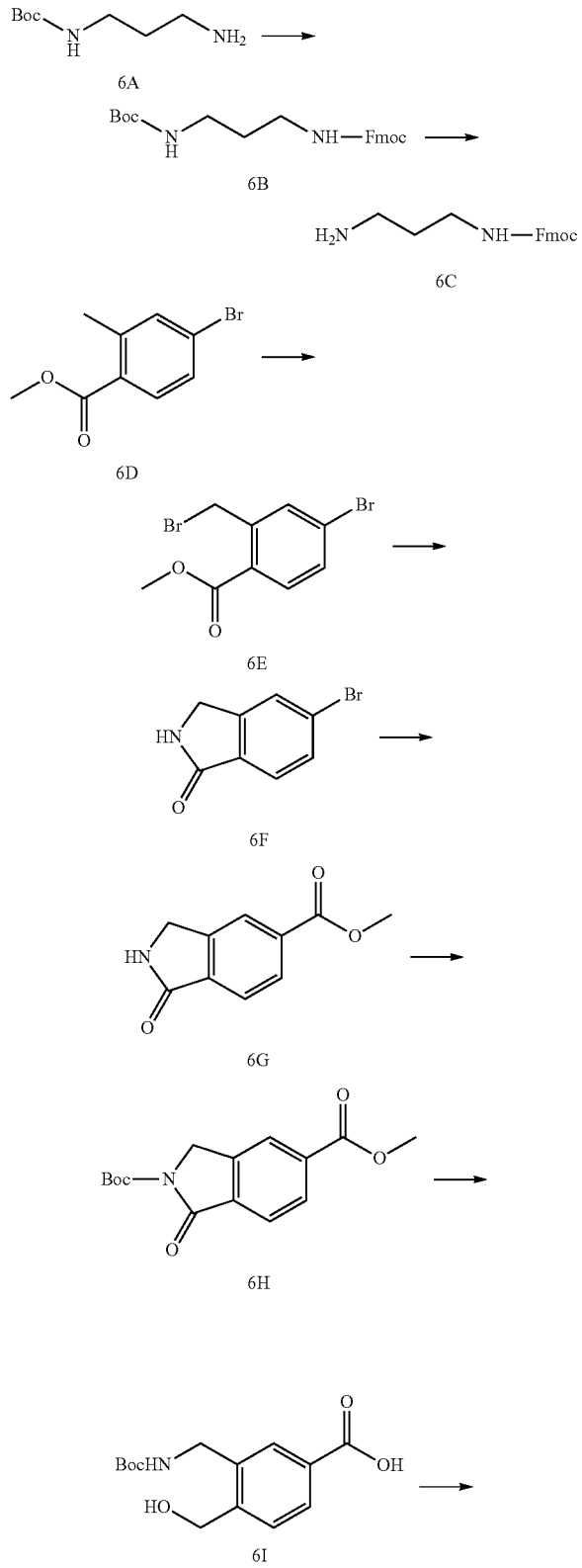

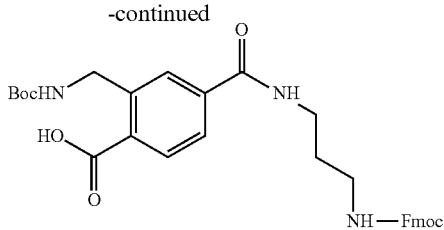

To a solution of 6A (10 g, 57.4 mmol) in CH₂Cl₂ (200 mL) was added aqueous saturated NaHCO₃ (200 mL), followed by FmocCl (17 g, 66 mmol). The mixture was stirred at room temperature overnight. The mixture was separated, and the organic layer was washed with water, brine, dried over Na₂SO₄ and concentrated in vacuum. The residue was purified with flash column chromatography to give 6B (15 g, 66%).

To a solution of 6B (15 g, 38 mmol) in CH₂Cl₂ (200 mL) was added TFA (100 mL) at 0° C. The mixture was stirred at room temperature for 3 hr. The mixture was concentrated in vacuum. The residue was poured into ice-water (200 mL), and then basified with aq. NaHCO₃ till pH>8. The mixture was filtered, and the filter cake was washed with water, dried in vacuo to give 6C (11 g, 98%) as white solid.

To a solution of 6D (50 g, 0.22 mol) in CCl₄ (750 mL) was added N-bromosuccinimide (38.9 g, 0.22 mol) and benzoyl peroxide (1.1 g, 4.4 mmol) at room temperature. The reaction mixture was stirred 4 hr at 60° C. while irradiated with a 250 watt lamp. The mixture was cooled to room temperature, washed with 1 M aq. NaOH, water, and dried over Na₂SO₄. The solvent was evaporated to afford the crude 6E (75 g) as oil, which was taken to next step directly.

The crude 6E (75 g) was suspended in NH₃/MeOH (2M, 750 mL) and concentrated ammonium hydroxide (250 mL) at room temperature for overnight. The mixture was filtered and the filter cake was dried in vacuo to give 6F (35 g, 75% for two steps) as white solid.

$^1$H-NMR (400 MHz, DMSO_d₆): 8.64-8.66(s, 1H), 7.83 (s, 1H), 7.66-7.68(d, 1H), 7.59-7.61(s, 1H), 4.37(s, 2H)

To a solution of 6F (6 g, 28 mmol) in MeOH (100 mL), palladium acetate (0.12 g), Et₃N (8.6 g, 85 mmol) and Xantphos (0.6 g) were added. The reaction mixture was stirred at 140° C. under CO (3 MPa) overnight. The mixture was cooled to room temperature and filtered. The filtrate was concentrated in vacuo to provide 6G (6 g).

$^1$H-NMR (400 MHz, DMSO_d₆): 8.82-8.84 (s, 1H), 8.16-8.18 (s, 1H), 8.05-8.07(s, 1H), 7.79-7.81(s, 1H), 4.44-4.46 (s, 2H), 3.90-3.92 (s, 3H)

To 6G (6 g) in CH₂Cl₂ (180 mL) was added di-tert-butyl dicarbonate (12.2 g, 56 mmol), Et₃N (2.8 g, 28 mmol) and DMAP (3.4 g, 28 mmol), The reaction mixture was stirred 2 hr at room temperature. The mixture was washed with 0.5 N HCl, water, dried over Na₂SO₄ and concentrated in vacuum. The crude product was purified by flash column chromatography to give 6H (4.2 g, 51% for two steps) as white solid.

$^1$H-NMR (400 MHz, CDCl₃): 8.15-8.17 (m, 2H), 7.96-7.98 (m, 1H), 4.80-4.82 (s, 2H), 3.96-3.98 (s, 3H), 1.59-1.61 (s, 9H)

To a solution of 6H (5.8 g, 20 mmol) in THF (100 mL) was added a solution of LiOH.H₂O (4.2 g, 100 mmol) in water (100 mL) with ice-bath. The reaction mixture was stirred for 5 hr at room temperature. Then the reaction mixture was concentrated in vacuum to remove THF. The aqueous phase was acidified with citric acid till PH<6, and then filtered. The filter cake was dried in vacuo to provide 6I (4.6 g, 78%) as a white solid.

¹H-NMR (400 MHz, DMSO_d₆): 7.86-7.98 (m, 3H), 7.38-7.40 (m, 1H), 4.48-4.49 (m, 2H),1.40-1.42 (s, 9H)

To a solution of 6I (3 g, 10.1 mmol) and 6C (3 g, 10.1 mmol) in DMF (30 mL) was added EDCI (1.9 g, 10.1 mmol), HOBt (1.3 g, 10.1 mmol) at room temperature. The mixture was stirred at ambient temperature for 2 hr. The three batches were combined, poured into water and extracted with EtOAc. The combined organic phases were washed with brine, dried over Na₂SO₄, filtered and concentrated in vacuum. The residue was purified by flash column chromatography to provide crude product (1.7 g). The crude product was recrystallized to give pure 6J (1.1 g, 6.3%) as a white solid.

¹H-NMR (400 MHz, DMSO_d₆): 13.21 (br, 1H), 8.55-8.53 (m, 1H), 7.89-7.87 (m, 4H), 7.76-7.67 (m, 3H), 7.43-7.23 (m, 6H), 4.50-4.20 (m, 5H), 3.32-3.24 (m, 2H), 3.07-3.02 (m, 2H), 1.70-1.65 (m, 2H), 1.40-1.27 (m, 9H). LC-MS: m/z=473.9 (M−100+1).

Synthesis of 4-((2-(((((9H-fluoren-9-yl)methoxy)carbonyl)amino)ethyl)sulfonyl)-2-(((tert-butoxycarbonyl)amino)methyl)benzoic acid

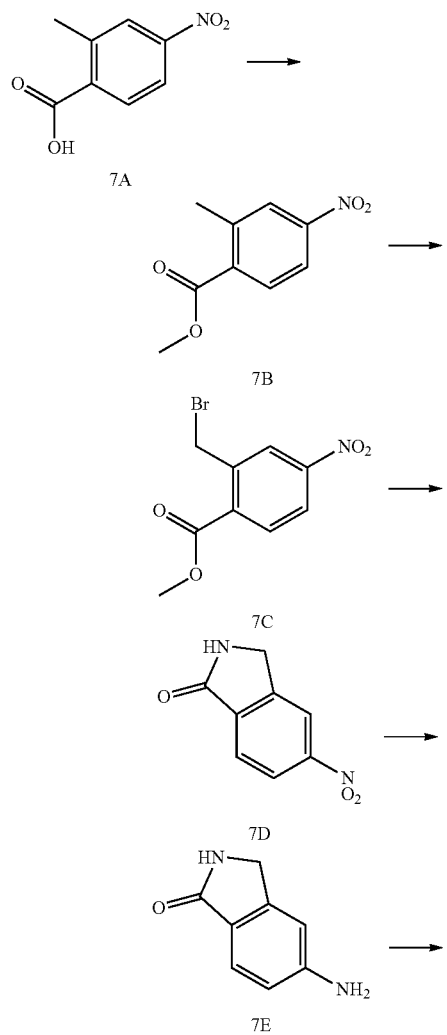

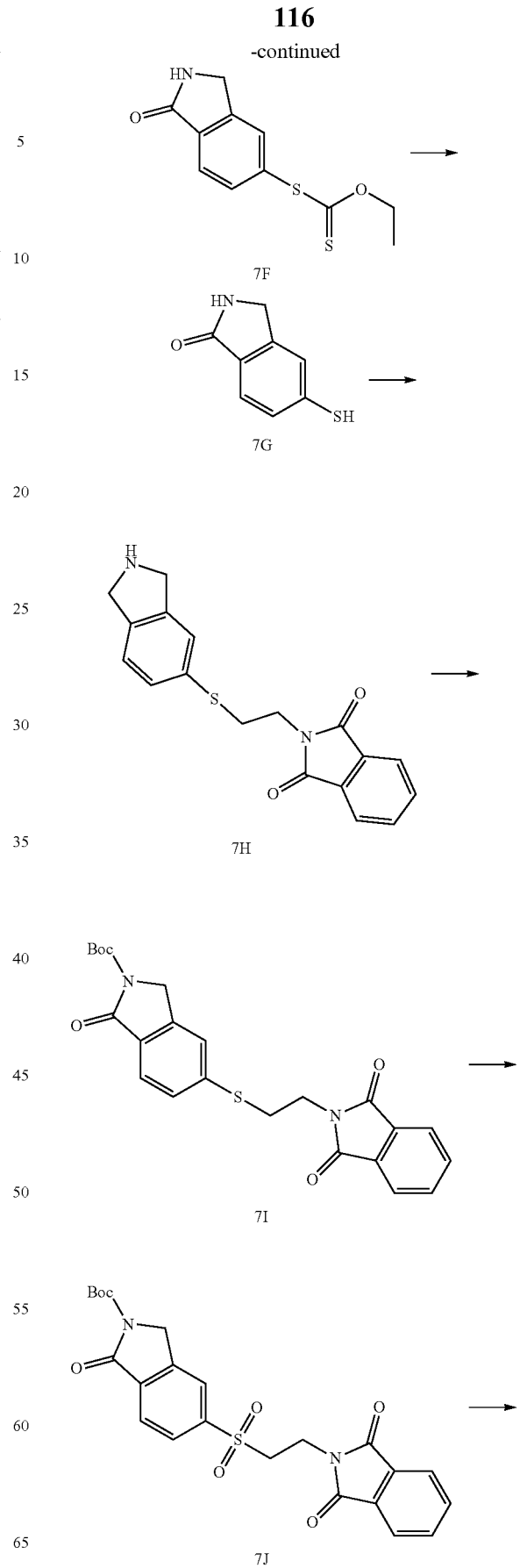

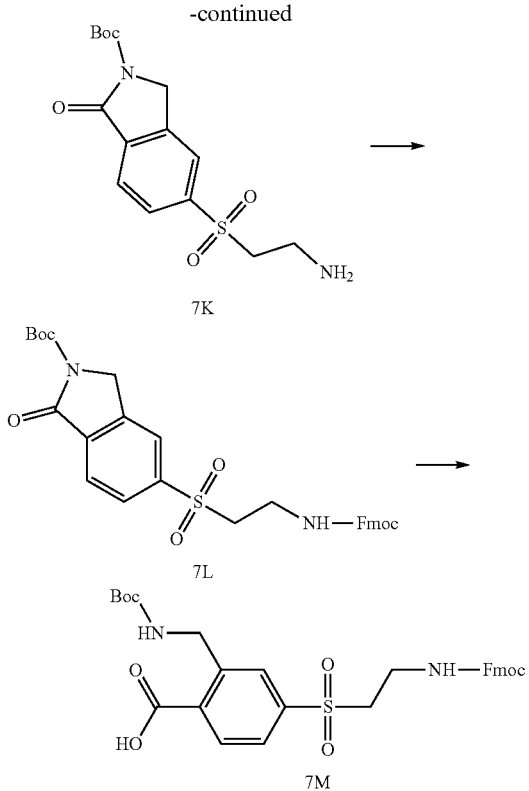

To a solution of 7A (50 g, 0.27 mol) in DMF (500 mL) was added K₂CO₃ (65 g, 0.54 mol). The mixture was cooled to 0° C., CH₃I was added dropwise. The reaction mixture was stirred 4 hr at room temperature. The mixture was extracted with EtOAc and washed with water, dried over Na₂SO₄ to afford crude 7B (55 g) as yellow oil.

To a solution of compound 7B (50 g, 0.26 mol) in CCl₄ (500 mL), N-bromosuccinimide (45.8 g, 0.26 mol) and benzoyl peroxide (0.12 g, 0.5 mmol) were added. The reaction mixture was stirred 4 hr at 60° C. The reaction mixture was cooled to RT and was washed with 1N NaOH and water and it was dried over Na₂SO₄, The solvent was evaporated to afford crude 7C (71 g) as yellow oil.

Crude 7C (70 g, 0.26 mol) was suspended in 2M NH₃ in MeOH (700 mL) and concentrated ammonium hydroxide (250 mL) at room temperature overnight. The mixture was filtered to afford crude 7D (35 g) as a white solid.

To a solution of 7D (35 g, 0.2 mol) in MeOH (350 mL) was added Pd/C (7 g), the mixture was stirred at 50° C. under H₂ at 50 psi for 2 hr. The mixture was filtered and concentrated in vacuum to afford crude 7E (30 g) as a white solid.

To a solution of 7E (30 g, 0.2 mol) in H₂O (540 mL) and HCl (45 mL) was added a solution of NaNO₂ (14 g, 0.2 mol) in H₂O (130 mL) at 0° C. After 45 min, to the reaction was added a solution of potassium O-methyl carbonodithioate (39 g, 0.24 mol) in H₂O (540 mL) at room temperature. The reaction mixture was stirred for 30 min. The mixture was acidified to pH 2 with 6N hydrochloric acid and filtered. The solid was washed with water and dried to give 7F (60 g) as a yellow solid.

¹H NMR (CDCl₃, 400 MHz): δ 8.76 (s, 1H), 7.76-7.78 (m, 2H), 7.63-7.65 (m, 1H), 4.58-4.63 (m, 2H), 4.42 (s, 2H), 1.23-1.28 (t, 3H).

A solution of 7F (60 g, 0.24 mol) in EtOH (600 mL) and KOH (46.5 g, mL) in H₂O (600 mL) was added. The reaction mixture was stirred for 30 min at 80° C. and then concentrated under pressure. Water was added and acidified to pH 2 with 6N hydrochloric acid and filtered. The solid was washed with water and dried to give 7G (25.2 g) as a yellow solid.

¹H NMR (CDCl₃, 400 MHz): δ 7.71-7.73 (d, 1H), 7.33-7.35 (d, 2H), 4.40 (s, 2H), 3.65 (d, 1H).

To a solution of 7G (25 g, 0.15 mol) in DMSO (400 mL), was added 2-(2-bromoethyl) isoindoline-1,3-dione (46.2 g, 0.18 mol) and K₂CO₃ (62.7 g, 2.15 mol). The reaction mixture was stirred 50° C. for 30 min. The reaction mixture was poured into ice water, stirred for 20 min and filtered to give 7H (48 g) as a yellow solid.

¹H NMR (DMSO-d₆, 400 MHz): δ 8.43 (s, 1H), 7.78-7.82 (m, 4H), 7.46-7.50 (t, 2H), 7.38-7.40 (s, 1H), 4.25 (s, 2H), 3.84-3.87 (t, 2H), 3.36-3.39 (t, 2H).

To a solution of 7H (35 g, 0.1 mol) in DMSO (700 mL) was added Boc₂O (27 g, 0.12 mol), Et₃N (10.4 g, 0.1 mol), DMAP (15.4 g, 0.13 mol) at room temperature. The mixture was stirred at 50° C. for 2 hr. The reaction mixture was poured into ice water, stirred for 30 min and filtered to give crude 7I (25 g) as a white solid.

To a solution of 7I (25 g, 57 mmol) in DCM (250 mL) was added m-CPBA (25 g, 0.14 mol) at 0° C. The mixture was stirred at ambient temperature for 1 hr and then quenched with sodium thiosulfate and extracted with DCM. The combined organic phases were washed with brine, dried over Na₂SO₄, filtered and concentrated and purification by column chromatography on silica gel to give crude 7J (30 g) as a white solid.

To a solution of 7J (25 g, 53 mmol) in EtOH (125 mL) was added hydrazine hydrate (50 mL) at rt. The mixture was stirred at 80° C. for 1 hr. The mixture was poured into water and extracted with DCM. To the organic layer was added saturated solution of NaHCO₃ (30 mL) and a solution of Fmoc-Cl (25.2 g, 97 mmol) in EtOAc (20 mL). The mixture was stirred at rt for 30 min. Then the reaction mixture was extracted with DCM. The combined organic phases were washed with brine, dried over Na₂SO₄, concentrated and purified by flash chromatography to give 7L (10 g) as a solid.

¹H NMR (CDCl₃, 400 MHz): δ 8.03-8.08 (t, 3H), 7.74-7.76 (d, 2H), 7.55-7.56 (d, 2H), 7.37-7.41 (t, 2H), 7.28-7.31 (t, 2H), 5.51 (bs, 1H), 4.82 (s, 2H), 4.34-4.36 (d, 2H), 4.17-4.18 (t, 1H), 3.65-3.66 (d, 2H), 3.37-3.38 (d, 2H), 1.60 (s, 9H).

To a solution of 7L (10 g, 18 mmol) in MeOH (250 mL) was added 1N LiOH (30 mL) at rt. The mixture was stirred at rt for 30 min. To the mixture was added a solution of Fmoc-Cl (25.2 g, 97 mmol) in EtOAc (20 mL), after 20 min. The mixture was acidified to pH 4 with citric acid and extracted with DCM. The combined organic phases were washed with brine, dried over Na₂SO₄, filtered and concentrated and purified by prep-HPLC (C18, 0.05% Formic Acid-H₂O/CH₃CN=60/40-30/70) to give 7M (980 mg) as a white solid.

¹H NMR (CDCl₃, 400 MHz): δ 8.02-8.10 (m, 3H), 7.75-7.77 (d, 2H), 7.55-7.57 (d, 2H), 7.38-7.42 (t, 2H), 7.29-7.32 (t, 2H), 5.46 (bs, 1H), 4.83 (s, 2H), 4.36-4.37 (d, 2H), 4.16-4.18 (t, 1H), 3.66-3.67 (d, 2H), 3.37 (bs, 2H), 1.61 (s, 9H). LC-MS: m/z=480.8 (M-100+1).

Synthesis of 4-(((((9H-fluoren-9-yl)methoxy)carbonyl)amino)methyl)-2-(((tert-butoxycarbonyl)amino)methyl)-6-methylbenzoic acid

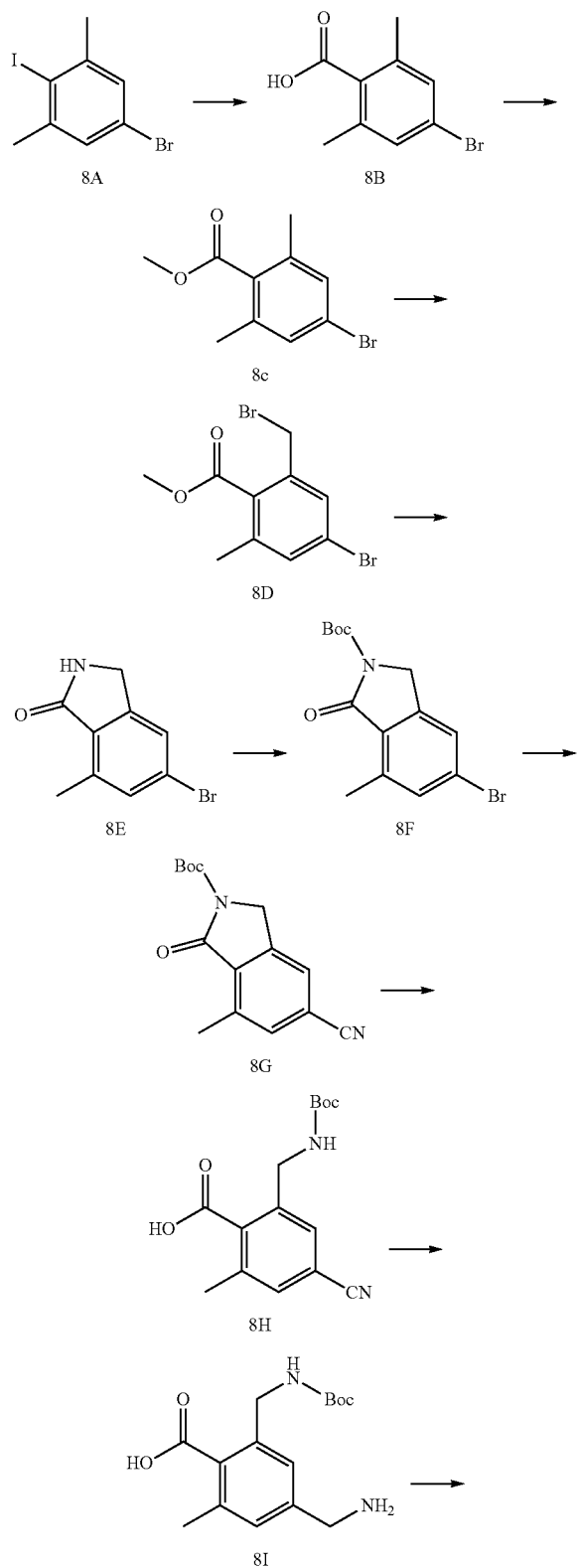

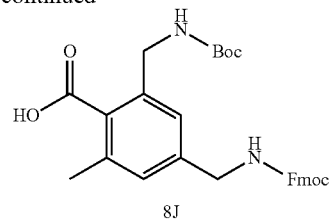

To the solution of 8A (100 g, 322 mmol) in THF (1 L) was added the solution of isoprorylmagnesium bromide in THF (485 mL, 1 M). The solution was stirred for 2 hrs. The resulting solution was poured into dry ice. After stirring for 1 h, the solution was quenched with water. The aqueous layer was adjusted to pH 5 with HCl and extracted with EtOAc. The combined organic layers were dried over $Na_2SO_4$, filtered, and evaporated in vacuum to afford crude 8B as a white solid (44 g, 60%).
$^1$H-NMR (400 MHz, DMSO_$d_6$): 7.24-7.25 (m, 2H), 2.40-2.42 (s, 6H)

To a solution of 8B (50 g, 219 mmol) in DMF (400 mL) was added $K_2CO_3$ (48.6 g, 352 mmol) and $CH_3I$ (32.7 g, 230 mmol), the mixture was stirred at room temperature overnight. The reaction was diluted with water and extracted with EtOAc. The combined organic layers were dried over $Na_2SO_4$, filtered, and evaporated in vacuum to afford the crude product which was purified by flash chromatography to afford 8C (50.3 g, 95%) as white solid.
$^1$H-NMR (400 MHz, DMSO_$d_6$): 7.19-7.21 (s, 2H), 3.89-3.91 (s, 3H), 2.27-2.29 (s, 6H)

To a solution of 8C (50 g, 0.22 mol) in $CCl_4$ (750 mL) was added N-bromosuccinimide (38.9 g, 0.22 mol) and benzoyl peroxide (1.1 g, 4.4 mmol) batchwise. The reaction mixture was stirred at 60° C. for 4 hrs. The reaction mixture was washed with 1N NaOH and water. The organic layer was dried over $Na_2SO_4$, filtered, and evaporated in vacuum to afford crude 8D (75 g) as a yellow oil.

The solution of crude 8D (75 g) in $NH_3$/MeOH (2 M, 750 mL) and concentrated ammonium hydroxide (250 mL) was stirred at room temperature overnight. The precipitate was filtered to provide 8E as a white solid (35 g).
$^1$H-NMR (400 MHz, DMSO_$D_6$): 8.49-8.51 (s, 1H), 7.58-7.60 (s, 1H), 7.43-7.44 (s, 1H), 4.29-4.30 (s, 2H), 2.58-2.59 (s, 3H)

To a solution of 8E (20 g, 88.9 mmol) and $Boc_2O$ (41 g, 188 mmol) in DCM (750 mL) was added $Et_3N$ (9.5 g, 94 mmol) and DMAP (11.7 g, 95.9 mmol) in one portion. The reaction mixture was stirred at room temperature for 2 hrs. The mixture was washed with 0.5N HCl and water. The organic layer was dried over $Na_2SO_4$, filtered, and evaporated in vacuum to afford the crude product which was purified by flash chromatography to afford 8F (25 g, 86.5%) as an white solid.
$^1$H-NMR (400 MHz, DMSO_$d_6$): 7.68-7.69 (s, 1H), 7.52-7.53 (s, 1H), 4.69-4.70 (s, 2H), 2.57-2.58 (s, 3H), 1.51-1.52 (s, 9H)

To a solution of 8F (1 g, 3.08 mmol) in DMF (10 mL) was added $Pd(PPh_3)_4$ (0.1 g, 3%) and $ZnCN_2$ (0.7 g, 6 mmol) in one batch. The reaction mixture was stirred at 100° C. under $N_2$ for 3 hrs. The mixture was cooled to room temperature and filtered. The filtrate was diluted with water and extracted with EtOAc. The combined organic layers were dried over $Na_2SO_4$, filtered, and evaporated in vacuum to afford the crude product which was purified by flash chromatography to afford 8G (0.75 g, 70%) as a white solid.

¹H-NMR (400 MHz, DMSO_d₆): 7.95-7.96 (s, 1H), 7.77-7.78 (s, 1H), 4.76-4.77 (s, 2H), 2.62-2.63 (s, 3H), 1.52-1.53 (s, 9H)

The solution of 8G (1.3 g, 4.48 mmol) in THF (40 mL) and LiOH solution (1 M, 10 mL) was stirred at room temperature for 5 hrs. The reaction was adjusted to pH 5 with HCl and extracted with EtOAc. The combined organic layers were dried over Na₂SO₄, filtered, and evaporated in vacuum to afford crude 8H (1.1 g) as a white solid.

To a solution of 8H (3 g, 10.3 mmol) in MeOH (30 mL) was added Rany Ni (0.3 g). The reaction mixture was stirred at room temperature overnight under H₂ atmosphere. The mixture was filtered and the filtrate was concentrated in vacuum to afford crude 8I (2.6 g) as a white solid.

To the solution of crude 8I (1 g) in DCM (10 mL) and saturated NaHCO₃ solution (10 mL) was added FmocCl (0.7 g, 1.0 eq.) in one portion. The mixture was stirred at room temperature overnight. The reaction was adjusted to pH 5 with HCl and extracted with EtOAc. The combined organic layers were dried over Na2SO4, filtered, and evaporated in vacuum to afford the crude product which was purified by flash chromatography to afford pure 8J (1.2 g).

1H-NMR (400 MHz, DMSO_d6): 7.84-7.90 (m, 3H), 7.68-7.70 (d, 2H), 7.39-7.43 (t, 2H), 7.30-7.34 (t, 2H), 7.17 (s, 1H), 6.98-7.01 (d, 2H), 4.30-4.32 (d, 2H), 4.20-4.24 (t, 1H), 4.13-4.14 (d, 4H), 2.26 (s, 3H), 1.37 (s, 9H). LC-MS: Neg m/z=514.9 (M−1).

Synthesis of (S)-2-(((9H-fluoren-9-yl)methoxy)carbonyl)-7-(tritylamino)-1,2,3,4-tetrahydroisoquinoline-3-carboxylic acid

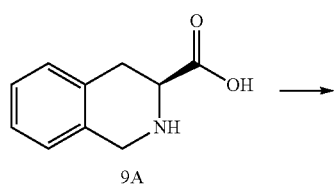
9A

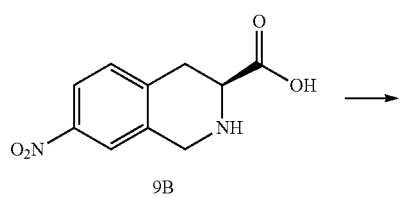
9B

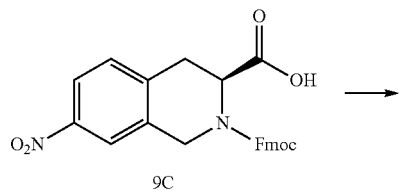
9C

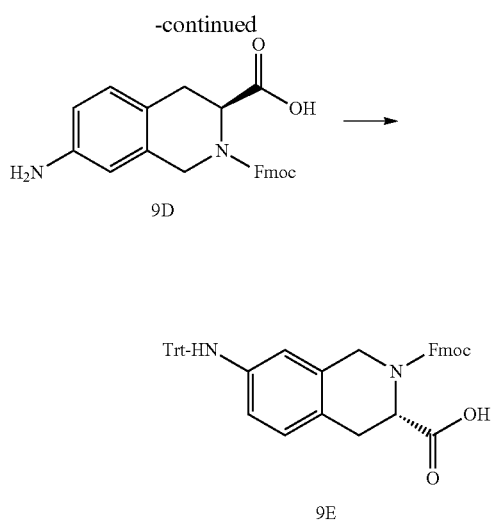
9D

9E

Concentrated HNO₃ (22 mL) was added dropwise to a stirred solution of 9A (30 g, 170 mmol) in concentrated H₂SO₄ (120 mL) at −20° C. The reaction mixture was stirred at −20° C. for 0.5 h then poured into ice water. The mixture was neutralization with ammonium hydroxide, then filtered and washed with water to give 9B as a white solid (35 g, 93%).

A solution of Fmoc-OSu (19.2 g, 81 mmol) in 1,4-dioxane (75 mL) was added to a solution of 9B (15 g, 67.5 mmol) in 10% Na₂CO₃ (120 mL) dropwise at 0° C. The mixture was stirred at room temperature for 2 h then acidified with 10% HCl and extracted with ethyl acetate. The organic phase was dried over Na₂SO₄, filtered, concentrated to give crude product and purified by flash chromatography to give 9C as a white solid (17.4 g, 58%).

¹H-NMR (400 MHz, CDCl₃): 7.93-8.10 (m, 2H), 7.69-7.78 (m, 2H), 7.48-7.58 (m, 2H), 7.21-7.43 (m, 5H), 5.15-5.16 (m, 1H), 4.80-4.84 (m, 1H), 4.47-4.60 (m, 3H), 4.20-4.30 (m,1H), 3.16-3.35 (m, 2H),

Pd/C (4.5 g) was added to a solution of 9C (11 g, 50 mmol) in methanol (500 mL). The reaction mixture was stirred under a hydrogen balloon overnight at room temperature. The mixture was filtered to remove the Pd/C and the solvent was removed to give the crude product. The crude compound was purified by pre-HPLC to give 9D as a white solid (3.1 g, 30%).

¹H-NMR (400 MHz, DMSO_d₆): 7.88-7.92 (m, 2H), 7.62-7.70 (m, 2H), 7.31-7.44 (m, 4H), 6.81-6.84 (m, 1H), 6.31-6.42 (m, 2H), 4.73-4.75 (m, 1H), 4.26-4.48 (m, 5H), 2.89-2.97 (m, 2H)

Trt-Cl (1.2 g, 4.3 mmol) and triethylamine (0.55 g, 5.4 mmol) were added to a solution of 9D (1.5 g, 3.6 mmol) in DCM (20 mL). The reaction was stirred at room temperature for 2 h. The mixture was washed with water, dried over Na₂SO₄ and concentrated to give crude product. The crude product was purified by silica gel column to give 9E as a pale yellow solid (1.5 g, 63%).

¹H-NMR (400 MHz, DMSO_d₆): 7.84-7.89 (m, 2H), 7.64-7.60 (m, 2H), 7.42-7.17 (m,19H), 6.87-6.55 (m, 2H), 6.37-6.15 (m, 2H), 4.65-4.6 (m, 1H), 4.30-4.08 (m, 5H), 2.97-2.72 (m, 6H), 2.51-2.49 (m, 1H), 1.09-1.05 (m, 9H). LC-MS: Pos m/z=415.0 (M-Trt+1).

Synthesis of (S)-2-(3-((S)-1-(9H-fluoren-9-yl)-13,13-dimethyl-3,11-dioxo-2,12-dioxa-4,10-diazatetradecan-9-yl)-4H-1,2,4-triazol-4-yl)-3-(tert-butoxy) propanoic acid

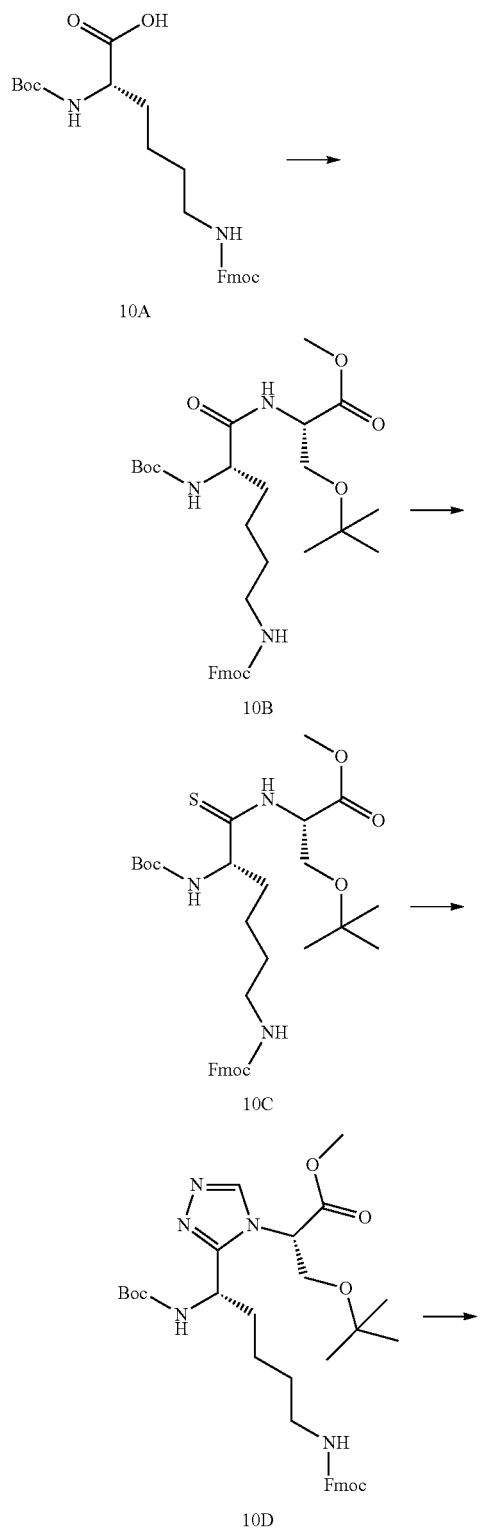

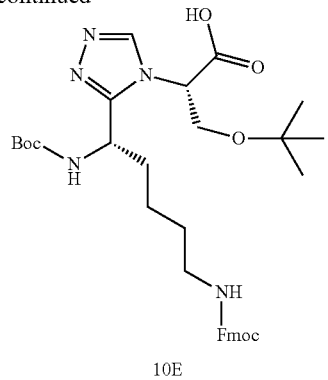

10E

To a solution of 10A (10 g, 21.4 mmol) in $CH_2Cl_2$ (100 mL) was added HOBT (3.5 g, 25.6 mmol) and EDCI (4.9 g, 25.6 mmol). The mixture was stirred at room temperature for 0.5 h. Then DIEA (5.5 g, 42.7 mmol) and H-Ser(tBu)-OMe (5.4 g, 25.6 mmol) were added. The mixture was stirred for 1 h. The mixture was washed with water, aq. $NaHCO_3$, brine, dried over $Na_2SO_4$ and concentrated in vacuum. The residue was purified with flash chromatography to give 10B (7.2 g, 53.9%) as white solid.

To a solution of 10B (7.2 g, 11.5 mmol) in toluene (72 mL) was added Lawensson's reagent (4.7 g, 11.5 mmol) at RT under $N_2$. The mixture was refluxed for 1 hr. The mixture was washed with water, brine, dried over $Na_2SO_4$ and concentrated in vacuum. The residue was purified with flash chromatography to give 10C (4.1 g, 55.6%) as yellow solid.

To a solution of 10C (4.1 g, 6.4 mmol) in THF (160 mL) was added formohydrazide (1.2 g, 19.2 mol) and $HgAC_2$ (6.1 g, 19.2 mmol) at room temperature. The reaction mixture was stirred 2 hr at room temperature. Water and EtOAc were added and the mixture was filtered. The organic layer was washed with water, brine, dried over $Na_2SO_4$ and concentrated in vacuum. The residue was dissolved in THF and added p-toluenesulfonic acid (0.1 g, 0.6 mmol). The mixture was stirred at room temperature overnight. The mixture was concentrated in vacuum and purified by pre-HPLC to give 10D (900 mg, 21.7%) as white solid.

To a solution of 10D (900 mg, 1.4 mmol) in MeOH (30 mL) and $H_2O$ (10 mL) was added NaOH (111 mg, 2.8 mmol) at 0° C. The reaction mixture was stirred 2 hr at 0° C. The mixture was added water and extracted with petroleum ether. The aqueous phase was acidized to pH 3 with HCl. The mixture was filtered, and the filter cake was washed with water, dried in vacua to give 10E (500 mg, 56.8%) as white solid.

$^1$H-NMR (400 MHz, $CDCl_3$): 8.69-8.62 (d, 1H), 7.76-7.72 (m, 2H), 7.59-7.52 (m, 2H), 7.40-7.35 (m, 2H), 7.31-7.28 (m, 2H), 5.60-5.44 (m, 2H), 4.93-4.75 (m, 2H), 4.41-4.35 (m, 2H), 4.21-3.86 (m, 3H), 3.17-3.05 (m, 2H), 2.08-2.00(m, 2H), 1.54-1.49 (m, 12H), 1.15-1.08 (m, 10H). LC-MS: m/z=636 (M+1).

Synthesis of (S)-6-((((9H-fluoren-9-yl)methoxy)carbonyl)amino)-2-(3-((R)-2-(tert-butoxy)-1-((tert-butoxycarbonyl)amino)ethyl)-4H-1,2,4-triazol-4-yl) hexanoic acid

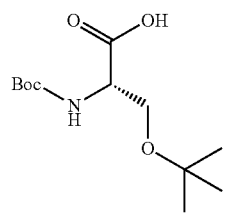

11A

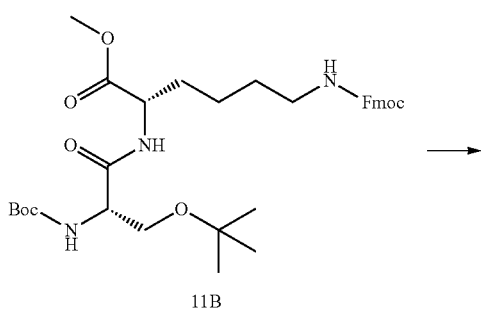

11B

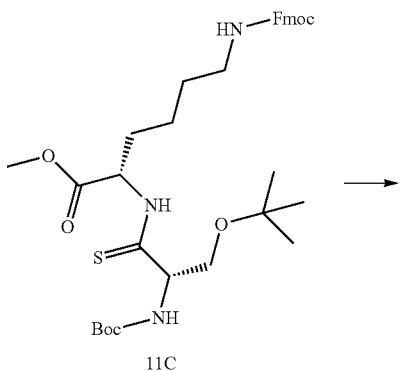

11C

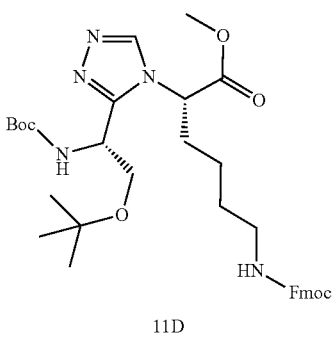

11D

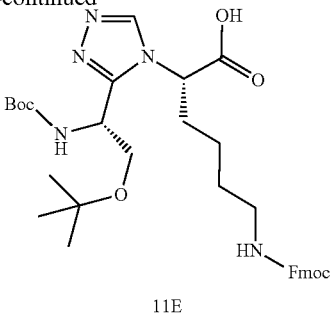

11E

To a solution of 11A (12.5 g, 48 mmol) in CH$_2$Cl$_2$ (125 mL) was added HOBT (7.8 g, 57.6 mmol) and EDCI (11 g, 57.6 mmol). The mixture was stirred at room temperature for 0.5 h. DIEA (12.7 g, 96 mmol) and H-Lys(Fmoc)-OMe (20 g, 48 mmol) were added. The mixture was stirred at room temperature for 1 h. The mixture was washed with water, aq. NaHCO$_3$, brine, dried over Na$_2$SO$_4$ and concentrated in vacuum. The residue was purified with column chromatography to give 11B (26 g, 86.3%) as white solid.

To a solution of 11B (26 g, 41.6 mmol) in toluene (260 mL) was added Lawensson's regant (16.8 g, 41.6 mmol) at RT under N$_2$. The mixture was refluxed for 1 hr. The mixture was washed with water, brine, dried over Na$_2$SO$_4$ and concentrated in vacuum. The residue was purified with column chromatography to give 11C (13 g, 57.5%) as yellow solid.

To a solution of 11C (13 g, 20.3 mmol) in THF (130 mL) was added formohydrazide (3.8 g, 60.8 mol) and HgAC$_2$ (19.4 g, 60.8 mmol) at room temperature. The reaction mixture was stirred 2 hr at room temperature. Water and EtOAc were added and the mixture was filtered. The organic layer was washed with water, brine, dried over Na$_2$SO$_4$ and concentrated in vacuum. The residue was dissolved in THF and added p-toluenesulfonic acid (0.3 g, 2.0 mmol). The mixture was stirred at room temperature overnight. The mixture was concentrated in vacuum and purified by pre-HPLC to give 11D (900 mg, 6.8%) as white solid.

To a solution of 11D (900 mg, 1.4 mmol) in MeOH (30 mL) and H$_2$O (10 mL) was added NaOH (111 mg, 2.8 mmol) at 0° C. The reaction mixture was stirred 2 hr at 0° C. The mixture was added water and extracted with petroleum ether. The aqueous phase was acidized to pH 3 with HCl. The mixture was filtered, and the filter cake was washed with water, dried in vacuo to give 11E (500 mg, 56.8%) as white solid.

$^1$H-NMR (400 MHz, CDCl$_3$): 8.51-8.38 (d, 1H), 7.74-7.73 (m, 2H), 7.59-7.52 (m, 2H), 7.39-7.35 (m, 2H), 7.29-7.27 (m, 2H), 6.00-5.99 (m, 1H), 5.30-4.94(m, 3H), 4.35-4.30 (m, 2H), 4.20-4.16 (m, 1H), 3.75-3.54 (m, 2H), 3.21-2.96(m, 2H), 2.27-1.90(m, 2H), 1.52-1.34 (m, 13H), 1.17-0.94 (m, 10H). LC-MS: m/z=636 [M+1].

Synthesis of (S)-2-(5-((S)-1-(9H-fluoren-9-yl)-13,13-dimethyl-3,11-dioxo-2,12-dioxa-4,10-diazatetradecan-9-yl)-1H-1,2,3-triazol-1-yl)propanoic acid

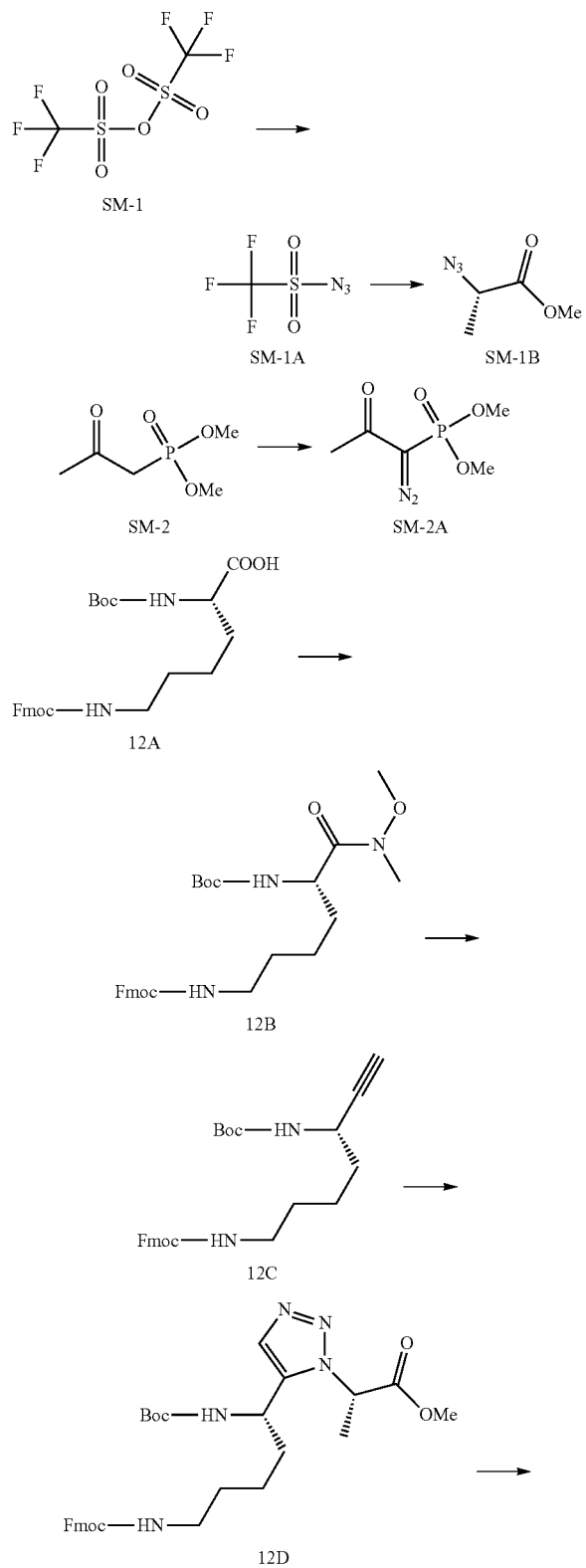

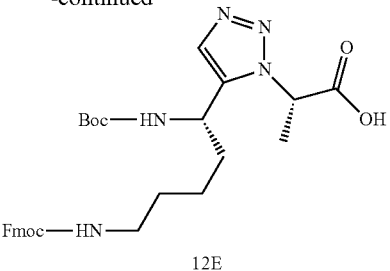

To a solution of NaN₃ (12.66 g, 194.7 mmol) in H₂O (10 ml) and DCM (44 ml) was added Tf₂O (6.3 ml, 37.2 mmol) in DCM (20 ml) dropwise, and the reaction mixture was stirred for 2 h. The organic phase was separated and washed with sat. NaHCO₃, brine, dried over MgSO₄, filtered to give the solution of SM-1A in DCM, which was used in next step directly.

To a solution of (S)-methyl 2-aminopropanoate hydrochloride (1.74 g, 12.5 mmol), K₂CO₃ (2.6 g, 18.7 mmol) and CuSO₄ 5H₂O (62.4 mg, 0.25 mmol) in DCM (10 ml) was added a solution of SM-1A in DCM. The resulting solution was stirred at room temperature overnight. The reaction mixture was diluted with water and extracted with DCM. The organic phase was dried over Na₂SO₄, filtered, concentrated in vacuum to give crude SM-1B (1.26 g, crude), which was used in next step without further purification. LC-MS: m/z=130.3 (M+1).

To a solution of SM-2 (5.0 g, 30 mmol) in CH₃CN (50 ml) was added K₂CO₃ (5.0 g, 36 mmol), the suspension was stirred at 40° C. for an hour and a solution of TsN₃ (6.53 g, 33 mmol) in CH₃CN (20 ml) was then added. The resulting mixture was stirred for an additional 2 hours and filtered over diatomaceous earth. The filtrate was concentrated in vacuum to give the crude which was purified by flash chromatography to give the desired product SM-2A (4.0 g, 69.4%).

$^1$H-NMR (400 MHz, CDC 3): 3.75-3.80(m, 6H), 2.18-2.20(m, 3H). LC-MS: m/z=193.1 (M+1).

A mixture of 12A (5.0 g, 10.68 mmol), EDCI (2.67 g, 13.9 mmol), HOBt (1.9 g, 13.9 mmol) and DIEA (2.3 ml, 13.9 mmol) and N,O-dimethylhydroxylamine hydrochloride (1.36 g, 13.9 mmole) were added in DCM (200 ml) and the resulting mixture was stirred at rt overnight. The reaction mixture was diluted with water, extracted with EtOAc, dried over MgSO₄, filtered, concentrated in vacuum to give the crude product, which was purified by flash chromatography to give 12B (6.59 g, ~100%).

To a solution of 12B (1.0 g, 2.0 mmol) in DCM (20 ml) was added DIBAL-H (6.0 ml, 5.87 mmol) dropwise at −78° C., and then the reaction mixture was stirred at −78° C. for 2 hours, excess of DIBAL-H was quenched by CH₃OH (1 ml), the reaction mixture was allowed to warm to 0° C., K₂CO₃ (0.81 g, 5.87 mmol) was added, and then intermediate SM-2A (0.752 g, 3.91 mmol) in DCM (20 ml) was added. The reaction mixture was stirred at room temperature overnight. The reaction mixture was diluted with DCM, washed with brine, dried over MgSO₄, filtered, concentrated in vacuum to give the crude, which was purified by flash chromatography to give 12C (640 mg, 71.4%).

To a solution of 12C (420 mg, 0.94 mmol), SM-1B (121 mg, 0.94 mmol) and CuSO₄ 5H₂O (2.4 mg, 0.0094 mmol) in EtOH (1.8 ml), H₂O (1.8 ml) and DCM (3 ml) was added sodium ascorbate (0.1 ml, 0.2 mmol, 2.0 M). The resulting mixture was stirred at room temperature overnight. The reaction mixture was diluted with EtOAc, washed with brine, dried over Na₂SO₄, filtered, concentrated to give the crude product (450 mg), which was purified by flash chromatography to give 12D (364 mg, 67.1%).

A solution of 12D (2.62 g, 4.5 mmol) in THF (10 ml) and LiOH (4.5 ml, 9 mmol, 2.0 M in water) was stirred at 0° C. for 10 min, and then the reaction mixture was acidified with citric acid. The reaction mixture was extracted with ethyl acetate, washed with brine, dried over Na₂SO₄, filtered, concentrated in vacuum to give the crude, which was purified by flash chromatography to give 12E (1.3 g).

¹H-NMR (400 MHz, MeOD): 7.9 (s, 1H), 7.78-7.80(d, 2H), 7.63-7.65(d, 2H), 7.36-7.38 (t,2H), 7.30-7.32(t,2H), 5.46(q, 1H), 4.76-4.80 (s, 1H),4.32-4.34(d, 2H), 4.18-4.20 (t,1H), 3.09-3.12 (t,2H), 2.89-2.93(d,1H), 2.77-2.81(d,1H), 1.81-1.98(m,5H), 1.18-1.65(m,13H). LC-MS: m/z=564.1 (M₊1); m/z=562.2 (M−1)

Synthesis of 2-(aminomethyl)-4-sulfamoylbenzoic acid

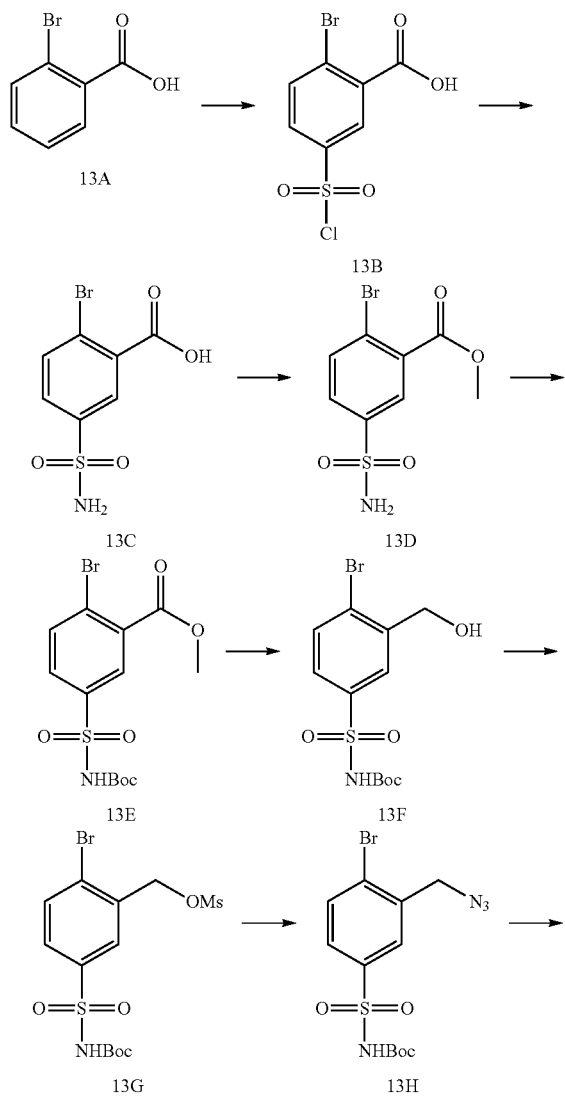

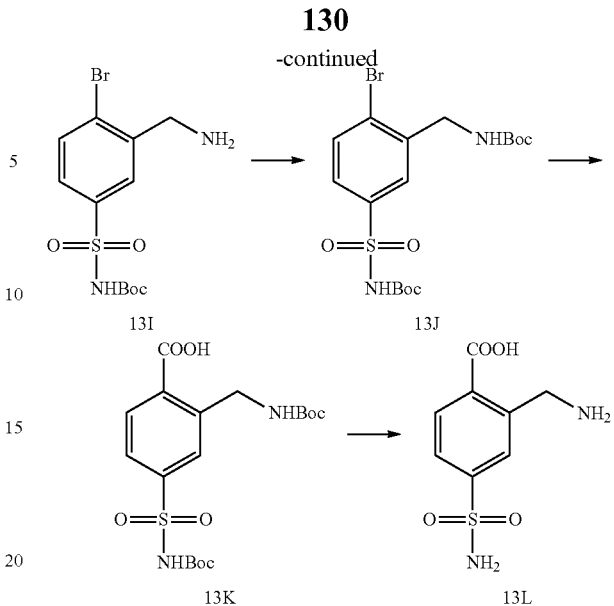

13A (25 g) was added to 100 mL chlorosulfonic acid and heated to 135-140° C. and stirred overnight. The reaction was cooled and poored on ice, filtered, washed with H₂O, dried over MgSO₄, and concentrated in vacuo to obtain yellow-brownish solid 13B (30 g).

At ice bath temperature 13B (30 g) was added to ammonia (150 mL) and stirred overnight. Water was added and pH was adjusted to 2 by HCl. The mixture was extracted with ethyl acetate. The organic layer was dried over MgSO₄ and concentrated in vacuo to give yellow-brownish solid 13C (23 g).

At ice bath temperature SOCl₂ (15 mL) was added dropwise to 13C (23 g) in methanol (500 mol). The reaction was stirred at room temperature overnight. After solvent removal saturated NaHCO₃ was added to the residue and extracted with ethyl acetate. The organic layer was dried over MgSO₄ and concentrated in vacuo to give 13D (25 g).

At ice bath temperature 13D (20 g), Di-tert-butyl dicarbonate (Boc₂O, 20 ml), DMAP (500 mg), and triethylamine (30 mL) were added to CH₂Cl₂ (150 mL) and stirred at room temperature overnight. The mixture was washed with H₂O, dried over MgSO₄, and concentrated in vacuo to give 13E (30 g).

At ice bath temperature 13E (15.6 g) was added batchwise to LiAlH₄ (10 g) in 1 L of anhydrous THF. The reaction was stirred at 0° C. for 2 hours and monitored by TLC. The reaction was quenched by saturated Na₂SO₄. 1 M NaOH (200 mL) was added. The mixture was filtered and extracted with ethyl acetate. After solvent evaporation the residue was purified with flash chromatography (CH₃OH: CH₂Cl₂ 1:20) to give yellow oil 13F (13.4 g).

At ice bath temperature MsCl (5 g, 3.4 mL) was slowly added to 13F (13.4 g) and triethylamine (12.7 mL) in anhydrous THF (120 mL). The reaction was warmed to room temperature and kept stirring for 4 hours. The reaction was quenched with saturated NaCl, extracted with ethyl acetate. Solvent was evaporated and the residue was purified with flash chromatography (CH₃OH: CH₂Cl₂ 1:20) gave white oil 13G (11.7 g).

13G (11.7 g) was dissolved in DMF (50 mL) followed by NaN₃ (4 g). The reaction was heated to 60° C. and stirred for 3 hours. The reaction was cooled to room temperature, quenched with H₂O and extracted with ethyl acetate. The organic layer was dried over MgSO₄ and concentrated in vacua to give 13H (7.4 g).

13H (7.4 g) and triphenyl phosphine (11 g) were added to THF (300 mL). The reaction was stirred at rt for 3 hours. After addition of H₂O (6 mL) the reaction was refluxed for another 5 hours. After cooled to rt, the reaction solution 13I was used directly for next step synthesis.

DMAP (400 mg), triethylamine (30 mL), Di-tert-butyl dicarbonate (Boc₂O, 20 ml) were added to reaction solution 13I. The reaction was stirred overnight at rt. After extraction with EtOAc, the combined organic layer was washed with 1 M HCl, saturated NaCl, dried over MgSO₄, and concentrated in vacuo. Purification by flash chromatography (ethyl acetate: petroleum ether 1:4) gave orange oil 13J (3.4 g).

At dry ice/acetone bath temperature, 2.5M/L BuLi (7 mL) was added dropwise to 13J (1.7 g) in anhydrous THF (60 mL) under N₂. The reaction was stirred for 1 hour at −70° C. before dry ice was added to the reaction. Stirring was continued for another 1 hour. Saturated NH₄Cl was used to quench the reaction and pH was adjusted to 11 with 2 M NaOH. After extraction with ethyl acetate, the pH of aqueous layer was adjusted to 3 with HCl. After extraction with ethyl acetate the organic layer was dried over MgSO₄ and concentrated in vacuo. The residue was purified with HPLC to give 13K (140 mg).

13K (140 mg) was dissolved in TFA/CH₂Cl₂ (1:1, 10 mL) and stirred at room temperature for 1 hour. After evaporation of solvent, the residue was purified by HPLC to give 13L (12.2 mg).

¹HNMR: (400 MHz, D₂O) δ 8.18 (d, 1H), 7.90-8.01 (2H), 4.39 (s, 2H). MS (m/z): 229 [M−H]⁺

(S)-6-(((((9H-fluoren-9-yl)methoxy)carbonyl)amino)-2-(5-((S)-1-((tert-butoxycarbonyl)amino)ethyl)-1H-tetrazol-1-yl)hexanoic acid

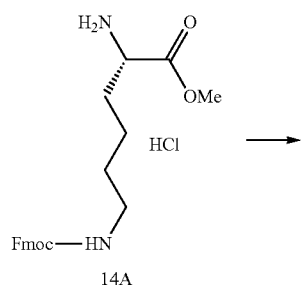

14A

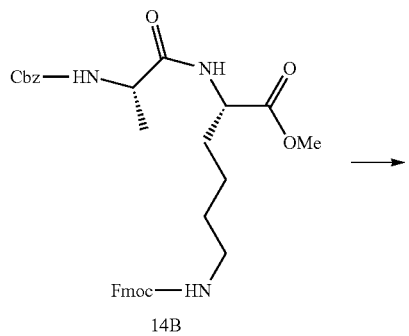

14B

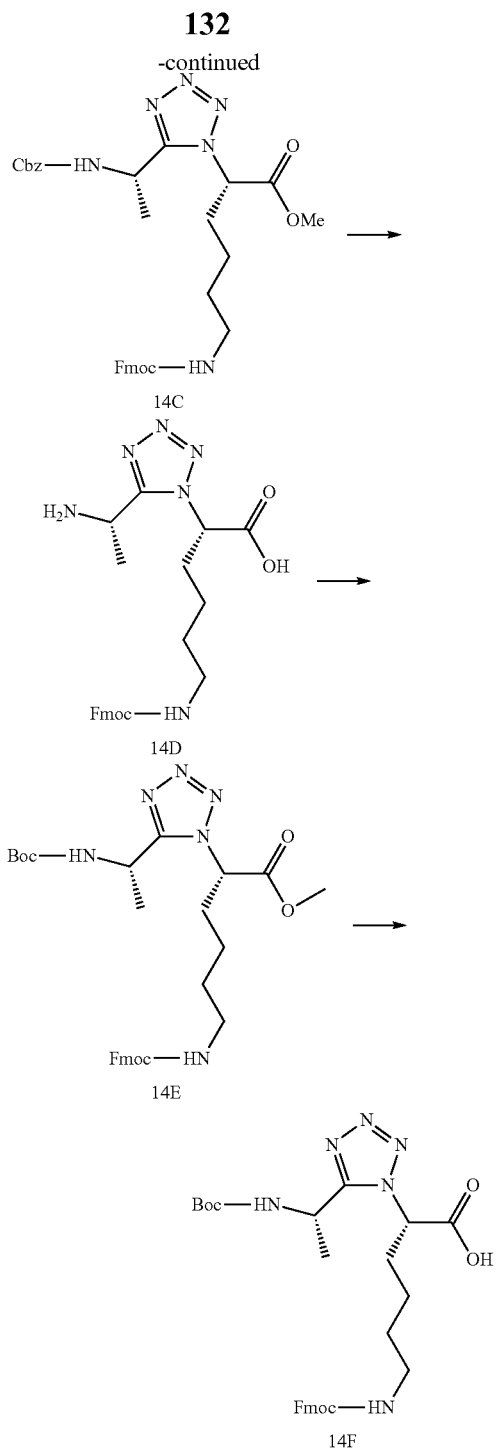

A mixture of 14A (2.0 g, 5.24 mmol), (S)-2-(((benzyloxy)carbonyl)amino)propanoic acid (1.3 g, 5.76 mmol), HATU (3.0 g, 7.86 mmol) and DIPEA (3.7 g, 28.82 mmol) in DCM (200 mL) was stirred at rt for 14 h, The reaction mixture was diluted with DCM and extracted with water, the organic layer was separated, concentrated in vacuo and purified by flash chromatography to give 14B (3.0 g) as a white solid.

To a solution of 14B (200 mg, 0.34 mmol) in 1,4-dioxane (5.0 mL) was added PCl₅ (142 mg, 0.68 mmol) and the mixture was stirred for 3 h. TMSN₃ (90 mg, 0.78 mmol) was added to the mixture. The reaction mixture was stirred 24 h and was quenched by ice water, extracted with EtOAc, and washed with NaHCO$_3$. The organic layers were combined, dried with Na$_2$SO$_4$, and concentrated in vacuo. The residue was purified by flash column chromatography on silica gel to give 14C (30 mg) as a white solid.

To a solution of 14C (20 mg) in DCM (5.0 mL) was added HBr (33% wt in AcOH) and anisole (0.5 mL). The reaction mixture was stirred at rt for 2 h, The mixture was concentrated to afford crude 14D as a brown solid (50 mg), which was used in the next step without further purification.

To crude 14D (50 mg) in DCM (5.0 mL) (Boc)$_2$O (0.2 mL) and Et$_3$N (0.4 mL) were added. The resulting mixture was stirred at rt for 2 h. The reaction was concentrated in vacuo and the residue was purified by prep-TLC to get 14E (10 mg) as a white solid.

14E (10 mg, 0.017 mmol) and Me$_3$SnOH (9.4 mg, 0.052 mmol) were dissolved in DCE (5.0 mL) and the resulting mixture was stirred under reflux for 12 h. The reaction was quenched with HCl (1N). After solvent evaporation the residue was purified by Prep-HPLC to give 14F (5.0 mg) as a white solid.

$^1$NMR (400 MHz, d$_6$-DMSO): (two diasteromers, dr=~2:1) δ 13.57 (br s, 1H), 7.89 (d, J=7.2 Hz, 2H), 7.79 (d, J=6.8 Hz, 0.37H, NH proton, minor diasteromer), 7.67 (d, J=7.2 Hz, 2H), 7.70-7.60 (br s, 0.62H, overlap, NH proton, major diasteromer), 7.41 (d, J=7.2 Hz, 2H), 7.33 (d, J=7.2 Hz, 2H), 7.26-7.23 (m, 1H, NH proton), 5.54-5.46 (m, 1H), 5.9-5.04 (m, 0.64H, major diasteromer), 4.99-4.92 (m, 0.33H, minor diasteromer), 4.29-4.15 (m, 3H), 2.95-2.89 (m, 2H), 2.32-2.16 (m, 2H), 1.48 and 1.45 (d, J=6.8 Hz, 3H, Me, overlap), 1.34 (s, 9H, Boc), 1.40-0.93 (m, 4H, overlap). LC-MS (ESI): m/z 565 [M+H]

Peptide Synthesis

Peptides in this disclosure were synthesized with solid phase method as C-terminal acids on Wang resin or as C-terminal amide on Rind amide resin using Fmoc chemistry. Peptides were synthesized using a 5-fold molar excess of Fmoc protected amino acids that were activated by 5-fold excess of diisopropylcarbodiimide (DIC) and 1-hydroxybenzotriazole (HOBT). Other coupling reagents such as HATU, HBTU, DEPBT, EDC, BOP can also be used instead. The commonly used amino acids and protective groups are as follows:
Fmoc-Cys(Trt)-OH, Fmoc-Asp(OtBu)-OH, Fmoc-Glu(OtBu)-OH, Fmoc-His(Trt)-OH, Fmoc-Lys(Boc)-OH, Fmoc-Asn(Trt)-OH, Fmoc-Gln(Trt)-OH, Fmoc-Arg(Pmc)-OH, Fmoc-Ser(tBu)-OH, Fmoc-Thr(tBu)-OH, Boc-Trp(Boc)-OH or Fmoc-Tyr(tBu)-OH.
Fmoc protecting groups were removed by treating the resin attached polypeptides with 20% piperidine/DMF. Ninhydrin (2,2-Dihydroxyindane-1,3-dione) test was used to monitor the progress of coupling. Each resin-bound polypeptide chain was cleaved from the solid support by treatment with TFA at room temperature for two hour with triisopropylsilane (TIS) and H$_2$O (5%) as the scanvagers. The cleaved peptide was precipitated in ice-cold diethyl ether. Alternatively, peptides can be synthesized on 4-methylbenzhyryl amine (MBHA) resin or 4-Hydroxymethyl-phenylacetamidomethyl (PAM) resin using Boc chemistry. The peptides are cleaved from the resin using HF/p-cresol for 1 hour at 0° C. followed by HF removal and ether precipitation.

General Protocol for Ester Formation

When the hydroxyl group of a pharmaceutically active agent is acylated by a promoiety, the activated ester of the promoiety is generated by the addition of DIC (1 mmol) to a solution of promoiety (2 mmol) in DCM (2 mL). DMAP (0.9 mmol, 244 mg) of is then added. This mixture is transferred to the reaction vessel containing the pharmaceutically active agent (0.5 mmol) and the reaction is stirred overnight. This protocol can be used for ester formation in small molecules as well as depsi-peptide synthesis.

Preparative Purification

Purification was performed using Agilent 1200 RP-HPLC with a 250×10 mm Phenomenex Jupiter (4μ particle size, 300 A° pore size) column. Solvent A contained 5% CH$_3$CN/0.1% TFA in deionized water, and solvent B contained 0.1% TFA in 100% CH$_3$CN. A linear gradient (0-70% B in 90 minutes) was employed and the flow rate was 4 ml/min and the fraction size was 5 ml. The correct fractions were combinted, freezed and lyophilized.

Determination of Half Life in PBS

Polypeptides GIVEQAA-NH$_2$ (SEQ ID NO: 57) and GIVEQAAY (SEQ ID NO: 58), two mimics of the N-terminus section of insulin A chain, were used as model peptides to determine the half lives of various promoieties linked to the N-terminus of the peptides through an amide bond. The model peptides were prepared with Fmoc chemistry, cleaved by TFA and purified by preparative RP-HPLC.

The promoiety capped model peptide was dissolved at 1 mg/mL concentration in PBS and the solution was incubated at 37° C. in a water bath. Samples were collected for analysis at different time points (e.g., 8 h, 16 h, 24 h, 48 h, 72 h, 96 h, 120 h). If the half life of a promoiety capped model peptide is significantly longer or shorter, the time frame for sampling analysis would be changed accordingly. The promoiety cleavage was quenched by lowering pH to 2 by addition of 0.1% TFA solution. RP-HPLC was used to monitor the cleavage reactions and the cleavage rates were quantitatively studied by measuring the peak areas of the promoiety capped and released model peptides. Agilent 6110 Quadrupole LC-MS was employed to verify the change of mass in the course of reaction.

The RP-HPLC analysis was performed using a Shimadzu LC-2010A HT system and a 150 mm×4.6 mm Zorbax 300SB-C18 column. The flow rate was 1 ml/mm. Solvent A contained 0.1% TFA/5% CH$_3$CN in deionized water, and solvent B contained 0.1% TFA in 100% CH$_3$CN. A linear gradient was employed (e.g., 10-70% B in 10 minutes).

The rate of cleavage was determined for the respective promoiety capped model peptides. The concentrations of the promoiety capped model peptides and the released model peptides were determined by their respective peak areas. The first order dissociation rate constant of a promoiety capped model peptide was determined by plotting the logarithm of [starting promoiety capped model peptide]/[remaining promoiety capped model peptide] at various time intervals. The half life for cleavage of a promoiety capped model peptide was calculated by using the equation and the slope derived from this plot.

The cleavage half lives of various promoieties linked to the model peptides were determined using the procedures described above. The data generated in these experiments is presented in Tables 1 and 2.

TABLE 1

Cleavage of various promoieties linked to the N terminus of model peptide X-GIVEQAAY
(SEQ ID NO: 59)

| X | t₁/₂ (h) | X | t₁/₂ (h) |
|---|---|---|---|
| (2-aminomethyl)benzoyl | 1028.0 | 4-(3-aminopropylcarbamoyl)-2-(aminomethyl)benzoyl | 112.1 |
| 2-(aminomethyl)pyridine-3-carbonyl | 457.5 | C10-NH-(CH₂)₃-NH-CO-(aminomethyl-pyridinyl)-carbonyl | 181.3 |
| 3-(aminomethyl)pyridine-2-carbonyl | 596.8 | 2-(carboxymethyl)benzoyl | 6.2 (pH 4) |
| 2-(2-aminomethylphenyl)acetyl (ketone linker) | 481.8 | 2-(carboxymethyl)benzoyl | 183.3 |
| Fmoc-HN-(Lys)-triazole-Ser-CO- | 79.7 | HO-CH₂-C(NH₂)-triazole-(Lys-NH-Fmoc)-CO- | 193.1 |
| NH₂-Ala-Indo2CA | 3.4 | NH₂-Ala-Tic | 58.9 |
| NH₂-Phe-Indo2CA | 9.7 | NH₂-dK(C10)-dTic | 50.6 |
| NH₂-Val-Indo2CA | 13.0 | NH₂-K(C10)-Tic | 46.9 |
| NH₂-K(C10)-Indo2CA | 6.0 | | |
| Mal-PEG2-Lys(C10)-Tic | | | 72.6 |

TABLE 1-continued

Cleavage of various promoieties linked to the N terminus of model peptide X-GIVEQAAY
(SEQ ID NO: 59)

| X | $t_{1/2}$ (h) | X | $t_{1/2}$ (h) |
|---|---|---|---|
| 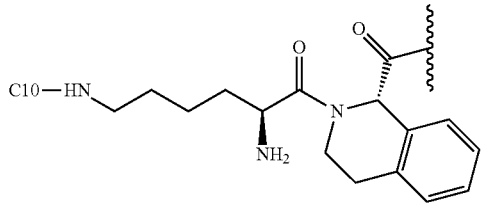 | | | 262.4 |

*C10 is decanoic acid
*indo2CA is indoline-2-carboxylic acid
*Tic is 1,2,3,4-tetrahydroisoquinoline-3-carboxylic acid

TABLE 2

Cleavage of various promoieties linked to the N terminus of model peptide X-GIVEQAA
(SEQ ID NO: 61)

| X | $t_{1/2}$ (h) | X | $t_{1/2}$ (h) |
|---|---|---|---|
| 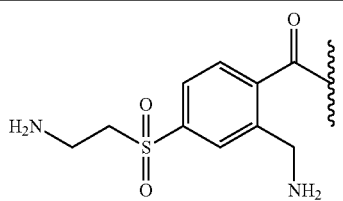 | 28.1 | 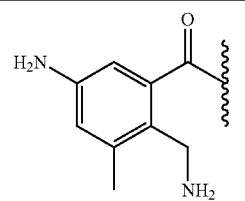 | 85.0 |
| 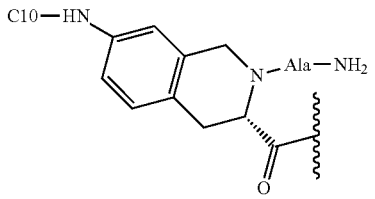 | 38.9 | 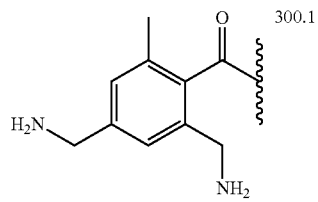 | 300.1 |

Half life for cleavage of the compound below is 779 h.

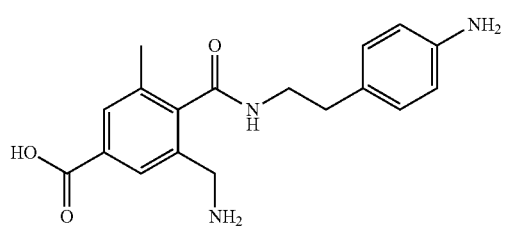 [SMILES: Cc1cc(C(=O)O)cc(CN)c1C(=O)NCCc1ccc(N)cc1]

Determination of Half Life in Serum

Promoiety capped model peptides X-G-dI-dV-dE-dQ-dA-dA were used in the assay. D amino acids were used to prevent other enzymatic cleavage of the model peptides. The peptides were dissolved in 100% serum and incubated at 37° C. Samples were collected for analysis at different time points (e.g., 1 h, 2 h, 4 h, 8 h, 12 h, 24 h, 48 h, 72 h, 96 h, and 120 h) If the half life of a promoiety capped model peptide is significantly longer or shorter, the time frame for sampling analysis would be changed accordingly.

The concentrations of the promoiety capped model peptides and the released parent model peptides were determined by their respective peak areas. The first order dissociation rate constant of a promoiety capped model peptide was determined by plotting the logarithm of [starting promoiety capped model peptide]/[remaining promoiety capped model peptide] at various time intervals. The half life for cleavage of a promoiety capped model peptide was calculated by using the equation and the slope derived from this plot.

TABLE 3

Cleavage of various promoieties linked to the N terminus of model peptide
X-G-dI-dV-dE-dQ-dA-dA

| X | $t_{1/2}$ (h) | X | $t_{1/2}$ (h) |
|---|---|---|---|
| (structure) | 96.4 | (structure) | 72.3 |
| (structure) | 91.5 | (structure) | 102.8 |
| (structure) | 39.9 | (structure) | 105.7 |

Synthesis of Exenatide Prodrugs

Four exenatide prodrugs have the sequences X-HGEGT-FTSDLSKQMEEEAVRLFIEWLKNGGPSSGAPPPS-NH$_2$ (SEQ ID NO: 62), X is linked to the α-amino group of histidine. The prodrugs were assembled by solid phase peptide synthesis using Fmoc chemistry.

X for exenatide prodrug 1 is as follows:

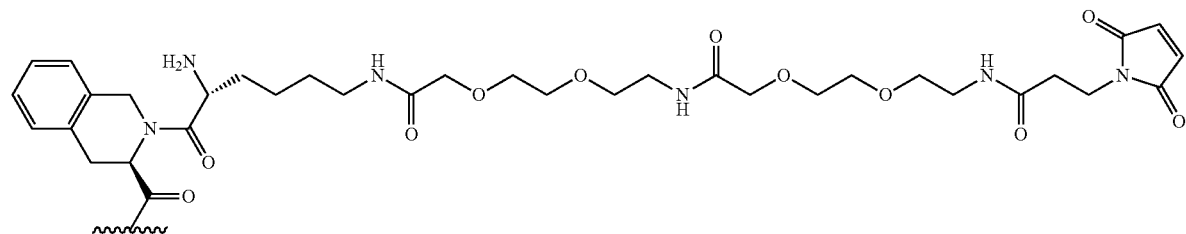 [SMILES: *C(=O)[C@H]1Cc2ccccc2CN1C(=O)[C@H](N)CCCCNC(=O)COCCOCCNC(=O)COCCOCCNC(=O)CCN1C(=O)C=CC1=O]

ESI: m/z=983.25 [M+5H]$^{5+}$, 1228.25 [M+4H]$^{4+}$

Exenatide prodrug 1 can be conjugated to human serum albumin in vivo or ex vivo.

Ex vivo conjugate formation of maleimido-activated prodrug and albumin

HSA (10 mg/ml) in 50 nM Tris buffer (pH 8.0) was mixed with excess (1.5 equivalent) maleimido activated promoiety and ethylenediamine tetraacetic acid (0.1 equivalent). The mixture was stirred at room temperature for 4 h. The resulting HSA-maleimido conjugate was purified from the excess unreacted promoiety by size exclusion chramotography (HiLoad 26/60 Superdex 75 prep grade) in PBS, pH 7.4, flow rate 2.5 ml/min. The correct fractions are identified by MALDI-TOF-MS, combined and lyophilized to give the desired conjugates.

The above can be used as a general protocol for thiol-maleimido reaction, such as a peptide containing a reactive cysteine or a pharmaceutically active agent with a reactive thiol group and a maleimido activated reagent (e.g., methoxy PEG maleimido reagent).

X for exenatide prodrug 2 is as follows:

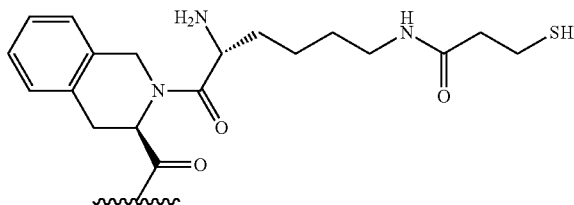 [SMILES: *C(=O)[C@H]1Cc2ccccc2CN1C(=O)[C@H](N)CCCCNC(=O)CCS]

ESI: m/z=1141.33 [M+4+H]$^{4+}$, 1521.62 [M+3H]$^{3+}$, 1529.50 [M+2H+Na]$^{3+}$

General Protocol for Reaction of Thiol-containing Prodrugs with Iodoacetyl Functioned PEG A pharmaceutically active peptide containing a reactive cysteine or a reactive thiol group can be pegylated by iodoacetyl-functioned PEG on the thiol group. The peptide is dissolved in 4 M urea/50 nM Tris buffer and excess (1.5-fold) iodoacetyl-functioned PEG is added and the mixture was stirred overnight at 4° C. The pegylated peptide was purified by preparative HPLC and the identity confirmed by mass spectrometry.

Reaction of exenatide prodrug 2 with iodoacetyl PEG4OK gave the pegylated exenatide prodrug. MALDI-TOF-MS: 44000-48000, broad peak. Calculated MS: 44560

X for exenatide prodrug 3 is as follows:

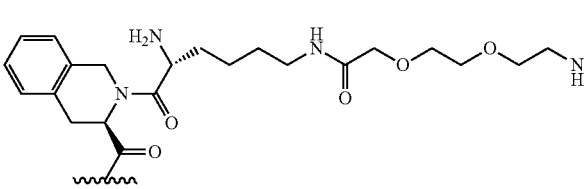

ESI: m/z=1271.66 [M+4H]$^{4+}$, 1695.83 [M+3H]$^{3+}$, 1703.31 [M+Na+2H]$^{3+}$

X for exenatide prodrug 4 is as follows:

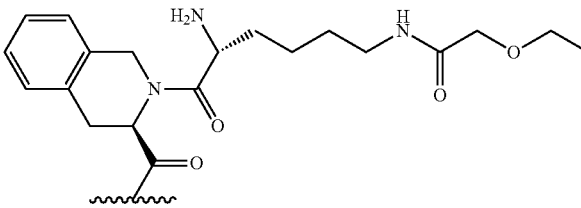

ESI: m/z=986.65 [M+5H]$^{5+}$

General Protocol for Reaction of Iodoacetyl Functioned Prodrug with Albumin

HSA (6.25 mg/ml) in Tris buffer was mixed with 1.2 M equivalent of iodoacetyl-peptide and stirred at room temperature overnight. The resulting HSA-prodrug conjugate was purified from the excess unreacted peptide by size exclusion chramotography (HiLoad 26/60 Superdex 75 prep grade) in PBS, pH 7.4, flow rate 2.5 m/min. The correct fractions were identified by MALDI-TOF-MS.

Reaction of exenatide prodrug 3 with human serum albumin gave the exenatide-albumin conjugate. MALDI-TOF-MS: 71420, broad peak. Calculated MS: 71383

Biological Activities of Exenatide Prodrugs in Plasma

Exenatide prodrug 1 human serum albumin conjugate (BK1411101-1411105), exenatide prodrug 2 PEG40K conjugate (BK1411201-1411205), and exenatide prodrug 3 albumin conjugate (BK1411301-1411304) were incubated in serum at 37° C. Samples were collected at different time points.

| | | | | | |
|---|---|---|---|---|---|
| BK1411101 | 0 h | BK1411102 | 24 h | BK1411103 | 72 h |
| BK1411104 | 96 h | BK1411105 | 144 h | | |
| BK1411201 | 0 h | BK1411202 | 24 h | BK1411103 | 36 h |
| BK1411104 | 48 h | BK1411105 | 60 h | | |
| BK1411301 | 0 h | BK1411302 | 12 h | BK1411303 | 24 h |
| BK1411304 | 72 h | | | | |

Exenatide prodrug 1 (BK1411001) was dissolved in PBS, diluted with serum and used directly.

To investigate the restored activities after cleavage of promoieties from exenatide prodrugs all samples were analyzied by GLP-1 receptor functional assay.

HEK293 cells stably expressing GLP-1 receptor constructed by WuXi AppTec were cultured in DMEM (Invitrogen, Cat# 11960077) supplemented with 10% FBS (GIBCO, Cat# 10099141). On the assay day, the cells were collected by Trypsin solution (0.05%; Invitrogen, cat #25300-062), washed twice with assay buffer (HBSS 1×(Invitrogen, Cat #14025) containing 5 mM HEPES, 0.1% BSA, pH 7.4), then mixed with Alexa Fluor® 647-anti cAMP antibody (1:100, LANCETM cAMP 384 Kit, PerkinElmer, Cat #AD0264). Serial dilutions of testing samples were incubated for 1 h at room temperature in OptiPlate-384, white (Perkin-Elmer, Cat #6007290). After incubation 12 micro liters of LANCE® cAMP Detection Mix were added to each well. The microplates were covered with TopSeal-A film (Perkin-Elmer) and incubated for 60 minutes at room temperature. At the end of incubation TR-FRET fluorescence were measured on EnVision (Ex: 340 nm, Em: 615 nm and 665 nm, Perkin-Elmer). Effective 50% concentrations were calculated by using GraphPad Prism 5. The results are shown in FIG. 1A-FIG. 1D.

Exenatide proved to be a highly potent GLP-1 receptor agonist in the assays. BK1411001, BK1411101, BK1411201, and BK1411301 displayed more than 100 folds reduction in activity, which were consistant with prodrug designs. The actual activities of four prodrugs might be even lower as small amount of exenatide may be released from the four prodrugs during incubation and made significant contribution to the activities in the assays. As time progressed an increasing amount of exenatide was released from the prodrugs and biological activities rose. In vitro results showed all four types of compounds worked well as exenatide prodrugs.

Figure 2A:
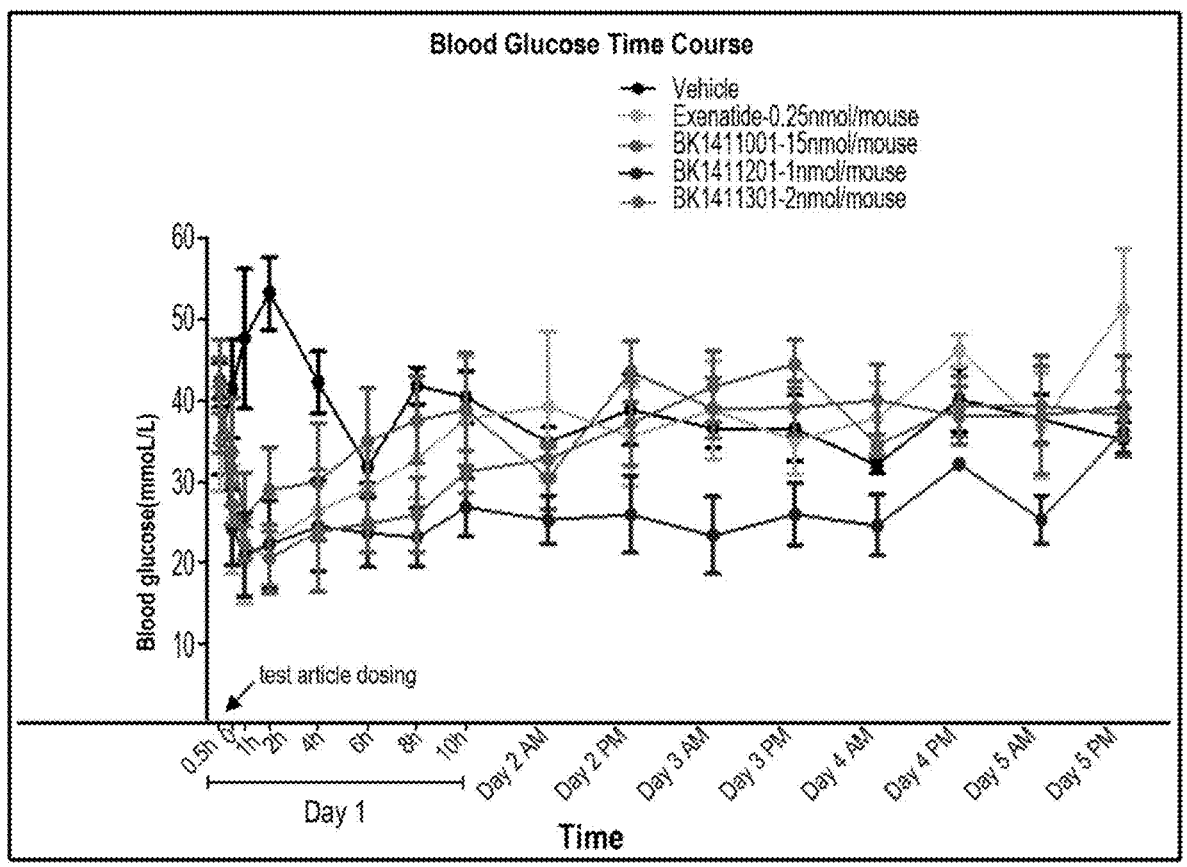
FIG. 2A and FIG. 2B show glucose lowering effects of exenatide and three exenatide prodrugs by single dose s.c. injection in db/db mice. All three exenatide prodrugs showed extended time of action in comparison to exenatide.
Figure 2B:
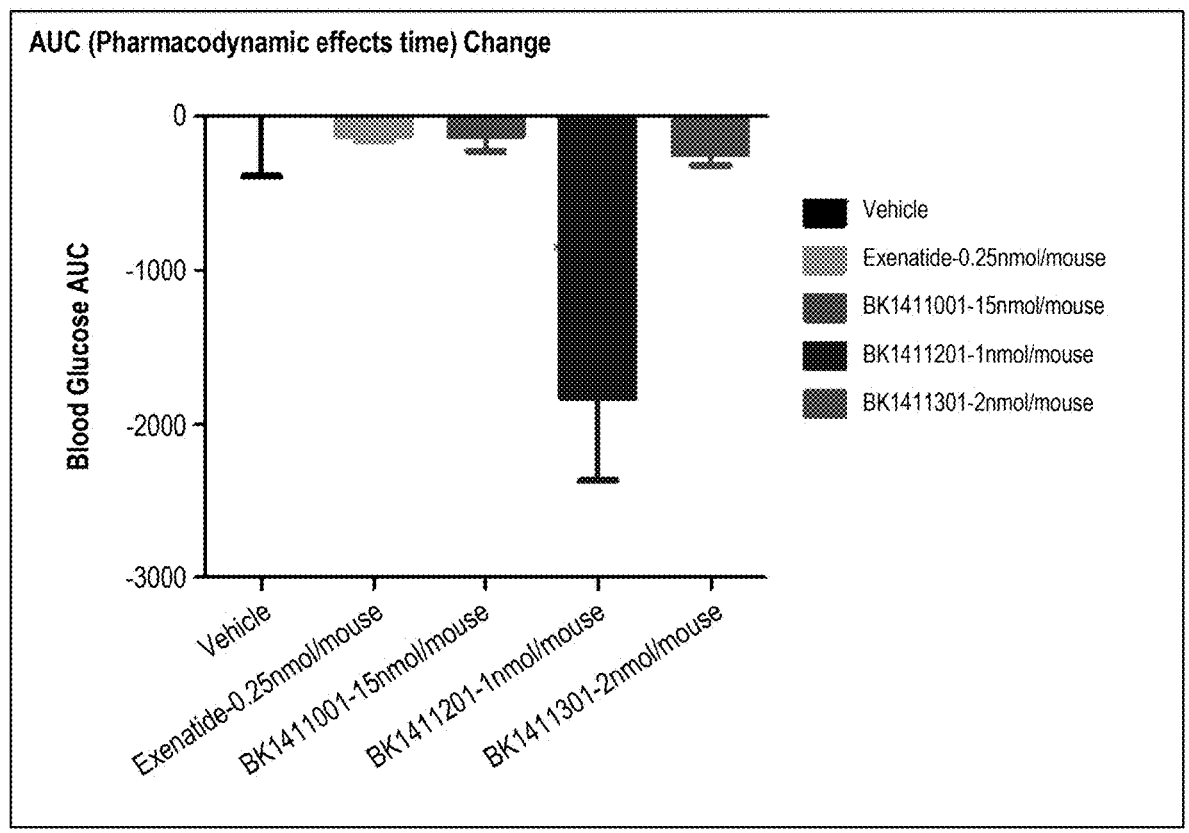

In vivo effects of exenatide prodrugs in mice db/db mice (body weight range 30-40g) were housed in the facility after arriving for at least one week for acclimation before the experiment. The baseline blood glucose was recorded for three days (day-3~day-1) before experiment at 10:00 am and 15:00 pm. The mice were randomly divided into 5 groups base on the blood glucose in the morning among three days. The mice were dosed with exenatide, exenatide prodrugs or vehicle s.c (single dose) in day 1 10:00 am. Blood glucose was recorded at multiple time points: Day1 30 min, 1h, 2h, 4h, 6h, 8h, 10h post dose. From day 2 blood glucose was measured at 10:00 am and 15:00 pm daily until the efficacy trend disappeared. Results of the experiment are shown in FIG. 2A and FIG. 2B.

At time point 0 h mice (n=3) were injected s.c. with either vehicle, exenatide, or exenatide prodrug 1 (BK1411001, 15 nmol/mouse), exenatide prodrug 2 PEG40K conjugate (BK1411201, 1 nmol/mouse), and exenatide prodrug 3 albumin conjugate (BK1411301, 2 nmol/mouse). The maximum effective time of the test articles are: Exenatide at 0.25 nmol<10 h; BK1411001 at 15 nmol<29 h; BK1411201 at 1 nmol<101 h; BK1411301 at 2 nmol<48 h. All the exenatide prodrugs displayed prolonged blood glucose lowering effect in comparison to that of exenatide. BK1411201 at 1 nmol and BK1411301 at 2 nmol had comparable maximum effect comparing to that of exenatide base on blood glucose data at 2 hr, while BK1411001 at 15 nmol was less potent. BK1411001 is designed to form a conjugate with serum albumin in vivo. It seems a large percentage of BK1411001 is quickly eliminated from system circulation before formation of albumin conjugate. Additionally, albumin Cys34-maleimido linkage is known to be unstable in mouse plasma and can be cleaved by retro-Michael reaction. This explains the relatively short duration of action of BK1411001 in comparison to BK1411301, which is conjugated to human serum albumin through a stable thioether bond. BK1411201 at 1 nmol showed the max AUC change. All the exenatide prodrugs are better than exenatide at 0.25 nmol.

Preparation of Long Acting Insulin Prodrugs

Sulfitolysis

Crude insulin A china or B china (0.5 mM, about 1-1.5 g) was dissolved in 150 ml fresh buffer comprising of 86 g Guanidine HCl, 1.8 g Tris, 5.2 g $Na_2SO_3$, 3.75 g $Na_2S_4O_6$. The pH was adjusted to about 8.5 and stirred at room temperature for 1 hour. Sephadex G10 column was used for desalting. A buffer: 0.05 M $NH_4HCO_3$, B buffer: 0.05 M $NH_4HCO_3$, 50% acetonitrile. The correct fractions were combined, frozen, and lyophilized.

Protection of Free Amino Groups on Insulin B Chain

Insulin B chain s-sulfonate (200 mg, 55.8 µmoles) and Di-tert-butyl dicarbonate ($Boc_2O$) (25 mg, 114.3 µmoles) were dissolved in 0.05 M $NH_4HCO_3$ (50 ml) in 20% acetonitrile. The reaction was stirred at room temperature overnight. The mixture was desalted with Sephadex G10 column. The correct fractions were combined, frozen, and lyophilized to give the diBoc-insulin B chain sulfonate (170 mg).

Combination of Human Insulin a and diBoc-insulin B Chain s-Sulfonates

Insulin A chain s-sulfonates (200 mg, 74 µmoles) and diBoc-insulin B chain s-sulfonates (100 mg, 26.3 µmoles) were dissolved in 0.1M glycine buffer (30 ml, pH 10.5). Dithiothreitol (DTT) (30.8 mg, 0.2 mmoles) was added. The reaction was stirred at 4° C. overnight. The reaction mixture was purified by preparative RP-HPLC (A: 0.05 M $NH_4HCO_3$ B: 0.05 M $NH_4HCO_3$, 50% acetonitrile) to give B1,B29-DiBoc insulin (52 mg)

Synthesis of a Pegylated Insulin Prodrug

To a mixture of N-hydroxysuccinimide (126.5 mg, 1.1 mmol) and 4-((3-((((9H-fluoren-9-yl) methoxy)carbonyyeamino)propyl)carbamoyl)-2-(((tert-butoxycarbonyl) amino)methyl)benzoic acid (573.6 mg, 1 mmol) in dioxane (120 mL) was added N,N'-dicyclohexylcarbodiimide (DCC) (227 mg, 1.1 mmol). The mixture was stirred overnight. The reaction mixture was filtered and washed with dioxane (3×10 mL). The combinted filtrate was evaporated to dryness to give crude 2,5-dioxopyrrolidin-1-yl 4-((3-((((9H-fluoren-9-yl) methoxy)carbonyl)amino)propyl) carbamoyl)-2-(((tert-butoxycarbonyl)amino)methyl)benzoate (388 mg) which was used in the next reaction without purification.

2,5-dioxopyrrolidin-1-yl 4-((3-((((9H-fluoren-9-yl) methoxy)carbonyl)amino) propyl)carbamoyl)-2-(((tert-butoxycarbonyeamino)methyl)benzoate (5 mg, 7.5 µmol) was added to B1,B29-diBoc-insulin (30 mg, 5 mol) and imidazole (17 mg, 250 µmol) in DMSO. After stirring overnight DMSO was removed and the residue was purified with RP-HPLC. The peptide was lyophilized. 20% piperidine/DMF (2 mL) was added to the peptide and the mixture was stirred at room temperature for 15 min. DMF was removed and the residue was purified with RP-HPLC to give A1 acylated B1, B29-diBoc insulin.

Methoxy PEG 40K succinimidyl carboxymethyl ester (200 mg, 5 µmol) and A1 acylated B1,B29-diBoc insulin (6.4 mg, 1 µmol) were dissolved in 0.1N bicine buffer (pH 8, 1.5 mL) and stirred at room temperature for 2 hours. The mixture was purified by RP-HPLC to give A1 pegylated B1,B29-diBoc-insulin.

A1 pegylated B1, B29-diBoc-insulin was dissolved in TFA/$H_2O$/phenol/thioanisole (85:5:5:5) (3 ml) and stirred for 15 min at room temperature. After removal of TFA, the crude product was purified with RP-HPLC to give the final pegylated insulin prodrug.

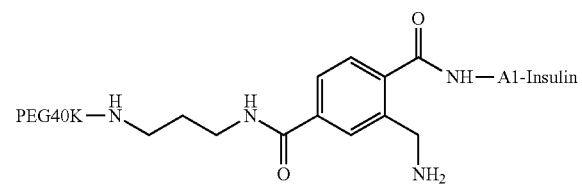

The identity of the peptide was confirmed by MALDI-TOF (broad peak centered at 46106). Calculated MS: 46041.

The half lives of insulin prodrugs in PBS and human plasma were determined using methodologies similar to those for model peptides. In vivo glucose lowering effect can be tested using methodologies similar to those used for exenatide prodrugs.

We claim:

1. A prodrug or a pharmaceutically acceptable salt thereof, comprising a nitrogen-containing or hydroxyl-containing drug or a pharmaceutically active agent conjugated to a promoiety via a covalent bond hydrolytically labile at physiological conditions, wherein the promoiety is of the following formula

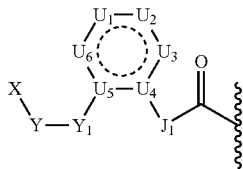

wherein $U_1$, $U_2$, $U_3$, $U_4$, $U_5$, and $U_6$ are independently selected from $CR_{12}$ and N;

X is HN—$R_0$, OH, or SH;

Y is selected from:
(1) N—$R_O$;
(2) C($R_p R_q$); and
(3) O or S, provided that X is not OH or SH;

$Y_1$ is selected from
(1) C($R_3 R_4$);
(2) C(O) or C(S), provided that Y is not C(O), C(S), SO, or $SO_2$;
(3) O, S, SO, or $SO_2$, provided that Y is not O or S;
(4) N—$R_n$; and
(5) a bond;

$J_1$ is a bond;

$R_0$, $R_O$, $R_p$, $R_q$, $R_n$, $R_3$, $R_4$, $R_{10}$, $R_{11}$, and $R_{12}$ are independently selected from hydrogen (H), lower alkyl, lower alkoxy, acyl, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, imino, amino lower alkyl, lower alkylamino, lower dialkylamino, hydroxyl, hydroxyl alkyl, nitro, nitrile (—CN), isonitrile (—NC), pyridyl, azido, azo, carboxyl, carboxamido, carbethoxy, thioalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, mercapto (or sulfhydryl);

or $R_0$, $R_O$, $R_3$, $R_4$, $R_{10}$, $R_{11}$, $R_{12}$, $R_n$, $R_p$, $R_q$ are independently selected from hydrogen (H), $C_1$-$C_{18}$ alkyl, $C_2$-$C_{18}$ alkenyl, ($C_1$-$C_{10}$ alkyl)OH, ($C_1$-$C_{10}$ alkyl)SH, ($C_2$-$C_3$ alkyl)$SCH_3$, ($C_1$-$C_4$ alkyl)$CONH_2$, ($C_1$-$C_{10}$ alkyl)COOH, ($C_1$-$C_{10}$ alkyl)$NH_2$, ($C_1$-$C_4$ alkyl)NHC(=$NH_2^+$)$NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl), ($C_0$-$C_4$ alkyl)($C_6$-$C_{10}$ aryl)$R_{16}$, ($C_1$-$C_4$ alkyl)($C_3$-$C_9$ heteroaryl), and ($C_1$-$C_{12}$ alkyl)($W_1$)($C_1$-$C_{12}$ alkyl), wherein $W_1$ is a heteroatom selected from N, S and O;
$R_{16}$ is selected from H, OH, halo, $C_1$-$C_7$ alkyl, $C_2$-$C_7$ alkenyl, $CF_3$, $OCF_3$, $NO_2$, CN, NC, $O(C_1$-$C_7$ alkyl), $CO_2H$, $CO_2(C_1$-$C_7$ alkyl), $NH(C_1$-$C_{10}$ alkyl), $O(C_1$-$C_{10}$ alkyl), aryl, and heteroaryl;

or two R groups, which are selected from $R_0$, $R_3$, $R_4$, $R_{10}$, $R_{11}$, $R_O$, $R_n$, $R_p$, $R_q$, and $R_{12}$, that are attached to the same atom or attached to two atoms separated by one bond, together with the atom(s) to which they are attached form a $C_3$-$C_8$ cycloalkyl, cycloalkenyl, or cycloalkynyl ring, or saturated or unsaturated heterocyclic ring optionally substituted by the at least one group other than hydrogen (H); or two R groups together with the atom(s) to which they are attached form an aromatic ring optionally substituted by the at least one group other than hydrogen (H), wherein the at least one group is selected from lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, imino, amino lower alkyl, lower alkylamino, lower dialkylamino, hydroxyl, hydroxyl alkyl, nitro, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, and mercapto (or sulfhydryl);

further wherein the prodrug is optionally conjugated to a modifying moiety of the following formula:

-L-M wherein:
L is a covalent bond or an optional linker selected from PEG, long chain fatty acids, natural or unnatural amino acids, dipeptides, —$(CH_2)_n$—, —$(CH_2CH_2O)_n$—, —O—, —S—, —C(O)—, —C(O)O—, —NH—, —NHC(O)CH$_2$—, —C(O)NH—, —SO$_2$CH$_2$CH$_2$—, —HNSO$_2$—, maleimide, and a combination of two or more of the above thereof, or any structure connecting a modifying moiety to a prodrug through a covalent bond; n is an integer in the range from 1 to 30;

M is a modifying moiety selected from hydrophilic moieties, lipophilic moieties, amphiphilic moieties, salt forming moieties, carrier proteins, a targeting agent, a diagnostic label, a fluorophore or enzymatic label, or combinations of two or more of the above thereof with appropriate spacer moieties, linker moieties, and terminating moieties, wherein the various moieties can be covalently coupled to one another by either hydrolyzable or non-hydrolyzable bonds.

2. The prodrug of claim 1, or a pharmaceutically acceptable salt thereof, wherein the promoiety is of the following formula

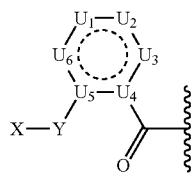

wherein X is HN—$R_0$, OH, or SH;

Y is selected from
(1) N—$R_O$;
(2) C($R_p R_q$); and
(3) O or S, provided that X is not OH or SH;

$U_1$, $U_2$, $U_3$, $U_4$, $U_5$, $U_6$, $R_0$, $R_o$, $R_p$ and $R_q$ are as defined in claim 1.

3. The prodrug of claim 2, or a pharmaceutically acceptable salt thereof, wherein the promoiety is of a formula selected from

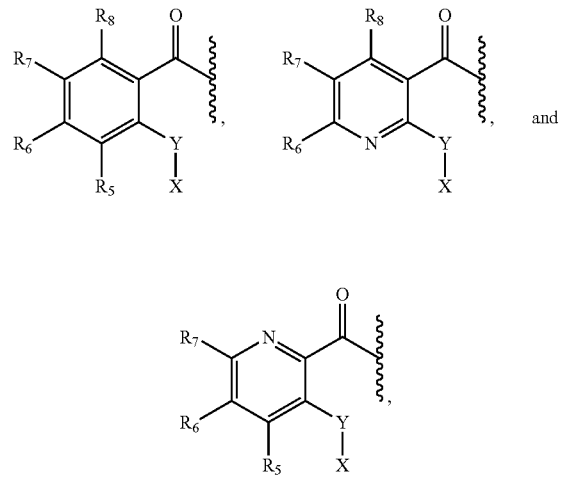

wherein

Y is selected from NH, N—$R_O$, O, provided that X is not OH or SH when Y is O;

X is HN—$R_0$ or OH;

$R_5$, $R_6$, $R_7$, and $R_8$ are independently selected from hydrogen (H), lower alkyl, lower alkoxy, acyl, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, imino, amino lower alkyl, lower alkylamino, lower dialkylamino, hydroxyl, hydroxyl alkyl, nitro, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, and mercapto (or sulfhydryl);

$R_o$, and $R_0$ are as defined in claim 2;

or two R groups selected from $R_5$, $R_6$, $R_7$, $R_8$, and $R_0$, $R_O$ that are attached to the same atom or attached to two atoms separated by one bond form a $C_3$-$C_8$ cycloalkyl, cycloalkenyl, or cycloalkynyl ring, or saturated or unsaturated heterocyclic ring optionally substituted by the at least one group; or two R groups together with the atoms to which they are attached form an aromatic ring optionally substituted by the at least one group.

4. The prodrug of claim 3, or a pharmaceutically acceptable salt thereof, wherein the promoiety is of a formula selected from

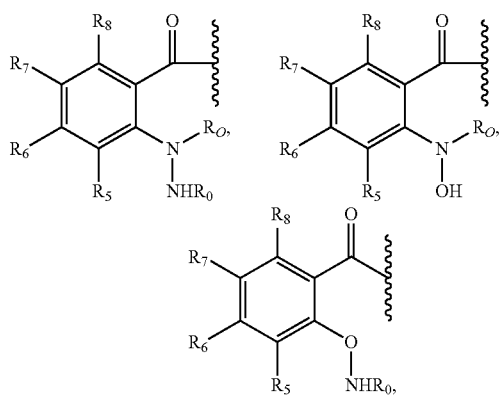

wherein $R_5$, $R_6$, $R_7$, $R_8$, $R_o$, and $R_0$ are as defined in claim 3.

5. The prodrug of claim 4, or a pharmaceutically acceptable salt thereof, wherein the promoiety is of a formula selected from

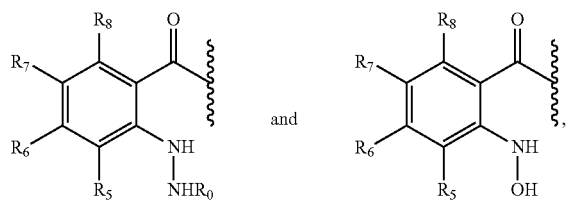

wherein $R_5$, $R_6$, $R_7$, $R_8$, and $R_0$ are as defined in claim 4.

6. The prodrug of claim 2, or a pharmaceutically acceptable salt thereof, wherein Y is $C(R_pR_q)$, when X is HN—$R_0$, wherein $R_0$ and $R_p$ together with the atoms to which they are attached can form a 4, 5, or 6 membered heterocyclic ring.

7. The prodrug of claim 1, or a pharmaceutically acceptable salt thereof, wherein the promoiety is of the following formula

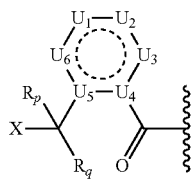

wherein $R_p$, $R_q$, X, $U_1$, $U_2$, $U_3$, $U_4$, $U_5$, and $U_6$ are as defined in claim 1.

8. The prodrug of claim 7, or a pharmaceutically acceptable salt thereof, wherein the promoiety is of a formula selected from

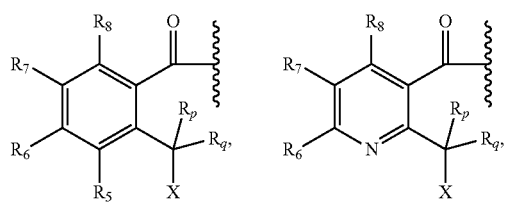

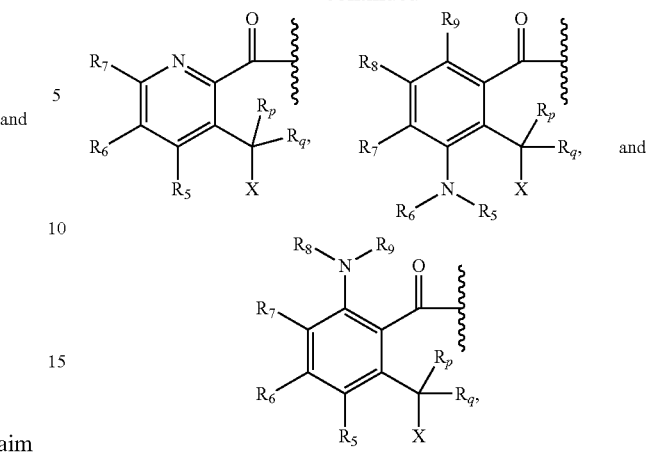

wherein $R_5$, $R_6$, $R_7$, $R_8$, and $R_9$ are independently selected from hydrogen (H), lower alkyl, lower alkoxy, acyl, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, imino, amino lower alkyl, lower alkylamino, lower dialkylamino, hydroxyl, hydroxyl alkyl, nitro, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, and mercapto (or sulfhydryl);

$R_p$, $R_q$, and X are as defined in claim 1;

or two R groups selected from $R_p$, $R_q$, $R_5$, $R_6$, $R_7$, $R_8$, and $R_9$ that are attached to the same atom or two atoms separated by one bond form a $C_3$-$C_8$ cycloalkyl, cycloalkenyl, or cycloalkynyl ring, or saturated or unsaturated heterocyclic ring optionally substituted by at least one group; or two R groups together with the atoms to which they are attached form an aromatic ring optionally substituted by at least one group.

9. The prodrug of claim 8, or a pharmaceutically acceptable salt thereof, wherein the promoiety is of the following formula

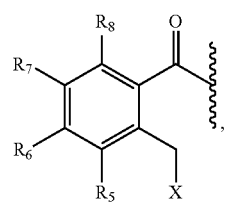

wherein $R_5$, $R_6$, $R_7$, $R_8$, and X are as defined in claim 8.

10. The prodrug of claim 9, or a pharmaceutically acceptable salt thereof, wherein the promoiety is of a formula selected from

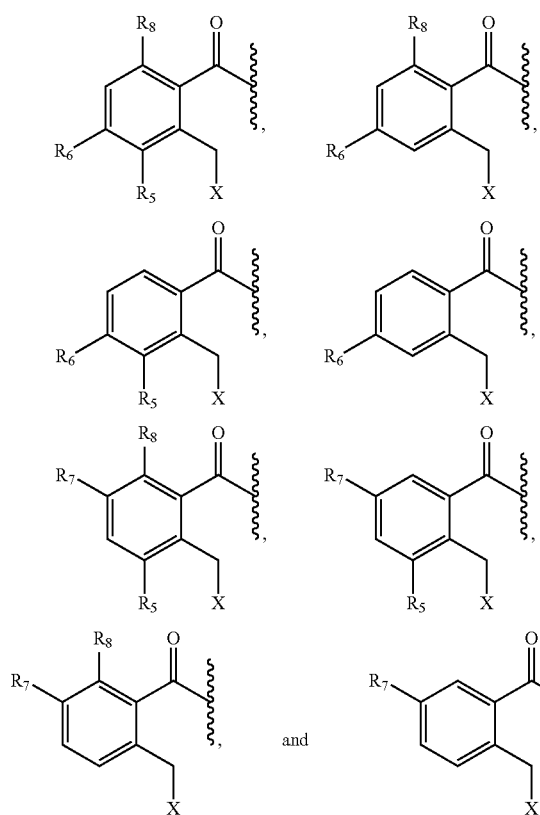

wherein

X is as defined in claims 9;

$R_5$, $R_6$, $R_7$, and $R_8$ are independently selected from the group hydrogen (H), lower alkyl, lower alkoxy, acyl, hydroxyl, amino, halogen, trifluoromethyl, trifluoromethoxy, nitrile, nitro, carboxylic acid, —$SO_2$—OH, —$SO_2$—$NR_{m1}R_{m2}$, —$SO_2$—$R_{m3}$, —O—$R_{m4}$, —S—$R_{m5}$, —N—$R_{m6}R_{m7}$, —C(O)$R_{m8}$, —C(O)O$R_{m9}$, —OC(O)$R_{m10}$, —NHC(O)$R_{m11}$, —C(O)N$R_{m12}R_{m13}$, —NHC(O)N$R_{m14}R_{m15}$, wherein $R_{m1}$, $R_{m2}$, $R_{m3}$, $R_{m4}$, $R_{m5}$, $R_{m6}$, $R_{m7}$, $R_{m8}$, $R_{m9}$, $R_{m10}$, $R_{m11}$, $R_{m12}$, $R_{m13}$, $R_{m14}$, and $R_{m15}$ are independently selected from hydrogen (H), ($C_1$-$C_{18}$) alkyl, aryl, ($C_1$-$C_{18}$ alkyl)OH, ($C_1$-$C_{18}$ alkyl)SH, ($C_1$-$C_{18}$ alkyl)COOH, ($C_1$-$C_{18}$ alkyl)$NH_2$, ($C_0$-$C_4$ alkyl)($C_3$-$C_6$ cycloalkyl), ($C_0$-$C_{10}$ alkyl)($C_2$-$C_5$ heterocyclic), ($C_0$-$C_4$ alkyl)($C_6$-$C_{10}$ aryl), and ($C_1$-$C_4$ alkyl)($C_3$-$C_9$heteroaryl).

11. The prodrug of claim 10, or a pharmaceutically acceptable salt thereof, wherein the promoiety is selected from

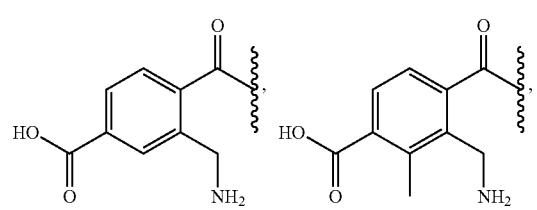

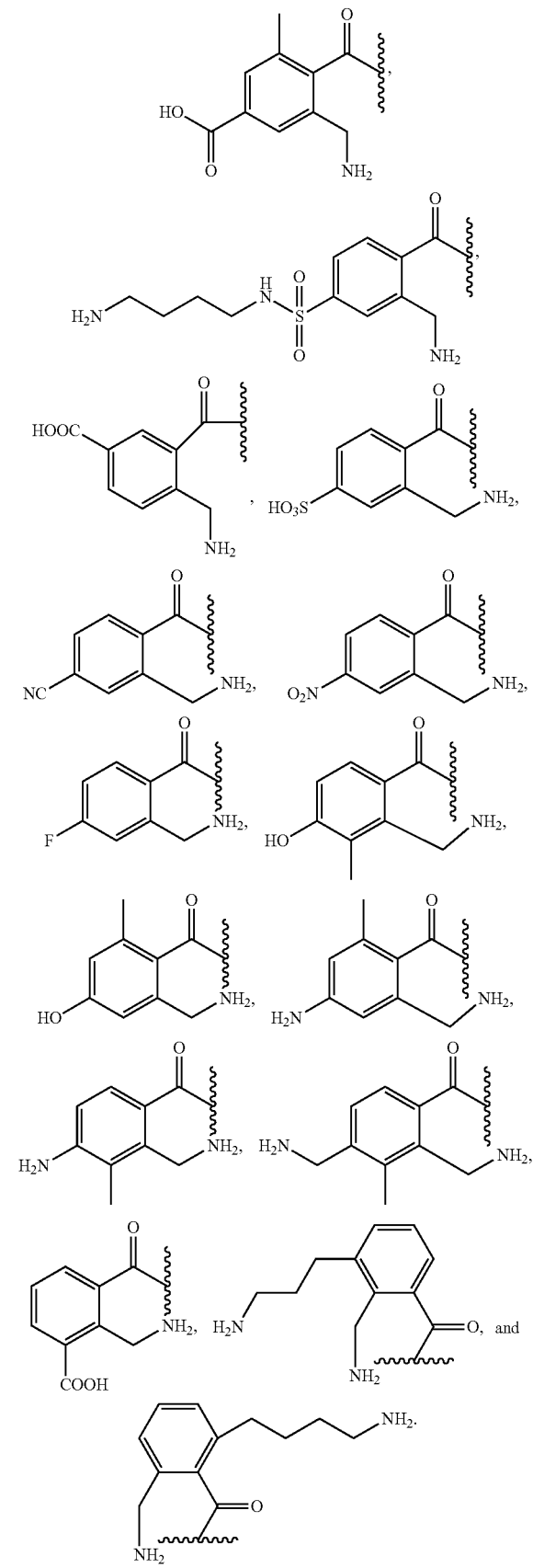

12. The prodrug of claim 10, or a pharmaceutically acceptable salt thereof, wherein the promoiety is of a formula selected from

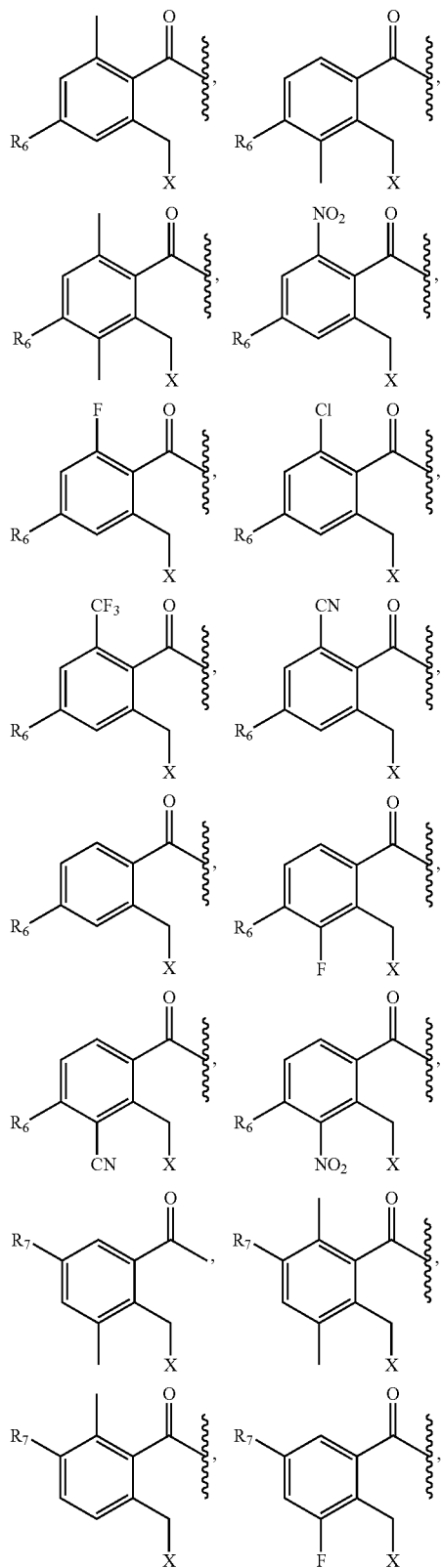

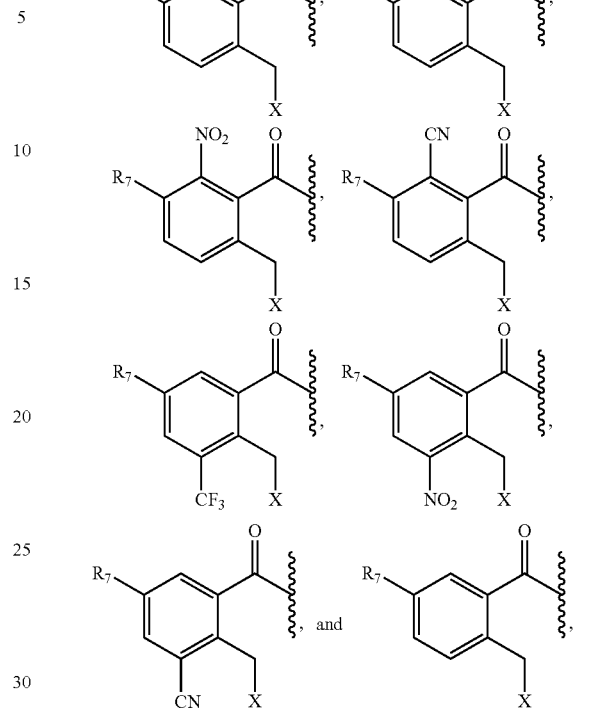

wherein $R_6$, $R_7$, and X are as defined in claim 10.

13. The prodrug of claim 12, or a pharmaceutically acceptable salt thereof, wherein X is OH or NH—$R_0$.

14. The prodrug of claim 13, or a pharmaceutically acceptable salt thereof, wherein X is OH.

15. The prodrug of claim 13, or a pharmaceutically acceptable salt thereof, wherein X is NH—$R_0$.

16. The prodrug of claim 13, or a pharmaceutically acceptable salt thereof, wherein X is $NH_2$.

17. The prodrug of claim 1, or a pharmaceutically acceptable salt thereof, wherein the promoiety is of a formula selected from

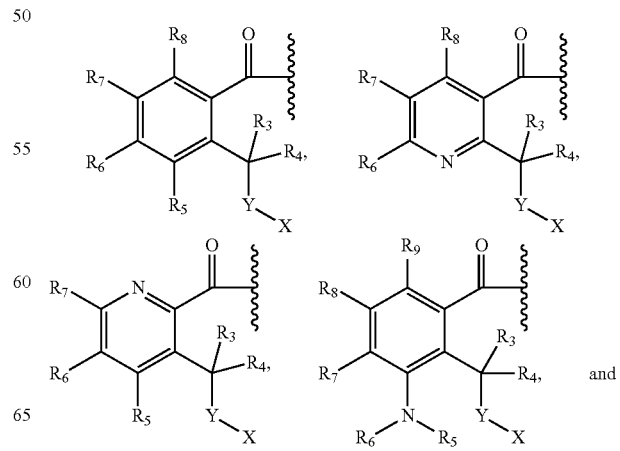

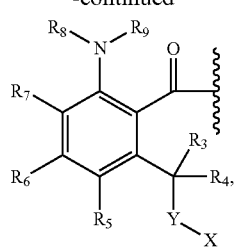

wherein

X, Y, R₃, and R₄ are as defined in claim 1,

R₅, R₆, R₇, R₈, and R₉ are independently selected from hydrogen (H), lower alkyl, lower alkoxy, acyl, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, imino, amino lower alkyl, lower alkylamino, lower dialkylamino, hydroxyl, hydroxyl alkyl, nitro, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, and mercapto (or sulfhydryl).

18. The prodrug of claim 1, or a pharmaceutically acceptable salt thereof, wherein the promoiety is of the following formula

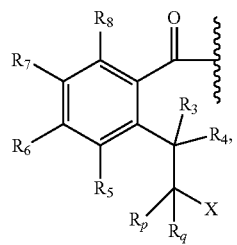

wherein $R_p$ and $R_q$ are as defined in claim 1.

19. The prodrug of claim 18, or a pharmaceutically acceptable salt thereof, wherein the promoiety is selected from

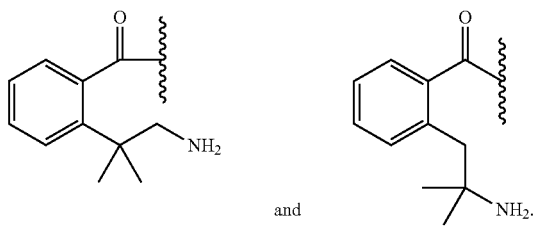 [SMILES: *C(=O)c1ccccc1C(C)(C)CN ; "and" ; *C(=O)c1ccccc1CC(C)(C)N]

20. The prodrug of claim 1, or a pharmaceutically acceptable salt thereof, wherein the promoiety is of a formula selected from

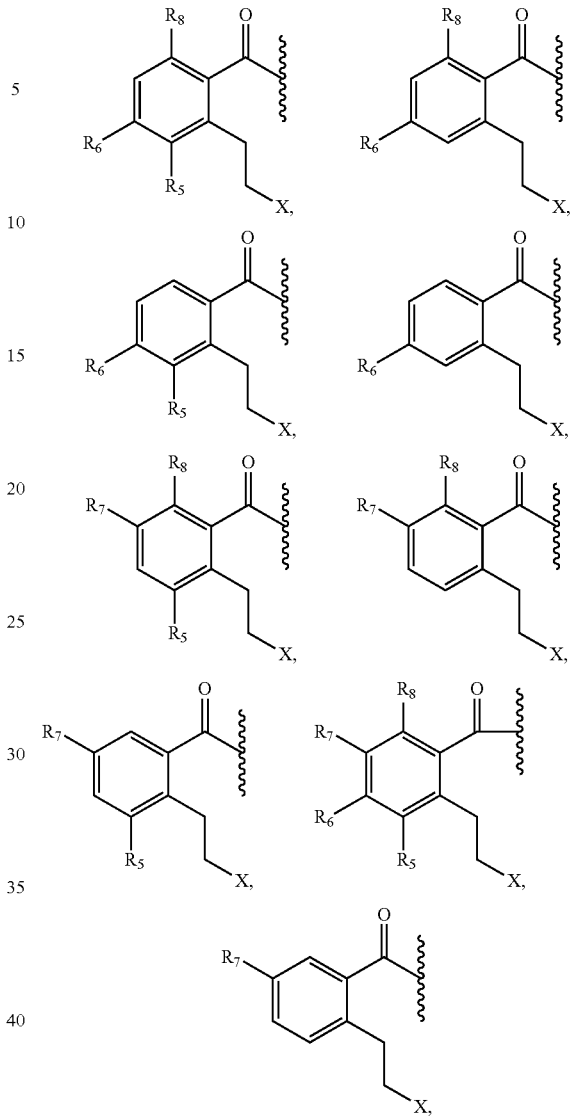

wherein

R₅, R₆, R₇, and R₈ are independently selected from hydrogen (H), lower alkyl, lower alkoxy, acyl, hydroxyl, amino, halogen, trifluoromethyl, trifluoromethoxy, nitrile, nitro, carboxylic acid, —SO₂—OH, —SO₂—NR$_{m1}$R$_{m2}$, —SO₂—R$_{m3}$, —O—R$_{m4}$, —S—Rm₅, —N—R$_{m6}$R$_{m7}$, —C(O)R$_{m8}$, —C(O)OR$_{m9}$, —OC(O)R$_{m10}$, —NHC(O)R$_{m11}$, —C(O)N$_{Rm12}$R$_{m13}$, and —NHC(O)NR$_{m14}$R$_{m15}$, wherein R$_{m1}$, R$_{m2}$, R$_{m3}$, R$_{m4}$, R$_{m5}$, R$_{m6}$, R$_{m7}$, R$_{m8}$, R$_{m9}$, R$_{m10}$, R$_{m11}$, R$_{m12}$, R$_{m13}$, R$_{m14}$, and R$_{m15}$ are independently selected from hydrogen (H), (C₁-C₁₈) alkyl, aryl, (C₁-C₁₈ alkyl)OH, (C₁-C₁₈ alkyl)SH, (C₁-C₁₈ alkyl)COOH, (C₁-C₁₈ alkyl)NH₂, (C₀-C₄ alkyl)(C₃-C₆ cycloalkyl), (C₀-C₁₀ alkyl)(C₂-C₅ heterocyclic), (C₀-C₄ alkyl)(C₆-C₁₀ aryl), and (C₁-C₄ alkyl)(C₃-C₉ heteroaryl);

X is OH or HN—R₀, wherein R₀ is as defined in claim 1.

21. The prodrug of claim 20, or a pharmaceutically acceptable salt thereof, wherein the promoiety is selected from

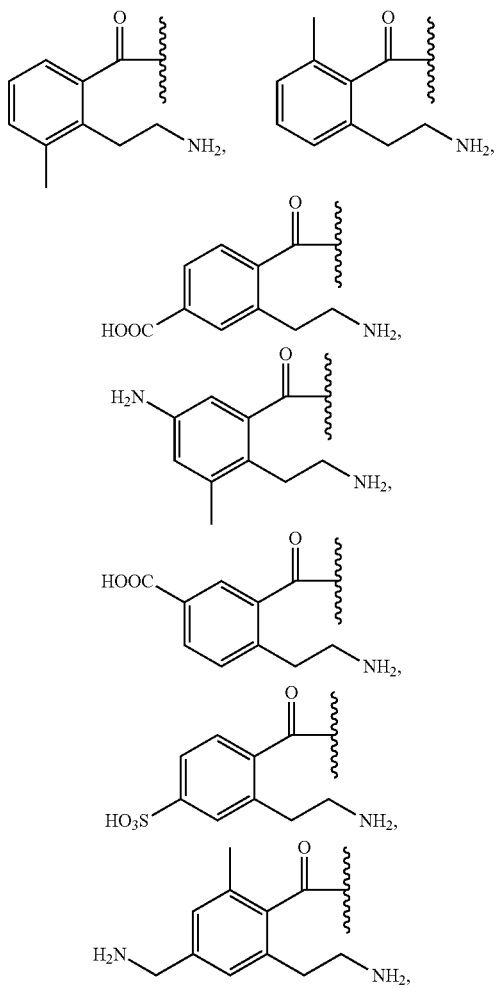

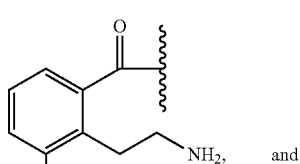

22. The prodrug of claim 1, or a pharmaceutically acceptable salt thereof, wherein the promoiety is of the following formula:

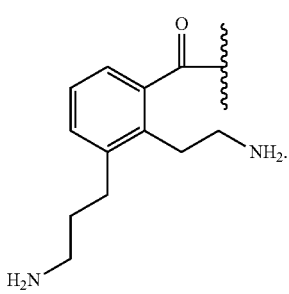

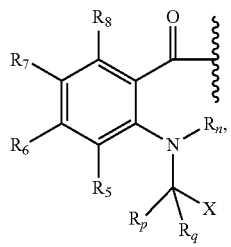

wherein X, $R_n$, $R_p$, and $R_q$ are as defined in claims 1;
$R_5$, $R_6$, $R_7$, and $R_8$ are independently selected from hydrogen (H), lower alkyl, lower alkoxy, acyl, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, imino, amino lower alkyl, lower alkylamino, lower dialkylamino, hydroxyl, hydroxyl alkyl, nitro, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, and mercapto (or sulfhydryl)

or two R groups selected from $R_p$, $R_q$, $R_5$, $R_6$, $R_7$, $R_8$ and $R_n$ that are attached to the same atom or two atoms separated by one bond form a $C_3$-$C_8$ cycloalkyl, cycloalkenyl, or cycloalkynyl ring, or saturated or unsaturated heterocyclic ring optionally substituted by at least one group; or two R groups together with the atoms to which they are attached form an aromatic ring optionally substituted by at least one group.

23. The prodrug of claim 1, or a pharmaceutically acceptable salt thereof, wherein the promoiety is of the following formula:

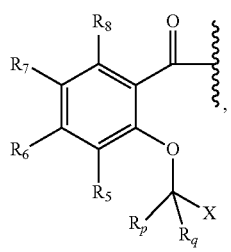

wherein X, $R_p$, $R_q$, are as defined in claimed 1;
$R_5$, $R_6$, $R_7$, and $R_8$ are independently selected from hydrogen (H), lower alkyl, lower alkoxy, acyl, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, imino, amino lower alkyl, lower alkylamino, lower dialkylamino, hydroxyl, hydroxyl alkyl, nitro, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, and mercapto (or sulfhydryl);

or two R groups selected from $R_p$, $R_q$, $R_5$, $R_6$, $R_7$, and $R_8$ that are attached to the same atom or two atoms separated by one bond form a $C_3$-$C_8$ cycloalkyl, cycloalkenyl, or cycloalkynyl ring, or saturated or unsaturated heterocyclic ring optionally substituted by at least one group; or two R groups together with the atoms to which they are attached form an aromatic ring optionally substituted by at least one group.

24. The prodrug of claim 1, or a pharmaceutically acceptable salt thereof, wherein the promoiety is of a formula selected from

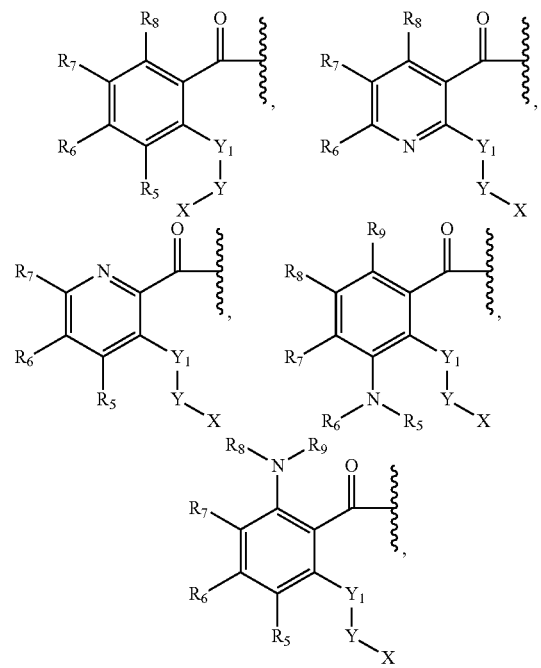

wherein

X and Y are as defined in claim 1;

$Y_1$ is C(O), C(S), SO, or $SO_2$;

$R_5$, $R_6$, $R_7$, $R_8$, and $R_9$ are independently selected from hydrogen (H), lower alkyl, lower alkoxy, acyl, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, imino, amino lower alkyl, lower alkylamino, lower dialkylamino, hydroxyl, hydroxyl alkyl, nitro, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, and mercapto (or sulfhydryl);

or two R groups selected from $R_5$, $R_6$, $R_7$, and $R_8$ that are attached to the same atom or two atoms separated by one bond form a $C_3$-$C_8$ cycloalkyl, cycloalkenyl, or cycloalkynyl ring, or saturated or unsaturated heterocyclic ring optionally substituted by at least one group; or two R groups together with the atoms to which they are attached form an aromatic ring optionally substituted by at least one group.

25. The prodrug of claim 24, or a pharmaceutically acceptable salt thereof, wherein $Y_1$ is C(O).

26. The prodrug of claim 24, or a pharmaceutically acceptable salt thereof, wherein Y is N—$R_o$ or C—$R_pR_q$, wherein $R_o$, $R_p$, and $R_q$ are as defined in claim 1.

27. The prodrug of claim 24, or a pharmaceutically acceptable salt thereof, wherein X is OH or HN—$R_0$, wherein $R_0$ is as defined in claim 1.

28. The prodrug of claim 1, or a pharmaceutically acceptable salt thereof, wherein the promoiety is of a formula selected from

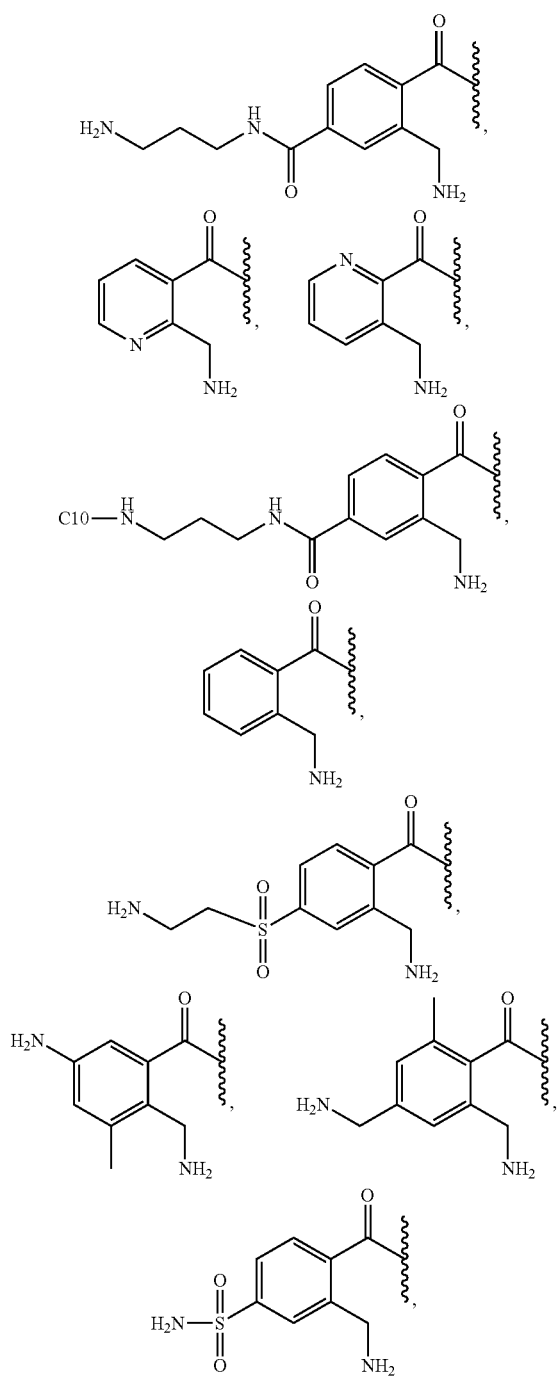

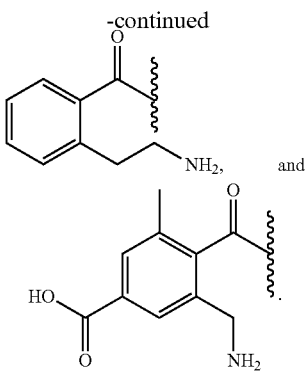
and

29. A pharmaceutical composition comprising a prodrug of claim 1 and a pharmaceutically acceptable excipient thereof.

30. The prodrug of claim 1, wherein a nitrogen-containing or hydroxyl-containing drug or a pharmaceutically active agent is selected from the group of agents falling into the following therapeutic categories: ACE-inhibitors; anti-anginal drugs; anti-arrhythmias; anti-asthmatics; anti-cholesterolemics; anti-convulsants; anti-depressants; anti-diarrhea preparations; anti-histamines; antihypertensive drugs; anti-infectives; anti-inflammatory agents; anti-lipid agents; antimanics; anti-nauseants; antistroke agents; anti-thyroid preparations; anti-tumor drugs; anti-tussives; anti-uricemic drugs; anti-viral agents; acne drugs; alkaloids; amino acid preparations; anabolic drugs; analgesics; anesthetics; angiogenesis inhibitors; antacids; anti-arthritics; antibiotics; anticoagulants; antiemetics; antiobesity drugs; antiparasitics; antipsychotics; antipyretics; antispasmodics; antithrombotic drugs; anxiolytic agents; appetite stimulants; appetite suppressants; beta blocking agents; bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypnotics; hypoglycemic agents; laxatives; migraine treatments; mucolytics; narcotics; neuroleptics; neuromuscular drugs; NSAIDS; peripheral vasodilators; prostaglandins; psychotropics; renin inhibitors; respiratory stimulants; steroids; stimulants; sympatholytics; thyroid preparations; tranquilizers; uterine relaxants; vaginal preparations; vasoconstrictors; vasodilators; vertigo agents; vitamins; and wound healing agents.

31. The prodrug of claim 1 or a pharmaceutically acceptable salt thereof, wherein X is SH or HN—$R_O$.

32. The prodrug of claim 1, or a pharmaceutically acceptable salt thereof, wherein the promoiety is of a formula selected from

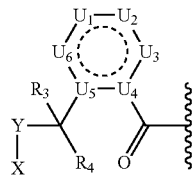

wherein X is HN—$R_0$, OH, or SH;

Y is selected from
(1) N—$R_O$;
(2) C($R_p R_q$); and
(3) O or S, provided that X is not OH or SH;
and wherein $U_1$, $U_2$, $U_3$, $U_4$, $U_5$, $U_6$, $R_3$, $R_4$, $R_0$, $R_o$, $R_p$ and $R_q$ are as defined in claim 1.

33. The prodrug of claim 32, or a pharmaceutically acceptable salt thereof, wherein Y is C($R_p R_q$), when X is HN—$R_0$, wherein $R_0$ and $R_p$ together with the atoms to which they are attached can form a 4, 5, or 6 membered heterocyclic ring.

34. The prodrug of claim 1, or a pharmaceutically acceptable salt thereof, wherein Y is C($R_p R_q$), when X is HN—$R_0$, wherein $R_0$ and $R_p$ together with the atoms to which they are attached can form a 4, 5, or 6 membered heterocyclic ring.

35. A prodrug of an insulin receptor binding analog comprises a modified A chain and B chain, wherein the A chain comprises a sequence of Z-$X_{-1}$ $X_0 X_1 I V X_4 X_5 C C X_8 X_9 X_{10} C X_{12} L X_{14} X_{15} L E X_{18} Y C X_{21} X_{22}$ (SEQ ID NO:24) and the B chain comprises a sequence of J-$X_{23-26}$ $X_{27} L C G X_{31} X_{32} L V X_{35} X_{36} L X_{38} X_{39} V C X_{42} X_{43} X_{44} G X_{46} X_{47}$ $X_{48} X_{49} X_{50} X_{51} X_{52} X_{53}$ (SEQ ID NO:25);
Z and J are independently hydrogen (H) or of a formula selected from

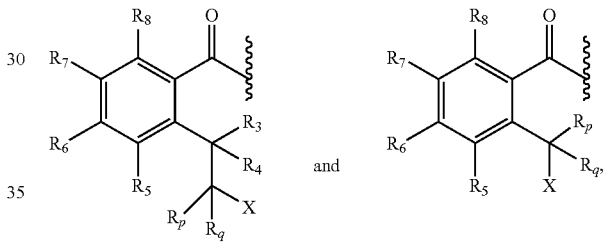
and wherein X is HN$R_0$, $NH_2$, or OH;
$R_0$, $R_p$, and $R_q$ are independently selected from hydrogen (H), lower alkyl, lower alkoxy, acyl, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, imino, amino lower alkyl, lower alkylamino, lower dialkylamino, hydroxyl, hydroxyl alkyl, nitro, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, and mercapto (or sulfhydryl);
$R_5$-$R_8$ are independently selected from hydrogen (H), lower alkyl, lower alkoxy, acyl, hydroxyl, amino, halogen, trifluoromethyl, trifloromethoxy, nitrile, nitro, carboxylic acid, —$SO_2$—OH, —$SO_2$—N$R_{m1}R_{m2}$, —$SO_2$—$R_{m3}$, —O—$R_{m4}$, —S—$R_{m5}$, —N—$R_{m6}R_{m7}$, —C(O)$R_{m8}$, —C(O)O$R_{m9}$, —OC(O)$R_{m10}$, —NHC(O)$R_{m11}$, —C(O)N$R_{m12}R_{m13}$, and —NHC(O)N$R_{m14}R_{m15}$, wherein $R_{m1}$, $R_{m2}$, $R_{m3}$, $R_{m4}$, $R_{m5}$, $R_{m6}$, $R_{m7}$, $R_{m8}$, $R_{m9}$, $R_{m10}$, $Rm_{11}$, $R_{m12}$, $R_{m13}$, $R_{m14}$, and $R_{m15}$ are independently selected from hydrogen (H), ($C_1$-$C_{18}$) alkyl, aryl, ($C_1$-$C_{18}$ alkyl)OH, ($C_1$-$C_{18}$ alkyl)SH, ($C_1$-$C_{18}$ alkyl)COOH, ($C_1$-$C_{18}$ alkyl)$NH_2$, ($C_0$-$C_4$ alkyl)($C_3$-$C_6$ cycloalkyl), ($C_0$-$C_{10}$ alkyl)($C_2$-$C_5$ heterocyclic), ($C_0$-$C_4$ alkyl)($C_6$-$C_{10}$aryl), and ($C_1$-$C_4$ alkyl)($C_3$-$C_9$ heteroaryl);

$X_{-1}$ is lysine, arginine, or deleted;
$X_0$ is lysine, arginine, or deleted;
$X_1$ is selected from sarcosine, D-alanine, D-leucine, D-lysine, D-glutamic acid, D-tryptophan, p-benzoyl-L-phenylalanine (Bpa), and glycine;
$X_4$ is aspartic acid or glutamic acid;
$X_5$ is aspartic acid, glutamic acid, asparagine, or glutamine;
$X_8$ is selected from 2,4-diaminobutyric acid (DAB), leucine, isoleucine, threonine, histidine, arginine, lysine, asparagine, glutamine, tryptophan, tyrosine, alanine, phenylalanine, valine, and methionine;
$X_9$ is alanine, serine, arginine, or lysine;
$X_{10}$ is isoleucine, serine, lysine, or arginine;
$X_{12}$ is aspartic acid or serine;
$X_{14}$ is tyrosine, phenylalanine, tryptophan, arginine, alanine, glutamic acid, histidine, or lysine;
$X_{15}$ is glutamine, leucine, arginine, or lysine;
$X_{18}$ is asparagine, methionine, or threonine;
$X_{21}$ is asparagine, aspartic acid, alanine, glycine, lysine, or arginine;
$X_{22}$ is lysine, arginine, lysine-lysine dipeptide, arginine-arginine dipeptide, or deleted;
$X_{23-26}$ is any codable amino acid except cysteine, a dipeptide or tripeptide comprising no cysteine, a tripeptide GPE, a tetrapeptide FVNQ, or deleted;
$X_{27}$ is histidine, threonine, arginine, or lysine;
$X_{31}$ is selected from threonine, alanine, serine, glycine, and α-aminoisobutyric acid;
$X_{32}$ is selected from histidine, aspartic acid, glutamic acid, homoglutamic acid, homocysteic acid, cysteic acid, arginine, and phenylalanine;
$X_{35}$ is glutamic acid or aspartic acid;
$X_{36}$ is alanine, threonine, or α-aminoisobutyric acid;
$X_{38}$ is selected from tyrosine, phenylalanine, and tryptophan;
$X_{39}$ is phenylalanine, tryptophan, or leucine;
$X_{42}$ is glycine, or alanine;
$X_{43}$ is glutamic acid, aspartic acid, or alanine;
$X_{44}$ is selected from arginine, lysine, aspartic acid, glutamic acid, and alanine;
$X_{46}$ is selected from phenylalaine, D-phenylalaine, D-tyrosine, D-alanine, and glycine;
$X_{47}$ is selected from tyrosine, phenylalanine, asparagine, and histidine;
$X_{48}$ is selected from tyrosine, D-tyrosine, phenylalanine, alanine, serine, histidine, D-alanine, D-tyrosine, glutamic acid, sarcosine, or deleted;
$X_{49}$ is selected from threonine, asparagine, arginine, glutamic acid, aspartic acid, lysine, serine, proline, or deleted;
$X_{50}$ is selected from proline, arginine, lysine, orthonine, glutamic acid, aspartic acid, or deleted;
$X_{51}$ is selected from proline, lysine, glutamic acid, aspartic acid, or deleted;
$X_{52}$ is threonine, alanine, glutamic acid, aspartic acid, or deleted;
$X_{53}$ is an arginine-arginine dipeptide, glutamic acid-glutamic acid dipeptide, aspartic acid-aspartic acid dipeptide, or deleted.

36. A prodrug comprising a single chain insulin having the sequence

J-$X_{23-26}$
$X_{27}$LCG$X_{31}X_{32}$LVE$X_{36}$L$X_{38}X_{39}$VC$X_{42}X_{43}X_{44}$G$X_{46}$
$X_{47}X_{48}X_{49}X_{50}X_{51}X_{52}X_{53}$-U-$X_{-1}$
$X_0X_1$IV$X_4X_5$CC$X_8X_9X_{10}$CSL$X_{14}X_{15}$LE$X_{18}$YC$X_{21}$
$X_{22}$ (SEQ ID NO:27), wherein J is a hydrogen (H) or of a formula selected from

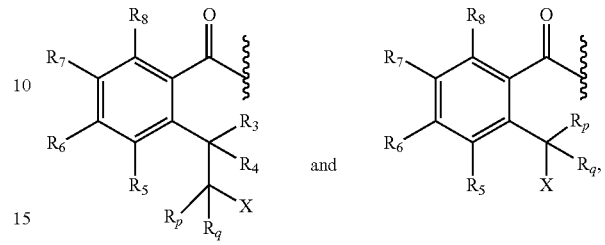

and

U is of a formula selected from

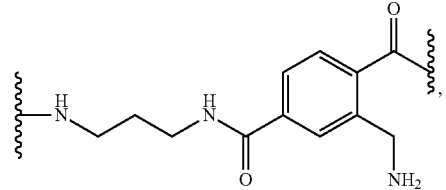

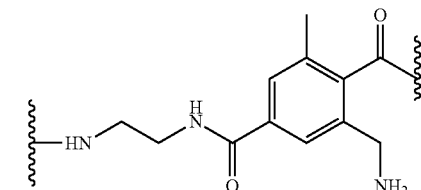

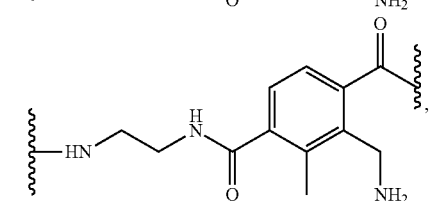

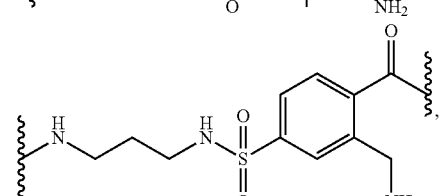

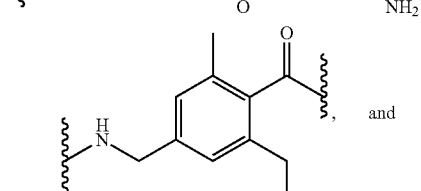, and

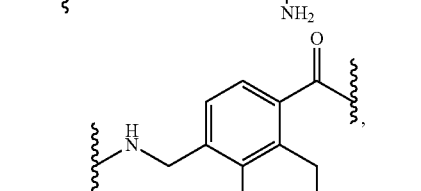

X is $HNR_0$, $NH_2$, or OH;

R$_0$, R$_p$, and R$_q$ are independently selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, imino, amino lower alkyl, lower alkylamino, lower dialkylamino, hydroxyl, hydroxyl alkyl, nitro, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, and mercapto (or sulfhydryl);

$R_5$-$R_8$ are independently selected from hydrogen (H), lower alkyl, lower alkoxy, acyl, hydroxyl, amino, halogen, trifluoromethyl, trifloromethoxy, nitrile, nitro, carboxylic acid, —$SO_2$—OH, —$SO_2$—$NR_{m1}R_{m2}$, —$SO_2$—$R_{m3}$, —O—$R_{m4}$, —S—$R_{m5}$, —N—$R_{m6}$,$R_{m7}$, —C(O)$R_{m8}$, —C(O)O$R_{m9}$, —OC(O)$R_{m10}$, —NHC(O)$R_{m11}$, —C(O)N$R_{m12}R_{m13}$, and —NHC(O)N$R_{m14}R_{m15}$, wherein $R_{m1}$, $R_{m2}$, $R_{m3}$, $R_{m4}$, $R_{m5}$, $R_{m6}$, $R_{m7}$, $R_{m8}$, $R_{m9}$, $R_{m10}$, $R_{m11}$, $R_{m12}$, $R_{m13}$, $R_{m14}$, and $R_{m15}$ are independently selected from hydrogen (H), ($C_1$-$C_{18}$) alkyl, aryl, ($C_1$-$C_{18}$ alkyl)OH, ($C_1$-$C_{18}$alkyl)SH, ($C_1$-$C_{18}$ alkyl)COOH, ($C_1$-$C_{18}$ alkyl)$NH_2$, ($C_0$-$C_4$ alkyl)($C_3$-$C_6$ cycloalkyl), ($C_0$-$C_{10}$ alkyl)($C_2$-$C_5$ heterocyclic), ($C_0$-$C_4$ alkyl)($C_6$-$C_{10}$ aryl), and ($C_1$-$C_4$ alkyl)($C_3$-$C_9$ heteroaryl);

$X_{-1}$ is lysine, arginine, or deleted;

$X_0$ is lysine, arginine, or deleted;

$X_1$ is selected from sarcosine, D-alanine, D-leucine, D-lysine, D-glutamic acid, D-tryptophan, p-benzoyl-L-phenylalanine (Bpa), and glycine;

$X_4$ is aspartic acid or glutamic acid;

$X_5$ is aspartic acid, glutamic acid, asparagine, or glutamine;

$X_8$ is selected from 2,4-diaminobutyric acid (DAB), leucine, isoleucine, threonine, histidine, arginine, lysine, asparagine, glutamine, tryptophan, tyrosine, alanine, phenylalanine, valine, and methionine;

$X_9$ is alanine, serine, arginine, or lysine;

$X_{10}$ is isoleucine, serine, lysine, or arginine;

$X_{12}$ is aspartic acid or serine;

$X_{14}$ is tyrosine, phenylalanine, tryptophan, arginine, alanine, glutamic acid, histidine, or lysine;

$X_{15}$ is glutamine, leucine, arginine, or lysine;

$X_{18}$ is asparagine, methionine, or threonine;

$X_{21}$ is asparagine, aspartic acid, alanine, glycine, lysine, or arginine;

$X_{22}$ is lysine, arginine, lysine-lysine dipeptide, arginine-arginine dipeptide, or deleted;

$X_{23-26}$ is any codable amino acid except cysteine, a dipeptide or tripeptide comprising no cysteine, a tripeptide GPE, a tetrapeptide FVNQ, or deleted;

$X_{27}$ is histidine, threonine, arginine, or lysine;

$X_{31}$ is selected from threonine, alanine, serine, glycine, and α-aminoisobutyric acid;

$X_{32}$ is selected from histidine, aspartic acid, glutamic acid, homoglutamic acid, homocysteic acid, cysteic acid, arginine, and phenylalanine;

$X_{35}$ is glutamic acid or aspartic acid;

$X_{36}$ is alanine, threonine, or α-aminoisobutyric acid;

$X_{38}$ is selected from tyrosine, phenylalanine, and tryptophan;

$X_{39}$ is phenylalanine, tryptophan, or leucine;

$X_{42}$ is glycine, or alanine;

$X_{43}$ is glutamic acid, aspartic acid, or alanine;

$X_{44}$ is selected from arginine, lysine, aspartic acid, glutamic acid, and alanine;

$X_{46}$ is selected from phenylalaine, D-phenylalaine, D-tyrosine, D-alanine, and glycine;

$X_{47}$ is selected from tyrosine, phenylalanine, asparagine, and histidine;

$X_{48}$ is selected from tyrosine, D-tyrosine, phenylalanine, alanine, serine, histidine, D-alanine, D-tyrosine, glutamic acid, sarcosine, or deleted;

$X_{49}$ is selected from threonine, asparagine, arginine, glutamic acid, aspartic acid, lysine, serine, proline, or deleted;

$X_{5O}$ is selected from proline, arginine, lysine, orthonine, glutamic acid, aspartic acid, or deleted;

$X_{51}$ is selected from proline, lysine, glutamic acid, aspartic acid, or deleted;

$X_{52}$ is threonine, alanine, glutamic acid, aspartic acid, or deleted;

$X_{53}$ is an arginine-arginine dipeptide, glutamic acid-glutamic acid dipeptide, aspartic acid-aspartic acid dipeptide, or deleted.

37. A prodrug comprising a GLP-1 receptor binding peptide having a sequence

J-$Xg_7Xg_8Xg_9GTXg_{12}TSDXg_{16}SXg_{18}Xg_{19}Xg_{20}EXg_{22}Xg_{23}Xg_{24}Xg_{25}Xg_{26}Xg_{27}F$
$Xg_{29}Xg_{30}WLXg_{33}Xg_{34}Xg_{35}Xg_{36}Xg_{37}Xg_{38}Xg_{39}Xg_{40}Xg_{41}Xg_{42}Xg_{43}Xg_{44}Xg_{45}Xg_{46}Xg_{47}Xg_{48}Xg_{49}$ (SEQ ID NO:49), wherein J is H or of a formula selected from

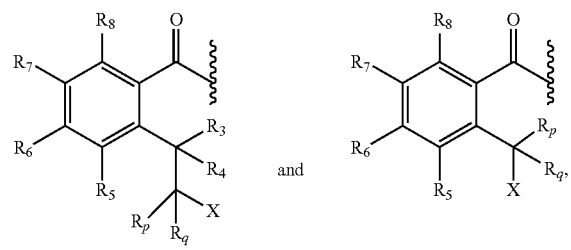

X is $HNR_0$, $NH_2$, or OH;

R$_0$, R$_p$, and R$_q$ are independently selected from hydrogen (H), lower alkyl, lower alkoxy, acyl, acyloxy, alkoxycarbonyl, aryl, phenyl, benzyl, halo, haloformyl, haloloweralkyl, trifluoromethyl, trifluoromethoxy, trichloromethyl, cyanato, isocyano, isocyanate, isothiocyanate, thiocyanate, lower alkylthio, amino, imino, amino lower alkyl, lower alkylamino, lower dialkylamino, hydroxyl, hydroxyl alkyl, nitro, nitrile (—CN), isonitrile (—NC), nitroso, pyridyl, azido, azo, carboxyl, carboxamido, carbethoxy, thiolalkyl, carbonate, carbamate group, loweralkylcarbamyl, diloweralkylcarbamyl, sulfonic acid group, sulfamide group, sulfonamide group, sulfonate group, sulfonyl, sulfoxide group, sulfide group, disulfide group, and mercapto (or sulfhydryl);

$R_5$-$R_8$ are independently selected from hydrogen (H), lower alkyl, lower alkoxy, acyl, hydroxyl, amino, halogen, trifluoromethyl, trifloromethoxy, nitrile, nitro, carboxylic acid, —$SO_2$—OH, —$SO_2$—$NR_{m1}R_{m2}$, —$SO_2$—$R_{m3}$, —O—$R_{m4}$, —S—$R_{m5}$, —N—$R_{m6}$,$R_{m7}$, —C(O)$R_{m8}$, —C(O)O$R_{m9}$, —OC(O)$R_{m10}$, —NHC(O)$R_{m11}$, —C(O)N$R_{m12}R_{m13}$, and —NHC(O)N$R_{m14}R_{m15}$, wherein $R_{m1}$, $R_{m2}$, $R_{m3}$, $R_{m4}$, $R_{m5}$, $R_{m6}$, $R_{m7}$, $R_{m8}$, $R_{m9}$, $R_{m10}$, $R_{m11}$, $R_{m12}$, $R_{m13}$, $R_{m14}$, and $R_{m15}$ are independently selected from hydrogen (H), ($C_1$-$C_{18}$) alkyl, aryl, ($C_1$-$C_{18}$ alkyl)OH, ($C_1$-$C_{18}$ alkyl)SH, ($C_1$-$C_{18}$ alkyl)COOH, ($C_1$-$C_{18}$ alkyl)$NH_2$, ($C_0$-$C_4$ alkyl)($C_3$-$C_6$ cycloalkyl), ($C_0$-$C_{10}$ alkyl)($C_2$-$C_5$ heterocyclic), ($C_0$-$C_4$ alkyl)($C_6$-$C_{10}$ aryl), and ($C_1$-$C_4$ alkyl)($C_3$-$C_9$ heteroaryl);

$Xg_7$ is selected from L-histidine, D-histidine, desamino-histidine, 2-amino-histidine, β-hydroxy-histidine, homohistidine, α-fluoromethyl-histidine, α-methyl-histidine, imidazopropionyl, arginine, and tyrosine;

$Xg_8$ is serine, D-serine, alanine, glycine, 2-aminoisobutyric acid, or valine;

$Xg_9$ is glutamic acid, glutamine, or proline;

$Xg_{12}$ is phenylalanine, tryptophan, tyrosine, or alanine;

$Xg_{16}$ is valine, tryptophan, isoleucine, leucine, phenylalanine, tyrosine, lysine, or cysteine;

$Xg_{18}$ is serine, tryptophan, tyrosine, phenylalanine, lysine, isoleucine, leucine, valine, or cysteine;

$Xg_{19}$ is tyrosine, tryptophan, or phenylalanine, glutamine, or alanine;

$Xg_{20}$ is leucine, phenylalanine, tyrosine, tryptophan, lysine, cysteine, or methione;

$Xg_{22}$ is glycine, glutamic acid, aspartic acid, serine, cysteine, or lysine;

$Xg_{23}$ is glutamine, glutamic acid, arginine, isoleucine, lysine, or cysteine;

$Xg_{24}$ is alanine, histidine, or arginine;

$Xg_{25}$ is alanine, glutamine, valine isoleucine, or leucine;

$Xg_{26}$ is lysine, cysteine, arginine, or glutamine;

$Xg_{27}$ is glutamic acid, aspartic acid, leucine, lysine, cysteine, or alanine;

$Xg_{29}$ is isoleucine or valine;

$Xg_{30}$ is alanine, asparagine, aspartic acid, glutamic acid, or glutamine;

$Xg_{33}$ is valine, leucine, lysine, cysteine, or methionine;

$Xg_{34}$ is lysine, alanine, asparagine, aspartic acid, arginine, cysteine, or glutamic acid;

$Xg_{35}$ is glycine, threonine, lysine, cysteine, or glutamine;

$Xg_{36}$ is glycine, lysine, cysteine, proline, or arginine;

$Xg_{37}$ is glycine, proline, serine, lysine, cysteine, $NH_2$, or deleted;

$Xg_{38}$ is serine, proline, histidine, cysteine, lysine, or deleted;

$Xg_{39}$ is serine, arginine, threonine, tryptophan, lysine, cysteine, or deleted;

$Xg_{40}$ is serine, glycine, asparagine, lysine, cysteine, or deleted;

$Xg_{41}$ is alanine, aspartic acid, arginine, glutamic acid, lysine, cysteine, glycine, or deleted;

$Xg_{42}$ is proline, alanine, tryptophan, $NH_2$, or deleted;

$Xg_{43}$ is proline, alanine, lysine, $NH_2$, or deleted;

$Xg_{44}$ is proline, alanine, arginine, lysine, histidine, $NH_2$, or deleted;

$Xg_{45}$ is serine, histidine, proline, lysine, arginine, cysteine, asparagine, $NH_2$ or deleted;

$Xg_{46}$ is histidine, serine, arginine, lysine, cysteine, isoleucine, $NH_2$ or deleted;

$Xg_{47}$ is histidine, serine, arginine, lysine, threonine, $NH_2$ or deleted;

$Xg_{48}$ is glutamine or deleted;

$Xg_{49}$ is $NH_2$ or deleted.

38. An insulin prodrug of the following formula

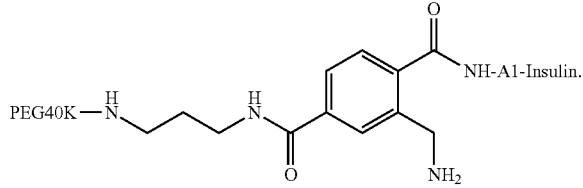

* * * * *